US011981938B2

(12) United States Patent
Szamecz et al.

(10) Patent No.: US 11,981,938 B2
(45) Date of Patent: May 14, 2024

(54) MICROORGANISMS AND METHODS FOR THE FERMENTATION OF CANNABINOIDS

(71) Applicant: Eleszto Genetika, Inc., Budapest (HU)

(72) Inventors: Bela Krisztian Szamecz, Budapest (HU); Szilvia Varszegi, Kalocsa (HU); Attila Nemeth, Budapest (HU); Lorand Szabo, Szentendre (HU); Abhinav Kumar, Pleasant Hill, CA (US)

(73) Assignee: ELESZTO GENETIKA, INC., Budapest (HU)

( * ) Notice: Subject to any disclaimer, the term of this patent is extended or adjusted under 35 U.S.C. 154(b) by 550 days.

(21) Appl. No.: 16/753,983

(22) PCT Filed: Oct. 4, 2018

(86) PCT No.: PCT/US2018/054400
§ 371 (c)(1),
(2) Date: Apr. 6, 2020

(87) PCT Pub. No.: WO2019/071000
PCT Pub. Date: Apr. 11, 2019

(65) Prior Publication Data

US 2021/0348137 A1 Nov. 11, 2021

Related U.S. Application Data

(60) Provisional application No. 62/686,884, filed on Jun. 19, 2018, provisional application No. 62/568,355, filed on Oct. 5, 2017.

(51) Int. Cl.

| | |
|---|---|
| ***C12N 9/10*** | (2006.01) |
| ***A61K 31/352*** | (2006.01) |
| ***C12N 1/21*** | (2006.01) |
| ***C12N 15/81*** | (2006.01) |
| ***C12P 7/42*** | (2006.01) |
| ***C12P 17/06*** | (2006.01) |

(52) U.S. Cl.
CPC .......... *C12N 9/1085* (2013.01); *A61K 31/352* (2013.01); *C12N 15/81* (2013.01); *C12P 7/42* (2013.01); *C12P 17/06* (2013.01)

(58) Field of Classification Search
None
See application file for complete search history.

(56) References Cited

U.S. PATENT DOCUMENTS

| | | | | |
|---|---|---|---|---|
| 2010/0286370 | A1* | 11/2010 | Gao | C07K 14/43595 536/23.1 |
| 2012/0144523 | A1* | 6/2012 | Page | C12N 9/1085 800/278 |
| 2016/0010126 | A1* | 1/2016 | Poulos | C12N 9/1085 435/146 |
| 2020/0283807 | A1* | 9/2020 | Mookerjee | C12Y 205/01 |

FOREIGN PATENT DOCUMENTS

| | | | | |
|---|---|---|---|---|
| WO | WO-2018200888 | A1 * | 11/2018 | C07C 63/04 |
| WO | 2019014490 | A1 | 1/2019 | |
| WO | 2019210404 | A1 | 11/2019 | |

OTHER PUBLICATIONS

Carvalho et al., Designing microorganisms for heterologous biosynthesis of cannabinoids, FEMS Yeast Res. 17, 2017, fox037. (Year: 2017).*

Agilent Technologies, pESC Yeast Epitope Tagging Vectors, Instruction Manual, 2015. (Year: 2015).*

Leber et al., Disrupted Short Chain Specific beta-Oxidation and Improved Synthase Expression Increase Synthesis of Short Chain Fatty Acids in *Saccharomyces cerevisiae*, Biotechnol. Bioeng. 113, 2016, 895-900. (Year: 2016).*

Lou et al., Complete biosynthesis of cannabinoids and their unnatural analogues in yeast, Nature 567, 2019, 123-26. (Year: 2019).*

Lorang et al., Green Fluorescent Protein Is Lighting Up Fungal Biology, Appl. Environ. Microbiol. 67, 2001, 1987-94. (Year: 2001).*

Albertsen et al., Diversion of Flux toward Sesquiterpene Production in *Saccharomyces cerevisiae* by Fusion of Host and Heterologous Enzymes, Appl. Environ. Microbiol. 77, 2011, 1033-40. (Year: 2011).*

Zirpel et al., J. Biotechnology (2017), 259:204-212.

Gen Bank Accession No. JP460119, Cannabis saliva PK15523.1_1.CasaPuKu mRNA sequence 102—[Cannabis saliva], Oct. 2011 [online]. Retrieved from—y the Internet <URL: https://www.ncbi.nlm.nih.gov/nuccore/JP460119> Entire document.

* cited by examiner

*Primary Examiner* — Todd M Epstein
(74) *Attorney, Agent, or Firm* — Gene J. Yao; Barnes & Thornburg LLP

(57) ABSTRACT

Disclosed herein are microorganism and methods that can be used for the synthesis of cannabigerolic acid (CBGA) and cannabinoids. The methods disclosed can be used to produce CBGA, $\Delta^9$-tetrahydrocannabinolic acid (THCA), cannabidiolic acid (CBDA), cannabichromenic acid (CBCA), $\Delta^9$-tetrahydrocannabinol (THC), cannabidiol (CBD), cannabichromene (CBC). Enzymes useful for the synthesis of CBGA and cannabinoids, include but are not limited to acyl activating enzyme (AAE1), polyketide synthase (PKS), olivetolic acid cyclase (OAC), prenyltransferase (PT), THCA synthase (THCAS), CBDA synthase (CBDAS), CBCA synthase (CBCAS), HMG-Co reductase (HMG1), and/or farnesyl pyrophosphate synthetase (ERG20). The microorganisms can also have one or more genes disrupted, such as gene that that controls beta oxidation of long chain fatty acids.

20 Claims, 5 Drawing Sheets

Specification includes a Sequence Listing.

MICROORGANISMS AND METHODS FOR THE FERMENTATION OF CANNABINOIDS

CROSS-REFERENCE TO RELATED APPLICATIONS

This application is a U.S. national stage filing of International Patent Application No. PCT/US2018/054400, filed Oct. 4, 2018, which claims the priority of U.S. Provisional Application Nos. 62/686,884, filed Jun. 19, 2018, and 62/568,355, filed Oct. 5, 2017.

SEQUENCE LISTING

The instant application contains a Sequence Listing which has been submitted electronically in ASCII format and is hereby incorporated by reference in its entirety. The ASCII copy was created on Sep. 19, 2018, is named INX00395_SL.txt and is 211,481 bytes in size.

BACKGROUND OF THE DISCLOSURE

*Cannabis sativa* (marijuana, hemp; Cannabaceae) is a medicinal and psychoactive herbal drug. Its unique effects are believed to be caused by cannabinoids, which include $\Delta^9$-tetrahydrocannabinol (THC) and more than 80 related metabolites. Medical marijuana and cannabinoid drugs are increasingly used to treat a range of diseases and conditions such as multiple sclerosis and chronic pain.

Currently, the production of cannabinoids for pharmaceutical or other use is through the extraction of cannabinoids from plants, for example *Cannabis sativa*, or by chemical synthesis.

There are several drawbacks of the natural production and extraction of cannabinoids from plants. It is often difficult to reproduce identical cannabinoid profiles in plants using an extraction process. In addition, extraction from *Cannabis sativa* produces a mixture of cannabinoids, which can be difficult to purify to provide a single compound needed for pharmaceutical applications.

The chemical synthesis of various cannabinoids is a costly process compared to extraction, but it provides the final product as single pure product, which is often required for pharmaceutical use.

The microbial fermentation-based production of cannabigerolic acid ("CBGA") or cannabinoids can be more economical, more robust, scalable, and can provide specific cannabinoid products for simplified isolation and purification versus current routes.

There are some known microbial fermentation processes. For example, WO 2016/010827 A1 and WO 2011/017798 A1 describe several processes. However, attempts at reproducing the methods disclosed therein, were unsuccessful: CBGA was not produced. The inventors have discovered a way to produce cannabinoids as described herein.

INCORPORATION BY REFERENCE

All publications, patents, and patent applications herein are incorporated by reference in their entireties to the same extent as if each individual publication, patent, or patent application was specifically and individually indicated to be incorporated by reference in its entirety. In the event of a conflict between a term herein and a term in an incorporated reference, the term herein controls.

SUMMARY

This application discloses microorganisms that are capable of producing CBGA and cannabinoids (e.g., THC), in an efficient manner, as well as methods of increasing the efficiency of CBGA and cannabinoid synthesis. The products that can be made by the processes and microorganism described herein can include, but are not limited to CBGA, $\Delta^9$-tetrahydrocannabinolic acid (THCA), cannabidiolic acid (CBDA), cannabichromenic acid (CBCA), $\Delta^9$-tetrahydrocannabinol (THC), cannabidiol (CBD), and cannabichromene (CBC).

Disclosed herein is a genetically modified microorganism comprising a polynucleotide that is at least 60% identical to SEQ ID NO: 2. The polynucleotide can encode an amino acid sequence that is at least 60% identical to SEQ ID NO: 1.

Disclosed herein is also a genetically modified microorganism comprising a polynucleotide that is at least 60% identical to SEQ ID NO: 26. The polynucleotide can encode an amino acid sequence that is at least 60% identical to SEQ ID NO: 27.

Disclosed herein is also a genetically modified microorganism comprising a polynucleotide that is at least 60% identical to SEQ ID NO: 31. The polynucleotide can encode an amino acid sequence that is at least 60% identical to SEQ ID NO: 32.

Disclosed herein is also a genetically modified microorganism comprising a polynucleotide that is at least 60% identical to SEQ ID NO: 37. The polynucleotide can encode an amino acid sequence that is at least 60% identical to SEQ ID NO: 38.

In some cases, the polynucleotide can encode for an enzyme that is capable of converting olivetolic acid to cannabigerolic acid. In other cases, the polynucleotide can encode for a protein having prenyltransferase activity.

In some cases, the genetically modified microorganism can further comprise one or more nucleic acids encoding for acyl activating enzyme (AAE1); polyketide synthase (PKS); olivetolic acid cyclase (OAC); THCA synthase (THCAS); CBDA synthase (CBDAS); CBCA synthase (CBCAS); HMG-Co reductase (HMG1); farnesyl pyrophosphate synthetase (ERG20); or any combination thereof. For example, if the microorganism comprises an AAE1, the AAE1 can be encoded by a polynucleotide sequence that is substantially identical to SEQ ID NO: 14. If the microorganism comprises a PKS, the PKS can be encoded by a polynucleotide sequence that is substantially identical to SEQ ID NO: 6. If the microorganism comprises an OAC, the OAC can be encoded by a polynucleotide sequence that is substantially identical to SEQ ID NO: 8. If the microorganism comprises a THCAS, the THCAS can be encoded by a polynucleotide sequence that is substantially identical to SEQ ID NO: 10. If the microorganism comprises a CBDAS, the CBDAS can be encoded by a polynucleotide sequence that is substantially identical to SEQ ID NO: 12. If the microorganism comprises a CBCAS, the CBCAS can be encoded by a polynucleotide sequence that is substantially identical to SEQ ID NO: 18. If the microorganism comprises a HMG1, the HMG1 comprises an amino acid sequence that is at least 90% identical to SEQ ID NO: 20 or 22. If the microorganism comprises an ERG20, the ERG20 comprises an amino acid sequence that is at least 90% identical to SEQ ID NO: 24.

In some cases, the microorganism can be a bacterium or a yeast. For example, the microorganism is a yeast. The yeast can be from the genus *Saccharomyces*. The yeast can be from the species *Saccharomyces cerevisiae*.

In some cases, the microorganism can comprise one or more genes that are disrupted. In some cases, the one or more genes that are disrupted can be from a pathway that controls beta oxidation of long chain fatty acids. In some cases, the one or more genes can be endogenous to the microorganism. In some cases, the one or more genes can be FOX1, FAA1, FAA4, FAT1, PXA1, PXA2, and/or PEX11. In some cases, the one or more gene is disrupted using a CRISPR/Cas system.

The genetically modified microorganism described throughout can be a microorganism that is capable of making cannabigerolic acid ("CBGA"). The genetically modified microorganism described throughout can be a microorganism that is capable of making a cannabinoid.

The cannabinoid produced by the genetically modified microorganism described throughout, can be $\Delta^9$-tetrahydrocannabinolic acid (THCA), cannabidiolic acid (CBDA), cannabichromenic acid (CBCA), $\Delta^9$-tetrahydrocannabinol (THC), cannabidiol (CBD), cannabichromene (CBC), or any combination thereof.

Disclosed herein is a method of making CBGA comprising (a) contacting a carbon substrate with a genetically modified microorganism, where the genetically modified microorganism comprises one or more polynucleotides encoding for i) acyl activating enzyme (AAE1); ii) a polyketide synthase (PKS), iii) a olivetolic acid cyclase (OAC), and iv) a prenyltransferase that comprises an amino acid sequence that is at least 60% identical to SEQ ID NO: 1; and (b) growing the genetically modified microorganism to make CBGA.

Disclosed herein is a method of making CBGA comprising (a) contacting a carbon substrate with a genetically modified microorganism, where the genetically modified microorganism comprises one or more polynucleotides encoding for i) acyl activating enzyme (AAE1); ii) a polyketide synthase (PKS), iii) a olivetolic acid cyclase (OAC), and iv) a prenyltransferase that comprises an amino acid sequence that is at least 60% identical to SEQ ID NO: 27; and (b) growing the genetically modified microorganism to make CBGA.

Disclosed herein is a method of making CBGA comprising (a) contacting a carbon substrate with a genetically modified microorganism, where the genetically modified microorganism comprises one or more polynucleotides encoding for i) acyl activating enzyme (AAE1); ii) a polyketide synthase (PKS), iii) a olivetolic acid cyclase (OAC), and iv) a prenyltransferase that comprises an amino acid sequence that is at least 60% identical to SEQ ID NO: 32; and (b) growing the genetically modified microorganism to make CBGA.

Disclosed herein is a method of making CBGA comprising (a) contacting a carbon substrate with a genetically modified microorganism, where the genetically modified microorganism comprises one or more polynucleotides encoding for i) acyl activating enzyme (AAE1); ii) a polyketide synthase (PKS), iii) a olivetolic acid cyclase (OAC), and iv) a prenyltransferase that comprises an amino acid sequence that is at least 60% identical to SEQ ID NO: 38; and (b) growing the genetically modified microorganism to make CBGA.

The methods can also further comprising isolating the CBGA from (b). The method can also further comprise converting CBGA into CBG, $\Delta^9$-tetrahydrocannabinolic acid; THC; cannabidiolic acid; CBD; cannabichromenic acid; CBC; other cannabinoid; or any combination thereof. This CBGA conversion can be completed outside the microorganism. In some cases, the conversion is a non-enzymatic conversion. In other cases, the conversion is an enzymatic conversion.

Also disclosed herein is a method of making a cannabinoid comprising (a) contacting a carbon substrate with a genetically modified microorganism, where the genetically modified microorganism comprises one or more polynucleotides encoding for i) acyl activating enzyme (AAE1); ii) a polyketide synthase (PKS), iii) a olivetolic acid cyclase (OAC), iv) a prenyltransferase that comprises an amino acid sequence that is at least 60% identical to SEQ ID NO: 1, and (v) a THCA synthase (THCAS); CBDA synthase (CBDAS), CBCA synthase (CBCAS), or any combination thereof; and (b) growing the genetically modified microorganism to make a cannabinoid.

Also disclosed herein is a method of making a cannabinoid comprising (a) contacting a carbon substrate with a genetically modified microorganism, where the genetically modified microorganism comprises one or more polynucleotides encoding for i) acyl activating enzyme (AAE1); ii) a polyketide synthase (PKS), iii) a olivetolic acid cyclase (OAC), iv) a prenyltransferase that comprises an amino acid sequence that is at least 60% identical to SEQ ID NO: 27, and (v) a THCA synthase (THCAS); CBDA synthase (CBDAS), CBCA synthase (CBCAS), or any combination thereof; and (b) growing the genetically modified microorganism to make a cannabinoid.

Also disclosed herein is a method of making a cannabinoid comprising (a) contacting a carbon substrate with a genetically modified microorganism, where the genetically modified microorganism comprises one or more polynucleotides encoding for i) acyl activating enzyme (AAE1); ii) a polyketide synthase (PKS), iii) a olivetolic acid cyclase (OAC), iv) a prenyltransferase that comprises an amino acid sequence that is at least 60% identical to SEQ ID NO: 32, and (v) a THCA synthase (THCAS); CBDA synthase (CBDAS), CBCA synthase (CBCAS), or any combination thereof; and (b) growing the genetically modified microorganism to make a cannabinoid.

Also disclosed herein is a method of making a cannabinoid comprising (a) contacting a carbon substrate with a genetically modified microorganism, where the genetically modified microorganism comprises one or more polynucleotides encoding for i) acyl activating enzyme (AAE1); ii) a polyketide synthase (PKS), iii) a olivetolic acid cyclase (OAC), iv) a prenyltransferase that comprises an amino acid sequence that is at least 60% identical to SEQ ID NO: 38, and (v) a THCA synthase (THCAS); CBDA synthase (CBDAS), CBCA synthase (CBCAS), or any combination thereof; and (b) growing the genetically modified microorganism to make a cannabinoid.

The methods can further comprise isolating the cannabinoid from (b).

The carbon substrate used in the methods can be a sugar, alcohol, and/or fatty acid. For example, the sugar, alcohol or fatty acid can include without limitation hexanoic acid, glucose, fructose, xylose, sucrose, dextrins, starch, xylan, cellulose, hemicellulose, arabinose, glycerol, ethanol, butanol, methanol, or any combination thereof. In some cases, the carbon substrate is hexanoic acid.

The methods can use the same or similar genetically modified microorganism described throughout. For example, if the microorganism comprises an AAE1, the AAE1 can be encoded by a polynucleotide sequence that is substantially identical to SEQ ID NO: 14. If the microorganism comprises a PKS, the PKS can be encoded by a polynucleotide sequence that is substantially identical to SEQ ID NO: 6. If the microorganism comprises an OAC, the OAC can be encoded by a polynucleotide sequence that is substantially identical to SEQ ID NO: 8.

The methods can use a microorganism that can further comprise one or more nucleic acids encoding for THCA synthase (THCAS); CBDA synthase (CBDAS), CBCA synthase (CBCAS); or any combination thereof. If the microorganism comprises a THCAS, the THCAS can be encoded by a polynucleotide sequence that is substantially identical to SEQ ID NO: 10. If the microorganism comprises a CBDAS, the CBDAS can be encoded by a polynucleotide sequence that is substantially identical to SEQ ID NO: 12. If the microorganism comprises a CBCAS, the CBCAS can be encoded by a polynucleotide sequence that is substantially identical to SEQ ID NO: 18. If the microorganism comprises an HMG1, the HMG1 comprises an amino acid sequence that is substantially identical to SEQ ID NO: 20 or 22. If the microorganism comprises an ERG20, the ERG20 comprises an amino acid sequence that is substantially identical to SEQ ID NO: 24. One or more of these enzymes can be present outside of a microorganism.

The methods can use a microorganism that can further comprise one or more genes that are disrupted. For example, the one or more genes that are disrupted can be from a pathway that controls beta oxidation of long chain fatty acids. In some cases, the one or more genes can be endogenous to the microorganism. In some cases, the one or more genes can comprise FOX1, FAA1, FAA4, FAT1, PXA1, PXA2, and/or PEX11.

In some cases, the methods can use a microorganism that can be a bacterium or a yeast. If a yeast, the yeast can be from the genus *Saccharomyces*, e.g., from the species *Saccharomyces cerevisiae*.

In some cases, the methods can produce CBGA. In other cases, the method can use a microorganism that produces THC. In other cases, the method can use a microorganism that produces CBD. In other cases, the method can use a microorganism that produces CBC.

Disclosed herein are also medicaments comprising a cannabinoid made by any one of the methods disclosed throughout, and a pharmaceutically acceptable excipient.

Also disclosed herein is a method of treating a disease or a symptom of a disease comprising administering a subject in need thereof the cannabinoid made by any described throughout.

Further disclosed herein are cannabinoids made by the microorganisms and/or the methods that are used for the manufacture of a medicament for the treatment of disease or symptom of disease. Additionally disclosed herein is a method of treating disease or symptom of disease comprising administering a subject in need thereof the medicament disclosed herein.

In some cases, the a disease or a symptom of a disease can be anorexia, multiple sclerosis, neurodegenerative disorders, epilepsy, glaucoma, osteoporosis, schizophrenia, bipolar disorder, post-traumatic stress disorder (PTSD), asthma, cardiovascular disorders, cancer, obesity, metabolic syndrome-related disorders, depression, anxiety, insomnia, emesis, pain, or inflammation.

Disclosed herein is a vector comprising a polynucleotide that is at least 60% identical to SEQ ID NO: 2 and a promoter suitable for expression in a yeast host. Also disclosed herein is a vector comprising a polynucleotide that is at least 60% identical to SEQ ID NO: 36 and a promoter suitable for expression in a yeast host. Also disclosed herein is a vector comprising a polynucleotide that is at least 60% identical to SEQ ID NO: 31 and a promoter suitable for expression in a yeast host. Also disclosed herein is a vector comprising a polynucleotide that is at least 60% identical to SEQ ID NO: 37 and a promoter suitable for expression in a yeast host.

Also disclosed herein is an isolated polynucleotide comprising a nucleotide sequence that is at least 60% identical to SEQ ID NO: 2. Also disclosed herein is an isolated polynucleotide comprising a nucleotide sequence that is at least 60% identical to SEQ ID NO: 26.

Also disclosed herein is an isolated polynucleotide comprising a nucleotide sequence that is at least 60% identical to SEQ ID NO: 31.

Also disclosed herein is an isolated polynucleotide comprising a nucleotide sequence that is at least 60% identical to SEQ ID NO: 37.

Further disclosed herein is a method of making a genetically modified microorganism capable of synthesizing CBGA comprising (a) contacting a microorganism with a polynucleotide that is at least 60% identical to SEQ ID NO: 2; and (b) growing the microorganism so that the polynucleotide is inserted into the microorganism.

Also disclosed herein is a method of making a genetically modified microorganism capable of synthesizing CBGA comprising (a) contacting a microorganism with a polynucleotide that is at least 60% identical to SEQ ID NO: 26; and (b) growing the microorganism so that the polynucleotide is inserted into the microorganism.

Also disclosed herein is a method of making a genetically modified microorganism capable of synthesizing CBGA comprising (a) contacting a microorganism with a polynucleotide that is at least 60% identical to SEQ ID NO: 31; and (b) growing the microorganism so that the polynucleotide is inserted into the microorganism.

Also disclosed herein is a method of making a genetically modified microorganism capable of synthesizing CBGA comprising (a) contacting a microorganism with a polynucleotide that is at least 60% identical to SEQ ID NO: 37; and (b) growing the microorganism so that the polynucleotide is inserted into the microorganism.

Also disclosed herein is a method of making a genetically modified microorganism capable of synthesizing cannabinoid comprising (a) contacting a microorganism with a polynucleotide that is at least 60% identical to SEQ ID NO: 2; and (b) growing the microorganism so that the polynucleotide is inserted into the microorganism.

Also disclosed herein is a method of making a genetically modified microorganism capable of synthesizing cannabinoid comprising (a) contacting a microorganism with a polynucleotide that is at least 60% identical to SEQ ID NO: 26; and (b) growing the microorganism so that the polynucleotide is inserted into the microorganism.

Also disclosed herein is a method of making a genetically modified microorganism capable of synthesizing cannabinoid comprising (a) contacting a microorganism with a polynucleotide that is at least 60% identical to SEQ ID NO: 31; and (b) growing the microorganism so that the polynucleotide is inserted into the microorganism.

Also disclosed herein is a method of making a genetically modified microorganism capable of synthesizing cannabinoid comprising (a) contacting a microorganism with a polynucleotide that is at least 60% identical to SEQ ID NO: 37; and (b) growing the microorganism so that the polynucleotide is inserted into the microorganism.

In some cases, the microorganism can translate the polynucleotide into an amino acid sequence that is at least 60% identical to SEQ ID NO: 1. In some cases, the microorganism can translate the polynucleotide into an amino acid sequence that is at least 60% identical to SEQ ID NO: 27. In some cases, the microorganism can translate the polynucleotide into an amino acid sequence that is at least 60% identical to SEQ ID NO: 32. In some cases, the microorganism can translate the polynucleotide into an amino acid sequence that is at least 60% identical to SEQ ID NO: 38. The polynucleotide can encode for a protein having prenyltransferase activity.

In some cases, the microorganism can be a bacterium or a yeast. If a yeast, the yeast can be from the genus *Saccharomyces*.

The microorganism can also comprise one or more additional polynucleotides that encodes for acyl activating enzyme (AAE1); polyketide synthase (PKS); olivetolic acid cyclase (OAC); THCA synthase (THCAS); CBDA synthase (CBDAS), CBCA synthase (CBCAS); HMG-Co reductase (HMG1); farnesyl pyrophosphate synthetase (ERG20); or any combination thereof.

In some cases, the method can comprise a genetically modified microorganism that comprises a polynucleotide encoding for an acyl activating enzyme (AAE1); polyketide synthase (PKS); olivetolic acid cyclase (OAC); and a prenyltransferase that is at least 60% identical to SEQ ID NO: 2.

The methods can result in a cannabinoid, where the cannabinoid is $\Delta^9$-tetrahydrocannabinolic acid (THCA), cannabidiolic acid (CBDA), cannabichromenic acid (CBCA), $\Delta^9$-tetrahydrocannabinol (THC), cannabidiol (CBD), cannabichromene (CBC), or any combination thereof.

Further disclosed is the use of a cannabinoid made by any one of the microorganisms or methods disclosed throughout for the manufacture of a medicament for recreational use. In some cases, the recreational use is delivered through inhalation, intravenously, oral, or topical. In some cases, the delivery is inhalation and completed through a vaporizer. In some cases, the delivery is intravenous and completed through a saline solution. In some cases, the delivery is oral and completed through food. In some cases, the delivery is oral and completed through drink. In some cases, the delivery is topical and completed through a patch. In some cases, the delivery is topical and completed through a lotion.

Further disclosed herein is a genetically modified microorganism that is capable of making a CBGA, which comprising a disruption of an endogenous gene that is FOX1

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE DISCLOSURE

Figure 1:
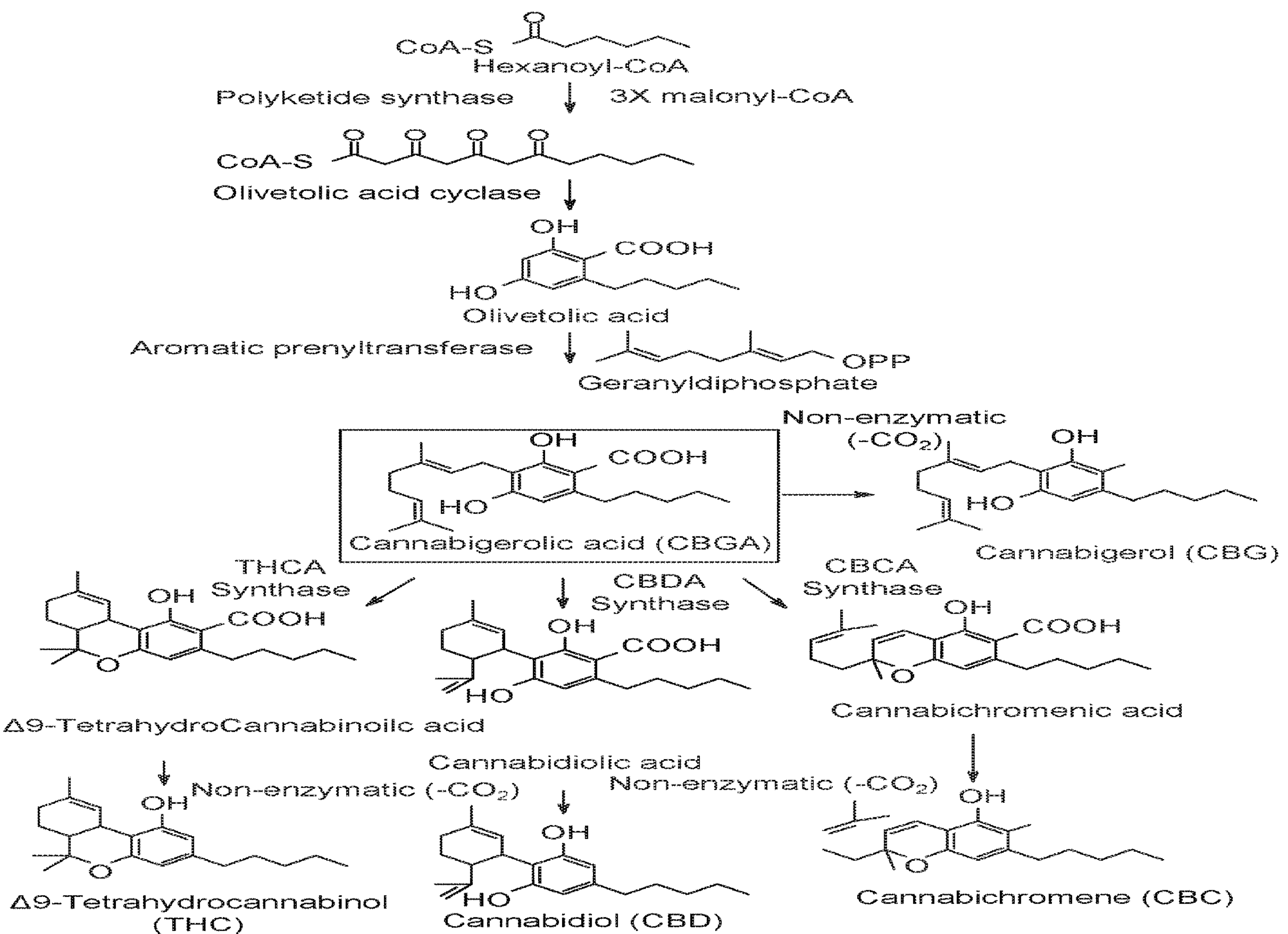
FIG. 1 shows the pathway from hexanoyl-CoA to CBGA. From CBGA, various cannabinoids can be made including but not limited to THC, CBD, CBC, and CBG.

The following description and examples illustrate embodiments of the invention in detail. It is to be understood that this invention is not limited to the particular embodiments described herein and as such can vary. Those of skill in the art will recognize that there are numerous variations and modifications of this invention, which are encompassed within its scope.

The cannabinoid biosynthetic pathway starts with acyl activating enzyme (AAE1) (also known hexanoyl-CoA synthetase) which converts hexanoic acid to hexanoyl-CoA, which is used as a substrate for a reaction involving two enzymes, polyketide synthase (PKS) and olivetolic acid cyclase (OAC), to form olivetolic acid. Olivetolic acid is then geranylated by a prenyltransferase enzyme (PT) to form cannabigerolic acid (CBGA), a branch-point intermediate that is converted by oxidocyclase enzymes to $\Delta^9$-tetrahydrocannabinolic acid (THCA), cannabidiolic acid (CBDA), and cannabichromenic acid (CBCA). These compounds undergo nonenzymatic decarboxylation to their neutral forms, THC and cannabidiol (CBD) and cannabichromene (CBC), respectively. CBGA is a key pathway intermediate that is an important compound for the preparation of both known, commercialized cannabinoids and compounds in development.

Described herein are genetically modified microorganisms, enzymes, polynucleotides, and methods to more efficiently produce CBGA or cannabinoids, including, THCA, CBDA, CBCA, THC, CBC and CBD.

Definitions

The term "about" in relation to a reference numerical value and its grammatical equivalents as used herein can include the numerical value itself and a range of values plus or minus 10% from that numerical value. For example, the amount "about 10" includes 10 and any amounts from 9 to 11. For example, the term "about" in relation to a reference numerical value can also include a range of values plus or minus 10%, 9%, 8%, 7%, 6%, 5%, 4%, 3%, 2%, or 1% from that value. In some cases, the numerical disclosed throughout can be "about" that numerical value even without specifically mentioning the term "about."

The term "genetic modification" or "genetically modified" and their grammatical equivalents as used herein can refer to one or more alterations of a nucleic acid, e.g., the nucleic acid within a microorganism's genome. For example, genetic modification can refer to alterations, additions, and/or deletion of nucleic acid (e.g., whole genes or fragments of genes).

The term "disrupting" and its grammatical equivalents as used herein can refer to a process of altering a gene, e.g., by deletion, insertion, mutation, rearrangement, or any combination thereof. For example, a gene can be disrupted by knockout. Disrupting a gene can be partially reducing or completely suppressing expression (e.g., mRNA and/or protein expression) of the gene. Disrupting can also include inhibitory technology, such as shRNA, siRNA, microRNA, dominant negative, or any other means to inhibit functionality or expression of a gene or protein.

The term "gene editing" and its grammatical equivalents as used herein can refer to genetic engineering in which one or more nucleotides are inserted, replaced, or removed from a genome. For example, gene editing can be performed using a nuclease (e.g., a natural-existing nuclease or an artificially engineered nuclease).

The terms "and/or" and "any combination thereof" and their grammatical equivalents as used herein, can be used interchangeably. These terms can convey that any combination is specifically contemplated. Solely for illustrative purposes, the following phrases "A, B, and/or C" or "A, B, C, or any combination thereof" can mean "A individually; B individually; C individually; A and B; B and C; A and C; and A, B, and C."

The term "sugar" and its grammatical equivalents as used herein can include, but are not limited to (i) simple carbohydrates, such as monosaccharides (e.g., glucose fructose, galactose, ribose); disaccharides (e.g., maltose, sucrose, lactose); oligosaccharides (e.g., raffinose, stachyose); or (ii) complex carbohydrates, such as starch (e.g., long chains of glucose, amylose, amylopectin); glycogen; fiber (e.g., cellulose, hemicellulose, pectin, gum, mucilage).

The term "alcohol" and its grammatical equivalents as used herein can include, but are not limited to any organic compound in which the hydroxyl functional group (—OH) is bound to a saturated carbon atom. For example, the term alcohol can include i) monohydric alcohols (e.g., methanol, ethanol, isopropyl alcohol, butanol, pentanol, cetyl alcohol); ii) polyhydric alcohols (e.g., ethylene glycol, propylene glycol, glycerol, erythritol, threitol, xylitol, mannitol, sorbitol, volemitol); iii) unsaturated aliphatic alcohols (e.g., allyl alcohol, geraniol, propargyl alcohol); or iv) alicyclic alcohols (e.g., inositol, menthol).

The term "fatty acid" and its grammatical equivalents as used herein can include, but are not limited to, a carboxylic acid with a long aliphatic chain, which is either saturated or unsaturated. Some examples of unsaturated fatty acids include but are not limited to myristoleic acid, sapienic acid; linoelaidic acid; α-linolenic acid; stearidonic acid; eicosapentaenoic acid; docosahexaenoic acid; linoleic acid; γ-linolenic acid; dihomo-γ-linolenic acid; arachidonic acid; docosatetraenoic acid; palmitoleic acid; vaccenic acid; paullinic acid; oleic acid; elaidic acid; gondoic acid; erucic acid; nervonic acid; and mead acid. Some examples of saturated fatty acids include but are not limited to propionic acid, butyric acid, valeric acid, hexanoic acid, enanthic acid, caprylic acid, pelargonic acid, capric acid, undecylic acid, lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, pentacosylic acid, cerotic acid, heptacosylic acid, montanic acid, nonacosylic acid, melissic acid, henatriacontylic acid, lacceroic acid, psyllic acid, geddic acid, ceroplastic acid, hexatriacontylic acid, heptatriacontanoic acid, and octatriacontanoic acid.

The term "substantially pure" and its grammatical equivalents as used herein can mean that a particular substance does not contain a majority of another substance. For example, "substantially pure CBGA" can mean at least 90% CBGA. In some instances, "substantially pure CBGA" can mean at least 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, 99.99%, 99.999%, or 99.9999% CBGA. For example, substantially pure CBGA can mean at least 70% CBGA. In some cases, substantially pure CBGA can mean at least 75% CBGA. In some cases, substantially pure CBGA can mean at least 80% CBGA. In some cases, substantially pure CBGA can mean at least 85% CBGA. In some cases, substantially pure CBGA can mean at least 90% CBGA. In some cases, substantially pure CBGA can mean at least 91% CBGA. In some cases, substantially pure CBGA can mean at least 92% CBGA. In some cases, substantially pure CBGA can mean at least 93% CBGA. In some cases, substantially pure CBGA can mean at least 94% CBGA. In some cases, substantially pure CBGA can mean at least 95% CBGA. In some cases, substantially pure CBGA can mean at least 96% CBGA. In some cases, substantially pure CBGA can mean at least 97% CBGA. In some cases, substantially pure CBGA can mean at least 98% CBGA. In some cases, substantially pure CBGA can mean at least 99% CBGA. In some cases, substantially pure CBGA can mean at least 99.9% CBGA. In some cases, substantially pure CBGA can mean at least 99.99% CBGA. In some cases, substantially pure CBGA can mean at least 99.999% CBGA. In some cases, substantially pure CBGA can mean at least 99.9999% CBGA.

The term "heterologous" and its grammatical equivalents as used herein can mean "derived from a different species." For example, a "heterologous gene" can mean a gene that is from a different species. In some instances, as "a yeast comprising a heterologous gene" can mean that the yeast contains a gene that is not from the same yeast. The gene can be from a different microorganism such as bacterium or from a different species such as a different yeast species.

The term "substantially identical" and its grammatical equivalents in reference to another sequence as used herein can mean at least 50% identical. In some instances, the term substantially identical refers to a sequence that is 55% identical. In some instances, the term substantially identical refers to a sequence that is 60% identical. In some instances, the term substantially identical refers to a sequence that is 65% identical. In some instances, the term substantially identical refers to a sequence that is 70% identical. In some instances, the term substantially identical refers to a sequence that is 75% identical. In some instances, the term substantially identical refers to a sequence that is 80% identical. In other instances, the term substantially identical refers to a sequence that is 81% identical. In other instances, the term substantially identical refers to a sequence that is 82% identical. In other instances, the term substantially identical refers to a sequence that is 83% identical. In other instances, the term substantially identical refers to a sequence that is 84% identical. In other instances, the term substantially identical refers to a sequence that is 85% identical. In other instances, the term substantially identical refers to a sequence that is 86% identical. In other instances, the term substantially identical refers to a sequence that is 87% identical. In other instances, the term substantially identical refers to a sequence that is 88% identical. In other instances, the term substantially identical refers to a sequence that is 89% identical. In some instances, the term substantially identical refers to a sequence that is 90% identical. In some instances, the term substantially identical refers to a sequence that is 91% identical. In some instances, the term substantially identical refers to a sequence that is 92% identical. In some instances, the term substantially identical refers to a sequence that is 93% identical. In some instances, the term substantially identical refers to a sequence that is 94% identical. In some instances, the term substantially identical refers to a sequence that is 95% identical. In some instances, the term substantially identical refers to a sequence that is 96% identical. In some instances, the term substantially identical refers to a sequence that is 97% identical. In some instances, the term substantially identical refers to a sequence that is 98% identical. In some instances, the term substantially identical refers to a sequence that is 99% identical. In order to determine the percentage of identity between two sequences, the two sequences are aligned, using for example the alignment method of Needleman and Wunsch (J. Mol. Biol., 1970, 48: 443), as revised by Smith and Waterman (Adv. Appl. Math., 1981, 2: 482) so that the highest order match is obtained between the two sequences and the number of identical amino acids/nucleotides is determined between the two sequences. For example, methods to calculate the percentage identity between two amino acid sequences are generally art recognized and include, for example, those described by Carillo and Lipton (SIAM J. Applied Math., 1988, 48:1073) and those described in Computational Molecular Biology, Lesk, e.d. Oxford University Press, New York, 1988, Biocomputing: Informatics and Genomics Projects. Generally, computer programs will be employed for such calculations. Computer programs that can be used in this regard include, but are not limited to, GCG (Devereux et al., Nucleic Acids Res., 1984, 12: 387) BLASTP, BLASTN and FASTA (Altschul et al., J. Molec. Biol., 1990:215:403). A particularly preferred method for determining the percentage identity between two polypeptides involves the Clustal W algorithm (Thompson, J D, Higgines, D G and Gibson T J, 1994, Nucleic Acid Res 22(22): 4673-4680 together with the BLOSUM 62 scoring matrix (Henikoff S & Henikoff, J G, 1992, Proc. Natl. Acad. Sci. USA 89: 10915-10919 using a gap opening penalty of 10 and a gap extension penalty of 0.1, so that the highest order match obtained between two sequences wherein at least 50% of the total length of one of the two sequences is involved in the alignment.

The term "polyketide synthase", "PKS", "tetraketide synthase", "olivetol synthase", "OLS", "OS" and their grammatical equivalents can be interchangeably used, as they refer to the same enzyme.

General

A cannabinoid is one of a class of diverse chemical compounds that acts on cannabinoid receptors. Cannabinoids can alter neurotransmitter release in the brain. Ligands for these receptor proteins include the endocannabinoids (produced naturally in the body by animals), the phytocannabinoids (found in cannabis and some other plants), and synthetic cannabinoids (manufactured artificially). The most notable cannabinoid is the phytocannabinoid tetrahydrocannabinol (THC), the primary psychoactive compound in cannabis. Cannabidiol (CBD) is another major constituent of the plant. There are at least 113 different cannabinoids isolated from cannabis, exhibiting varied effects.

Cannabinoids can be useful in treating the side effects of cancer and cancer treatment. For example, one of the severe side effects of chemotherapy is loss of appetite. Marinol (containing delta-9-THC API) has been used to effectively treat this side effect. Other medical uses of cannabinoids include but are not limited to anti-inflammatory activity, blocking cell growth, preventing the growth of blood vessels that supply tumors, antiviral activity, and relieving muscle spasms caused by multiple sclerosis.

Disclosed herein are microorganisms and methods of making CBGA or cannabinoids.

Microrganisms Used in the Synthesis of Cannabinoids

Cell-Types

The cells that can be used include but are not limited to plant or animal cells, fungus, yeast, algae, or bacterium. The cells can be prokaryotes or in some cases can be eukaryotes. For example, the cell can be a *Saccharomyces cerevisiae, Yarrowia hpolyhca*, or *Escherichia coli*, or any other cell disclosed throughout.

In certain cases, the cells are not naturally capable of producing CBGA or cannabinoids (e.g., THC, CBD or CBC). In some cases, the cells are able to produce CBGA or cannabinoids but at a low level. By implementation of the methods described herein, the cells can be modified such that the level of CBGA or cannabinoids in the cells is higher relative to the level of CBGA or the same cannabinoid produced in the unmodified cells.

In some cases, the modified cell is capable of producing a substrate capable of being converted into a CBGA or a cannabinoid, however, the cells is not capable of naturally producing a cannabinoids. The genetically modified microorganisms in some cases are unable to produce a substrate capable of being converted into a CBGA or a cannabinoid (for example, hexanoic acid), and the substrate capable of being converted into a CBGA or a cannabinoid is provided to the cells as part of the cell's growth medium. In this case, the genetically modified microorganism can process the substrate into a desired product such as CBGA, THC, CBD, or CBC.

The cell can naturally comprise one or more enzyme capable of catalyzing one or more of the reactions: Hexanoyl-CoA to Olivetolic Acid; Olivetolic Acid to CBGA; CBGA to THCA; CBGA to CBDA; CBGA to CBCA; THCA to THC; CBDA to CBD; or CBCA to CBC.

Enzymes

The cells disclosed can be genetically modified with one or more enzymes that are capable of producing CBGA or a cannabinoid, and other pathway intermediates such as olivetolic acid. The cells disclosed can also be genetically modified with one or more enzymes that are capable of assisting in or enhancing the ability of the cell to produce CBGA or a cannabinoid, and other pathway intermediate (as disclosed throughout).

The cell can be modified to include an enzyme that can perform any one of the following reactions: hexanoic acid to hexanoyl-CoA, hexanoyl-CoA to olivetolic Acid; olivetolic Acid to CBGA; CBGA to THCA; CBGA to CBDA; CBGA to CBCA; THCA to THC; CBDA to CBD; or CBCA to CBC. For example, the cell can be modified with one or more of the following enzymes: polyketide synthase (PKS); olivetolic acid cyclase (OAC); prenyltransferase (PT); THCA synthase (THCAS); CBDA synthase (CBDAS), CBCA synthase (CBCAS); or any combination thereof. Additional enzymes that can be included include but are not limited to HMG-CoA reductase, ERG20 reductase, or both. These enzymes can either be endogenous to the cell or heterologous. However, in some cases, even if the enzyme is endogenous, it can be made to be overexpressed. The heterologous enzymes can also be overexpressed.

In some cases, two or more consecutive enzymes in the pathway from a carbon substrate (e.g., sugar) to any of the cannabinoids described throughout (e.g., THCA, CBDA, CBCA, THC, CBD, or CBC) can be used. In some cases, three or more consecutive enzymes in the pathway can be used. In some cases, four or more consecutive enzymes in the pathway can be used. In some cases, five or more consecutive enzymes in the pathway can be used. In some cases, six or more consecutive enzymes in the pathway can be used. In some cases, seven or more consecutive enzymes in the pathway can be used. In some cases, eight or more consecutive enzymes in the pathway can be used. In some cases, nine or more consecutive enzymes in the pathway can be used. In some cases, ten or more consecutive enzymes in the pathway can be used.

In some cases, when an acyl activating enzyme (AAE1) is desired, the AAE1 can be encoded by an amino acid sequence that is substantially identical to SEQ ID NO: 13. In some cases, the AAE1 can be encoded by an amino acid sequence that is at least 50% identical to SEQ ID NO: 13. In some cases, the AAE1 can be encoded by an amino acid sequence that is at least 55% identical to SEQ ID NO: 13. In some cases, the AAE1 can be encoded by an amino acid sequence that is at least 60% identical to SEQ ID NO: 13. In some cases, the AAE1 can be encoded by an amino acid sequence that is at least 65% identical to SEQ ID NO: 13. In some cases, the AAE1 can be encoded by an amino acid sequence that is at least 70% identical to SEQ ID NO: 13. In some cases, the AAE1 can be encoded by an amino acid sequence that is at least 75% identical to SEQ ID NO: 13. In some cases, the AAE1 can be encoded by an amino acid sequence that is at least 80% identical to SEQ ID NO: 13. In some cases, the AAE1 can be encoded by an amino acid sequence that is at least 81% identical to SEQ ID NO: 13. In some cases, the AAE1 can be encoded by an amino acid sequence that is at least 82% identical to SEQ ID NO: 13. In some cases, the AAE1 can be encoded by an amino acid sequence that is at least 83% identical to SEQ ID NO: 13. In some cases, the AAE1 can be encoded by an amino acid sequence that is at least 84% identical to SEQ ID NO: 13. In some cases, the AAE1 can be encoded by an amino acid sequence that is at least 85% identical to SEQ ID NO: 13. In some cases, the AAE1 can be encoded by an amino acid sequence that is at least 86% identical to SEQ ID NO: 13. In some cases, the AAE1 can be encoded by an amino acid sequence that is at least 87% identical to SEQ ID NO: 13. In some cases, the AAE1 can be encoded by an amino acid sequence that is at least 88% identical to SEQ ID NO: 13. In some cases, the AAE1 can be encoded by an amino acid sequence that is at least 89% identical to SEQ ID NO: 13. In some cases, the AAE1 can be encoded by an amino acid sequence that is at least 90% identical to SEQ ID NO: 13. In some cases, the AAE1 can be encoded by an amino acid sequence that is at least 91% identical to SEQ ID NO: 13. In some cases, the AAE1 can be encoded by an amino acid sequence that is at least 92% identical to SEQ ID NO: 13. In some cases, the AAE1 can be encoded by an amino acid sequence that is at least 93% identical to SEQ ID NO: 13. In some cases, the AAE1 can be encoded by an amino acid sequence that is at least 94% identical to SEQ ID NO: 13. In some cases, the AAE1 can be encoded by an amino acid sequence that is at least 95% identical to SEQ ID NO: 13. In some cases, the AAE1 can be encoded by an amino acid sequence that is at least 96% identical to SEQ ID NO: 13. In some cases, the AAE1 can be encoded by an amino acid sequence that is at least 97% identical to SEQ ID NO: 13. In some cases, the AAE1 can be encoded by an amino acid sequence that is at least 98% identical to SEQ ID NO: 13. In some cases, the AAE1 can be encoded by an amino acid sequence that is at least 99% identical to SEQ ID NO: 13. In some cases, the AAE1 can be encoded by an amino acid sequence that is identical to SEQ ID NO: 13. In some cases, the amino acid sequence can be optimized to correspond to amino acid usage within a specific host organism/cell.

In some cases when a polyketide synthase (PKS) is desired, the PKS can be encoded by an amino acid sequence that is substantially identical to SEQ ID NO: 5. In some cases, the PKS can be encoded by an amino acid sequence that is at least 50% identical to SEQ ID NO: 5. In some cases, the PKS can be encoded by an amino acid sequence that is at least 55% identical to SEQ ID NO: 5. In some cases, the PKS can be encoded by an amino acid sequence that is at least 60% identical to SEQ ID NO: 5. In some cases, the PKS can be encoded by an amino acid sequence that is at least 65% identical to SEQ ID NO: 5. In some cases, the PKS can be encoded by an amino acid sequence that is at least 70% identical to SEQ ID NO: 5. In some cases, the PKS can be encoded by an amino acid sequence that is at least 75% identical to SEQ ID NO: 5. In some cases, the PKS can be encoded by an amino acid sequence that is at least 80% identical to SEQ ID NO: 5. In some cases, the PKS can be encoded by an amino acid sequence that is at least 81% identical to SEQ ID NO: 5. In some cases, the PKS can be encoded by an amino acid sequence that is at least 82% identical to SEQ ID NO: 5. In some cases, the PKS can be encoded by an amino acid sequence that is at least 83% identical to SEQ ID NO: 5. In some cases, the PKS can be encoded by an amino acid sequence that is at least 84% identical to SEQ ID NO: 5. In some cases, the PKS can be encoded by an amino acid sequence that is at least 85% identical to SEQ ID NO: 5. In some cases, the PKS can be encoded by an amino acid sequence that is at least 86% identical to SEQ ID NO: 5. In some cases, the PKS can be encoded by an amino acid sequence that is at least 87% identical to SEQ ID NO: 5. In some cases, the PKS can be encoded by an amino acid sequence that is at least 88% identical to SEQ ID NO: 5. In some cases, the PKS can be encoded by an amino acid sequence that is at least 89% identical to SEQ ID NO: 5. In some cases, the PKS can be encoded by an amino acid sequence that is at least 90% identical to SEQ ID NO: 5. In some cases, the PKS can be encoded by an amino acid sequence that is at least 91% identical to SEQ ID NO: 5. In some cases, the PKS can be encoded by an amino acid sequence that is at least 92% identical to SEQ ID NO: 5. In some cases, the PKS can be encoded by an amino acid sequence that is at least 93% identical to SEQ ID NO: 5. In some cases, the PKS can be encoded by an amino acid sequence that is at least 94% identical to SEQ ID NO: 5. In some cases, the PKS can be encoded by an amino acid sequence that is at least 95% identical to SEQ ID NO: 5. In some cases, the PKS can be encoded by an amino acid sequence that is at least 96% identical to SEQ ID NO: 5. In some cases, the PKS can be encoded by an amino acid sequence that is at least 97% identical to SEQ ID NO: 5. In some cases, the PKS can be encoded by an amino acid sequence that is at least 98% identical to SEQ ID NO: 5. In some cases, the PKS can be encoded by an amino acid sequence that is at least 99% identical to SEQ ID NO: 5. In some cases, the PKS can be encoded by an amino acid sequence that is identical to SEQ ID NO: 5. In some cases, the amino acid sequence can be optimized to correspond to amino acid usage within a specific host organism/cell.

In some cases when an olivetolic acid cyclase (OAC) is desired, the OAC can be encoded by an amino acid sequence that is substantially identical to SEQ ID NO: 7. In some cases, the OAC can be encoded by an amino acid sequence that is at least 50% identical to SEQ ID NO: 7. In some cases, the OAC can be encoded by an amino acid sequence that is at least 55% identical to SEQ ID NO: 7. In some cases, the OAC can be encoded by an amino acid sequence that is at least 60% identical to SEQ ID NO: 7. In some cases, the OAC can be encoded by an amino acid sequence that is at least 65% identical to SEQ ID NO: 7. In some cases, the OAC can be encoded by an amino acid sequence that is at least 70% identical to SEQ ID NO: 7. In some cases, the OAC can be encoded by an amino acid sequence that is at least 75% identical to SEQ ID NO: 7. In some cases, the OAC can be encoded by an amino acid sequence that is at least 80% identical to SEQ ID NO: 7. In some cases, the OAC can be encoded by an amino acid sequence that is at least 81% identical to SEQ ID NO: 7. In some cases, the OAC can be encoded by an amino acid sequence that is at least 82% identical to SEQ ID NO: 7. In some cases, the OAC can be encoded by an amino acid sequence that is at least 83% identical to SEQ ID NO: 7. In some cases, the OAC can be encoded by an amino acid sequence that is at least 84% identical to SEQ ID NO: 7. In some cases, the OAC can be encoded by an amino acid sequence that is at least 85% identical to SEQ ID NO: 7. In some cases, the OAC can be encoded by an amino acid sequence that is at least 86% identical to SEQ ID NO: 7. In some cases, the OAC can be encoded by an amino acid sequence that is at least 87% identical to SEQ ID NO: 7. In some cases, the OAC can be encoded by an amino acid sequence that is at least 88% identical to SEQ ID NO: 7. In some cases, the OAC can be encoded by an amino acid sequence that is at least 89% identical to SEQ ID NO: 7. In some cases, the OAC can be encoded by an amino acid sequence that is at least 90% identical to SEQ ID NO: 7. In some cases, the OAC can be encoded by an amino acid sequence that is at least 91% identical to SEQ ID NO: 7. In some cases, the OAC can be encoded by an amino acid sequence that is at least 92% identical to SEQ ID NO: 7. In some cases, the OAC can be encoded by an amino acid sequence that is at least 93% identical to SEQ ID NO: 7. In some cases, the OAC can be encoded by an amino acid sequence that is at least 94% identical to SEQ ID NO: 7. In some cases, the OAC can be encoded by an amino acid sequence that is at least 95% identical to SEQ ID NO: 7. In some cases, the OAC can be encoded by an amino acid sequence that is at least 96% identical to SEQ ID NO: 7. In some cases, the OAC can be encoded by an amino acid sequence that is at least 97% identical to SEQ ID NO: 7. In some cases, the OAC can be encoded by an amino acid sequence that is at least 98% identical to SEQ ID NO: 7. In some cases, the OAC can be encoded by an amino acid sequence that is at least 99% identical to SEQ ID NO: 7. In some cases, the OAC can be encoded by an amino acid sequence that is identical to SEQ ID NO: 7. In some cases, the amino acid sequence can be optimized to correspond to amino acid usage within a specific host organism/cell.

In some cases when a prenyltransferase (PT) is desired, the PT can be encoded by an amino acid sequence that is substantially identical to any one of SEQ ID NOs: 1, 27, 32, or 38. In some cases, the amino acid sequence encoding a prenyltransferase can be at least 50% identical to any one of SEQ ID NOs: 1, 27, 32, or 38. In some cases, the amino acid sequence encoding a prenyltransferase can be at least 55% identical to any one of SEQ ID NOs: 1, 27, 32, or 38. In some cases, the amino acid sequence encoding a prenyltransferase can be at least 60% identical to any one of SEQ ID NOs: 1, 27, 32, or 38. In some cases, the amino acid sequence encoding a prenyltransferase can be at least 65% identical to any one of SEQ ID NOs: 1, 27, 32, or 38. In some cases, the amino acid sequence encoding a prenyltransferase can be at least 70% identical to any one of SEQ ID NOs: 1, 27, 32, or 38. In some cases, the amino acid sequence encoding a prenyltransferase can be at least 75% identical to any one of SEQ ID NOs: 1, 27, 32, or 38. In some cases, the amino acid sequence encoding a prenyltransferase can be at least 80% identical to any one of SEQ ID NOs: 1, 27, 32, or 38. In some cases, the amino acid sequence encoding a prenyltransferase can be at least 81% identical to any one of SEQ ID NOs: 1, 27, 32, or 38. In some cases, the amino acid sequence encoding a prenyltransferase can be at least 82% identical to any one of SEQ ID NOs: 1, 27, 32, or 38. In some cases, the amino acid sequence encoding a prenyltransferase can be at least 83% identical to any one of SEQ ID NOs: 1, 27, 32, or 38. In some cases, the amino acid sequence encoding a prenyltransferase can be at least 84% identical to any one of SEQ ID NOs: 1, 27, 32, or 38. In some cases, the amino acid sequence encoding a prenyltransferase can be at least 85% identical to any one of SEQ ID NOs: 1, 27, 32, or 38. In some cases, the amino acid sequence encoding a prenyltransferase can be at least 86% identical to any one of SEQ ID NOs: 1, 27, 32, or 38. In some cases, the amino acid sequence encoding a prenyltransferase can be at least 87% identical to any one of SEQ ID NOs: 1, 27, 32, or 38. In some cases, the amino acid sequence encoding a prenyltransferase can be at least 88% identical to any one of SEQ ID NOs: 1, 27, 32, or 38. In some cases, the amino acid sequence encoding a prenyltransferase can be at least 89% identical to any one of SEQ ID NOs: 1, 27, 32, or 38. In some cases, the amino acid sequence encoding a prenyltransferase can be at least 90% identical to any one of SEQ ID NOs: 1, 27, 32, or 38. In some cases, the amino acid sequence encoding a prenyltransferase can be at least 91% identical to any one of SEQ ID NOs: 1, 27, 32, or 38. In some cases, the amino acid sequence encoding a prenyltransferase can be at least 92% identical to any one of SEQ ID NOs: 1, 27, 32, or 38. In some cases, the amino acid sequence encoding a prenyltransferase can be at least 93% identical to any one of SEQ ID NOs: 1, 27, 32, or 38. In some cases, the amino acid sequence encoding a prenyltransferase can be at least 94% identical to any one of SEQ ID NOs: 1, 27, 32, or 38. In some cases, the amino acid sequence encoding a prenyltransferase can be at least 95% identical to any one of SEQ ID NOs: 1, 27, 32, or 38. In some cases, the amino acid sequence encoding a prenyltransferase can be at least 96% identical to any one of SEQ ID NOs: 1, 27, 32, or 38. In some cases, the amino acid sequence encoding a prenyltransferase can be at least 97% identical to any one of SEQ ID NOs: 1, 27, 32, or 38. In some cases, the amino acid sequence encoding a prenyltransferase can be at least 98% identical to any one of SEQ ID NOs: 1, 27, 32, or 38. In some cases, the amino acid sequence encoding a prenyltransferase can be at least 99% identical to any one of SEQ ID NOs: 1, 27, 32, or 38. In some cases, the amino acid sequence encoding a prenyltransferase can be identical to any one of SEQ ID NOs: 1, 27, 32, or 38. In some cases, the amino acid sequence can be optimized to correspond to amino acid usage within a specific host organism/cell.

Additionally, other enzymes can be used to make different products. These enzymes can include a THCA synthase (THCAS); CBDA synthase (CBDAS), CBCA synthase (CBCAS), or any combination thereof.

In some cases, when a THCA synthase (THCAS) is desired, the THCAS can be encoded by an amino acid sequence that is substantially identical to SEQ ID NO: 9. In some cases, the amino acid sequence encoding a THCAS can be at least 50% identical to SEQ ID NO: 9. In some cases, the amino acid sequence encoding a THCAS can be at least 55% identical to SEQ ID NO: 9. In some cases, the amino acid sequence encoding a THCAS can be at least 60% identical to SEQ ID NO: 9. In some cases, the amino acid sequence encoding a THCAS can be at least 65% identical to SEQ ID NO: 9. In some cases, the amino acid sequence encoding a THCAS can be at least 70% identical to SEQ ID NO: 9. In some cases, the amino acid sequence encoding a THCAS can be at least 75% identical to SEQ ID NO: 9. In some cases, the amino acid sequence encoding a THCAS can be at least 80% identical to SEQ ID NO: 9. In some cases, the amino acid sequence encoding a THCAS can be at least 81% identical to SEQ ID NO: 9. In some cases, the amino acid sequence encoding a THCAS can be at least 82% identical to SEQ ID NO: 9. In some cases, the amino acid sequence encoding a THCAS can be at least 83% identical to SEQ ID NO: 9. In some cases, the amino acid sequence encoding a THCAS can be at least 84% identical to SEQ ID NO: 9. In some cases, the amino acid sequence encoding a THCAS can be at least 85% identical to SEQ ID NO: 9. In some cases, the amino acid sequence encoding a THCAS can be at least 86% identical to SEQ ID NO: 9. In some cases, the amino acid sequence encoding a THCAS can be at least 87% identical to SEQ ID NO: 9. In some cases, the amino acid sequence encoding a THCAS can be at least 88% identical to SEQ ID NO: 9. In some cases, the amino acid sequence encoding a THCAS can be at least 89% identical to SEQ ID NO: 9. In some cases, the amino acid sequence encoding a THCAS can be at least 90% identical to SEQ ID NO: 9. In some cases, the amino acid sequence encoding a THCAS can be at least 91% identical to SEQ ID NO: 9. In some cases, the amino acid sequence encoding a THCAS can be at least 92% identical to SEQ ID NO: 9. In some cases, the amino acid sequence encoding a THCAS can be at least 93% identical to SEQ ID NO: 9. In some cases, the amino acid sequence encoding a THCAS can be at least 94% identical to SEQ ID NO: 9. In some cases, the amino acid sequence encoding a THCAS can be at least 95% identical to SEQ ID NO: 9. In some cases, the amino acid sequence encoding a THCAS can be at least 96% identical to SEQ ID NO: 9. In some cases, the amino acid sequence encoding a THCAS can be at least 97% identical to SEQ ID NO: 9. In some cases, the amino acid sequence encoding a THCAS can be at least 98% identical to SEQ ID NO: 9. In some cases, the amino acid sequence encoding a THCAS can be at least 99% identical to SEQ ID NO: 9. In some cases, the amino acid sequence encoding a THCAS can be identical to SEQ ID NO: 9. In some cases, the amino acid sequence can be optimized to correspond to amino acid usage within a specific host organism/cell. The use of a THCAS, in some cases, can result in the enzymatic synthesis of Δ9-tetrahydrocannabinol (THC) and the accumulation of THC within the cell or culture medium.

In some cases, when a CBDA synthase (CBDAS) is desired, the CBDAS can be encoded by an amino acid sequence that is substantially identical to SEQ ID NO: 11. In some cases, the amino acid sequence encoding a CBDAS can be at least 50% identical to SEQ ID NO: 11. In some cases, the amino acid sequence encoding a CBDAS can be at least 55% identical to SEQ ID NO: 11. In some cases, the amino acid sequence encoding a CBDAS can be at least 60% identical to SEQ ID NO: 11. In some cases, the amino acid sequence encoding a CBDAS can be at least 65% identical to SEQ ID NO: 11. In some cases, the amino acid sequence encoding a CBDAS can be at least 70% identical to SEQ ID NO: 11. In some cases, the amino acid sequence encoding a CBDAS can be at least 75% identical to SEQ ID NO: 11. In some cases, the amino acid sequence encoding a CBDAS can be at least 80% identical to SEQ ID NO: 11. In some cases, the amino acid sequence encoding a CBDAS can be at least 81% identical to SEQ ID NO: 11. In some cases, the amino acid sequence encoding a CBDAS can be at least 82% identical to SEQ ID NO: 11. In some cases, the amino acid sequence encoding a CBDAS can be at least 83% identical to SEQ ID NO: 11. In some cases, the amino acid sequence encoding a CBDAS can be at least 84% identical to SEQ ID NO: 11. In some cases, the amino acid sequence encoding a CBDAS can be at least 85% identical to SEQ ID NO: 11. In some cases, the amino acid sequence encoding a CBDAS can be at least 86% identical to SEQ ID NO: 11. In some cases, the amino acid sequence encoding a CBDAS can be at least 87% identical to SEQ ID NO: 11. In some cases, the amino acid sequence encoding a CBDAS can be at least 88% identical to SEQ ID NO: 11. In some cases, the amino acid sequence encoding a CBDAS can be at least 89% identical to SEQ ID NO: 11. In some cases, the amino acid sequence encoding a CBDAS can be at least 90% identical to SEQ ID NO: 11. In some cases, the amino acid sequence encoding a CBDAS can be at least 91% identical to SEQ ID NO: 11. In some cases, the amino acid sequence encoding a CBDAS can be at least 92% identical to SEQ ID NO: 11. In some cases, the amino acid sequence encoding a CBDAS can be at least 93% identical to SEQ ID NO: 11. In some cases, the amino acid sequence encoding a CBDAS can be at least 94% identical to SEQ ID NO: 11. In some cases, the amino acid sequence encoding a CBDAS can be at least 95% identical to SEQ ID NO: 11. In some cases, the amino acid sequence encoding a CBDAS can be at least 96% identical to SEQ ID NO: 11. In some cases, the amino acid sequence encoding a CBDAS can be at least 97% identical to SEQ ID NO: 11. In some cases, the amino acid sequence encoding a CBDAS can be at least 98% identical to SEQ ID NO: 11. In some cases, the amino acid sequence encoding a CBDAS can be at least 99% identical to SEQ ID NO: 11. In some cases, the amino acid sequence encoding a CBDAS can be identical to SEQ ID NO: 11. In some cases, the amino acid sequence can be optimized to correspond to amino acid usage within a specific host organism/cell. The use of a CBDAS in some cases can result in the enzymatic synthesis of cannabidiol (CBD) and the accumulation of CBD within the cell or culture medium.

In some cases, when a CBCA synthase (CBCAS) is desired, the CDCS can be encoded by an amino acid sequence that is substantially identical to SEQ ID NO: 17. In some cases, the amino acid sequence encoding a CBCAS can be at least 50% identical to SEQ ID NO: 17. In some cases, the amino acid sequence encoding a CBCAS can be at least 55% identical to SEQ ID NO: 17. In some cases, the amino acid sequence encoding a CBCAS can be at least 60% identical to SEQ ID NO: 17. In some cases, the amino acid sequence encoding a CBCAS can be at least 65% identical to SEQ ID NO: 17. In some cases, the amino acid sequence encoding a CBCAS can be at least 70% identical to SEQ ID NO: 17. In some cases, the amino acid sequence encoding a CBCAS can be at least 75% identical to SEQ ID NO: 17. In some cases, the amino acid sequence encoding a CBCAS can be at least 80% identical to SEQ ID NO: 17. In some cases, the amino acid sequence encoding a CBCAS can be at least 81% identical to SEQ ID NO: 17. In some cases, the amino acid sequence encoding a CBCAS can be at least 82% identical to SEQ ID NO: 17. In some cases, the amino acid sequence encoding a CBCAS can be at least 83% identical to SEQ ID NO: 17. In some cases, the amino acid sequence encoding a CBCAS can be at least 84% identical to SEQ ID NO: 17. In some cases, the amino acid sequence encoding a CBCAS can be at least 85% identical to SEQ ID NO: 17. In some cases, the amino acid sequence encoding a CBCAS can be at least 86% identical to SEQ ID NO: 17. In some cases, the amino acid sequence encoding a CBCAS can be at least 87% identical to SEQ ID NO: 17. In some cases, the amino acid sequence encoding a CBCAS can be at least 88% identical to SEQ ID NO: 17. In some cases, the amino acid sequence encoding a CBCAS can be at least 89% identical to SEQ ID NO: 17. In some cases, the amino acid sequence encoding a CBCAS can be at least 90% identical to SEQ ID NO: 17. In some cases, the amino acid sequence encoding a CBCAS can be at least 91% identical to SEQ ID NO: 17. In some cases, the amino acid sequence encoding a CBCAS can be at least 92% identical to SEQ ID NO: 17. In some cases, the amino acid sequence encoding a CBCAS can be at least 93% identical to SEQ ID NO: 17. In some cases, the amino acid sequence encoding a CBCAS can be at least 94% identical to SEQ ID NO: 17. In some cases, the amino acid sequence encoding a CBCAS can be at least 95% identical to SEQ ID NO: 17. In some cases, the amino acid sequence encoding a CBCAS can be at least 96% identical to SEQ ID NO: 17. In some cases, the amino acid sequence encoding a CBCAS can be at least 97% identical to SEQ ID NO: 17. In some cases, the amino acid sequence encoding a CBCAS can be at least 98% identical to SEQ ID NO: 17. In some cases, the amino acid sequence encoding a CBCAS can be at least 99% identical to SEQ ID NO: 17. In some cases, the amino acid sequence encoding a CBCAS can be identical to SEQ ID NO: 17. In some cases, the amino acid sequence can be optimized to correspond to amino acid usage within a specific host organism/cell. The use of a CBCAS in some cases can result in the enzymatic synthesis of cannabichromene (CBC) and the accumulation of CBC within the cell or culture medium.

The various combinations of enzymes can be used to make a desired product such as olivetolic acid; CBGA; THCA; CBDA; CBCA; THC; CBD; CBC, or any combination thereof.

The enzymes disclosed throughout can be from a plant. For example, the enzymes can be from a plant that is from the genus *Cannabis*. More specifically, *Cannabis* plants that can be used include, but are not limited to *Cannabis sativa, Cannabis indica*, and *Cannabis ruderalis*. Other plants that can be used can be from the genus *Echinacea, Acmella* (e.g., *Acmella oleracea*), *Helichrysum* (e.g., *Helichrysum umbraculigerum*), *Radula* (e.g., *Radula marginata*), *Theobroma* (e.g., *Theobroma cacao*), and/or *Piper* (e.g., *Piper nigrum*).

Additional enzymes can be added in order to improve the production of CBGA or cannabinoids. For example, a gene encoding an HMG-CoA reductase, such as HMG1, can be used to increase cannabinoid titers. In some instances, the titer of CBGA can be increased by expressing HMG1. Additionally, HMG1 can be in different forms. For example, a truncated form of HMG1 can be used to increase cannabinoid titers. Other enzymes such as Farnesyl pyrophosphate synthetase, which is encoded by the gene ERG20 can be used to increase cannabinoid/CBGA titers. Additionally, ERG20 can be in different forms, such as mutant forms.

In cases where a HMG-CoA reductase (HMG1) is desired, the HMG1 can be encoded by a nucleic acid sequence that is substantially identical to SEQ ID NO: 19 or 21. For example, the HMG1 can be encoded by a nucleic acid sequence that is at least 50%, 60%, 70%, 80%, 85%, 90%, 95%, 96%, 97%, 98% or 99% identical to any one of SEQ ID NO: 19 or 21. In some cases, the nucleic acid sequence can be at least 50% identical to SEQ ID NO: 19 or 21. In some cases, the nucleic acid sequence can be at least 60% identical to SEQ ID NO: 19 or 21. In some cases, the nucleic acid sequence can be at least 65% identical to SEQ ID NO: 19 or 21. In some cases, the nucleic acid sequence can be at least 70% identical to SEQ ID NO: 19 or 21. In some cases, the nucleic acid sequence can be at least 75% identical to SEQ ID NO: 19 or 21. In some cases, the nucleic acid sequence can be at least 80% identical to SEQ ID NO: 19 or 21. In some cases, the nucleic acid sequence can be at least 81% identical to SEQ ID NO: 19 or 21. In some cases, the nucleic acid sequence can be at least 82% identical to SEQ ID NO: 19 or 21. In some cases, the nucleic acid sequence can be at least 83% identical to SEQ ID NO: 19 or 21. In some cases, the nucleic acid sequence can be at least 84% identical to SEQ ID NO: 19 or 21. In some cases, the nucleic acid sequence can be at least 85% identical to SEQ ID NO: 19 or 21. In some cases, the nucleic acid sequence can be at least 86% identical to SEQ ID NO: 19 or 21. In some cases, the nucleic acid sequence can be at least 87% identical to SEQ ID NO: 19 or 21. In some cases, the nucleic acid sequence can be at least 88% identical to SEQ ID NO: 19 or 21. In some cases, the nucleic acid sequence can be at least 89% identical to SEQ ID NO: 19 or 21. In some cases, the nucleic acid sequence can be at least 90% identical to SEQ ID NO: 19 or 21. In some cases, the nucleic acid sequence can be at least 91% identical to SEQ ID NO: 19 or 21. In some cases, the nucleic acid sequence can be at least 92% identical to SEQ ID NO: 19 or 21. In some cases, the nucleic acid sequence can be at least 93% identical to SEQ ID NO: 19 or 21. In some cases, the nucleic acid sequence can be at least 94% identical to SEQ ID NO: 19 or 21. In some cases, the nucleic acid sequence can be at least 95% identical to SEQ ID NO: 19 or 21. In some cases, the nucleic acid sequence can be at least 96% identical to SEQ ID NO: 19 or 21. In some cases, the nucleic acid sequence can be at least 97% identical to SEQ ID NO: 19 or 21. In some cases, the nucleic acid sequence can be at least 98% identical to SEQ ID NO: 19 or 21. In some cases, the nucleic acid sequence can be at least 99% identical to SEQ ID NO: 19 or 21. In some cases, the nucleic acid sequence can be identical to SEQ ID NO: 19 or 21. Further, codon optimized polynucleotides (for a particular host cell/organism) for the above referenced sequences can be used herein.

In cases where a farnesyl pyrophosphate synthetase (ERG20) is used, the ERG20 can be encoded by a nucleic acid sequence that is substantially identical to SEQ ID NO: 23. For example, the ERG20 can be encoded by an nucleic acid sequence that is at least 50%, 60%, 70%, 80%, 85%, 90%, 95%, 96%, 97%, 98% or 99% identical to SEQ ID NO: 23. In some cases, the nucleic acid ERG20 can be at least 50% identical to SEQ ID NO: 23. In some cases, the nucleic acid can be at least 60% identical to SEQ ID NO: 23. In some cases, the nucleic acid can be at least 65% identical to SEQ ID NO: 23. In some cases, the nucleic acid can be at least 70% identical to SEQ ID NO: 23. In some cases, the nucleic acid can be at least 75% identical to SEQ ID NO: 23. In some cases, the nucleic acid can be at least 80% identical to SEQ ID NO: 23. In some cases, the nucleic acid can be at least 81% identical to SEQ ID NO: 23. In some cases, the nucleic acid can be at least 82% identical to SEQ ID NO: 23. In some cases, the nucleic acid can be at least 83% identical to SEQ ID NO: 23. In some cases, the nucleic acid can be at least 84% identical to SEQ ID NO: 23. In some cases, the nucleic acid can be at least 85% identical to SEQ ID NO: 23. In some cases, the nucleic acid can be at least 86% identical to SEQ ID NO: 23. In some cases, the nucleic acid can be at least 87% identical to SEQ ID NO: 23. In some cases, the nucleic acid can be at least 88% identical to SEQ ID NO: 23. In some cases, the nucleic acid can be at least 89% identical to SEQ ID NO: 23. In some cases, the nucleic acid can be at least 90% identical to SEQ ID NO: 23. In some cases, the nucleic acid can be at least 91% identical to SEQ ID NO: 23.

In some cases, the nucleic acid can be at least 92% identical to SEQ ID NO: 23. In some cases, the nucleic acid can be at least 93% identical to SEQ ID NO: 23. In some cases, the nucleic acid can be at least 94% identical to SEQ ID NO: 23. In some cases, the nucleic acid can be at least 95% identical to SEQ ID NO: 23. In some cases, the nucleic acid can be at least 96% identical to SEQ ID NO: 23. In some cases, the nucleic acid can be at least 97% identical to SEQ ID NO: 23. In some cases, the nucleic acid can be at least 98% identical to SEQ ID NO: 23. In some cases, the nucleic acid can be at least 99% identical to SEQ ID NO: 23. In some cases, the nucleic acid can be identical to SEQ ID NO: 23. Further, codon optimized polynucleotides (for a particular host cell/organism) for the above referenced sequences can be used herein.

In some cases, the enzymes described herein can be a fragment thereof. The fragment can still retain its respective biological activity. For example, a fragment of the prenyltransferase can be used as long as the activity of the fragment retains its biological activity.

The enzymes or fragments thereof described throughout can also be in some cases can be fused or linked together. Any fragment linker can be used to link the two or more of the enzymes or fragments thereof together. In some cases, the linker can be any random array of amino acid sequences. In some cases, linkers such as the T2A linker (SEQ ID NO: 15 (amino acid) or 16 (nucleic acid)) can be used.

The fused or linked enzymes can be two or more of any of the enzymes described throughout. For example, the disclosed prenyltransferase can be linked with a CBDA synthase. The resulting fused or linked enzyme can produce increased cannabidiol titers compared to separate enzymes that are not linked or fused. Additionally, other enzymes such as prenyltransferase and THCA synthase can be fused or linked. The resulting fused or linked enzyme can produce increased THC titers compared to separate enzymes that are not linked or fused. Enzymes that can catalyze the product of another enzyme can be fused or linked. For example AAE1 can be fused or linked to PKS. In some cases, OAC can be fused or linked to PKS. This can in some cases, increase the speed of two or more enzymatic conversions due to the proximity of the enzymatic substrates/products.

Vectors

Polynucleotide constructs prepared for introduction into a prokaryotic or eukaryotic host can typically, but not always, comprise a replication system (i.e. vector) recognized by the host, including the intended polynucleotide fragment encoding the desired polypeptide, and can but not necessarily, also include transcription and translational initiation regulatory sequences operably linked to the polypeptide-encoding segment. Expression systems (such as expression vectors) can include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, mRNA stabilizing sequences, nucleotide sequences homologous to host chromosomal DNA, and/or a multiple cloning site. Signal peptides can also be included where appropriate, for example from secreted polypeptides of the same or related species, which allow the protein to cross and/or lodge in cell membranes or be secreted from the cell.

The vectors can be constructed using standard methods (see, e.g., Sambrook et al., Molecular Biology: A Laboratory Manual, Cold Spring Harbor, N.Y. 1989; and Ausubel, et al., Current Protocols in Molecular Biology, Greene Publishing, Co. N.Y., 1995).

The manipulation of polynucleotides that encode the enzymes disclosed herein is typically carried out in recombinant vectors. Numerous vectors are publicly available, including bacterial plasmids, bacteriophage, artificial chromosomes, episomal vectors and gene expression vectors, which can all be employed. A vector can be selected to accommodate a polynucleotide encoding a protein of a desired size. Following recombinant modification of a selected vector, a suitable host cell (e.g., the microorganisms described herein) is transfected or transformed with the vector. Each vector contains various functional components, which generally include a cloning site, an origin of replication and at least one selectable marker gene. A vector can additionally possess one or more of the following elements: an enhancer, promoter, and transcription termination and/or other signal sequences. Such sequence elements can be optimized for the selected host species. Such sequence elements can be positioned in the vicinity of the cloning site, such that they are operatively linked to the gene encoding a preselected enzyme.

Vectors, including cloning and expression vectors, can contain nucleic acid sequences that enable the vector to replicate in one or more selected microorganisms. For example, the sequence can be one that enables the vector to replicate independently of the host chromosomal DNA and can include origins of replication or autonomously replicating sequences. Such sequences are well known for a variety of bacteria, yeast and viruses. For example, the origin of replication from the plasmid pBR322 is suitable for most Gram-negative bacteria, the 2 micron plasmid origin is suitable for yeast, and various viral origins (e.g. SV40, adenovirus) are useful for cloning vectors.

A cloning or expression vector can contain a selection gene (also referred to as a selectable marker). This gene encodes a protein necessary for the survival or growth of transformed microorganisms in a selective culture medium. Microorganisms not transformed with the vector containing the selection gene will therefore not survive in the culture medium. Typical selection genes encode proteins that confer resistance to antibiotics and other toxins, e.g. ampicillin, neomycin, methotrexate, hygromycin, thiostrepton, apramycin or tetracycline, complement auxotrophic deficiencies, or supply critical nutrients not available in the growth media.

The replication of vectors can be performed in *E. coli*. An *E. coli*-selectable marker, for example, the β-lactamase gene that confers resistance to the antibiotic ampicillin, can be of use. These selectable markers can be obtained from *E. coli* plasmids, such as pBR322 or a pUC plasmid such as pUC18 or pUC19, or pUC119.

Some exemplary vectors that can be used in the methods and microorganisms/cells are SEQ ID NO: 3 and 4. SEQ ID NO: 3 is also called the RUNM000898_511.1 vector, which comprises a *Saccharomyces cerevisiae* 2μ replication origin, a URA3 gene as an auxotrophic marker and the PKS and OAC genes under the regulation of the bidirectional GAL1/GAL10 promoter. SEQ ID NO: 4 is the bCBGA0098 vector that comprises a *Saccharomyces cerevisiae* 2μ replication origin, a LEU2 gene as an auxotrophic marker, and the AAE1 and PT genes under the regulation of the bidirectional GAL1/GAL10 promoter.

SEQ ID NO: 25 is a bCBGA0306 is a vector that comprises the *Saccharomyces cerevisiae* 2μ replication origin, the LEU2 gene as an auxotrophic marker and the PT gene under the regulation of the bidirectional GAL1/GAL10 promoter.

SEQ ID NO: 34 is the RUNM001233_51.1 vector comprising the *Saccharomyces cerevisiae* 2μ replication origin, the URA3 gene as an auxotrophic marker and the THCA synthase gene under the regulation of the bidirectional GAL1/GAL10 promoter.

SEQ ID NO: 35 is the RUNM001210_96.1 vector comprising the *Saccharomyces cerevisiae* 2μ replication origin, the URA3 gene as an auxotrophic marker, the PKS and OAC genes under the regulation of the bidirectional GAL1/GAL10 promoter and the AAE1 gene under the regulation of the STES promoter.

SEQ ID NO: 36 is the bCBGA0409 vector comprising the *Saccharomyces cerevisiae* 2μ replication origin, the LEU2 gene as an auxotrophic marker, the THCA synthase and PT genes under the regulation of the bidirectional GAL1/GAL10 promoter.

SEQ ID NO: 29 is the bCBGA0385 vector comprising the *Saccharomyces cerevisiae* 2μ replication origin, the LEU2 gene as an auxotrophic marker and the GFP-dPT gene under the regulation of the bidirectional GAL1/GAL10 promoter.

SEQ ID NO: 30 is the bCBGA0305 vector comprising the *Saccharomyces cerevisiae* 2μ replication origin, the TRP1 gene as an auxotrophic marker and the AAE1 gene under the regulation of the bidirectional GAL1/GAL10 promoter.

SEQ ID NO: 33 is the bCBGA0559 vector comprising the *Saccharomyces cerevisiae* 2μ replication origin, the LEU2 gene as an auxotrophic marker and the ERG20mut-dPT gene under the regulation of the bidirectional GAL1/GAL10 promoter.

Promoters

Vectors can contain a promoter that is recognized by the host microorganism. The promoter can be operably linked to a coding sequence of interest. Such a promoter can be inducible or constitutive. Polynucleotides are operably linked when the polynucleotides are in a relationship permitting them to function in their intended manner.

Different promoters can be used to drive the expression of the genes. For example, if temporary gene expression (i.e., non-constitutively expressed) is desired, expression can be driven by inducible promoters.

In some cases, some of the genes disclosed can be expressed temporarily. In other words, the genes are not constitutively expressed. The expression of the genes can be driven by inducible or repressible promoters. For example, the inducible or repressible promoters that can be used include but are not limited to: (a) sugars such as arabinose and lactose (or non metabolizable analogs, e.g., isopropyl β-D-1-thiogalactopyranoside (IPTG)); (b) metals such as lanthanum, copper, calcium; (c) temperature; (d) Nitrogen-source; (e) oxygen; (f) cell state (growth or stationary); (g) metabolites such as phosphate; (h) CRISPRi; (i) jun; (j) fos, (k) metallothionein and/or (1) heat shock.

Constitutively expressed promoters can also be used in the vector systems herein. For example, the expression of some of the genes disclosed throughout can be controlled by constitutively active promoters. For examples, the promoters that can be used include but are not limited to p.Bba.J23111, J23111, and J23100.

Promoters suitable for use with prokaryotic hosts can, for example, include but are not limited to the α-lactamase and lactose promoter systems, alkaline phosphatase, the tryptophan (trp) promoter system, the erythromycin promoter, apramycin promoter, hygromycin promoter, methylenomycin promoter and hybrid promoters such as the tac promoter. Promoters for use in bacterial systems will also generally contain a Shine-Dalgarno sequence operably linked to the coding sequence.

Generally, a strong promoter can be employed to provide for high level transcription and expression of the desired product.

One or more promoters of a transcription unit can be an inducible promoter. For example, a GFP can be expressed from a constitutive promoter while an inducible promoter drives transcription of a gene coding for one or more enzymes as disclosed herein and/or the amplifiable selectable marker.

Some vectors can contain prokaryotic sequences that facilitate the propagation of the vector in bacteria. Thus, the vectors can have other components such as an origin of replication (e.g., a nucleic acid sequence that enables the vector to replicate in one or more selected microorganisms), antibiotic resistance genes for selection in bacteria, and/or an amber stop codon which can permit translation to read through the codon. Additional selectable gene(s) can also be incorporated. Generally, in cloning vectors the origin of replication is one that enables the vector to replicate independently of the host chromosomal DNA, and includes origins of replication or autonomously replicating sequences. Such sequences can include the ColEl origin of replication in bacteria or other known sequences.

Genes

The genetically modified microorganisms can comprise a nucleic acid sequence encoding for one or more enzymes that are capable of catalyzing one or more of the following reactions: hexanoic acid to hexanoyl-CoA; hexanoyl-CoA to olivetolic Acid; olivetolic Acid to CBGA; CBGA to THCA; CBGA to CBDA; CBGA to CBCA; THCA to THC; CBDA to CBD; or CBCA to CBC. For example, the genetically modified microorganism can comprise a nucleic acid sequence encoding for one or more of the following enzymes: acyl activating enzyme (AAE1); polyketide synthase (PKS); olivetolic acid cyclase (OAC); prenyltransferase (PT); THCA synthase (THCAS); CBDA synthase (CBDAS), CBCA synthase (CBCAS); or any combination thereof. The nucleic acid sequence in some cases can be within a vector. In some cases, the nucleic acid sequences do not need to be within a vector but rather integrated into the microorganism's genome or isolated. In some cases, the isolated nucleic acids can be inserted into the genome of the cell/microorganism used. In some cases, the isolated nucleic acid is inserted into the genome at a specific locus, where the isolated nucleic acid can be expressed in sufficient amounts.

In some cases, two or more genes encoding for consecutive enzymes in the pathway from a carbon substrate (e.g., sugar) to any of the cannabinoids described throughout (e.g., THCA, CBDA, CBCA, THC, CBD, or CBC) can be used. In some cases, three or more genes encoding for consecutive enzymes in the pathway can be used. In some cases, four or more genes encoding for consecutive enzymes in the pathway can be used. In some cases, five or more genes encoding for consecutive enzymes in the pathway can be used. In some cases, six or more genes encoding for consecutive enzymes in the pathway can be used. In some cases, seven or more genes encoding for consecutive enzymes in the pathway can be used. In some cases, eight or more genes encoding for consecutive enzymes in the pathway can be used. In some cases, nine or more genes encoding for consecutive enzymes in the pathway can be used. In some cases, ten or more genes encoding for consecutive enzymes in the pathway can be used.

In some cases, when an acyl activating enzyme (AAE1) is desired, the AAE1 can be encoded by a nucleic acid sequence that is substantially identical to SEQ ID NO: 14. For example, the AAE1 can be encoded by a polynucleotide that is at least 50%, 60%, 70%, 80%, 85%, 90%, 95%, 96%, 97%, 98% or 99% identical to SEQ ID NO: 14. In some cases, the AAE1 can be at least 50% identical to SEQ ID NO: 14. In some cases, the AAE1 can be at least 60% identical to SEQ ID NO: 14. In some cases, the AAE1 can be at least 65% identical to SEQ ID NO: 14. In some cases, the AAE1 can be at least 70% identical to SEQ ID NO: 14. In some cases, the AAE1 can be at least 75% identical to SEQ ID NO: 14. In some cases, the AAE1 can be at least 80% identical to SEQ ID NO: 14. In some cases, the AAE1 can be at least 81% identical to SEQ ID NO: 14. In some cases, the AAE1 can be at least 82% identical to SEQ ID NO: 14. In some cases, the AAE1 can be at least 83% identical to SEQ ID NO: 14. In some cases, the AAE1 can be at least 84% identical to SEQ ID NO: 14. In some cases, the AAE1 can be at least 85% identical to SEQ ID NO: 14. In some cases, the AAE1 can be at least 86% identical to SEQ ID NO: 14. In some cases, the AAE1 can be at least 87% identical to SEQ ID NO: 14. In some cases, the AAE1 can be at least 88% identical to SEQ ID NO: 14. In some cases, the AAE1 can be at least 89% identical to SEQ ID NO: 14. In some cases, the AAE1 can be at least 90% identical to SEQ ID NO: 14. In some cases, the AAE1 can be at least 91% identical to SEQ ID NO: 14. In some cases, the AAE1 can be at least 92% identical to SEQ ID NO: 14. In some cases, the AAE1 can be at least 93% identical to SEQ ID NO: 14. In some cases, the AAE1 can be at least 94% identical to SEQ ID NO: 14. In some cases, the AAE1 can be at least 95% identical to SEQ ID NO: 14. In some cases, the AAE1 can be at least 96% identical to SEQ ID NO: 14. In some cases, the AAE1 can be at least 97% identical to SEQ ID NO: 14. In some cases, the AAE1 can be at least 98% identical to SEQ ID NO: 14. In some cases, the AAE1 can be at least 99% identical to SEQ ID NO: 14. In some cases, the AAE1 can be identical to SEQ ID NO: 14. Further, codon optimized polynucleotides (for a particular host cell/organism) for the above referenced sequences can be used herein.

In cases where a polyketide synthase (PKS) is used, the PKS can be encoded by a nucleic acid sequence that is substantially identical to SEQ ID NO: 6. For example, the PKS can be encoded by a polynucleotide that is at least 50%, 60%, 70%, 80%, 85%, 90%, 95%, 96%, 97%, 98% or 99% identical to SEQ ID NO: 6. In some cases, the PKS can be at least 50% identical to SEQ ID NO: 6. In some cases, the PKS can be at least 60% identical to SEQ ID NO: 6. In some cases, the PKS can be at least 65% identical to SEQ ID NO: 6. In some cases, the PKS can be at least 70% identical to SEQ ID NO: 6. In some cases, the PKS can be at least 75% identical to SEQ ID NO: 6. In some cases, the PKS can be at least 80% identical to SEQ ID NO: 6. In some cases, the PKS can be at least 81% identical to SEQ ID NO: 6. In some cases, the PKS can be at least 82% identical to SEQ ID NO: 6. In some cases, the PKS can be at least 83% identical to SEQ ID NO: 6. In some cases, the PKS can be at least 84% identical to SEQ ID NO: 6. In some cases, the PKS can be at least 85% identical to SEQ ID NO: 6. In some cases, the PKS can be at least 86% identical to SEQ ID NO: 6. In some cases, the PKS can be at least 87% identical to SEQ ID NO: 6. In some cases, the PKS can be at least 88% identical to SEQ ID NO: 6. In some cases, the PKS can be at least 89% identical to SEQ ID NO: 6. In some cases, the PKS can be at least 90% identical to SEQ ID NO: 6. In some cases, the PKS can be at least 91% identical to SEQ ID NO: 6. In some cases, the PKS can be at least 92% identical to SEQ ID NO: 6. In some cases, the PKS can be at least 93% identical to SEQ ID NO: 6. In some cases, the PKS can be at least 94% identical to SEQ ID NO: 6. In some cases, the PKS can be at least 95% identical to SEQ ID NO: 6. In some cases, the PKS can be at least 96% identical to SEQ ID NO: 6. In some cases, the PKS can be at least 97% identical to SEQ ID NO: 6. In some cases, the PKS can be at least 98% identical to SEQ ID NO: 6. In some cases, the PKS can be at least 99% identical to SEQ ID NO: 6. In some cases, the PKS can be identical to SEQ ID NO: 6. Further, codon optimized polynucleotides (for a particular host cell/organism) for the above referenced sequences can be used herein.

In cases where an olivetolic acid cyclase (OAC) is used, the OAC can be encoded by a nucleic acid sequence that is substantially identical to SEQ ID NO: 8. For example, the OAC can be encoded by a polynucleotide that is at least 50%, 60%, 70%, 80%, 85%, 90%, 95%, 96%, 97%, 98% or 99% identical to SEQ ID NO: 8. In some cases, the OAC can be at least 50% identical to SEQ ID NO: 8. In some cases, the OAC can be at least 60% identical to SEQ ID NO: 8. In some cases, the OAC can be at least 65% identical to SEQ ID NO: 8. In some cases, the OAC can be at least 70% identical to SEQ ID NO: 8. In some cases, the OAC can be at least 75% identical to SEQ ID NO: 8. In some cases, the OAC can be at least 80% identical to SEQ ID NO: 8. In some cases, the OAC can be at least 81% identical to SEQ ID NO: 8. In some cases, the OAC can be at least 82% identical to SEQ ID NO: 8. In some cases, the OAC can be at least 83% identical to SEQ ID NO: 8. In some cases, the OAC can be at least 84% identical to SEQ ID NO: 8. In some cases, the OAC can be at least 85% identical to SEQ ID NO: 8. In some cases, the OAC can be at least 86% identical to SEQ ID NO: 8. In some cases, the OAC can be at least 87% identical to SEQ ID NO: 8. In some cases, the OAC can be at least 88% identical to SEQ ID NO: 8. In some cases, the OAC can be at least 89% identical to SEQ ID NO: 8. In some cases, the OAC can be at least 90% identical to SEQ ID NO: 8. In some cases, the OAC can be at least 91% identical to SEQ ID NO: 8. In some cases, the OAC can be at least 92% identical to SEQ ID NO: 8. In some cases, the OAC can be at least 93% identical to SEQ ID NO: 8. In some cases, the OAC can be at least 94% identical to SEQ ID NO: 8. In some cases, the OAC can be at least 95% identical to SEQ ID NO: 8. In some cases, the OAC can be at least 96% identical to SEQ ID NO: 8. In some cases, the OAC can be at least 97% identical to SEQ ID NO: 8. In some cases, the OAC can be at least 98% identical to SEQ ID NO: 8. In some cases, the OAC can be at least 99% identical to SEQ ID NO: 8. In some cases, the OAC can be identical to SEQ ID NO: 8. Further, codon optimized polynucleotides (for a particular host cell/organism) for the above referenced sequences can be used herein.

In cases where a prenyltransferase (PT) is used, the PT can be encoded by a nucleic acid sequence that is substantially identical to any one of SEQ ID NOs: 2, 26, 31, or 37. For example, the PT can be encoded by a polynucleotide that is at least 50%, 60%, 70%, 80%, 85%, 90%, 95%, 96%, 97%, 98% or 99% identical to any one of SEQ ID NOs: 2, 26, 31, or 37. In some cases, the PT can be at least 50% identical to any one of SEQ ID NOs: 2, 26, 31, or 37. In some cases, the PT can be at least 60% identical to any one of SEQ ID NOs: 2, 26, 31, or 37. In some cases, the PT can be at least 65% identical to any one of SEQ ID NOs: 2, 26, 31, or 37. In some cases, the PT can be at least 70% identical to any one of SEQ ID NOs: 2, 26, 31, or 37. In some cases, the PT can be at least 75% identical to any one of SEQ ID NOs: 2, 26, 31, or 37. In some cases, the PT can be at least 80% identical to any one of SEQ ID NOs: 2, 26, 31, or 37. In some cases, the PT can be at least 81% identical to any one of SEQ ID NOs: 2, 26, 31, or 37. In some cases, the PT can be at least 82% identical to any one of SEQ ID NOs: 2, 26, 31, or 37. In some cases, the PT can be at least 83% identical to any one of SEQ ID NOs: 2, 26, 31, or 37. In some cases, the PT can be at least 84% identical to any one of SEQ ID NOs: 2, 26, 31, or 37. In some cases, the PT can be at least 85% identical to any one of SEQ ID NOs: 2, 26, 31, or 37. In some cases, the PT can be at least 86% identical to any one of SEQ ID NOs: 2, 26, 31, or 37. In some cases, the PT can be at least 87% identical to any one of SEQ ID NOs: 2, 26, 31, or 37. In some cases, the PT can be at least 88% identical to any one of SEQ ID NOs: 2, 26, 31, or 37. In some cases, the PT can be at least 89% identical to any one of SEQ ID NOs: 2, 26, 31, or 37. In some cases, the PT can be at least 90% identical to any one of SEQ ID NOs: 2, 26, 31, or 37. In some cases, the PT can be at least 91% identical to any one of SEQ ID NOs: 2, 26, 31, or 37. In some cases, the PT can be at least 92% identical to any one of SEQ ID NOs: 2, 26, 31, or 37. In some cases, the PT can be at least 93% identical to any one of SEQ ID NOs: 2, 26, 31, or 37. In some cases, the PT can be at least 94% identical to any one of SEQ ID NOs: 2, 26, 31, or 37. In some cases, the PT can be at least 95% identical to any one of SEQ ID NOs: 2, 26, 31, or 37. In some cases, the PT can be at least 96% identical to any one of SEQ ID NOs: 2, 26, 31, or 37. In some cases, the PT can be at least 97% identical to any one of SEQ ID NOs: 2, 26, 31, or 37. In some cases, the PT can be at least 98% identical to any one of SEQ ID NOs: 2, 26, 31, or 37. In some cases, the PT can be at least 99% identical to any one of SEQ ID NOs: 2, 26, 31, or 37. In some cases, the PT can be identical to any one of SEQ ID NOs: 2, 26, 31, or 37. Further, codon optimized polynucleotides (for a particular host cell/organism) for the above referenced sequences can be used herein.

In cases where a THCA synthase (THCAS) is used, the THCAS can be encoded by a nucleic acid sequence that is substantially identical to SEQ ID NO: 10. For example, the THCAS can be encoded by a polynucleotide that is at least 50%, 60%, 70%, 80%, 85%, 90%, 95%, 96%, 97%, 98% or 99% identical to SEQ ID NO: 10. In some cases, the THCAS can be at least 50% identical to SEQ ID NO: 10. In some cases, the THCAS can be at least 60% identical to SEQ ID NO: 10. In some cases, the THCAS can be at least 65% identical to SEQ ID NO: 10. In some cases, the THCAS can be at least 70% identical to SEQ ID NO: 10. In some cases, the THCAS can be at least 75% identical to SEQ ID NO: 10. In some cases, the THCAS can be at least 80% identical to SEQ ID NO: 10. In some cases, the THCAS can be at least 81% identical to SEQ ID NO: 10. In some cases, the THCAS can be at least 82% identical to SEQ ID NO: 10. In some cases, the THCAS can be at least 83% identical to SEQ ID NO: 10. In some cases, the THCAS can be at least 84% identical to SEQ ID NO: 10. In some cases, the THCAS can be at least 85% identical to SEQ ID NO: 10. In some cases, the THCAS can be at least 86% identical to SEQ ID NO: 10. In some cases, the THCAS can be at least 87% identical to SEQ ID NO: 10. In some cases, the THCAS can be at least 88% identical to SEQ ID NO: 10. In some cases, the THCAS can be at least 89% identical to SEQ ID NO: 10. In some cases, the THCAS can be at least 90% identical to SEQ ID NO: 10. In some cases, the THCAS can be at least 91% identical to SEQ ID NO: 10. In some cases, the THCAS can be at least 92% identical to SEQ ID NO: 10. In some cases, the THCAS can be at least 93% identical to SEQ ID NO: 10. In some cases, the THCAS can be at least 94% identical to SEQ ID NO: 10. In some cases, the THCAS can be at least 95% identical to SEQ ID NO: 10. In some cases, the THCAS can be at least 96% identical to SEQ ID NO: 10. In some cases, the THCAS can be at least 97% identical to SEQ ID NO: 10. In some cases, the THCAS can be at least 98% identical to SEQ ID NO: 10. In some cases, the THCAS can be at least 99% identical to SEQ ID NO: 10. In some cases, the THCAS can be identical to SEQ ID NO: 10. Further, codon optimized polynucleotides (for a particular host cell/organism) for the above referenced sequences can be used herein.

In cases where a CBDA synthase (CBDAS) is used, the CBDAS can be encoded by a nucleic acid sequence that is substantially identical to SEQ ID NO: 12. For example, the CBDAS can be encoded by a polynucleotide that is at least 50%, 60%, 70%, 80%, 85%, 90%, 95%, 96%, 97%, 98% or 99% identical to SEQ ID NO: 12. In some cases, the CBDAS can be at least 50% identical to SEQ ID NO: 12. In some cases, the CBDAS can be at least 60% identical to SEQ ID NO: 12. In some cases, the CBDAS can be at least 65% identical to SEQ ID NO: 12. In some cases, the CBDAS can be at least 70% identical to SEQ ID NO: 12. In some cases, the CBDAS can be at least 75% identical to SEQ ID NO: 12. In some cases, the CBDAS can be at least 80% identical to SEQ ID NO: 12. In some cases, the CBDAS can be at least 81% identical to SEQ ID NO: 12. In some cases, the CBDAS can be at least 82% identical to SEQ ID NO: 12. In some cases, the CBDAS can be at least 83% identical to SEQ ID NO: 12. In some cases, the CBDAS can be at least 84% identical to SEQ ID NO: 12. In some cases, the CBDAS can be at least 85% identical to SEQ ID NO: 12. In some cases, the CBDAS can be at least 86% identical to SEQ ID NO: 12. In some cases, the CBDAS can be at least 87% identical to SEQ ID NO: 12. In some cases, the CBDAS can be at least 88% identical to SEQ ID NO: 12. In some cases, the CBDAS can be at least 89% identical to SEQ ID NO: 12. In some cases, the CBDAS can be at least 90% identical to SEQ ID NO: 12. In some cases, the CBDAS can be at least 91% identical to SEQ ID NO: 12. In some cases, the CBDAS can be at least 92% identical to SEQ ID NO: 12. In some cases, the CBDAS can be at least 93% identical to SEQ ID NO: 12. In some cases, the CBDAS can be at least 94% identical to SEQ ID NO: 12. In some cases, the CBDAS can be at least 95% identical to SEQ ID NO: 12. In some cases, the CBDAS can be at least 96% identical to SEQ ID NO: 12. In some cases, the CBDAS can be at least 97% identical to SEQ ID NO: 12. In some cases, the CBDAS can be at least 98% identical to SEQ ID NO: 12. In some cases, the CBDAS can be at least 99% identical to SEQ ID NO: 12. In some cases, the CBDAS can be identical to SEQ ID NO: 12. Further, codon optimized polynucleotides (for a particular host cell/organism) for the above referenced sequences can be used herein.

In cases where a CBCA synthase (CBCAS) is used, the CBCAS can be encoded by a nucleic acid sequence that is substantially identical to SEQ ID NO: 18. For example, the CBCAS can be encoded by a polynucleotide that is at least 50%, 60%, 70%, 80%, 85%, 90%, 95%, 96%, 97%, 98% or 99% identical to SEQ ID NO: 18. In some cases, the CBCAS can be at least 50% identical to SEQ ID NO: 18. In some cases, the CBCAS can be at least 60% identical to SEQ ID NO: 18. In some cases, the CBCAS can be at least 65% identical to SEQ ID NO: 18. In some cases, the CBCAS can be at least 70% identical to SEQ ID NO: 18. In some cases, the CBCAS can be at least 75% identical to SEQ ID NO: 18. In some cases, the CBCAS can be at least 80% identical to SEQ ID NO: 18. In some cases, the CBCAS can be at least 81% identical to SEQ ID NO: 18. In some cases, the CBCAS can be at least 82% identical to SEQ ID NO: 18. In some cases, the CBCAS can be at least 83% identical to SEQ ID NO: 18. In some cases, the CBCAS can be at least 84% identical to SEQ ID NO: 18. In some cases, the CBCAS can be at least 85% identical to SEQ ID NO: 18. In some cases, the CBCAS can be at least 86% identical to SEQ ID NO: 18. In some cases, the CBCAS can be at least 87% identical to SEQ ID NO: 18. In some cases, the CBCAS can be at least 88% identical to SEQ ID NO: 18. In some cases, the CBCAS can be at least 89% identical to SEQ ID NO: 18. In some cases, the CBCAS can be at least 90% identical to SEQ ID NO: 18. In some cases, the CBCAS can be at least 91% identical to SEQ ID NO: 18. In some cases, the CBCAS can be at least 92% identical to SEQ ID NO: 18. In some cases, the CBCAS can be at least 93% identical to SEQ ID NO: 18. In some cases, the CBCAS can be at least 94% identical to SEQ ID NO: 18. In some cases, the CBCAS can be at least 95% identical to SEQ ID NO: 18. In some cases, the CBCAS can be at least 96% identical to SEQ ID NO: 18. In some cases, the CBCAS can be at least 97% identical to SEQ ID NO: 18. In some cases, the CBCAS can be at least 98% identical to SEQ ID NO: 18. In some cases, the CBCAS can be at least 99% identical to SEQ ID NO: 18. In some cases, the CBCAS can be identical to SEQ ID NO: 18. Further, codon optimized polynucleotides (for a particular host cell/organism) for the above referenced sequences can be used herein.

The genetically modified microorganism can also further comprise one or more nucleic acids encoding for enzymes (in some cases heterologous enzymes), including but not limited to HMG1, ERG20, and/or isoforms and mutants thereof.

In cases where a HMG-CoA reductase (HMG1) is used, the HMG1 comprises an amino acid sequence that is substantially identical to SEQ ID NO: 20 or 22. For example, the HMG1 can be encoded by an amino acid sequence that is at least 50%, 60%, 70%, 80%, 85%, 90%, 95%, 96%, 97%, 98% or 99% identical to SEQ ID NO: 20 or 22. In some cases, the amino acid sequence can be at least 50% identical to SEQ ID NO: 20 or 22. In some cases, the amino acid sequence can be at least 60% identical to SEQ ID NO: 20 or 22. In some cases, the amino acid sequence can be at least 65% identical to SEQ ID NO: 20 or 22. In some cases, the amino acid sequence can be at least 70% identical to SEQ ID NO: 20 or 22. In some cases, the amino acid sequence can be at least 75% identical to SEQ ID NO: 20 or 22. In some cases, the amino acid sequence can be at least 80% identical to SEQ ID NO: 20 or 22. In some cases, the amino acid sequence can be at least 81% identical to SEQ ID NO: 20 or 22. In some cases, the amino acid sequence can be at least 82% identical to SEQ ID NO: 20 or 22. In some cases, the amino acid sequence can be at least 83% identical to SEQ ID NO: 20 or 22. In some cases, the amino acid sequence can be at least 84% identical to SEQ ID NO: 20 or 22. In some cases, the amino acid sequence can be at least 85% identical to SEQ ID NO: 20 or 22. In some cases, the amino acid sequence can be at least 86% identical to SEQ ID NO: 20 or 22. In some cases, the amino acid sequence can be at least 87% identical to SEQ ID NO: 20 or 22. In some cases, the amino acid sequence can be at least 88% identical to SEQ ID NO: 20 or 22. In some cases, the amino acid sequence can be at least 89% identical to SEQ ID NO: 20 or 22. In some cases, the amino acid sequence can be at least 90% identical to SEQ ID NO: 20 or 22. In some cases, the amino acid sequence can be at least 91% identical to SEQ ID NO: 20 or 22. In some cases, the amino acid sequence can be at least 92% identical to SEQ ID NO: 20 or 22. In some cases, the amino acid sequence can be at least 93% identical to SEQ ID NO: 20 or 22. In some cases, the amino acid sequence can be at least 94% identical to SEQ ID NO: 20 or 22. In some cases, the amino acid sequence can be at least 95% identical to SEQ ID NO: 20 or 22. In some cases, the amino acid sequence can be at least 96% identical to SEQ ID NO: 20 or 22. In some cases, the amino acid sequence can be at least 97% identical to SEQ ID NO: 20 or 22. In some cases, the amino acid sequence can be at least 98% identical to SEQ ID NO: 20 or 22. In some cases, the amino acid sequence can be at least 99% identical to SEQ ID NO: 20 or 22. In some cases, the amino acid sequence can be identical to SEQ ID NO: 20 or 22.

In cases where a farnesyl pyrophosphate synthetase (ERG20) is used, the ERG20 comprises an amino acid sequence that is substantially identical to SEQ ID NO: 24. For example, the ERG20 can comprise an amino acid sequence that is at least 50%, 60%, 70%, 80%, 85%, 90%, 95%, 96%, 97%, 98% or 99% identical to SEQ ID NO: 24. In some cases, the amino acid sequence can be at least 50% identical to SEQ ID NO: 24. In some cases, the amino acid sequence can be at least 60% identical to SEQ ID NO: 24. In some cases, the amino acid sequence can be at least 65% identical to SEQ ID NO: 24. In some cases, the amino acid sequence can be at least 70% identical to SEQ ID NO: 24. In some cases, the amino acid sequence can be at least 75% identical to SEQ ID NO: 24. In some cases, the amino acid sequence can be at least 80% identical to SEQ ID NO: 24. In some cases, the amino acid sequence can be at least 81% identical to SEQ ID NO: 24. In some cases, the amino acid sequence can be at least 82% identical to SEQ ID NO: 24. In some cases, the amino acid sequence can be at least 83% identical to SEQ ID NO: 24. In some cases, the amino acid sequence can be at least 84% identical to SEQ ID NO: 24. In some cases, the amino acid sequence can be at least 85% identical to SEQ ID NO: 24. In some cases, the amino acid sequence can be at least 86% identical to SEQ ID NO: 24. In some cases, the amino acid sequence can be at least 87% identical to SEQ ID NO: 24. In some cases, the amino acid sequence can be at least 88% identical to SEQ ID NO: 24. In some cases, the amino acid sequence can be at least 89% identical to SEQ ID NO: 24. In some cases, the amino acid sequence can be at least 90% identical to SEQ ID NO: 24. In some cases, the amino acid sequence can be at least 91% identical to SEQ ID NO: 24. In some cases, the amino acid sequence can be at least 92% identical to SEQ ID NO: 24. In some cases, the amino acid sequence can be at least 93% identical to SEQ ID NO: 24. In some cases, the amino acid sequence can be at least 94% identical to SEQ ID NO: 24. In some cases, the amino acid sequence can be at least 95% identical to SEQ ID NO: 24. In some cases, the amino acid sequence can be at least 96% identical to SEQ ID NO: 24. In some cases, the amino acid sequence can be at least 97% identical to SEQ ID NO: 24. In some cases, the amino acid sequence can be at least 98% identical to SEQ ID NO: 24. In some cases, the amino acid sequence can be at least 99% identical to SEQ ID NO: 24. In some cases, the amino acid sequence can be identical to SEQ ID NO: 24.

Modifying Endogenous Gene Expression

The genetically modified microorganisms disclosed herein can have their endogenous genes regulated. This can be useful, for example, when there is negative feedback to the expression of a desired polypeptide, such as any of the enzymes described throughout including but not limited to acyl activating enzyme (AAE1); polyketide synthase (PKS); olivetolic acid cyclase (OAC); prenyltransferase (PT); THCA synthase (THCAS); CBDA synthase (CBDAS), CBCA synthase (CBCAS); HMG-CoA reductase (HMG1); farnesyl pyrophosphate synthetase (ERG20); or any combination thereof. Modifying one or more negative regulator can lead to increased expression of a desired polypeptide, and in some cases, increase the production level of the cannabinoids.

Modifying the expression of endogenous genes can be achieved in a variety of ways. For example, antisense or RNA interference approaches can be used to down-regulate expression of the polynucleotides of the present disclosure, e.g., as a further mechanism for modulating cellular phenotype. That is, antisense sequences of the polynucleotides of the present disclosure, or subsequences thereof, can be used to block expression of naturally occurring homologous polynucleotide sequences. In particular, constructs comprising a desired polypeptide coding sequence, including fragments thereof, in antisense orientation, or combinations of sense and antisense orientation, can be used to decrease or effectively eliminate the expression of the desired polypeptide in a cell or plant and obtain an improvement in shelf life as is described herein. Accordingly, this can be used to "knock-out" the desired polypeptide or homologous sequences thereof. A variety of sense and antisense technologies, e.g., as set forth in Lichtenstein and Nellen (Antisense Technology: A Practical Approach IRL Press at Oxford University, Oxford, England, 1997), can be used. Sense or antisense polynucleotide can be introduced into a cell, where they are transcribed. Such polynucleotides can include both simple oligonucleotide sequences and catalytic sequences such as ribozymes.

Other methods for a reducing or eliminating expression (i.e., a "knock-out" or "knockdown") of a desired polypeptide in a transgenic cell or plant can be done by introduction of a construct which expresses an antisense of the desired polypeptide coding strand or fragment thereof. For antisense suppression, the desired polypeptide cDNA or fragment thereof is arranged in reverse orientation (with respect to the coding sequence) relative to the promoter sequence in the expression vector. Further, the introduced sequence need not always correspond to the full length cDNA or gene, and need not be identical to the cDNA or gene found in the cell or plant to be transformed.

Additionally, the antisense sequence need only be capable of hybridizing to the target gene or RNA of interest. Thus, where the introduced polynucleotide sequence is of shorter length, a higher degree of homology to the endogenous transcription factor sequence will be needed for effective antisense suppression. While antisense sequences of various lengths can be utilized, in some embodiments, the introduced antisense polynucleotide sequence in the vector is at least 10, 20, 30, 40, 50, 100 or more nucleotides in length in certain embodiments. Transcription of an antisense construct as described results in the production of RNA molecules that comprise a sequence that is the reverse complement of the mRNA molecules transcribed from the endogenous gene to be repressed.

Other methods for a reducing or eliminating expression can be done by introduction of a construct that expresses siRNA that targets a desired polypeptide (e.g., CBGA synthesis polypeptide). In certain embodiments, siRNAs are short (20 to 24-bp) double-stranded RNA (dsRNA) with phosphorylated 5' ends and hydroxylated 3' ends with two overhanging nucleotides.

Other methods for a reducing or eliminating expression can be done by insertion mutagenesis using the T-DNA of *Agrobacterium tumefaciens* or a selection marker cassette or any other non-sense DNA fragments. After generating the insertion mutants, the mutants can be screened to identify those containing the insertion in the CBGA synthesis polypeptide (or other desired polypeptide) gene. Plants containing one or more transgene insertion events at the desired gene can be crossed to generate homozygous plant for the mutation, as described in Koncz et al., (Methods in *Arabidopsis* Research; World Scientific, 1992).

Suppression of gene expression can also be achieved using a ribozyme. Ribozymes are RNA molecules that possess highly specific endoribonuclease activity. The production and use of ribozymes are disclosed in U.S. Pat. Nos. 4,987,071 and 5,543,508. Synthetic ribozyme sequences including antisense RNAs can be used to confer RNA cleaving activity on the antisense RNA, such that endogenous mRNA molecules that hybridize to the antisense RNA are cleaved, which in turn leads to an enhanced antisense inhibition of endogenous gene expression.

A cell or plant gene can also be modified by using the Cre-lox system (for example, as described in U.S. Pat. No. 5,658,772). A cellular or plant genome can be modified to include first and second lox sites that are then contacted with a Cre recombinase. If the lox sites are in the same orientation, the intervening DNA sequence between the two sites is excised. If the lox sites are in the opposite orientation, the intervening sequence is inverted.

In addition, silencing approach using short hairpin RNA (shRNA) system, and complementary mature CRISPR RNA (crRNA) by CRISPR/Cas system, and virus inducing gene silencing (VIGS) system can also be used to make down regulated or knockout of synthase mutants. Dominant negative approaches can also be used to make down regulated or knockout of desired polypeptides.

The RNA-guided endonuclease can be derived from a clustered regularly interspersed short palindromic repeats (CRISPR)/CRISPR-associated (Cas) system. The CRISPR/Cas system can be a type I, a type II, or a type III system. Non-limiting examples of suitable CRISPR/Cas proteins include Cas3, Cas4, Cas5, Cas5e (or CasD), Cas6, Cas6e, Cas6f, Cas7, Cas8a1, Cas8a2, Cas8b, Cas8c, Cas9, Cas10, Cas10d, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csz1, Csx15, Csf1, Csf2, Csf3, Csf4, and Cul966.

In general, CRISPR/Cas proteins comprise at least one RNA recognition and/or RNA binding domain. RNA recognition and/or RNA binding domains interact with guide RNAs. CRISPR/Cas proteins can also comprise nuclease domains (i.e., DNase or RNase domains), DNA binding domains, helicase domains, RNAse domains, protein-protein interaction domains, dimerization domains, as well as other domains.

The CRISPR/Cas-like protein can be a wild type CRISPR/Cas protein, a modified CRISPR/Cas protein, or a fragment of a wild type or modified CRISPR/Cas protein. The CRISPR/Cas-like protein can be modified to increase nucleic acid binding affinity and/or specificity, alter an enzyme activity, and/or change another property of the protein. For example, nuclease (i.e., DNase, RNase) domains of the CRISPR/Cas-like protein can be modified, deleted, or inactivated. Alternatively, the CRISPR/Cas-like protein can be truncated to remove domains that are not essential for the function of the fusion protein. The CRISPR/Cas-like protein can also be truncated or modified to optimize the activity of the effector domain of the fusion protein.

One method to silence a desired gene (or a CBGA synthesis polypeptide gene) is virus induced gene silencing (known to the art as VIGS). In general, in plants infected with unmodified viruses, the viral genome is targeted. However, when viral vectors have been modified to carry inserts derived from host genes (e.g. portions of sequences encoding a desired polypeptide such as CBGA synthesis polypeptide), the process is additionally targeted against the corresponding mRNAs. Thus disclosed is a method of producing a plant expressing reduced levels of a desired gene (such as CBGA synthesis polypeptide) or other desired gene(s), the method comprising (a) providing a plant expressing a desired gene (e.g., a CBGA synthesis polypeptide); and (b) reducing expression of the desired gene in the plant using virus induced gene silencing.

In some cases, one or more genes can be disrupted. In some cases, the one or more genes can be from the pathway that controls beta oxidation of long chain fatty acids. For example, in some cases, the one or more genes that can be disrupted can be any one of FOX1, FAA1, FAA4, FAT1, PXA1, PXA2, and/or PEX11. Any of the methods described throughout, can be used to disrupt one or more of the genes.

In some cases, the one or more genes that can be disrupted can comprise FOX1. For example, a sequence that is substantially identical to SEQ ID NO: 39 can be targeted for disruption. Any of the methods described throughout, can be used to disrupt the FOX1 gene, for example, but use of the CRISPR/Cas system or the use of RNAi technology. As few as a single nucleotide needs to be altered to have a disruptive effect to FOX1 or other genes that are targeted for disruption.

Isolated Polynucleic Acids

The genes described throughout can be in the form of an isolated polynucleic acid. In other words, the genes can be in forms that do not exist in nature, isolated from a chromosome. The isolated polynucleic acids can comprise a nucleic acid sequence of one or more genes encoding a: (i) acyl activating enzyme (AAE1); (ii) polyketide synthase (PKS); (iii) olivetolic acid cyclase (OAC); (iv) prenyltransferase (PT); (v) THCA synthase (THCAS); (vi) CBDA synthase (CBDAS); and/or (vii) CBCA synthase (CBCAS). For example, the isolated polynucleic acid can comprise a PKS gene. The isolated polynucleic acid can comprise an OAC gene. The isolated polynucleic acid can comprise a PT gene. The isolated polynucleic acid can comprise a THCAS gene. The isolated polynucleic acid can comprise a CBDAS gene. The isolated polynucleic acid can comprise a CBCAS gene. The isolated polynucleic acid can comprise an AAE1 gene.

In some cases, the isolated polynucleic acid can encode an acyl activating enzyme (AAE1). For example, the isolated polynucleic acid can comprise a nucleotide sequence that is substantially identical to SEQ ID NO: 14. In some cases, the isolated polynucleic acid can comprise a nucleotide sequence that is at least 60%, 65%, 70%, 75%, 80%, 85%, 90%, 91%, 92%, 93%, 94%, 95%, 96%, 97%, 98%, 99%, 99.9%, 99.99%, 99.999%, or 99.9999% identical to SEQ ID NO: 14. In some cases, the isolated polynucleic acid can comprise a nucleotide sequence that is at least 60% identical to SEQ ID NO: 14. In some cases, the isolated polynucleic acid can comprise a nucleotide sequence that is at least 65% identical to SEQ ID NO: 14. In some cases, the isolated polynucleic acid can comprise a nucleotide sequence that is at least 70% identical to SEQ ID NO: 14. In some cases, the isolated polynucleic acid can comprise a nucleotide sequence that is at least 75% identical to SEQ ID NO: 14. In some cases, the isolated polynucleic acid can comprise a nucleotide sequence that is at least 80% identical to SEQ ID NO: 14. In some cases, the isolated polynucleic acid can comprise a nucleotide sequence that is at least 81% identical to SEQ ID NO: 14. In some cases, the isolated polynucleic acid can comprise a nucleotide sequence that is at least 82% identical to SEQ ID NO: 14. In some cases, the isolated polynucleic acid can comprise a nucleotide sequence that is at least 83% identical to SEQ ID NO: 14. In some cases, the isolated polynucleic acid can comprise a nucleotide sequence that is at least 84% identical to SEQ ID NO: 14. In some cases, the isolated polynucleic acid can comprise a nucleotide sequence that is at least 85% identical to SEQ ID NO: 14. In some cases, the isolated polynucleic acid can comprise a nucleotide sequence that is at least 86% identical to SEQ ID NO: 14. In some cases, the isolated polynucleic acid can comprise a nucleotide sequence that is at least 87% identical to SEQ ID NO: 14. In some cases, the isolated polynucleic acid can comprise a nucleotide sequence that is at least 88% identical to SEQ ID NO: 14. In some cases, the isolated polynucleic acid can comprise a nucleotide sequence that is at least 89% identical to SEQ ID NO: 14. In some cases, the isolated polynucleic acid can comprise a nucleotide sequence that is at least 90% identical to SEQ ID NO: 14. In some cases, the isolated polynucleic acid can comprise a nucleotide sequence that is at least 91% identical to SEQ ID NO: 14. In some cases, the isolated polynucleic acid can comprise a nucleotide sequence that is at least 92% identical to SEQ ID NO: 14. In some cases, the isolated polynucleic acid can comprise a nucleotide sequence that is at least 93% identical to SEQ ID NO: 14. In some cases, the isolated polynucleic acid can comprise a nucleotide sequence that is at least 94% identical to SEQ ID NO: 14. In some cases, the isolated polynucleic acid can comprise a nucleotide sequence that is at least 95% identical to SEQ ID NO: 14. In some cases, the isolated polynucleic acid can comprise a nucleotide sequence that is at least 96% identical to SEQ ID NO: 14. In some cases, the isolated polynucleic acid can comprise a nucleotide sequence that is at least 97% identical to SEQ ID NO: 14. In some cases, the isolated polynucleic acid can comprise a nucleotide sequence that is at least 98% identical to SEQ ID NO: 14. In some cases, the isolated polynucleic acid can comprise a nucleotide sequence that is at least 99% identical to SEQ ID NO: 14. In some cases, the isolated polynucleic acid can comprise a nucleotide sequence that is identical to SEQ ID NO: 14.

In some cases, the isolated polynucleic acid can encode a polyketide synthase (PKS). For example, the isolated polynucleic acid can comprise a nucleotide sequence that is substantially identical to SEQ ID NO: 6. In some cases, the isolated polynucleic acid can comprise a nucleotide sequence that is at least 60%, 65%, 70%, 75%, 80%, 85%, 90%, 91%, 92%, 93%, 94%, 95%, 96%, 97%, 98%, 99%, 99.9%, 99.99%, 99.999%, or 99.9999% identical to SEQ ID NO: 6. In some cases, the isolated polynucleic acid can comprise a nucleotide sequence that is at least 60% identical to SEQ ID NO: 6. In some cases, the isolated polynucleic acid can comprise a nucleotide sequence that is at least 65% identical to SEQ ID NO: 6. In some cases, the isolated polynucleic acid can comprise a nucleotide sequence that is at least 70% identical to SEQ ID NO: 6. In some cases, the isolated polynucleic acid can comprise a nucleotide sequence that is at least 75% identical to SEQ ID NO: 6. In some cases, the isolated polynucleic acid can comprise a nucleotide sequence that is at least 80% identical to SEQ ID NO: 6. In some cases, the isolated polynucleic acid can comprise a nucleotide sequence that is at least 81% identical to SEQ ID NO: 6. In some cases, the isolated polynucleic acid can comprise a nucleotide sequence that is at least 82% identical to SEQ ID NO: 6. In some cases, the isolated polynucleic acid can comprise a nucleotide sequence that is at least 83% identical to SEQ ID NO: 6. In some cases, the isolated polynucleic acid can comprise a nucleotide sequence that is at least 84% identical to SEQ ID NO: 6. In some cases, the isolated polynucleic acid can comprise a nucleotide sequence that is at least 85% identical to SEQ ID NO: 6. In some cases, the isolated polynucleic acid can comprise a nucleotide sequence that is at least 86% identical to SEQ ID NO: 6. In some cases, the isolated polynucleic acid can comprise a nucleotide sequence that is at least 87% identical to SEQ ID NO: 6. In some cases, the isolated polynucleic acid can comprise a nucleotide sequence that is at least 88% identical to SEQ ID NO: 6. In some cases, the isolated polynucleic acid can comprise a nucleotide sequence that is at least 89% identical to SEQ ID NO: 6. In some cases, the isolated polynucleic acid can comprise a nucleotide sequence that is at least 90% identical to SEQ ID NO: 6. In some cases, the isolated polynucleic acid can comprise a nucleotide sequence that is at least 91% identical to SEQ ID NO: 6. In some cases, the isolated polynucleic acid can comprise a nucleotide sequence that is at least 92% identical to SEQ ID NO: 6. In some cases, the isolated polynucleic acid can comprise a nucleotide sequence that is at least 93% identical to SEQ ID NO: 6. In some cases, the isolated polynucleic acid can comprise a nucleotide sequence that is at least 94% identical to SEQ ID NO: 6. In some cases, the isolated polynucleic acid can comprise a nucleotide sequence that is at least 95% identical to SEQ ID NO: 6. In some cases, the isolated polynucleic acid can comprise a nucleotide sequence that is at least 96% identical to SEQ ID NO: 6. In some cases, the isolated polynucleic acid can comprise a nucleotide sequence that is at least 97% identical to SEQ ID NO: 6. In some cases, the isolated polynucleic acid can comprise a nucleotide sequence that is at least 98% identical to SEQ ID NO: 6. In some cases, the isolated polynucleic acid can comprise a nucleotide sequence that is at least 99% identical to SEQ ID NO: 6. In some cases, the isolated polynucleic acid can comprise a nucleotide sequence that is identical to SEQ ID NO: 6.

In some cases, the isolated polynucleic acid can encode an olivetolic acid cyclase (OAC). For example, the isolated polynucleic acid can comprise a nucleotide sequence that is substantially identical to SEQ ID NO: 8. In some cases, the isolated polynucleic acid can comprise a nucleotide sequence that is at least 60%, 65%, 70%, 75%, 80%, 85%, 90%, 91%, 92%, 93%, 94%, 95%, 96%, 97%, 98%, 99%, 99.9%, 99.99%, 99.999%, or 99.9999% identical to SEQ ID NO: 8. In some cases, the isolated polynucleic acid can comprise a nucleotide sequence that is at least 60% identical to SEQ ID NO: 8. In some cases, the isolated polynucleic acid can comprise a nucleotide sequence that is at least 65% identical to SEQ ID NO: 8. In some cases, the isolated polynucleic acid can comprise a nucleotide sequence that is at least 70% identical to SEQ ID NO: 8. In some cases, the isolated polynucleic acid can comprise a nucleotide sequence that is at least 75% identical to SEQ ID NO: 8. In some cases, the isolated polynucleic acid can comprise a nucleotide sequence that is at least 80% identical to SEQ ID NO: 8. In some cases, the isolated polynucleic acid can comprise a nucleotide sequence that is at least 81% identical to SEQ ID NO: 8. In some cases, the isolated polynucleic acid can comprise a nucleotide sequence that is at least 82% identical to SEQ ID NO: 8. In some cases, the isolated polynucleic acid can comprise a nucleotide sequence that is at least 83% identical to SEQ ID NO: 8. In some cases, the isolated polynucleic acid can comprise a nucleotide sequence that is at least 84% identical to SEQ ID NO: 8. In some cases, the isolated polynucleic acid can comprise a nucleotide sequence that is at least 85% identical to SEQ ID NO: 8. In some cases, the isolated polynucleic acid can comprise a nucleotide sequence that is at least 86% identical to SEQ ID NO: 8. In some cases, the isolated polynucleic acid can comprise a nucleotide sequence that is at least 87% identical to SEQ ID NO: 8. In some cases, the isolated polynucleic acid can comprise a nucleotide sequence that is at least 88% identical to SEQ ID NO: 8. In some cases, the isolated polynucleic acid can comprise a nucleotide sequence that is at least 89% identical to SEQ ID NO: 8. In some cases, the isolated polynucleic acid can comprise a nucleotide sequence that is at least 90% identical to SEQ ID NO: 8. In some cases, the isolated polynucleic acid can comprise a nucleotide sequence that is at least 91% identical to SEQ ID NO: 8. In some cases, the isolated polynucleic acid can comprise a nucleotide sequence that is at least 92% identical to SEQ ID NO: 8. In some cases, the isolated polynucleic acid can comprise a nucleotide sequence that is at least 93% identical to SEQ ID NO: 8. In some cases, the isolated polynucleic acid can comprise a nucleotide sequence that is at least 94% identical to SEQ ID NO: 8. In some cases, the isolated polynucleic acid can comprise a nucleotide sequence that is at least 95% identical to SEQ ID NO: 8. In some cases, the isolated polynucleic acid can comprise a nucleotide sequence that is at least 96% identical to SEQ ID NO: 8. In some cases, the isolated polynucleic acid can comprise a nucleotide sequence that is at least 97% identical to SEQ ID NO: 8. In some cases, the isolated polynucleic acid can comprise a nucleotide sequence that is at least 98% identical to SEQ ID NO: 8. In some cases, the isolated polynucleic acid can comprise a nucleotide sequence that is at least 99% identical to SEQ ID NO: 8. In some cases, the isolated polynucleic acid can comprise a nucleotide sequence that is identical to SEQ ID NO: 8.

In some cases, the isolated polynucleic acid can encode a prenyltransferase (PT). For example, the isolated polynucleic acid can comprise a nucleotide sequence that is substantially identical to any one of SEQ ID NOs: 2, 26, 31, or 37. In some cases, the isolated polynucleic acid can comprise a nucleotide sequence that is at least 60%, 65%, 70%, 75%, 80%, 85%, 90%, 91%, 92%, 93%, 94%, 95%, 96%, 97%, 98%, 99%, 99.9%, 99.99%, 99.999%, or 99.9999% identical to any one of SEQ ID NOs: 2, 26, 31, or 37. In some cases, the isolated polynucleic acid can comprise a nucleotide sequence that is at least 60% identical to any one of SEQ ID NOs: 2, 26, 31, or 37. In some cases, the isolated polynucleic acid can comprise a nucleotide sequence that is at least 65% identical to any one of SEQ ID NOs: 2, 26, 31, or 37. In some cases, the isolated polynucleic acid can comprise a nucleotide sequence that is at least 70% identical to any one of SEQ ID NOs: 2, 26, 31, or 37. In some cases, the isolated polynucleic acid can comprise a nucleotide sequence that is at least 75% identical to any one of SEQ ID NOs: 2, 26, 31, or 37. In some cases, the isolated polynucleic acid can comprise a nucleotide sequence that is at least 80% identical to any one of SEQ ID NOs: 2, 26, 31, or 37. In some cases, the isolated polynucleic acid can comprise a nucleotide sequence that is at least 81% identical to any one of SEQ ID NOs: 2, 26, 31, or 37. In some cases, the isolated polynucleic acid can comprise a nucleotide sequence that is at least 82% identical to any one of SEQ ID NOs: 2, 26, 31, or 37. In some cases, the isolated polynucleic acid can comprise a nucleotide sequence that is at least 83% identical to any one of SEQ ID NOs: 2, 26, 31, or 37. In some cases, the isolated polynucleic acid can comprise a nucleotide sequence that is at least 84% identical to any one of SEQ ID NOs: 2, 26, 31, or 37. In some cases, the isolated polynucleic acid can comprise a nucleotide sequence that is at least 85% identical to any one of SEQ ID NOs: 2, 26, 31, or 37. In some cases, the isolated polynucleic acid can comprise a nucleotide sequence that is at least 86% identical to any one of SEQ ID NOs: 2, 26, 31, or 37. In some cases, the isolated polynucleic acid can comprise a nucleotide sequence that is at least 87% identical to any one of SEQ ID NOs: 2, 26, 31, or 37. In some cases, the isolated polynucleic acid can comprise a nucleotide sequence that is at least 88% identical to any one of SEQ ID NOs: 2, 26, 31, or 37. In some cases, the isolated polynucleic acid can comprise a nucleotide sequence that is at least 89% identical to any one of SEQ ID NOs: 2, 26, 31, or 37. In some cases, the isolated polynucleic acid can comprise a nucleotide sequence that is at least 90% identical to any one of SEQ ID NOs: 2, 26, 31, or 37. In some cases, the isolated polynucleic acid can comprise a nucleotide sequence that is at least 91% identical to any one of SEQ ID NOs: 2, 26, 31, or 37. In some cases, the isolated polynucleic acid can comprise a nucleotide sequence that is at least 92% identical to any one of SEQ ID NOs: 2, 26, 31, or 37. In some cases, the isolated polynucleic acid can comprise a nucleotide sequence that is at least 93% identical to any one of SEQ ID NOs: 2, 26, 31, or 37. In some cases, the isolated polynucleic acid can comprise a nucleotide sequence that is at least 94% identical to any one of SEQ ID NOs: 2, 26, 31, or 37. In some cases, the isolated polynucleic acid can comprise a nucleotide sequence that is at least 95% identical to any one of SEQ ID NOs: 2, 26, 31, or 37. In some cases, the isolated polynucleic acid can comprise a nucleotide sequence that is at least 96% identical to any one of SEQ ID NOs: 2, 26, 31, or 37. In some cases, the isolated polynucleic acid can comprise a nucleotide sequence that is at least 97% identical to any one of SEQ ID NOs: 2, 26, 31, or 37. In some cases, the isolated polynucleic acid can comprise a nucleotide sequence that is at least 98% identical to any one of SEQ ID NOs: 2, 26, 31, or 37. In some cases, the isolated polynucleic acid can comprise a nucleotide sequence that is at least 99% identical to any one of SEQ ID NOs: 2, 26, 31, or 37. In some cases, the isolated polynucleic acid can comprise a nucleotide sequence that is identical to any one of SEQ ID NOs: 2, 26, 31, or 37.

In some cases, the isolated polynucleic acid can encode a THCA synthase (THCAS). For example, the isolated polynucleic acid can comprise a nucleotide sequence that is substantially identical to SEQ ID NO: 10. In some cases, the isolated polynucleic acid can comprise a nucleotide sequence that is at least 60%, 65%, 70%, 75%, 80%, 85%, 90%, 91%, 92%, 93%, 94%, 95%, 96%, 97%, 98%, 99%, 99.9%, 99.99%, 99.999%, or 99.9999% identical to SEQ ID NO: 10. In some cases, the isolated polynucleic acid can comprise a nucleotide sequence that is at least 60% identical to SEQ ID NO: 10. In some cases, the isolated polynucleic acid can comprise a nucleotide sequence that is at least 65% identical to SEQ ID NO: 10. In some cases, the isolated polynucleic acid can comprise a nucleotide sequence that is at least 70% identical to SEQ ID NO: 10. In some cases, the isolated polynucleic acid can comprise a nucleotide sequence that is at least 75% identical to SEQ ID NO: 10. In some cases, the isolated polynucleic acid can comprise a nucleotide sequence that is at least 80% identical to SEQ ID NO: 10. In some cases, the isolated polynucleic acid can comprise a nucleotide sequence that is at least 81% identical to SEQ ID NO: 10. In some cases, the isolated polynucleic acid can comprise a nucleotide sequence that is at least 82% identical to SEQ ID NO: 10. In some cases, the isolated polynucleic acid can comprise a nucleotide sequence that is at least 83% identical to SEQ ID NO: 10. In some cases, the isolated polynucleic acid can comprise a nucleotide sequence that is at least 84% identical to SEQ ID NO: 10. In some cases, the isolated polynucleic acid can comprise a nucleotide sequence that is at least 85% identical to SEQ ID NO: 10. In some cases, the isolated polynucleic acid can comprise a nucleotide sequence that is at least 86% identical to SEQ ID NO: 10. In some cases, the isolated polynucleic acid can comprise a nucleotide sequence that is at least 87% identical to SEQ ID NO: 10. In some cases, the isolated polynucleic acid can comprise a nucleotide sequence that is at least 88% identical to SEQ ID NO: 10. In some cases, the isolated polynucleic acid can comprise a nucleotide sequence that is at least 89% identical to SEQ ID NO: 10. In some cases, the isolated polynucleic acid can comprise a nucleotide sequence that is at least 90% identical to SEQ ID NO: 10. In some cases, the isolated polynucleic acid can comprise a nucleotide sequence that is at least 91% identical to SEQ ID NO: 10. In some cases, the isolated polynucleic acid can comprise a nucleotide sequence that is at least 92% identical to SEQ ID NO: 10. In some cases, the isolated polynucleic acid can comprise a nucleotide sequence that is at least 93% identical to SEQ ID NO: 10. In some cases, the isolated polynucleic acid can comprise a nucleotide sequence that is at least 94% identical to SEQ ID NO: 10. In some cases, the isolated polynucleic acid can comprise a nucleotide sequence that is at least 95% identical to SEQ ID NO: 10. In some cases, the isolated polynucleic acid can comprise a nucleotide sequence that is at least 96% identical to SEQ ID NO: 10. In some cases, the isolated polynucleic acid can comprise a nucleotide sequence that is at least 97% identical to SEQ ID NO: 10. In some cases, the isolated polynucleic acid can comprise a nucleotide sequence that is at least 98% identical to SEQ ID NO: 10. In some cases, the isolated polynucleic acid can comprise a nucleotide sequence that is at least 99% identical to SEQ ID NO: 10. In some cases, the isolated polynucleic acid can comprise a nucleotide sequence that is identical to SEQ ID NO: 10.

In some cases, the isolated polynucleic acid can encode a CBDA synthase (CBDAS). For example, the isolated polynucleic acid can comprise a nucleotide sequence that is substantially identical to SEQ ID NO: 12. In some cases, the isolated polynucleic acid can comprise a nucleotide sequence that is at least 60%, 65%, 70%, 75%, 80%, 85%, 90%, 91%, 92%, 93%, 94%, 95%, 96%, 97%, 98%, 99%, 99.9%, 99.99%, 99.999%, or 99.9999% identical to SEQ ID NO: 12. In some cases, the isolated polynucleic acid can comprise a nucleotide sequence that is at least 60% identical to SEQ ID NO: 12. In some cases, the isolated polynucleic acid can comprise a nucleotide sequence that is at least 65% identical to SEQ ID NO: 12. In some cases, the isolated polynucleic acid can comprise a nucleotide sequence that is at least 70% identical to SEQ ID NO: 12. In some cases, the isolated polynucleic acid can comprise a nucleotide sequence that is at least 75% identical to SEQ ID NO: 12. In some cases, the isolated polynucleic acid can comprise a nucleotide sequence that is at least 80% identical to SEQ ID NO: 12. In some cases, the isolated polynucleic acid can comprise a nucleotide sequence that is at least 81% identical to SEQ ID NO: 12. In some cases, the isolated polynucleic acid can comprise a nucleotide sequence that is at least 82% identical to SEQ ID NO: 12. In some cases, the isolated polynucleic acid can comprise a nucleotide sequence that is at least 83% identical to SEQ ID NO: 12. In some cases, the isolated polynucleic acid can comprise a nucleotide sequence that is at least 84% identical to SEQ ID NO: 12. In some cases, the isolated polynucleic acid can comprise a nucleotide sequence that is at least 85% identical to SEQ ID NO: 12. In some cases, the isolated polynucleic acid can comprise a nucleotide sequence that is at least 86% identical to SEQ ID NO: 12. In some cases, the isolated polynucleic acid can comprise a nucleotide sequence that is at least 87% identical to SEQ ID NO: 12. In some cases, the isolated polynucleic acid can comprise a nucleotide sequence that is at least 88% identical to SEQ ID NO: 12. In some cases, the isolated polynucleic acid can comprise a nucleotide sequence that is at least 89% identical to SEQ ID NO: 12. In some cases, the isolated polynucleic acid can comprise a nucleotide sequence that is at least 90% identical to SEQ ID NO: 12. In some cases, the isolated polynucleic acid can comprise a nucleotide sequence that is at least 91% identical to SEQ ID NO: 12. In some cases, the isolated polynucleic acid can comprise a nucleotide sequence that is at least 92% identical to SEQ ID NO: 12. In some cases, the isolated polynucleic acid can comprise a nucleotide sequence that is at least 93% identical to SEQ ID NO: 12. In some cases, the isolated polynucleic acid can comprise a nucleotide sequence that is at least 94% identical to SEQ ID NO: 12. In some cases, the isolated polynucleic acid can comprise a nucleotide sequence that is at least 95% identical to SEQ ID NO: 12. In some cases, the isolated polynucleic acid can comprise a nucleotide sequence that is at least 96% identical to SEQ ID NO: 12. In some cases, the isolated polynucleic acid can comprise a nucleotide sequence that is at least 97% identical to SEQ ID NO: 12. In some cases, the isolated polynucleic acid can comprise a nucleotide sequence that is at least 98% identical to SEQ ID NO: 12. In some cases, the isolated polynucleic acid can comprise a nucleotide sequence that is at least 99% identical to SEQ ID NO: 12. In some cases, the isolated polynucleic acid can comprise a nucleotide sequence that is identical to SEQ ID NO: 12.

In some cases, the isolated polynucleic acid can encode a CBCA synthase (CBCAS). For example, the isolated polynucleic acid can comprise a nucleotide sequence that is substantially identical to SEQ ID NO: 18. In some cases, the isolated polynucleic acid can comprise a nucleotide sequence that is at least 60%, 65%, 70%, 75%, 80%, 85%, 90%, 91%, 92%, 93%, 94%, 95%, 96%, 97%, 98%, 99%, 99.9%, 99.99%, 99.999%, or 99.9999% identical to SEQ ID NO: 18. In some cases, the isolated polynucleic acid can comprise a nucleotide sequence that is at least 60% identical to SEQ ID NO: 18. In some cases, the isolated polynucleic acid can comprise a nucleotide sequence that is at least 65% identical to SEQ ID NO: 18. In some cases, the isolated polynucleic acid can comprise a nucleotide sequence that is at least 70% identical to SEQ ID NO: 18. In some cases, the isolated polynucleic acid can comprise a nucleotide sequence that is at least 75% identical to SEQ ID NO: 18. In some cases, the isolated polynucleic acid can comprise a nucleotide sequence that is at least 80% identical to SEQ ID NO: 18. In some cases, the isolated polynucleic acid can comprise a nucleotide sequence that is at least 81% identical to SEQ ID NO: 18. In some cases, the isolated polynucleic acid can comprise a nucleotide sequence that is at least 82% identical to SEQ ID NO: 18. In some cases, the isolated polynucleic acid can comprise a nucleotide sequence that is at least 83% identical to SEQ ID NO: 18. In some cases, the isolated polynucleic acid can comprise a nucleotide sequence that is at least 84% identical to SEQ ID NO: 18. In some cases, the isolated polynucleic acid can comprise a nucleotide sequence that is at least 85% identical to SEQ ID NO: 18. In some cases, the isolated polynucleic acid can comprise a nucleotide sequence that is at least 86% identical to SEQ ID NO: 18. In some cases, the isolated polynucleic acid can comprise a nucleotide sequence that is at least 87% identical to SEQ ID NO: 18. In some cases, the isolated polynucleic acid can comprise a nucleotide sequence that is at least 88% identical to SEQ ID NO: 18. In some cases, the isolated polynucleic acid can comprise a nucleotide sequence that is at least 89% identical to SEQ ID NO: 18. In some cases, the isolated polynucleic acid can comprise a nucleotide sequence that is at least 90% identical to SEQ ID NO: 18. In some cases, the isolated polynucleic acid can comprise a nucleotide sequence that is at least 91% identical to SEQ ID NO: 18. In some cases, the isolated polynucleic acid can comprise a nucleotide sequence that is at least 92% identical to SEQ ID NO: 18. In some cases, the isolated polynucleic acid can comprise a nucleotide sequence that is at least 93% identical to SEQ ID NO: 18. In some cases, the isolated polynucleic acid can comprise a nucleotide sequence that is at least 94% identical to SEQ ID NO: 18. In some cases, the isolated polynucleic acid can comprise a nucleotide sequence that is at least 95% identical to SEQ ID NO: 18. In some cases, the isolated polynucleic acid can comprise a nucleotide sequence that is at least 96% identical to SEQ ID NO: 18. In some cases, the isolated polynucleic acid can comprise a nucleotide sequence that is at least 97% identical to SEQ ID NO: 18. In some cases, the isolated polynucleic acid can comprise a nucleotide sequence that is at least 98% identical to SEQ ID NO: 18. In some cases, the isolated polynucleic acid can comprise a nucleotide sequence that is at least 99% identical to SEQ ID NO: 18. In some cases, the isolated polynucleic acid can comprise a nucleotide sequence that is identical to SEQ ID NO: 18.

In some cases, the isolated polynucleic acid can encode a HMG-CoA reductase (HMG1). For example, the isolated polynucleic acid can encode an amino acid sequence that is substantially identical to SEQ ID NO: 20 or 22. In some cases, the amino acid sequence is at least 50%, 60%, 70%, 80%, 85%, 90%, 95%, 96%, 97%, 98% or 99% identical to SEQ ID NO: 20 or 22. In some cases, the amino acid sequence is at least 50% identical to SEQ ID NO: 20 or 22. In some cases, the amino acid sequence is at least 60% identical to SEQ ID NO: 20 or 22. In some cases, the amino acid sequence at least 65% identical to SEQ ID NO: 20 or 22. In some cases, the amino acid sequence is at least 70% identical to SEQ ID NO: 20 or 22. In some cases, the amino acid sequence is at least 75% identical to SEQ ID NO: 20 or 22. In some cases, the amino acid sequence is at least 80% identical to SEQ ID NO: 20 or 22. In some cases, the amino acid sequence is at least 81% identical to SEQ ID NO: 20 or 22. In some cases, the amino acid sequence is at least 82% identical to SEQ ID NO: 20 or 22. In some cases, the amino acid sequence is at least 83% identical to SEQ ID NO: 20 or 22. In some cases, the amino acid sequence is at least 84% identical to SEQ ID NO: 20 or 22. In some cases, the amino acid sequence is at least 85% identical to SEQ ID NO: 20 or 22. In some cases, the amino acid sequence is at least 86% identical to SEQ ID NO: 20 or 22. In some cases, the amino acid sequence is at least 87% identical to SEQ ID NO: 20 or 22. In some cases, the amino acid sequence is at least 88% identical to SEQ ID NO: 20 or 22. In some cases, the amino acid sequence is at least 89% identical to SEQ ID NO: 20 or 22. In some cases, the amino acid sequence is at least 90% identical to SEQ ID NO: 20 or 22. In some cases, the amino acid sequence is at least 91% identical to SEQ ID NO: 20 or 22. In some cases, the amino acid sequence is at least 92% identical to SEQ ID NO: 20 or 22. In some cases, the amino acid sequence is at least 93% identical to SEQ ID NO: 20 or 22. In some cases, the amino acid sequence is at least 94% identical to SEQ ID NO: 20 or 22. In some cases, the amino acid sequence is at least 95% identical to SEQ ID NO: 20 or 22. In some cases, the amino acid sequence is at least 96% identical to SEQ ID NO: 20 or 22. In some cases, the amino acid sequence is at least 97% identical to SEQ ID NO: 20 or 22. In some cases, the amino acid sequence is at least 98% identical to SEQ ID NO: 20 or 22. In some cases, the amino acid sequence is at least 99% identical to SEQ ID NO: 20 or 22. In some cases, the amino acid sequence is identical to SEQ ID NO: 20 or 22.

In some cases, the isolated polynucleic acid can encode a farnesyl pyrophosphate synthetase (ERG20). For example, the isolated polynucleic acid can encode an amino acid sequence that is substantially identical to SEQ ID NO: 24. In some cases, the amino acid sequence is at least 50%, 60%, 70%, 80%, 85%, 90%, 95%, 96%, 97%, 98% or 99% identical to SEQ ID NO: 24. In some cases, the amino acid sequence is at least 50% identical to SEQ ID NO: 24. In some cases, the amino acid sequence is at least 60% identical to SEQ ID NO: 24. In some cases, the amino acid sequence is at least 65% identical to SEQ ID NO: 24. In some cases, the amino acid sequence is at least 70% identical to SEQ ID NO: 24. In some cases, the amino acid sequence is at least 75% identical to SEQ ID NO: 24. In some cases, the amino acid sequence is at least 80% identical to SEQ ID NO: 24. In some cases, the amino acid sequence is at least 81% identical to SEQ ID NO: 24. In some cases, the amino acid sequence is at least 82% identical to SEQ ID NO: 24. In some cases, the amino acid sequence is at least 83% identical to SEQ ID NO: 24. In some cases, the amino acid sequence is at least 84% identical to SEQ ID NO: 24. In some cases, the amino acid sequence is at least 85% identical to SEQ ID NO: 24. In some cases, the amino acid sequence is at least 86% identical to SEQ ID NO: 24. In some cases, the amino acid sequence is at least 87% identical to SEQ ID NO: 24. In some cases, the amino acid sequence is at least 88% identical to SEQ ID NO: 24. In some cases, the amino acid sequence is at least 89% identical to SEQ ID NO: 24. In some cases, the amino acid sequence is at least 90% identical to SEQ ID NO: 24. In some cases, the amino acid sequence is at least 91% identical to SEQ ID NO: 24. In some cases, the amino acid sequence is at least 92% identical to SEQ ID NO: 24. In some cases, the amino acid sequence is at least 93% identical to SEQ ID NO: 24. In some cases, the amino acid sequence is at least 94% identical to SEQ ID NO: 24. In some cases, the amino acid sequence is at least 95% identical to SEQ ID NO: 24. In some cases, the amino acid sequence is at least 96% identical to SEQ ID NO: 24. In some cases, the amino acid sequence is at least 97% identical to SEQ ID NO: 24. In some cases, the amino acid sequence is at least 98% identical to SEQ ID NO: 24. In some cases, the amino acid sequence is at least 99% identical to SEQ ID NO: 24. In some cases, the amino acid sequence is identical to SEQ ID NO: 24.

Methods of Making Genetically Modified Microorganisms

Disclosed herein is a method of making a genetically modified microorganism capable of converting a carbon substrate into CBGA. Also disclosed herein is a method of making a genetically modified microorganism capable of converting a carbon substrate into a cannabinoid.

In some cases, the microorganism can be made by contacting the microorganism with one or more polynucleotides. The polynucleotides can be a vector. The polynucleotides can also comprise one or more genes encoding for an enzymes.

In some cases, the microorganism can be grown so that the polynucleotides are inserted into the microorganism. In some cases, the insertion can be done any method, e.g., transfections, transformation, etc. The insertion of the microorganism can be by plasmid or in some cases the insertion can lead to a stable integration of the plasmid into the chromosome of the microorganism.

The genes encoding for an enzymes can include (i) acyl activating enzyme (AAE1); (ii) polyketide synthase (PKS); (iii) olivetolic acid cyclase (OAC); (iv) prenyltransferase (PT); (v) THCA synthase (THCAS); (vi) CBDA synthase (CBDAS); and/or (vii) CBCA synthase (CBCAS). In some further cases, the genes encoding for an enzyme can include (viii) a HMG-Co reductase (HMG1) and/or (ix) a farnesyl pyrophosphate synthetase (ERG20).

In some cases, the microorganism can be contacted with a polynucleotide that encodes for a prenyltransferase (PT). In some cases, the PT can be encoded by a nucleotide sequence that is substantially identical to SEQ ID NO: 2. In some cases, the polynucleotide can be translated into an amino acid sequence that is substantially identical to SEQ ID NO: 1. In some cases, the PT can be encoded by a nucleotide sequence that is substantially identical to SEQ ID NO: 26. In some cases, the polynucleotide can be translated into an amino acid sequence that is substantially identical to SEQ ID NO: 27. In some cases, the PT can be encoded by a nucleotide sequence that is substantially identical to SEQ ID NO: 31. In some cases, the polynucleotide can be translated into an amino acid sequence that is substantially identical to SEQ ID NO: 32. In some cases, the PT can be encoded by a nucleotide sequence that is substantially identical to SEQ ID NO: 37. In some cases, the polynucleotide can be translated into an amino acid sequence that is substantially identical to SEQ ID NO: 38.

In some cases, the microorganism can also be contacted with a polynucleotide that encodes for an AAE1. In some cases, the AAE1 is encoded by a polynucleotide sequence that is substantially identical to SEQ ID NO: 14. In some cases, the polynucleotide can be translated into an amino acid sequence that is substantially identical to SEQ ID NO: 13.

In some cases, the microorganism can also be contacted with a polynucleotide that encodes for a PKS. In some cases, the PKS encoded by a polynucleotide sequence that is substantially identical to SEQ ID NO: 6. In some cases, the polynucleotide can be translated into an amino acid sequence that is substantially identical to SEQ ID NO: 5.

In some cases, the microorganism can also be contacted with a polynucleotide that encodes for an OAC. In some cases, the OAC encoded by a polynucleotide sequence that is substantially identical to SEQ ID NO: 8. In some cases, the polynucleotide can be translated into an amino acid sequence that is substantially identical to SEQ ID NO: 7.

In some cases, the microorganism can also be contacted with a polynucleotide that encodes for a THCAS. In some cases, the THCAS encoded by a polynucleotide sequence that is substantially identical to SEQ ID NO: 10. In some cases, the polynucleotide can be translated into an amino acid sequence that is substantially identical to SEQ ID NO: 9.

In some cases, the microorganism can also be contacted with a polynucleotide that encodes for a CBDAS. In some cases, the CBDAS encoded by a polynucleotide sequence that is substantially identical to SEQ ID NO: 12. In some cases, the polynucleotide can be translated into an amino acid sequence that is substantially identical to SEQ ID NO: 11.

In some cases, the microorganism can also be contacted with a polynucleotide that encodes for a CBCAS. In some cases, the CBCAS encoded by a polynucleotide sequence that is substantially identical to SEQ ID NO: 18. In some cases, the polynucleotide can be translated into an amino acid sequence that is substantially identical to SEQ ID NO: 17.

In some cases, the microorganism can also be contacted with a polynucleotide that encodes for an HMG-Co reductase (HMG1). In some cases, the HMG1 encoded by a polynucleotide sequence that is substantially identical to SEQ ID NO: 19 or 21. In some cases, the polynucleotide can be translated into an amino acid sequence that is substantially identical to SEQ ID NO: 20 or 22.

In some cases, the microorganism can also be contacted with a polynucleotide that encodes for a farnesyl pyrophosphate synthetase (ERG20). In some cases, the ERG20 encoded by a polynucleotide sequence that is substantially identical to SEQ ID NO: 23. In some cases, the polynucleotide can be translated into an amino acid sequence that is substantially identical to SEQ ID NO: 24.

The microorganism can be any type of microorganism that is disclosed throughout. For example, the microorganism can be a bacterium or a yeast.

The cannabinoid that can be made can be one or more of the following: cannabinoid is $\Delta^9$-tetrahydrocannabinolic acid (THCA), cannabidiolic acid (CBDA), cannabichromenic acid (CBCA), $\Delta^9$-tetrahydrocannabinol (THC), cannabidiol (CBD), cannabichromene (CBC), or any combination thereof.

Exemplary Genetically Modified Microorganisms

Disclosed herein is a genetically modified microorganism capable of converting a carbon substrate into CBGA or a cannabinoid.

The genetically modified microorganism can comprise a heterologous polynucleotide encoding an acyl activating enzyme (AAE1); polyketide synthase (PKS); olivetolic acid cyclase (OAC); and/or prenyltransferase (PT). In some cases, two or more polynucleotides encoding AAE1, PKS, OAC, and/or PT can be present within the genetically modified microorganism. In some cases, three of the polynucleotides encoding AAE1, PKS, OAC, and/or PT can be present within the genetically modified microorganism. In some cases, all four of the polynucleotides encoding AAE1, PKS, OAC, and PT can be present within the genetically modified microorganism.

Additionally, the genetically modified microorganism can further comprise polynucleotides encoding for a THCA synthase (THCAS); a CBDA synthase (CBDAS), a CBCA synthase (CBCAS), an HMG-Co reductase (HMG1) and/or a farnesyl pyrophosphate synthetase (ERG20). In some cases, the polynucleotides can be heterologous. In some cases, two or more polynucleotides encoding THCAS, CBDAS, CBCAS, HMG1, and/or ERG20 can be present within the genetically modified microorganism. In some cases, three or more of the polynucleotides encoding THCAS, CBDAS, CBCAS, HMG1, and/or ERG20 can be present within the genetically modified microorganism.

Should an AAE1 be present within the genetically modified microorganism, the AAE1 can be encoded by an amino acid sequence that is substantially identical to SEQ ID NO: 13. In some cases, the AAE1 can be encoded by a polynucleotide sequence that is substantially identical to SEQ ID NO: 14.

Should a PKS be present within the genetically modified microorganism, the PKS can be encoded by an amino acid sequence that is substantially identical to SEQ ID NO: 5. In some cases, the PKS can be encoded by a polynucleotide sequence that is substantially identical to SEQ ID NO: 6.

Should an OAC be present within the genetically modified microorganism, the OAC can be encoded by an amino acid sequence that is substantially identical to SEQ ID NO: 7. In some cases, the OAC can be encoded by a polynucleotide sequence that is substantially identical to SEQ ID NO: 8.

Should a PT be present within the genetically modified microorganism, the PT can be encoded by an amino acid sequence that is substantially identical to any one of SEQ ID NOs: 1, 27, 32, or 38. In some cases, the PT can be encoded by a polynucleotide sequence that is substantially identical to any one of SEQ ID NOs: 2, 26, 31, or 37.

Should a THCAS be present within the genetically modified microorganism, the THCAS can be encoded by an amino acid sequence that is substantially identical to SEQ ID NO: 9. In some cases, the THCAS can be encoded by a polynucleotide sequence that is substantially identical to SEQ ID NO: 10.

Should a CBDAS be present within the genetically modified microorganism, the CBDAS can be encoded by an amino acid sequence that is substantially identical to SEQ ID NO: 11. In some cases, the CBDAS can be encoded by a polynucleotide sequence that is substantially identical to SEQ ID NO: 12.

Should a CBCAS be present within the genetically modified microorganism, the CBCAS can be encoded by an amino acid sequence that is substantially identical to SEQ ID NO: 17. In some cases, the CBCAS can be encoded by a polynucleotide sequence that is substantially identical to SEQ ID NO: 18.

Should a HMG1 be present within the genetically modified microorganism, the HMG1 can be encoded by a nucleic acid sequence that is substantially identical to SEQ ID NO: 19 or 21. In some cases, the HMG1 comprises an amino acid sequence that is substantially identical to SEQ ID NO: 20 or 22.

Should an ERG20 be present within the genetically modified microorganism, the ERG20 can be encoded by a nucleic acid sequence that is substantially identical to SEQ ID NO: 23. In some cases, the ERG20 comprises an amino acid sequence that is substantially identical to SEQ ID NO: 24.

In certain cases, the genetically modified microorganism can be a yeast or bacterium. Should the genetically modified microorganism be a yeast, the yeast can be from the genus *Saccharomyces*. More specifically, the yeast can be from the species *Saccharomyces cerevisiae*. Should the genetically modified microorganism be a bacterium, the bacterium can be from the genus *Escherichia*, e.g., *Escherichia coli*.

The genetically modified microorganism can use hexanoic acid. In some cases, the genetically modified microorganism can use sugar as a substrate. In some cases, the genetically modified microorganism can make a CBGA or a cannabinoid. If a cannabinoid is made, in some cases, the cannabinoid can be Δ9-tetrahydrocannabinol (THC), cannabidiol (CBD), and/or cannabichromene (CBC).

Fermentation Methods and Processes

In general, the microorganisms disclosed herein should be placed in fermentation conditions that are appropriate to convert a carbon source (such as a sugar, alcohol, and/or fatty acid) to CBGA or a cannabinoid (e.g., THC, CBD, CBC). Reaction conditions that should be considered include temperature, media flow rate, pH, media redox potential, agitation rate (if using a continuous stirred tank reactor), inoculum level, maximum substrate concentrations and rates of introduction of the substrate to the bioreactor to ensure that substrate level does not become limiting, and maximum product concentrations to avoid product inhibition.

In some cases, non-genetically modified microorganisms can be used to increase CBGA or cannabinoid production. For example, cells taken from organisms that naturally produce cannabinoids can be used. These cells can be isolated and once isolated they can be used in a fermentation process.

Fermentation Conditions

The fermentation conditions described herein are applicable to any and all methods disclosed throughout the application.

pH can have a profound effect on overall CBGA or cannabinoid production. Therefore, pH adjustments should be made in some cases.

In some cases, the pH during fermentation can vary from 4 to 10. In some instances, the pH can be from 5 to 9; 6 to 8; 6.1 to 7.9; 6.2 to 7.8; 6.3 to 7.7; 6.4 to 7.6; or 6.5 to 7.5. For example, the pH can be from 6.6 to 7.4. In some instances, the pH can be from 5 to 9. In some instances, the pH can be from 6 to 8. In some instances, the pH can be from 6.1 to 7.9. In some instances, the pH can be from 6.2 to 7.8. In some instances, the pH can be from 6.3 to 7.7. In some instances, the pH can be from 6.4 to 7.6. In some instances, the pH can be from 5.5 to 7.5. In some instances, the pH can be from 6.5 to 7.5. In some instances the pH used for the fermentation can be greater than 6. In some instances the pH used for the fermentation can be lower than 10.

Temperature

Temperature can also be adjusted based on cell, microorganism, or enzyme sensitivity. For example, the temperature used during fermentation, can from 27° C. to 45° C. In other instances, the temperature of the fermentation can be from 27° C. to 45° C.; 28° C. to 44° C.; 29° C. to 43° C.; 30° C. to 42° C.; 31° C. to 41° C.; 32° C. to 40° C. For example, the temperature can be from 36° C. to 39° C. (e.g., 36° C., 37° C., 38° C., or 39° C. In some instances, the temperature can be from 27° C. to 45° C. In some instances, the temperature can be from 28° C. to 44° C. In some instances, the temperature can be from 29° C. to 43° C. In some instances, the temperature can be from 30° C. to 42° C. In some instances, the temperature can be from 31° C. to 41° C. In some instances, the temperature can be from 32° C. to 40° C.

Gases

Availability of oxygen and other gases such as gaseous $CO_2$ can affect yield and fermentation rate. For example, when considering oxygen availability, the percent of dissolved oxygen (DO) within the fermentation media can be from 1% to 40%. In certain instances, the DO concentration can be from 1.5% to 35%; 2% to 30%; 2.5% to 25%; 3% to 20%; 4% to 19%; 5% to 18%; 6% to 17%; 7% to 16%; 8% to 15%; 9% to 14%; 10% to 13%; or 11% to 12%. For example, in some cases the DO concentration can be from 2% to 30%. In other cases, the DO can be from 3% to 20%. In some instances, the DO can be from 4% to 10%. In some cases, the DO can be from 1.5% to 35%. In some cases, the DO can be from 2.5% to 25%. In some cases, the DO can be from 4% to 19%. In some cases, the DO can be from 5% to 18%. In some cases, the DO can be from 6% to 17%. In some cases, the DO can be from 7% to 16%. In some cases, the DO can be from 8% to 15%. In some cases, the DO can be from 9% to 14%. In some cases, the DO can be from 10% to 13%. In some cases, the DO can be from 11% to 12%.

For example, when considering atmospheric $CO_2$, the percent of atmospheric $CO_2$ within an incubator can be from 0% to 10%. In some cases, atmospheric $CO_2$ can help to control the pH within cell culture medium. pH contain within cell culture media is dependent on a balance of dissolved $CO_2$ and bicarbonate ($HCO_3$). Changes in atmospheric $CO_2$ can alter the pH of the medium. In certain instances, the atmospheric $CO_2$ can be from 0% to 10%; 0.01% to 9%; 0.05% to 8%; 0.1% to 7%; 0.5% to 6%; 1% to 5%; 2% to 4%; 3% to 6%; 4% to 7%; 2% to 6%; or 5% to 10%. For example, in some cases the atmospheric $CO_2$ can be from 0% to 10%. In other cases, the atmospheric $CO_2$ can be from 0.01% to 9%. In some instances, the atmospheric $CO_2$ can be from 0.05% to 8%. In some cases, the atmospheric $CO_2$ can be from 0.1% to 7%. In some cases, the atmospheric $CO_2$ can be from 0.5% to 6%. In some cases, the atmospheric $CO_2$ can be from 1% to 5%. In some cases, the atmospheric $CO_2$ can be from 2% to 4%. In some cases, the atmospheric $CO_2$ can be from 3% to 6%. In some cases, the atmospheric $CO_2$ can be from 4% to 7%. In some cases, the atmospheric $CO_2$ can be from 2% to 6%. In some cases, the atmospheric $CO_2$ can be from 5% to 10%.

Bioreactors

Fermentation reactions can be carried out in any suitable bioreactor. In some embodiments of the invention, the bioreactor can comprise a first, growth reactor in which the microorganisms or cells are cultured, and a second, fermentation reactor, to which broth from the growth reactor is fed and in which most of the fermentation product (for example, CBGA or cannabinoids) is produced.

Media

The medium used to ferment CBGA or cannabinoid with the microorganisms described throughout can include hexanoic acid. For example, in some cases, the media can comprise a combination of hexanoic acid, yeast extract, peptone, and glucose. In certain cases, the media can comprise 10 g/L of yeast extract, 20 g/L peptone, 20 g/L glucose and 100 mg/L hexanoic acid. In some cases, hexanoic acid can be used in an amount of 1 mg/L to 1 g/L. In some cases, hexanoic acid can be used in an amount of 10 mg/ to 900 mg/L. In some cases, hexanoic acid can be used in an amount of 25 mg/ to 800 mg/L. In some cases, hexanoic acid can be used in an amount of 50 mg/ to 700 mg/L. In some cases, hexanoic acid can be used in an amount of 75 mg/ to 600 mg/L. In some cases, hexanoic acid can be used in an amount of 100 mg/ to 500 mg/L. In some cases, hexanoic acid can be used in an amount of 125 mg/ to 400 mg/L. In some cases, hexanoic acid can be used in an amount of 150 mg/ to 300 mg/L. In some cases, hexanoic acid can be used in an amount of 175 mg/ to 250 mg/L. In some cases, hexanoic acid can be used in an amount of 50 mg/ to 250 mg/L. In some cases, hexanoic acid can be used in an amount of 75 mg/ to 200 mg/L. In some cases, hexanoic acid can be used in an amount of 90 mg/ to 150 mg/L.

In other cases, olivetolic acid can be used to ferment CBGA or cannabinoids with the microorganism described throughout. For example, in some cases, the media can comprise a combination of olivetolic acid, yeast extract, peptone, and glucose. In certain cases, the media can comprise 10 g/L of yeast extract, 20 g/L peptone, 20 g/L glucose and 40 mg/L hexanoic acid. In some cases, olivetolic acid can be used in an amount of 1 mg/ to 1 g/L. In some cases, olivetolic acid can be used in an amount of 5 mg/ to 900 mg/L. In some cases, olivetolic acid can be used in an amount of 10 mg/ to 800 mg/L. In some cases, olivetolic acid can be used in an amount of 15 mg/ to 700 mg/L. In some cases, olivetolic acid can be used in an amount of 20 mg/ to 600 mg/L. In some cases, olivetolic acid can be used in an amount of 25 mg/ to 500 mg/L. In some cases, olivetolic acid can be used in an amount of 30 mg/ to 400 mg/L. In some cases, olivetolic acid can be used in an amount of 35 mg/ to 300 mg/L. In some cases, olivetolic acid can be used in an amount of 40 mg/ to 200 mg/L. In some cases, olivetolic acid can be used in an amount of 50 mg/ to 150 mg/L. In some cases, olivetolic acid can be used in an amount of 10 mg/ to 100 mg/L. In some cases, olivetolic acid can be used in an amount of 20 mg/ to 75 mg/L. In some cases, olivetolic acid can be used in an amount of 30 mg/ to 50 mg/L.

Product Recovery

The fermentation of the microorganisms disclosed herein can produce a fermentation broth comprising a desired product (e.g., CBGA or cannabinoid) and/or one or more by-products as well as the cells/microorganisms (e.g., a genetically modified microorganism), in a nutrient medium.

In certain embodiments the CBGA produced in the fermentation reaction is converted to a cannabinoid, such as THC, CBD, and/or CDC. This conversion can happen directly from the fermentation broth. However, in other embodiments, the CBGA can be first recovered from the fermentation broth before conversion to a cannabinoid such as THC, CBD, and/or CDC.

In some cases, the CBGA can be continuously removed from a portion of broth and recovered as purified the CBGA. In particular embodiments, the recovery of the CBGA includes passing the removed portion of the broth containing the CBGA through a separation unit to separate the microorganisms (e.g., genetically modified microorganism) from the broth, to produce a cell-free CBGA containing permeate, and returning the microorganisms to the bioreactor. Additional nutrients can be added to the media to replenish its nutrients before it is returned to the bioreactor. The cell-free CBGA permeate can then be stored or be used for subsequent conversion to cannabinoids (or other desired product).

Also, if the pH of the broth was adjusted during recovery of CBGA, the pH should be re-adjusted to a similar pH to that of the broth in the fermentation bioreactor, before being returned to the bioreactor.

Subsequent purification steps can involve treating the post-fermentation CBGA product using methods known in the art to recover individual product species of interest to high purity.

In one example, CBGA extracted in an organic phase can be transferred to an aqueous solution. In some cases, the organic solvent can be evaporated by heat and/or vacuum, and the resulting powder can be dissolved in an aqueous solution of suitable pH. The aqueous phase can then be removed by decantation, centrifugation, or another method. For example, when the organic solvent is ethyl acetate, the resulting powder from evaporation is dissolved in a water: acetonitrile mixture (50:50 ratio).

The same methods as described above can be applied to cannabinoids, should they be produced.

CBGA or Cannabinoid Production Levels

The microorganisms and the methods herein can produce CBGA or cannabinoids at surprisingly high efficiency, more so than other known CBGA or cannabinoids fermentation processes. For example, the microorganisms and the methods disclosed herein can convert a carbon substrate (such as sugar, alcohol, and/or fatty acid) at a rate of greater than 0.01%. For example, the methods disclosed herein can convert a carbon substrate at a rate of greater than 0.02%; 0.03%; 0.04%; 0.05%; 0.06%; 0.07%; 0.08%; 0.09%; or 0.10%.

The genetic modifications to the cells described throughout can be made to produce CBGA or cannabinoids over what would have been made without any genetic modifications. For example, compared to a non-genetically altered cell, the genetically modified microorganisms described throughout can produce CBGA or cannabinoids greater than 1.1 times (compared to the production levels of a non-genetically modified microorganism or non-genetically altered cell). In some cases, the genetically modified microorganisms described throughout can produce CBGA or cannabinoids greater than 1.2; 1.3; 1.4; 1.5; 1.6; 1.7; 1.8; 1.9; 2.0; 2.5; 3.0; 3.5; 4.0; 4.5; 5.0; 6.0; 7.0; 8.0; 9.0; 10.0; 12.5; 15.0; 17.5; 20.0; 25.0; 30.0; 50.0; 75.0; or 100.0 times compared to the production level of a non-genetically modified microorganism (or non-genetically altered cell).

In some cases, the cannabinoid can be THC, CBD, CBC, or any combination thereof.

Methods of Making CBGA or Cannabinoids

The genetically modified cells or microorganisms described throughout can be used to make CBGA and/or cannabinoids, e.g., THC, CBD, and CBC. A substrate capable of being converted into a CBGA or a cannabinoid can be brought in contact with one or more of the following enzymes: acyl activating enzyme (AAE1); polyketide synthase (PKS); olivetolic acid cyclase (OAC); prenyltransferase (PT); THCA synthase (THCAS); CBDA synthase (CBDAS), CBCA synthase (CBCAS), HMG-Co reductase (HMG1), and/or farnesyl pyrophosphate synthetase (ERG20).

The CBGA or cannabinoids (e.g., THC, CBD, CBC) produced can be recovered and isolated from the modified cells. The CBGA or cannabinoids in some cases can be secreted into the media of a cell culture, in which the CBGA or cannabinoids is extracted directly from the media. In some cases, the CBGA or cannabinoids can be within the cell itself, and the cells will need to be lysed in order to recover the respective CBGA or cannabinoids. In some instances, both cases can be true, where some CBGA or cannabinoids are secreted and some remains within the cells. In this case, either method or both methods can be used.

Accordingly, disclosed herein is a method of making CBGA or a cannabinoid comprising (a) contacting the genetically modified microorganism with a medium comprising a carbon source, and (b) growing the genetically modified microorganism to produce the CBGA or cannabinoid. The genetically modified microorganism can comprise any microorganism disclosed throughout. For example, the microorganism can be a genetically modified microorganism capable of converting a carbon substrate into CBGA or a cannabinoid, the genetically modified microorganism comprising a heterologous nucleic acid encoding one or more of the enzymes disclosed throughout (e.g., microorganism can comprise a nucleic acid sequence encoding for one or more of the following enzymes: acyl activating enzyme (AAE1); polyketide synthase (PKS); olivetolic acid cyclase (OAC); prenyltransferase (PT); THCA synthase (THCAS); CBDA synthase (CBDAS), CBCA synthase (CBCAS); HMG-Co reductase (HMG1); farnesyl pyrophosphate synthetase (ERG20); or any combination thereof).

The carbon source can be any carbon source that can be used by the microorganism. In some cases, the carbon source can be a sugar, alcohol, and/or fatty acid. For example, the sugar, alcohol or fatty acid can include without limitation hexanoic acid, glucose, fructose, xylose, sucrose, dextrins, starch, xylan, cellulose, hemicellulose, arabinose, glycerol, ethanol, butanol, methanol, or any combination thereof. In some cases, the carbon source can be hexanoic acid. In some cases, the carbon source can be olivetolic acid. In other cases, the carbon source can be a mixture of one or more different types of carbon sources.

The cannabinoid produced by the methods disclosed throughout can be any cannabinoid including but not limited to $\Delta^9$-tetrahydrocannabinolic acid (THCA), cannabigerolic acid (CBGA); cannabidiolic acid (CBDA), cannabichromenic acid (CBCA), $\Delta^9$-tetrahydrocannabinol (THC), cannabidiol (CBD), cannabichromene (CBC), or any combination thereof.

In some cases, the medium does not contain any cells. In other words, this reaction is performed in the media in vitro. In some cases, the reaction does not occur within a cell. For example, the conversion of hexanoic acid to hexanoyl-CoA can occur outside of a cell. In some cases, the conversion of hexanoyl-CoA to olivetolic acid can occur outside of a cell. In some cases, the conversion of olivetolic acid to CBGA can occur outside of a cell. In some cases, the conversion of CBGA to Δ9-tetrahydrocannabinolic acid can occur outside of a cell. In some cases, the conversion of Δ9-tetrahydrocannabinolic acid to Δ9-tetrahydrocannabinol can occur outside of a cell. In some cases, the conversion of CBGA to cannabidiolic acid can occur outside of a cell. In some cases, the conversion of cannabidiolic acid to cannabidiol can occur outside of a cell. In some cases, the conversion of CBGA to cannabichromenic acid can occur outside of a cell. In some cases, the conversion of cannabichromenic acid to cannabichromene can occur outside of a cell.

In some cases, the cannabinoid, such as CBGA can be converted outside of a cell. For example, once CBGA is produced, it can be either isolated (from the cell or the cell media or both). Once isolated it can be converted, enzymatically or non-enzymatically into other a different product, such as another type of cannabinoid. In some cases, the CBGA is just secreted into the media by the microorganism that synthesized it, and then the CBGA is directly converted enzymatically or non-enzymatically into other a different product, such as another type of cannabinoid.

In some cases, this reaction is contained within a cell that's within cell culture media. In other words, the reaction is performed in vivo. For example, the conversion of hexanoic acid to hexanoyl-CoA can occur within a cell. In some cases, the conversion of hexanoyl-CoA to olivetolic acid can occur within a cell. In some cases, the conversion of olivetolic acid to CBGA can occur within a cell. In some cases, the conversion of CBGA to Δ9-tetrahydrocannabinolic acid can occur within a cell. In some cases, the conversion of Δ9-tetrahydrocannabinolic acid to Δ9-tetrahydrocannabinol can occur within a cell. In some cases, the conversion of CBGA to cannabidiolic acid can occur within a cell. In some cases, the conversion of cannabidiolic acid to cannabidiol can occur within a cell. In some cases, the conversion of CBGA to cannabichromenic acid can occur within a cell. In some cases, the conversion of cannabichromenic acid to cannabichromene can occur within a cell.

In some cases, there is a combination of the two. Some reactions along the pathway can occur within a cell, whereas some of the reactions along the pathway occur outside of a cell.

In some cases, the medium is cell culture media. In other instances, the medium is water or other liquid in which the cells (for in vivo reactions) can survive (such as saline buffered water). In other instances, the medium is water or other liquid in which the enzymes (for in vitro reactions) are active.

The CBGA or cannabinoids produced herein can be useful inter alia in the manufacture of pharmaceutical compositions. Thus, disclosed herein is a method of making a pharmaceutical composition by using the products disclosed herein. In some cases, the CBGA or cannabinoids are mixed with excipients to produce pharmaceutical compositions.

Upon completion of the methods or reactions described throughout, the amount of a particular cannabinoid, e.g., THCA, CBDA, CBCA, THC, CBD, or CBC, present in the reaction mixture can be at least 50% (w/w), at least 60% (w/w), at least 70% (w/w), at least 80% (w/w), at least 90% (w/w), at least, 95% (w/w), or at least 99% (w/w) of the total cannabinoids in the reaction mixture. In some instances, the reaction mixture comprises CBGA in a weight percentage of least 50% (w/w), at least 60% (w/w), at least 70% (w/w), at least 80% (w/w), at least 90% (w/w), at least 95% (w/w), or at least 99% (w/w) of total cannabinoids in the reaction mixture.

Upon completion of the methods or reactions described throughout, the amount of a particular cannabinoid, e.g., THCA, CBDA, CBCA, THC, CBD, or CBC, present in the reaction mixture can be less than 25% (w/w), less than 20% (w/w), less than 15% (w/w), less than 10% (w/w), less than 5% (w/w), or less than 1% (w/w) of the total cannabinoids in the reaction mixture. In some instances, the reaction mixture comprises CBGA in a weight percentage of less than 25% (w/w), less than 20% (w/w), less than 15% (w/w), less than 10% (w/w), less than 5% (w/w), or less than 1% (w/w) of total cannabinoids in the reaction mixture.

Exemplary Uses of the CBGA or Cannabinoids

Preparations of CBGA or cannabinoids obtained can be used for any and all uses. The CBGA or cannabinoids can be isolated and sold as purified products. Or these purified products (e.g., CBGA) can be a feedstock to make additional cannabinoids.

The cannabinoids made can be used to manufacture medicinal compounds.

Accordingly, in one aspect, disclosed is a use of CBGA as a feedstock compound in the manufacture of a cannabinoid. In another aspect, disclosed is a use of a cannabinoid in the manufacture of a medicinal composition.

Pharmaceutical Compositions and Routes of Administration

The cannabinoids (e.g., THC, CBD, and/or CDC) can include pharmaceutically acceptable derivatives or prodrugs thereof. A "pharmaceutically acceptable derivative" can mean means any pharmaceutically acceptable salt, ester, salt of an ester, pro-drug or other derivative thereof.

Pharmaceutically acceptable salts of the compounds of this invention include those derived from pharmaceutically acceptable inorganic and organic acids and bases. Examples of suitable acid salts include acetate, adipate, benzoate, benzenesulfonate, butyrate, citrate, digluconate, dodecylsulfate, formate, fumarate, glycolate, hemisulfate, heptanoate, hexanoate, hydrochloride, hydrobromide, hydroiodide, lactate, maleate, malonate, methanesulfonate, 2-naphthalenesulfonate, nicotinate, nitrate, palmoate, phosphate, picrate, pivalate, propionate, salicylate, succinate, sulfate, tartrate, tosylate and undecanoate. Salts derived from appropriate bases include alkali metal (e.g., sodium), alkaline earth metal (e.g., magnesium), ammonium and $N\text{-(alkyl)}_4^+$ salts.

For preparing pharmaceutical compositions from the compounds of the present invention, pharmaceutically acceptable carriers include either solid or liquid carriers. Solid form preparations include powders, tablets, pills, capsules, cachets, suppositories, and dispersible granules. A solid carrier can be one or more substances, which also acts as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton PA In powders, the carrier is a finely divided solid, which is in a mixture with the finely divided active component. In tablets, the active component is mixed with the carrier having the necessary binding properties in suitable proportions and compacted in the shape and size desired.

Suitable solid excipients are carbohydrate or protein fillers include, but are not limited to sugars, including lactose, sucrose, mannitol, or sorbitol; starch from corn, wheat, rice, potato, or other plants; cellulose such as methyl cellulose, hydroxypropylmethyl-cellulose, or sodium carboxymethylcellulose; and gums including arabic and tragacanth; as well as proteins such as gelatin and collagen. If desired, disintegrating or solubilizing agents are added, such as the cross-linked polyvinyl pyrrolidone, agar, alginic acid, or a salt thereof, such as sodium alginate.

Liquid form preparations include solutions, suspensions, and emulsions, for example, water or water/propylene glycol solutions. For parenteral injection, liquid preparations can be formulated in solution in aqueous polyethylene glycol solution.

The pharmaceutical preparation can be a unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

Exemplary uses of the Cannabinoids

Preparations of cannabinoids (e.g., CBGA, THCA, CBDA, CBCA, THC, CBD, and CBC) obtained can be used for any and all uses. The cannabinoids can be isolated and sold as purified products. Or these purified products can be a feedstock to make additional types of cannabinoids. For example, purified CBGA can be used as a feedstock to make other cannabinoids such as THCA, CBDA, CBCA, THC, CBD, and CBC.

The cannabinoids made in the processes described throughout can be used to manufacture medicinal compounds. Accordingly, in one aspect, disclosed is a use of cannabinoids as a feedstock compound in the manufacture of a medicinal compound. For example, the cannabinoids can be subsequently processed to prepare a pharmaceutical formulation.

Pharmaceutical Compositions and Routes of Administration

The cannabinoids also include pharmaceutically acceptable derivatives thereof. A "pharmaceutically acceptable derivative" means any pharmaceutically acceptable salt, ester, salt of an ester, or other derivative thereof.

Pharmaceutically acceptable salts of the compounds of this invention include those derived from pharmaceutically acceptable inorganic and organic acids and bases. Examples of suitable acid salts include acetate, adipate, benzoate, benzenesulfonate, butyrate, citrate, digluconate, dodecylsulfate, formate, fumarate, glycolate, hemisulfate, heptanoate, hexanoate, hydrochloride, hydrobromide, hydroiodide, lactate, maleate, malonate, methanesulfonate, 2-naphthalenesulfonate, nicotinate, nitrate, palmoate, phosphate, picrate, pivalate, propionate, salicylate, succinate, sulfate, tartrate, tosylate and undecanoate. Salts derived from appropriate bases include alkali metal (e.g., sodium), alkaline earth metal (e.g., magnesium), ammonium and N-$(alkyl)_4^+$ salts.

For preparing pharmaceutical compositions from the compounds of the present invention, pharmaceutically acceptable carriers include either solid or liquid carriers. Solid form preparations include powders, tablets, pills, capsules, cachets, suppositories, and dispersible granules. A solid carrier can be one or more substances, which also acts as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton PA In powders, the carrier is a finely divided solid, which is in a mixture with the finely divided active component. In tablets, the active component is mixed with the carrier having the necessary binding properties in suitable proportions and compacted in the shape and size desired.

Suitable solid excipients are carbohydrate or protein fillers include, but are not limited to sugars, including lactose, sucrose, mannitol, or sorbitol; starch from corn, wheat, rice, potato, or other plants; cellulose such as methyl cellulose, hydroxypropylmethyl-cellulose, or sodium carboxymethylcellulose; and gums including arabic and tragacanth; as well as proteins such as gelatin and collagen. If desired, disintegrating or solubilizing agents are added, such as the cross-linked polyvinyl pyrrolidone, agar, alginic acid, or a salt thereof, such as sodium alginate.

Liquid form preparations include solutions, suspensions, and emulsions, for example, water or water/propylene glycol solutions. For parenteral injection, liquid preparations can be formulated in solution in aqueous polyethylene glycol solution.

The pharmaceutical preparation can be a unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

One particular delivery system can be through the pulmonary system. In some cases, the cannabinoid can be for into a liquid and vaporized so that it can be inhaled. See e.g., U.S. Pat. No. 9,326,967. Vaporization of cannabinoids and delivery through the pulmonary system can result in quick absorption through the circulatory system and can provide extremely fast systemic effects. Further, vaporization can mimic one of the preferred ways in which natural cannabinoids are inhaled.

Additional delivery system that can work by intravenous injections. See e.g., WO2013009928A1. Similar to vaporization, this intravenous injection can provide extremely fast systemic effects.

Oral delivery systems, such as, delivery through the gastrointestinal tract, can be used to deliver the cannabinoids. For example, the oral delivery system can be in the form of a pharmaceutical dosage unit, food, drink, or anything that can be delivered through the gastrointestinal tract.

Treatment of Disease and Symptoms of Disease

The cannabinoids can be used to treat disease, in particular to treat disease of people that are in need thereof. This includes treating one or more symptoms of the diseases. For example, the cannabinoids can be used to treat one of more of the following diseases: anorexia, multiple sclerosis, neurodegenerative disorders, such as Parkinson's disease, Huntington's disease, Tourette's syndrome, and Alzheimer's disease, epilepsy, glaucoma, osteoporosis, schizophrenia, bipolar disorder, post-traumatic stress disorder (PTSD), asthma, cardiovascular disorders, cancer, obesity, or metabolic syndrome-related disorders.

The cannabinoids can be used to treat one or more symptoms of disease, such as depression, anxiety, insomnia, emesis, pain, or inflammation.

Some of the diseases or symptom of disease can be exclusive to humans, but other diseases or symptom of disease can be shared in more than one animal, such as in all mammals.

Recreational Uses

The cannabinoids produced by the microorganism and methods described throughout can be used for recreational use. For example, the cannabinoids, such as $\Delta^9$-tetrahydrocannabinolic acid (THCA), cannabidiolic acid (CBDA), cannabichromenic acid (CBCA), $\Delta^9$-tetrahydrocannabinol (THC), cannabidiol (CBD), cannabichromene (CBC), or any combination thereof, can be used for non-medical uses.

In some cases, the cannabinoid can be formed into a liquid and vaporized so that it can be inhaled. See e.g., U.S. Pat. No. 9,326,967. Vaporization of cannabinoids and delivery through the pulmonary system can be used and can be preferred by some recreational users. For example, recreational users who do not like the smell of burning cannabis or those that are afraid of the effects of inhaling burning substances, can use this method. Further, since this method is not invasive and can be used almost anywhere, recreational users can prefer this method.

In some cases, the cannabinoid can be formed into something that can be injected, e.g., injected intravenously. This method can be used in order to deliver substances quickly and efficiently within the blood stream. For example, this liquid can be injected into the saline solution (colloquially known as "IV") used in hospitals to keep patients hydrated. Further, intravenous injections can be used by recreational users for immediate effects. In some cases, the intravenous cannabinoid injections can be used to treat other drug addictions, such as heroin addiction.

In additional cases, the cannabinoids produced from the microorganisms and methods described throughout can be used as an additive to food or drink. For example, the cannabinoids can be used, for example, in baked goods, such as brownies or cakes. Additionally, the cannabinoids can be added to a beverage such as water, soda, beer, liquor, etc.

Other recreational ways to use the cannabinoids include but are not limited to patches; (similar to nicotine patches); topically (such as in lotions); sprays (breath freshener), or tinctures (mouth drops).

The disclosure is now described with reference to the following examples. These examples are provided for the purpose of illustration only and the disclosure should in no way be construed as being limited to these examples, but rather should be construed to encompass any and all variations which become evident as a result of the teaching provided herein.

EXAMPLES

Example 1—Plasmid Construction

A prenyltransferase of interest was identified. The amino acid sequence (SEQ ID NO: 1) was used by Genscript to design and synthesize the yeast codon optimized sequence coding for the prenyltransferase and used in the experiments.

Plasmids were constructed using the GeneArt Seamless Cloning and Assembly from Thermo Fisher Scientific. The RUNM000898_511.1 vector (SEQ ID NO: 3) contained the *Saccharomyces cerevisiae* 2μ replication origin, the URA3 gene as an auxotrophic marker and the PKS and OAC genes under the regulation of the bidirectional GAL1/GAL10 promoter. The bCBGA0098 vector (SEQ ID NO: 4) contained the *Saccharomyces cerevisiae* 2μ replication origin, the LEU2 gene as an auxotrophic marker and the AAE1 and PT genes under the regulation of the bidirectional GAL1/GAL10 promoter. The bCBGA0306 vector (SEQ ID NO: 25) contained the *Saccharomyces cerevisiae* 2μ replication origin, the LEU2 gene as an auxotrophic marker and the PT gene under the regulation of the bidirectional GAL1/GAL10 promoter.

Example 2—Strain Construction

The parental strain for all examples was the *Saccharomyces cerevisiae* CEN.PK2-1C strain. Its genotype is: MATA, ura3-52; trp1-289; leu2-3, 112; his3Δ1; MAL2-$8^C$; SUC2.

A mutant ERG20 allele was integrated into the GAL80 locus of the host. First, a plasmid was constructed carrying an ERG20 allele with two mutations: F96W and N127W. Second, the ERG20 allele together with the adjacent HygMX cassette was amplified in a PCR reaction and flanking sequences of the chromosomal GAL80 coding sequence were incorporated during the PCR reaction using oligonucleotides with 5' extensions. Third, this DNA fragment was transformed into the host strain by electroporation. Finally, the strain with integrated mutant ERG20 sequence at the GAL80 locus were identified by its hygromycin B resistance and referred to as yCBGA0172.

Plasmids RUNM000898_511.1 (SEQ ID NO: 3) and bCBGA0098 (SEQ ID NO: 4) were transformed into the yCBGA0172 strain by electroporation. Transformants were selected by their leucine and uracil prototrophy on SD/MSG minimal medium (20 g/L glucose, 1.7 g/L yeast nitrogen base w/o ammonium sulphate and amino acids, 1 g/L monosodium glutamic acid, 20 g/L agar when solid medium is to be used) supplemented with histidine and tryptophan.

In another example plasmid bCBGA0306 (SEQ ID NO: 25) and the VVN4655922 plasmid were transformed into the yCBGA0172 strain by electroporation. The plasmid VVN4655922 encodes for the *Saccharomyces cerevisiae* HMG1 gene truncated of the first 530 amino acids and has the *Saccharomyces cerevisiae* TRP1 gene as an auxotrophic selection marker. Transformants were selected by their leucine and tryptophan prototrophies on SD/MSG minimal medium supplemented with histidine and uracil.

Example 3—Growth

Transformant colonies were picked and inoculated into separate wells of a 96-well deep well plate. Each well contained 400 μl SD/MSG liquid medium supplemented with histidine and tryptophan. These inoculums were grown overnight at 30° C. and shaken at 300 rpm with 50 mm shaking diameter.

After the overnight growth the samples were centrifuged, the supernatant discarded and cells transformed with plasmids RUNM000898_511.1 and bCBGA0098 were re-suspended in 400 μl YPD-HXA (10 g/L yeast extract, 20 g/L peptone, 20 g/L glucose and 100 mg/L hexanoic acid) medium. In case of cultures transformed with plasmids bCBGA0306 and VVN4655922 the pelleted cells were re-suspended in 400 μl YPD-OLA (10 g/L yeast extract, 20 g/L peptone, 20 g/L glucose and 40 mg/L olivetolic acid) medium.

Then samples were grown for 16 hours at 30° C. and shaken at 300 rpm with 50 mm shaking diameter and 16 μl 50% glucose was added to the samples. Samples grown in YPD-OLA medium were supplemented additionally with 20 μl of 800 mg/L olivetolic acid solution too.

Finally, samples were grown for additional 32 hours and were analyzed for CBGA titers.

Example 4—Sample Processing and Analytics

The samples were processed by adding 400 μl acetonitrile, then shaken for 5 minutes at 30° C. at 300 rpm with 50 mm throw. The samples were then centrifuged at 400 rpm for 5 minutes. 200 μl of supernatant were transferred into a new 96 well plate.

The new 96 well plate were transferred to a Waters Acquity UPLC (Binary pump)-TQD MS and set with the following parameters:

Instrument: Waters Acquity UPLC (Binary pump)-TQD MS

Stationary phase: Agilent Eclipse Plus C18 RRHD 1.8 mm, 2.1×50 mm

Mobile phase A: water 0.1% FA

Mobil phase B: acetonitrile 0.1% FA

Gradient info:

| Time [min] | % A | % B |
|---|---|---|
| 0 | 55 | 45 |
| 0.5 | 45 | 55 |
| 0.6 | 30 | 70 |
| 2.0 | 30 | 70 |
| 2.1 | 0 | 100 |
| 2.2 | 0 | 100 |
| 2.3 | 55 | 45 |

Flow: 0.4 mL/min

Column temp: 35° C.

Detection: Acquity TQD, MRM Mode (361.2>>219.1; 361.2>>149.0; 361.2>>237.1; 361.2>>343.2)

Figure 2:
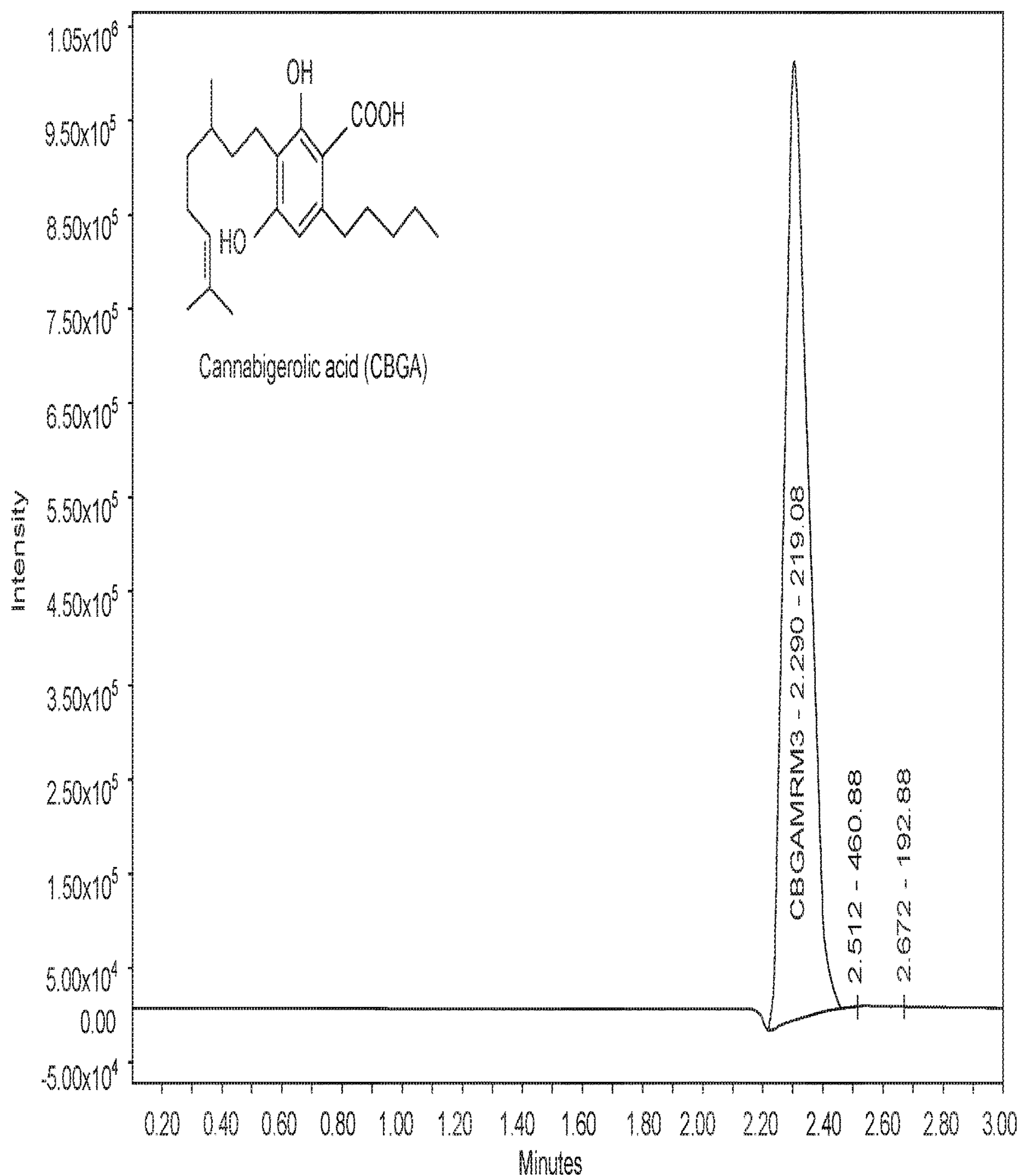
FIG. 2 shows a representative chromatogram of one sample compared to a CBGA standard. This indicates that CBGA is made by our strains since our sample and the CBGA standard overlap.

Using the strains and methods described above CBGA was produced at 200 μg/L concentration when YPD-HXA medium was used and at 15 mg/L concentration when YPD-OLA medium was used. A representative chromatogram of the sample and the CBGA standard can be seen in FIG. 2.

Example 5—Additional Prenyl Transferases

A modified sequence with higher prenyl transferase activity was constructed and referred to as GFP-dPT (polynucleotide sequence: SEQ ID NO: 26; amino acid sequence: SEQ ID NO: 27). The GFP-dPT gene is a fusion of two polynucleotide sequences: a gene of a modified fluorescent protein yEVenus (SEQ ID NO: 28) from the plasmid pKT90 and a truncated version of SEQ ID NO: 2 missing its first 246 nucleotides.

Plasmids were constructed using the GeneArt Seamless Cloning and Assembly from Thermo Fisher Scientific. The bCBGA0385 vector (SEQ ID NO: 29) contained the *Saccharomyces cerevisiae* 2μ replication origin, the LEU2 gene as an auxotrophic marker and the GFP-dPT gene under the regulation of the bidirectional GAL1/GAL10 promoter. The bCBGA0305 vector (SEQ ID NO: 30) contained the *Saccharomyces cerevisiae* 2μ replication origin, the TRP1 gene as an auxotrophic marker and the AAE1 gene under the regulation of the bidirectional GAL1/GAL10 promoter.

For testing the GFP-dPT activity a new parental strain was constructed: a polynucleotide fragment of the RUNM000898_511.1 vector coding for OAC, PKS and URA3 genes was transformed into the strain yCBGA0172 by electroporation. The strain with OAC, PKS and URA3 genes inserted was identified by its uracil prototrophy on SD/MSG minimal medium supplemented with histidine, tryptophan and leucine and referred to as yCBGA0189.

In an another experiment a polynucleotide fragment coding for the truncated version of HMG1 gene lacking its first 530 amino acids and a KanMX cassette was transformed into the strain yCBGA0172 by electroporation. The strain with truncated HMG1 gene inserted was identified by its G418 resistance and referred to as yCBGA0197.

The strain yCBGA0197 was transformed with a vector coding for the *Saccharomyces cerevisiae* HO gene and URA3 gene. The plasmid was cured and a clone with MAT alpha mating type was identified using standard laboratory methods. Finally, this MAT alpha clone was mated with yCBGA0189 and the isolated diploid strain is referred to as yCBGA0201.

Plasmids bCBGA0305 and bCBGA0385 were transformed into the yCBGA0201 strain by electroporation. Transformants were selected by their leucine and tryptophan prototrophies on SD/MSG minimal medium supplemented with histidine.

In another example plasmid bCBGA0385 was transformed into the yCBGA0197 strain by electroporation. Transformants were selected by their leucine prototrophy on SD/MSG minimal medium supplemented with histidine, uracil and tryptophan.

Transformant colonies were picked and inoculated into separate wells of a 96-well deep well plate. Each well contained 400 μl SD/MSG liquid medium supplemented with histidine in case of strains containing both bCBGA0305 and bCBGA3085 and with histidine, uracil and tryptophan in case of strains containing bCBGA0385 plasmid alone. These inoculums were grown overnight at 30° C. and shaken at 300 rpm with 50 mm shaking diameter.

After the overnight growth the samples were centrifuged, the supernatant discarded and cells re-suspended in 400 μl YPD-HXA (10 g/L yeast extract, 20 g/L peptone, 20 g/L glucose and 100 mg/L hexanoic acid) medium or 400 μl YPD-80OLA (10 g/L yeast extract, 20 g/L peptone, 20 g/L glucose and 80 mg/L olivetolic acid) medium. In case of cultures transformed with only bCBGA0385 plasmid the YPD-80OLA medium was used.

The samples were grown for 16 hours at 30° C. and shaken at 300 rpm with 50 mm shaking diameter and 16 μl 50% glucose was added to the samples.

Finally, samples were grown for additional 32 hours and were analyzed for CBGA titers as described in "Example 4—Sample processing and analytics".

Using the strains and methods described above CBGA was produced at 11 mg/L concentration when YPD-HXA medium was used and at 50 mg/L concentration when YPD-80OLA medium was used.

Example 6—Mutant Prenyl Transferase

Another modified sequence with increased prenyl transferase activity was constructed and referred to as ERG20mut-dPT (polynucleotide sequence: SEQ ID NO: 31; amino acid sequence: SEQ ID NO: 32). The ERG20mut-dPT gene is a fusion of two polynucleotide sequences: ERG20 gene with F96W and N127W mutations and a truncated version of SEQ ID NO: 2 missing its first 246 nucleotides.

Plasmid was constructed using the GeneArt Seamless Cloning and Assembly from Thermo Fisher Scientific. The bCBGA0559 vector (SEQ ID NO: 33) contained the *Saccharomyces cerevisiae* 2μ replication origin, the LEU2 gene as an auxotrophic marker and the ERG20mut-dPT gene under the regulation of the bidirectional GAL1/GAL10 promoter.

bCBGA0559 was transformed into the yCBGA0197 strain by electroporation. Transformants were selected by their leucine prototrophy on SD/MSG minimal medium supplemented with histidine, uracil and tryptophan.

Transformant colonies were picked and inoculated into separate wells of a 96-well deep well plate. Each well contained 400 μl SD/MSG liquid medium supplemented with histidine, uracil and tryptophan. These inoculums were grown overnight at 30° C. and shaken at 300 rpm with 50 mm shaking diameter.

After the overnight growth the samples were centrifuged, the supernatant discarded and cells re-suspended in 400 μl YPD-120OLA (10 g/L yeast extract, 20 g/L peptone, 20 g/L glucose and 120 mg/L olivetolic acid) medium.

Then samples were grown for 16 hours at 30° C. and shaken at 300 rpm with 50 mm shaking diameter and 16 μl 50% glucose was added to the samples.

Finally, samples were grown for additional 32 hours and were analyzed for CBGA titers as described in Example 4—Sample processing and analytics.

Using the strains and methods described above CBGA was produced at 90 mg/L concentration.

Example 7—ERG20 Promoter Truncation yCBGA0237 strain was constructed by deleting the HygMX and KanMX cassettes form the yCBGA0197 strain and inserting the GFP-dPT gene under the regulation of the bidirectional GAL1/GAL10 promoter into the YJL144W locus by replacing the native YJL144W ORF. Two more strains were constructed by deleting different fragments from the promoter of the native ERG20 allele of the yCBGA0237 strain. The yCBGA0253 strain contains a 133 nucleotide long deletion between 143 and 275 nucleotides upstream of the translational start site. The yCBGA0254 strain contains a 422 nucleotide long deletion between 69 and 490 nucleotides upstream of the translational start site.

Strains yCBGA0237, yCBGA0253 and yCBGA0254 were inoculated into separate wells of a 96-well deep well plate. Each well contained 400 μl SD/MSG liquid medium supplemented with histidine, leucine, uracil and tryptophan. These inoculums were grown overnight at 30° C. and shaken at 300 rpm with 50 mm shaking diameter.

After the overnight growth 40 μl of the samples were transferred into 360 μl YPD-120OLA (10 g/L yeast extract, 20 g/L peptone, 20 g/L glucose and 120 mg/L olivetolic acid) medium.

Then samples were grown for 16 hours at 30° C. and shaken at 300 rpm with 50 mm shaking diameter and 16 μl 50% glucose was added to the samples.

Finally, samples were grown for additional 32 hours and were analyzed for CBGA titers as described in Example 4—Sample processing and analytics.

Using the strains and methods described above, yCBGA0237 strain produced 53 mg/L CBGA and yCBGA0253 and yCBGA0254 reached 96 and 78 mg/L CBGA concentration, respectively.

Example 8—Olivetolic Acid conversion to THCA

A plasmid was constructed using the GeneArt Seamless Cloning and Assembly from Thermo Fisher Scientific. The RUNM001233_51.1 vector (SEQ ID NO: 34) contained the *Saccharomyces cerevisiae* 2,t replication origin, the URA3 gene as an auxotrophic marker and the THCA synthase gene under the regulation of the bidirectional GAL1/GAL10 promoter.

For testing the olivetolic acid conversion into THCA the RUNM001233_51.1 and bCBGA0385 vectors were transformed into the strain yCBGA0197 by electroporation. Transformants were selected by their leucine and uracil prototrophies on SD/MSG minimal medium supplemented with histidine and tryptophan.

Transformant colonies were picked and inoculated into separate wells of a 96-well deep well plate. Each well contained 400 μl SC-URA-LEU (6.7 g/L Yeast Nitrogen Base, 1.6 g/L Amino Acid Drop Out mix without uracil and leucine, 22 g/L glucose, buffered to pH 6.0). These inoculums were grown for 48 hours at 30° C. and shaken at 300 rpm with 50 mm shaking diameter.

After the 48 hours growth period the samples were centrifuged, the supernatant discarded and cells re-suspended in 400 μl YPD-120OLA (10 g/L yeast extract, 20 g/L peptone, 20 g/L glucose and 120 mg/L olivetolic acid) medium.

Then samples were grown for 16 hours at 30° C. and shaken at 300 rpm with 50 mm shaking diameter and 16 μl 50% glucose was added to the samples.

Finally, samples were grown for additional 32 hours and were analyzed for THCA and CBGA titers as described below.

Using the strains and methods described above CBGA was produced at 2 mg/L concentration while THCA was produced at 84 mg/L concentration.

Example 9—Hexanoic Acid Conversion to THCA

Plasmids were constructed using the GeneArt Seamless Cloning and Assembly from Thermo Fisher Scientific. The RUNM001210_96.1 vector (SEQ ID NO: 35) contained the *Saccharomyces cerevisiae* 2μ replication origin, the URA3 gene as an auxotrophic marker, the PKS and OAC genes under the regulation of the bidirectional GAL1/GAL10 promoter and the AAE1 gene under the regulation of the STES promoter. The bCBGA0409 vector (SEQ ID NO: 36) contained the *Saccharomyces cerevisiae* 2μ replication origin, the LEU2 gene as an auxotrophic marker, the THCA synthase and PT genes under the regulation of the bidirectional GAL1/GAL10 promoter.

The yCBGA0251 strain was constructed by inserting the ERG20mut-dPT gene under the regulation of the bidirectional GAL1/GAL10 promoter into the YMR145C locus by replacing the native YMR145C ORF of the yCBGA0237 strain. The yCBGA0269 strain was constructed by deleting a 133 nucleotide long fragment between 143 and 275 nucleotides upstream of the translational start site of the native ERG20 allele of the yCBGA0251 strain. Plasmids RUNM001210_96.1 and bCBGA0409 were transformed into the yCBGA0269 strain by electroporation. Transformants were selected by their uracil and leucine prototrophy on SD/MSG minimal medium supplemented with histidine and tryptophan.

Transformant colonies were picked and inoculated into separate wells of a 96-well deep well plate. Each well contained 400 μl SC-URA-LEU (6.7 g/L Yeast Nitrogen Base, 1.6 g/L Amino Acid Drop Out mix without uracil and leucine, 22 g/L glucose, buffered to pH 6.0). These inoculums were grown for 48 hours at 30° C. and shaken at 300 rpm with 50 mm shaking diameter. After the 48 hours growth period 40 μl samples of these cultures were inoculated into 360 μl YPD-HXA (10 g/L yeast extract, 20 g/L peptone, 20 g/L glucose and 100 mg/L hexanoic acid) medium. Then samples were grown for 16 hours at 30° C. and shaken at 300 rpm with 50 mm shaking diameter and 40 μg hexanoic acid dissolved in 8 μl ethanol was added to the samples. Finally, samples were grown for additional 32 hours and were analyzed for THCA and CBGA titers as described below.

Using the strains and methods described above CBGA was produced at 34 mg/L concentration while THCA was produced at 23 mg/L concentration.

Example 10—Additional Sample Processing

The samples from examples 8 and 9 were processed by dilution with acetonitrile:water mixture (the composition of the mixture depends on the dilution factor, to reach 50% acetonitrile content for further processing), then shaken for 5 minutes at 30° C. at 300 rpm with 50 mm throw. The samples were then centrifuged at 400 rpm for 5 minutes. 200 μl of supernatant were transferred into a new 96 well plate.

The new 96 well plate were transferred to a Waters Acquity UPLC (Binary pump)-TQD MS and set with the following parameters:

Instrument: Waters Acquity UPLC (Binary pump)-TQD MS

Stationary phase: Agilent Eclipse Plus C18 RRHD 1.8 mm, 2.1×50 mm

Mobile phase A: water 0.1% FA

Mobil phase B: acetonitrile 0.1% FA

Gradient info:

| Time [min] | A [%] | B [%] |
|---|---|---|
| 0 | 55 | 45 |
| 0.5 | 45 | 55 |
| 0.6 | 30 | 70 |
| 2.0 | 30 | 70 |
| 2.1 | 5 | 95 |
| 3.1 | 5 | 95 |
| 3.2 | 55 | 45 |
| 5.5 | 55 | 45 |

Flow: 0.4 mL/min

Column temp: 35° C.

Detection: Acquity TQD, MRM Mode (361.2>>219.1; 361.2>>149.0; 361.2>>237.1; 361.2>>343.2); UV at 280 nm wavelength.

Figure 3:
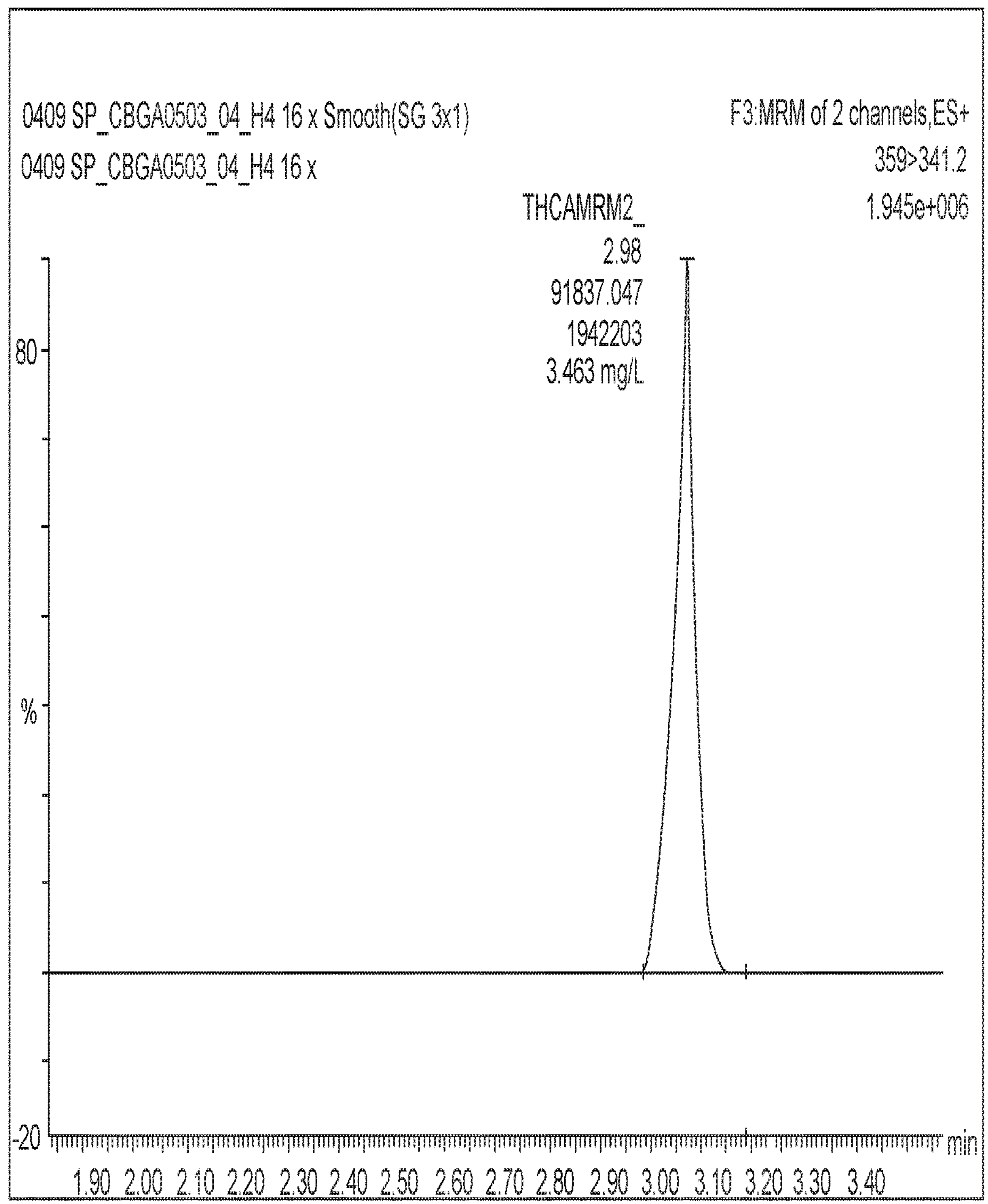
FIG. 3 shows a representative MRM chromatogram of a THCA containing sample produced by the microorganism described throughout.
Figure 4:
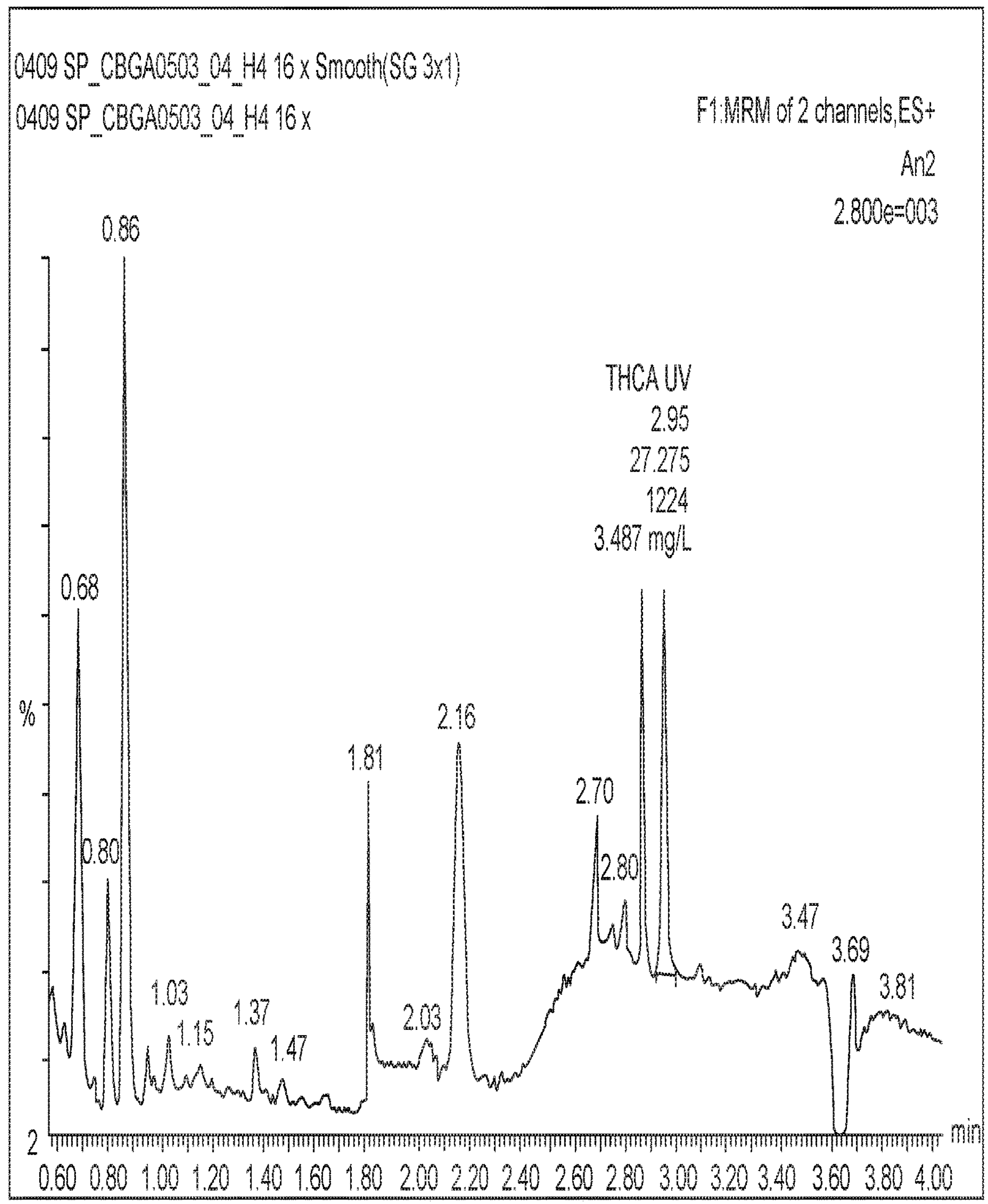
FIG. 4 shows a representative UV chromatogram of a THCA containing sample produced by the microorganism described throughout.

Representative chromatograms of a THCA containing sample can be seen in FIG. 3 (MRM chromatogram) and FIG. 4 (UV chromatogram).

Example 11—Preventing Hexanoic Acid Degradation and Increasing CBGA Titers

Cannabinoid production can be limited by the availability of hexanoic acid. We tested to see if the availability of hexanoic acid can be increased by knocking out several genes of the beta-oxidation pathway. In particular, we tested to see if hexanoic acid degradation could be prevented or minimized. Deletion of FAA1, FAA4, FAT1, PXA1, PXA2 and PEX11 had no obvious effect on hexanoic acid titers: after 24 hours of growth in YPD-HXA medium the hexanoic acid concentration was dropped below 5% of the original level (no heterologous cannabinoid pathway genes present). In other words, hexanoic degradation was not affected. A wild type control strain performed similarly, resulting in less than 5% final hexanoic acid concentration. However, deletion of the FOX1 gene (a.k.a. PDX1, systematic name YGL205W) increased hexanoic acid titers. The knockout of FOX1 eliminated HXA degradation almost completely: 95% of the original hexanoic concentration was still present at the end of the 24 hour long growth period.

Yeast strains having the ability to make CBGA were also knocked out for the FOX1 gene. yCBGA0326 strain was constructed by first, inserting the PKS and OAC genes under the regulation of the bidirectional GAL1/GAL10 promoter and the AAE1 gene under the regulation of the HXK1 promoter into the YGL202W locus replacing the native YGL202W ORF, second, inserting the PKS and OAC genes under the regulation of the bidirectional GAL1/GAL10 promoter and the AAE1 gene under the regulation of the HXK1 promoter into the DPP1 locus replacing the native DPP1 ORF, third, inserting the PKS and OAC genes under the regulation of the bidirectional GAL1/GAL10 promoter into the BTS1 locus replacing the native BTS1 ORF. yCBGA0373 strain was constructed by deleting the FOX1 gene, more specifically the nucleotide fragment between −73 and 3243 relative to the translational start site.

Strains yCBGA0326 and yCBGA0373 were inoculated into separate wells of a 96-well deep well plate. Each well contained 400 μl SC liquid medium (6.7 g/L Yeast Nitrogen Base, 1.6 g/L Amino Acid Drop Out mix without uracil and leucine, 22 g/L glucose, buffered to pH 6.0, supplemented with leucine and uracil). These inoculums were grown for 48 hours at 30° C. and shaken at 300 rpm with 50 mm shaking diameter. After the 48 hours growth period 40 μl samples of these cultures were inoculated into 360 μl YPD-50HXA (10 g/L yeast extract, 20 g/L peptone, 20 g/L glucose and 50 mg/L hexanoic acid) medium. Then samples were grown for 24 hours at 30° C. and shaken at 300 rpm with 50 mm shaking diameter, then 20 μg hexanoic acid dissolved in 8 μl ethanol was added to the samples. Finally, samples were grown for additional 24 hours and four replicates of both strains were analyzed for CBGA titers.

Figure 5A:
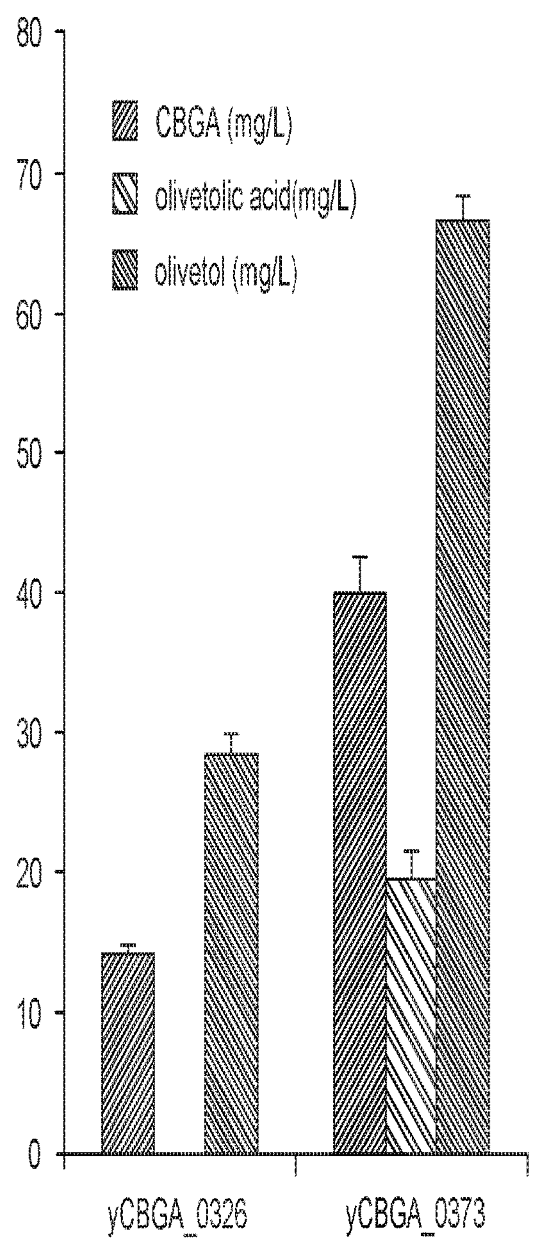
FIG. 5 shows the ability of two different yeast strains to produce CBGA, olivetolic acid, and olivetol. yCBGA_0373 strain with a knocked out FOX1 gene produced more CBGA, olivetolic acid, and olivetol compared to its parental yCBGA_0326 strain with wild type FOX1 gene. Error bars show standard deviation of the four replicates measured.
Figure 5B:
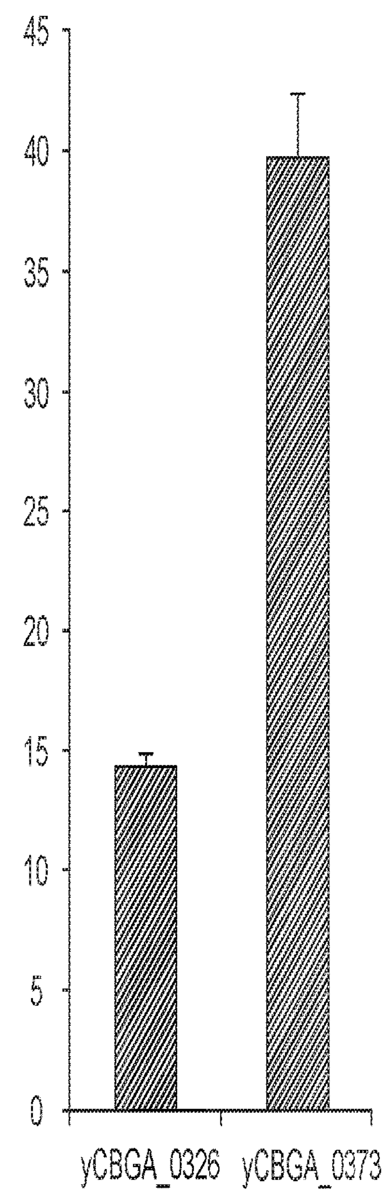

Using the methods described above, CBGA, olivetol, and olivetol acid titers were measured. As seen in FIG. 5, yCBGA0326 produced 14.3 mg/L CBGA and 28.4 mg/L olivetol while the strain yCBGA0373 deleted for the FOX1 gene produced 39.7 mg/L CBGA, 19.6 mg/L olivetolic acid and 66.1 mg/L olivetol.

We claim:

1. A genetically modified microorganism comprising a polynucleotide encoding a polypeptide having prenyltransferase activity, the polypeptide comprising an amino acid sequence comprising SEQ ID NO: 27 or 32.

2. The genetically modified microorganism of claim 1, wherein the microorganism is a bacterium or a yeast.

3. The genetically modified microorganism of claim 1, wherein the microorganism is a yeast.

4. The genetically modified microorganism of claim 3, wherein the yeast is from the species *Saccharomyces cerevisiae.*

5. The genetically modified microorganism of claim 1, wherein one or more genes are disrupted.

6. The genetically modified microorganism of claim 5, wherein the one or more disrupted genes is from a pathway that controls beta oxidation of long chain fatty acids.

7. The genetically modified microorganism of claim 5, wherein the one or more disrupted genes are endogenous to the microorganism.

8. The genetically modified microorganism of claim 5, wherein the one or more disrupted genes is FOX1, FAA1, FAA4, FAT1, PXA1, PXA2, and/or PEX11.

9. The genetically modified microorganism of claim 5, wherein a FOX1 gene is disrupted.

10. The genetically modified microorganism of claim 1, further comprising one or more polynucleotides encoding: an acyl activating enzyme (AAE1); a polyketide synthase (PKS); an olivetolic acid cyclase (OAC); a tetrahydrocannabinolic acid synthase (THCAS); a cannabidiolic acid synthase (CBDAS); a cannabichromenic acid synthase (CBCAS); a HMG-Co reductase (HMG1); and/or a farnesyl pyrophosphate synthetase (ERG20).

11. The genetically modified microorganism of claim 10, wherein: the AAE1 comprises an amino acid sequence that is at least 90% identical to SEQ ID NO: 13; the PKS comprises an amino acid sequence that is at least 90% identical to SEQ ID NO: 5; the OAC comprises an amino acid sequence that is at least 90% identical to SEQ ID NO: 7; the THCAS comprises an amino acid sequence that is at least 90% identical to SEQ ID NO: 9; the CBDAS comprises an amino acid sequence that is at least 90% identical to SEQ ID NO: 11; the CBCAS comprises an amino acid sequence that is at least 90% identical to SEQ ID NO: 17; the HMG1 comprises an amino acid sequence that is at least 90% identical to SEQ ID NO: 20 or 22; and/or the ERG20 comprises an amino acid sequence that is at least 90% identical to SEQ ID NO: 24.

12. A method of making a cannabinoid, the method comprising contacting the genetically modified microorganism of claim 10 with hexanoic acid and a second carbon substrate.

13. The method of claim 12, wherein the second carbon substrate is a sugar, alcohol, and/or fatty acid.

14. The method of claim 12, wherein the second carbon substrate is glucose, fructose, xylose, sucrose, dextrins, starch, xylan, cellulose, hemicellulose, arabinose, glycerol, ethanol, butanol, methanol, or any combination thereof.

15. A method of making the genetically modified microorganism of claim 1, the method comprising contacting a microorganism with a polynucleotide encoding a polypeptide having prenyltransferase activity, the polypeptide comprising an amino acid sequence comprising SEQ ID NO: 27 or 32.

16. The method of claim 15, further comprising contacting the microorganism with one or more additional polynucleotides that encode for: acyl activating enzyme (AAE1); polyketide synthase (PKS); olivetolic acid cyclase (OAC); THCA synthase (THCAS); CBDA synthase (CBDAS), CBCA synthase (CBCAS), HMG-Co reductase (HMG1), and/or farnesyl pyrophosphate synthetase (ERG20).

17. The genetically modified microorganism of claim 1, further comprising one or more polynucleotides encoding: an acyl activating enzyme (AAE1); a polyketide synthase (PKS); and an olivetolic acid cyclase (OAC).

18. The genetically modified microorganism of claim 17, wherein: the AAE1 comprises an amino acid sequence that is at least 90% identical to SEQ ID NO: 13; the PKS comprises an amino acid sequence that is at least 90% identical to SEQ ID NO: 5; and the OAC comprises an amino acid sequence that is at least 90% identical to SEQ ID NO: 7.

19. A method of making a cannabinoid, the method comprising contacting the genetically modified microorganism of claim 17 with hexanoic acid and a second carbon substrate.

20. A vector comprising: a) a polynucleotide encoding a polypeptide having prenyltransferase activity, the polypeptide comprising an amino acid sequence comprising SEQ ID NO: 27 or 32; and b) a promoter suitable for expression in a yeast host.

* * * * *

SEQUENCE LISTING

```
<160> NUMBER OF SEQ ID NOS: 39

<210> SEQ ID NO 1
<211> LENGTH: 398
<212> TYPE: PRT
<213> ORGANISM: Unknown
<220> FEATURE:
<223> OTHER INFORMATION: New/Synthetic sequence

<400> SEQUENCE: 1

Met Gly Leu Ser Leu Val Cys Thr Phe Ser Phe Gln Thr Asn Tyr His
1               5                   10                  15

Thr Leu Leu Asn Pro His Asn Lys Asn Pro Lys Asn Ser Leu Leu Ser
            20                  25                  30

Tyr Gln His Pro Lys Thr Pro Ile Ile Lys Ser Ser Tyr Asp Asn Phe
        35                  40                  45

Pro Ser Lys Tyr Cys Leu Thr Lys Asn Phe His Leu Leu Gly Leu Asn
    50                  55                  60

Ser His Asn Arg Ile Ser Ser Gln Ser Arg Ser Ile Arg Ala Gly Ser
65                  70                  75                  80

Asp Gln Ile Glu Gly Ser Pro His His Glu Ser Asp Asn Ser Ile Ala
                85                  90                  95

Thr Lys Ile Leu Asn Phe Gly His Thr Cys Trp Lys Leu Gln Arg Pro
            100                 105                 110

Tyr Val Val Lys Gly Met Ile Ser Ile Ala Cys Gly Leu Phe Gly Arg
        115                 120                 125

Glu Leu Phe Asn Asn Arg His Leu Phe Ser Trp Gly Leu Met Trp Lys
    130                 135                 140

Ala Phe Phe Ala Leu Val Pro Ile Leu Ser Phe Asn Phe Phe Ala Ala
145                 150                 155                 160

Ile Met Asn Gln Ile Tyr Asp Val Asp Ile Asp Arg Ile Asn Lys Pro
                165                 170                 175

Asp Leu Pro Leu Val Ser Gly Glu Met Ser Ile Glu Thr Ala Trp Ile
            180                 185                 190

Leu Ser Ile Ile Val Ala Leu Thr Gly Leu Ile Val Thr Ile Lys Leu
        195                 200                 205

Lys Ser Ala Pro Leu Phe Val Phe Ile Tyr Ile Phe Gly Ile Phe Ala
    210                 215                 220

Gly Phe Ala Tyr Ser Val Pro Pro Ile Arg Trp Lys Gln Tyr Pro Phe
225                 230                 235                 240

Thr Asn Phe Leu Ile Thr Ile Ser Ser His Val Gly Leu Ala Phe Thr
                245                 250                 255

Ser Tyr Ser Ala Thr Thr Ser Ala Leu Gly Leu Pro Phe Val Trp Arg
            260                 265                 270

Pro Ala Phe Ser Phe Ile Ile Ala Phe Met Thr Val Met Gly Met Thr
        275                 280                 285

Ile Ala Phe Ala Lys Asp Ile Ser Asp Ile Glu Gly Asp Ala Lys Tyr
    290                 295                 300

Gly Val Ser Thr Val Ala Thr Lys Leu Gly Ala Arg Asn Met Thr Phe
305                 310                 315                 320

Val Val Ser Gly Val Leu Leu Leu Asn Tyr Leu Val Ser Ile Ser Ile
```

```
            325                 330                 335

Gly Ile Ile Trp Pro Gln Val Phe Lys Ser Asn Ile Met Ile Leu Ser
            340                 345                 350

His Ala Ile Leu Ala Phe Cys Leu Ile Phe Gln Thr Arg Glu Leu Ala
        355                 360                 365

Leu Ala Asn Tyr Ala Ser Ala Pro Ser Arg Gln Phe Phe Glu Phe Ile
    370                 375                 380

Trp Leu Leu Tyr Tyr Ala Glu Tyr Phe Val Tyr Val Phe Ile
385                 390                 395
```

<210> SEQ ID NO 2
<211> LENGTH: 1197
<212> TYPE: DNA
<213> ORGANISM: Unknown
<220> FEATURE:
<223> OTHER INFORMATION: New/Synthetic sequence

<400> SEQUENCE: 2

```
atgggtttat ctttggtctg tactttttca tttcaaacta attaccatac attgttaaat     60

ccacataata agaaccctaa aaattctttg ttgtcatatc aacatccaaa aactccaatt    120

attaaatctt cttatgataa ttttccatct aagtactgtt tgactaaaaa tttccatttg    180

ttaggtttaa attctcataa tagaatttct tcacaatcaa gatcaattag agctggttct    240

gatcaaattg aaggttcacc acatcatgaa tctgataact caatcgcaac taaaattttg    300

aactttggtc atacatgttg gaaattgcaa agaccatacg ttgttaaggg tatgatttct    360

attgcttgtg gtttatttgg tagagaattg tttaataaca gacatttgtt ttcttggggt    420

ttgatgtgga aagcattttt cgcattagtt ccaatcttgt cttttaattt ctttgctgca    480

atcatgaacc aaatatatga tgttgatatt gatagaatta ataagccaga tttgccattg    540

gtttctggtg aaatgtcaat cgaaactgct tggattttat ctatcatcgt tgcattgact    600

ggtttgatcg ttacaattaa attaaaatca gctccattgt tcgtttttat atatatcttc    660

ggtatcttcg ctggttttgc atactctgtt ccaccaatta gatggaagca ataccctttt    720

actaatttct tgatcacaat ttcttcacat gttggtttgg cttttacttc ttactcagct    780

actacatctg cattaggttt gccatttgtt tggaggccag ctttttcttt tattatcgct    840

tttatgactg ttatgggtat gacaatcgct ttcgcaaagg atatctctga tattgaaggt    900

gacgctaaat acggtgtttc aactgttgct acaaaattgg gtgcaagaaa catgactttc    960

gttgtttctg gtgttttgtt gttgaactat ttggtttcta tctcaatcgg tattatttgg   1020

ccacaagttt ttaaatctaa catcatgatc ttgtcacatg ctatcttggc attctgtttg   1080

atcttccaaa caagagaatt agctttggca aattatgctt ctgcaccatc aagacaattt   1140

ttcgagttta tttggttgtt gtactacgct gaatattttg tttacgtttt tatttga      1197
```

<210> SEQ ID NO 3
<211> LENGTH: 8794
<212> TYPE: DNA
<213> ORGANISM: Artificial Sequence
<220> FEATURE:
<223> OTHER INFORMATION: RUNM000898_511.1

<400> SEQUENCE: 3

```
ttttggtttt aattttcttg gagtgtaatc aaaaattaac aacttttccc agaatgatct     60

gtaaacgtca ccaaaaccaa catgtgctgg atgaataatg taatcttgga tagtttcaac    120

agattcgaat gtaacttcaa cgatatgagt gtaaccttct tctttctttt gtgtaacatc    180
```

```
tttaccccaa taaacatcct tcatagctgg gatgatgtta accaaattaa cgtaagtctt    240
gaaaaattct tctttttgtg cttctgtaat ttcatcttta aacttcaaaa cgatcaaatg    300
cttaacagcc atttatattg aattttcaaa aattcttact tttttttgg atggacgcaa    360
agaagtttaa taatcatatt acatggcatt accaccatat acatatccat atctaatctt    420
acttatatgt tgtggaaatg taaagagccc cattatctta gcctaaaaaa accttctctt    480
tggaactttc agtaatacgc ttaactgctc attgctatat tgaagtacgg attagaagcc    540
gccgagcggg cgacagccct ccgacggaag actctcctcc gtgcgtcctc gtcttcaccg    600
gtcgcgttcc tgaaacgcag atgtgcctcg cgccgcactg ctccgaacaa taaagattct    660
acaatactag cttttatggt tatgaagagg aaaaattggc agtaacctgg ccccacaaac    720
cttcaaatta acgaatcaaa ttaacaacca taggatgata atgcgattag ttttttagcc    780
ttatttctgg ggtaattaat cagcgaagcg atgatttttg atctattaac agatatataa    840
atggaaaagc tgcataacca ctttaactaa tactttcaac attttcagtt tgtattactt    900
cttattcaaa tgtcataaaa gtatcaacaa aaaattgtta atatacctct atactttaac    960
gtcaaggaga aaaaactata atgaatcatt tgagagctga aggtccagca tcagttttgg   1020
ctattggtac tgcaaaccca gaaaacatct tgatccaaga tgaatttcca gattattact   1080
tcagagttac taagtcagaa catatgacac aattgaagga aaagtttaga aagatctgtg   1140
ataagtctat gattagaaaa agaaattgtt tcttgaacga agaacatttg aagcaaaacc   1200
caagattagt tgaacatgaa atgcaaacat tggatgctag acaagatatg ttggttgttg   1260
aagttccaaa gttgggtaaa gatgcatgtg ctaaagcaat taaagaatgg ggtcaaccaa   1320
agtctaagat cactcatttg atttttacat cagcatctac tacagatatg ccaggtgctg   1380
attaccattg tgcaaagttg ttgggtttgt caccatctgt taagagagtt atgatgtacc   1440
aattaggttg ttacggtggt ggtactgttt tgagaatcgc taaggatatc gcagaaaaca   1500
ataagggtgc tagagtcttg gcagtttgtt gtgatatcat ggcttgtttg tttagaggtc   1560
catcagattc tgatttggaa ttgttagttg gtcaagctat tttggtgac ggtgctgcag   1620
ctgttattgt tggtgcagaa ccagatgaat cagttggtga aagaccaatc ttcgaattag   1680
tttcaactgg tcaaacaatt ttgccaaatt ctgaaggtac aattggtggt catatcagag   1740
aagctggttt gatcttcgat ttgcataaag atgttccaat gttgatctct aacaacatcg   1800
aaaagtgttt gatcgaagct tttactccaa tcggtatctc agattggaac tctattttct   1860
ggattacaca tccaggtggt aaagcaatct tggataaggt tgaagaaaaa ttggatttga   1920
agaaagaaaa atttgttgat tcaagacatg ttttgtctga acatggtaac atgtcttcat   1980
ctactgtttt gttcgttatg gatgaattga gaaagagatc attagaagag ggtaaatcta   2040
ctacaggtga cggttttgaa tggggtgttt tatttggttt tggtccaggt ttgacagttg   2100
aaagagttgt tgttagatct gttccaatta aatactaagt gaatttactt taaatcttgc   2160
atttaaataa attttctttt tatagcttta tgacttagtt tcaatttata tactatttta   2220
atgacatttt cgattcattg attgaaagct ttgtgttttt tcttgatgcg ctattgcatt   2280
gttcttgtct ttttcgccac atgtaatatc tgtagtagat acctgataca ttgtggatgc   2340
tgagtgaaat tttagttaat aatggaggcg ctcttaataa ttttggggat attggctttt   2400
ttttttaaag tttacaaatg aattttttcc gccaggataa cgattctgaa gttactctta   2460
gcgttcctat cggtacagcc atcaaatcat gcctataaat catgcctata tttgcgtgca   2520
```

```
gtcagtatca tctacagaat ttcatcattt tttttttatt cttttttttg atttcggttt   2580
ccttgaaatt tttttgattc ggtaatctcc gaacagaagg aagaacgaag gaaggagcac   2640
agacttagat tggtatatat acgcatatgt agtgttgaag aaacatgaaa ttgcccagta   2700
ttcttaaccc aactgcacag aacaaaaacc tgcaggaaac gaagataaat catgtcgaaa   2760
gctacatata aggaacgtgc tgctactcat cctagtcctg ttgctgccaa gctatttaat   2820
atcatgcacg aaaagcaaac aaacttgtgt gcttcattgg atgttcgtac caccaaggaa   2880
ttactggagt tagttgaagc attaggtccc aaaatttgtt tactaaaaac acatgtggat   2940
atcttgactg atttttccat ggagggcaca gttaagccgc taaaggcatt atccgccaag   3000
tacaattttt tactcttcga agacagaaaa tttgctgaca ttggtaatac agtcaaattg   3060
cagtactctg cgggtgtata cagaatagca gaatgggcag acattacgaa tgcacacggt   3120
gtggtgggcc caggtattgt tagcggtttg aagcaggcgg cagaagaagt aacaaaggaa   3180
cctagaggcc ttttgatgtt agcagaattg tcatgcaagg gctccctatc tactggagaa   3240
tatactaagg gtactgttga cattgcgaag agcgacaaag attttgttat cggctttatt   3300
gctcaaagag acatgggtgg aagagatgaa ggttacgatt ggttgattat gacacccggt   3360
gtgggtttag atgacaaggg agacgcattg ggtcaacagt atagaaccgt ggatgatgtg   3420
gtctctacag gatctgacat tattattgtt ggaagaggac tatttgcaaa gggaagggat   3480
gctaaggtag agggtgaacg ttacagaaaa gcaggctggg aagcatattt gagaagatgc   3540
ggccagcaaa actaaaaaac tgtattataa gtaaatgcat gtatactaaa ctcacaaatt   3600
agagcttcaa tttaattata tcagttatta cccaatcaga tctgctgcat taatgaatcg   3660
gccaacgcgc ggggagaggc ggtttgcgta ttgggcgctc ttccgcttcc tcgctcactg   3720
actcgctgcg ctcggtcgtt cggctgcggc gagcggtatc agcatcgatg aattccacgg   3780
actatagact atactagtat actccgtcta ctgtacgata cacttccgct caggtccttg   3840
tcctttaacg aggccttacc actcttttgt tactctattg atccagctca gcaaaggcag   3900
tgtgatctaa gattctatct tcgcgatgta gtaaaactag ctagaccgag aaagagacta   3960
gaaatgcaaa aggcacttct acaatggctg ccatcattat tatccgatgt gacgctgcag   4020
cttctcaatg atattcgaat acgctttgag gagatacagc ctaatatccg acaaactgtt   4080
ttacagattt acgatcgtat ttgttaccca tcattgaatt ttgaacatcc gaacctggga   4140
gttttccctg aaacagatag tatatttgaa cctgtataat aatatatagt ctagcgcttt   4200
acggaagaca atgtatgtat ttcggttcct ggagaaacta ttgcatctat tgcataggta   4260
atcttgcacg tcgcatcccc ggttcatttt ctgcgtttcc atcttgcact tcaatagcat   4320
atctttgtta acgaagcatc tgtgcttcat tttgtagaac aaaaatgcaa cgcgagagcg   4380
ctaatttttc aaacaaagaa tctgagctgc atttttacag aacagaaatg caacgcgaaa   4440
gcgctatttt accaacgaag aatctgtgct tcatttttgt aaaacaaaaa tgcaacgcga   4500
gagcgctaat tttcaaaca aagaatctga gctgcatttt tacagaacag aaatgcaacg   4560
cgagagcgct attttaccaa caaagaatct atacttcttt tttgttctac aaaaatgcat   4620
cccgagagcg ctatttttct aacaaagcat cttagattac tttttttctc ctttgtgcgc   4680
tctataatgc agtctcttga taactttttg cactgtaggt ccgttaaggt tagaagaagg   4740
ctactttggt gtctattttc tcttccataa aaaaagcctg actccacttc ccgcgtttac   4800
tgattactag cgaagctgcg ggtgcatttt ttcaagataa aggcatcccc gattatattc   4860
tataccgatg tggattgcgc atactttgtg aacagaaagt gatagcgttg atgattcttc   4920
```

```
attggtcaga aaattatgaa cggtttcttc tattttgtct ctatatacta cgtataggaa   4980
atgtttacat tttcgtattg ttttcgattc actctatgaa tagttcttac tacaattttt   5040
ttgtctaaag agtaatacta gagataaaca taaaaaatgt agaggtcgag tttagatgca   5100
agttcaagga gcgaaaggtg gatgggtagg ttatataggg atatagcaca gagatatata   5160
gcaaagagat acttttgagc aatgtttgtg gaagcggtat tcgcaatatt ttagtagctc   5220
gttacagtcc ggtgcgtttt tggttttttg aaagtgcgtc ttcagagcgc ttttggtttt   5280
caaaagcgct ctgaagttcc tatactttct agagaatagg aacttcggaa taggaacttc   5340
aaagcgtttc cgaaaacgag cgcttccgaa aatgcaacgc gagctgcgca catacagctc   5400
actgttcacg tcgcacctat atctgcgtgt tgcctgtata tatatataca tgagaagaac   5460
ggcatagtgc gtgtttatgc ttaaatgcgt acttatatgc gtctatttat gtaggatgaa   5520
aggtagtcta gtacctcctg tgatattatc ccattccatg cggggtatcg tatgcttcct   5580
tcagcactac cctttagctg ttctatatgc tgccactcct caattggatt agtctcatcc   5640
ttcaatgcta tcatttcctt tgatattgga tcatatgcat agtaccgaga aactagtgcg   5700
aagtagtgat caggtattgc tgttatctga tgagtatacg ttgtcctggc cacggcagaa   5760
gcacgcttat cgctccaatt tcccacaaca ttagtcaact ccgttaggcc cttcattgaa   5820
agaaatgagg tcatcaaatg tcttccaatg tgagattttg ggccattttt tatagcaaag   5880
attgaataag gcgcattttt cttcaaagct ttattgtacg atctgactaa gttatctttt   5940
aataattggt attcctgttt attgcttgaa gaattgccgg tcctatttac tcgttttagg   6000
actggttcag aattcatcga tgctcactca aaggcggtaa tacggttatc cacagaatca   6060
ggggataacg caggaaagaa catgtgagca aaaggccagc aaaaggccag gaaccgtaaa   6120
aaggccgcgt tgctggcgtt tttccatagg ctccgccccc ctgacgagca tcacaaaaat   6180
cgacgctcaa gtcagaggtg gcgaaacccg acaggactat aaagatacca ggcgtttccc   6240
cctggaagct ccctcgtgcg ctctcctgtt ccgaccctgc cgcttaccgg atacctgtcc   6300
gcctttctcc cttcgggaag cgtggcgctt tctcatagct cacgctgtag gtatctcagt   6360
tcggtgtagg tcgttcgctc caagctgggc tgtgtgcacg aaccccccgt tcagcccgac   6420
cgctgcgcct tatccggtaa ctatcgtctt gagtccaacc cggtaagaca cgacttatcg   6480
ccactggcag cagccactgg taacaggatt agcagagcga ggtatgtagg cggtgctaca   6540
gagttcttga agtggtggcc taactacggc tacactagaa gacagtattt ggtatctgcg   6600
ctctgctgaa gccagttacc ttcggaaaaa gagttggtag ctcttgatcc ggcaaacaaa   6660
ccaccgctgg tagcggtggt ttttttgttt gcaagcagca gattacgcgc agaaaaaaag   6720
gatctcaaga agatcctttg atcttttcta cggggtctga cgctcagtgg aacgaaaact   6780
cacgttaagg gattttggtc atgagattat caaaaaggat cttcacctag atccttttaa   6840
attaaaaatg aagttttaaa tcaatctaaa gtatatatga gtaaacttgg tctgacagtt   6900
accaatgctt aatcagtgag gcacctatct cagcgatctg tctatttcgt tcatccatag   6960
ttgcctgact ccccgtcgtg tagataacta cgatacggga gggcttacca tctggcccca   7020
gtgctgcaat gataccgcga gacccacgct caccggctcc agatttatca gcaataaacc   7080
agccagccgg aagggccgag cgcagaagtg gtcctgcaac tttatccgcc tccatccagt   7140
ctattaattg ttgccgggaa gctagagtaa gtagttcgcc agttaatagt ttgcgcaacg   7200
ttgttgccat tgctacaggc atcgtggtgt cacgctcgtc gtttggtatg gcttcattca   7260
```

```
gctccggttc ccaacgatca aggcgagtta catgatcccc catgttgtgc aaaaaagcgg   7320
ttagctcctt cggtcctccg atcgttgtca gaagtaagtt ggccgcagtg ttatcactca   7380
tggttatggc agcactgcat aattctctta ctgtcatgcc atccgtaaga tgcttttctg   7440
tgactggtga gtactcaacc aagtcattct gagaatagtg tatgcggcga ccgagttgct   7500
cttgcccggc gtcaatacgg gataataccg cgccacatag cagaacttta aaagtgctca   7560
tcattggaaa acgttcttcg gggcgaaaac tctcaaggat cttaccgctg ttgagatcca   7620
gttcgatgta acccactcgt gcacccaact gatcttcagc atcttttact ttcaccagcg   7680
tttctgggtg agcaaaaaca ggaaggcaaa atgccgcaaa aaagggaata agggcgacac   7740
ggaaatgttg aatactcata ctcttccttt ttcaatatta ttgaagcatt tatcagggtt   7800
attgtctcat gagcggatac atatttgaat gtatttagaa aaataaacaa ataggggttc   7860
cgcgcacatt tccccgaaaa gtgccacctg acgtctaaga aaccattatt atcatgacat   7920
taacctataa aaataggcgt atcacgaggc cctttcgtct cgcgcgtttc ggtgatgacg   7980
gtgaaaacct ctgacacatg cagctcccgg agacggtcac agcttgtctg taagcggatg   8040
ccgggagcag acaagcccgt cagggcgcgt cagcgggtgt tggcgggtgt cggggctggc   8100
ttaactatgc ggcatcagag cagattgtac tgagagtgca ccatatgcgg tgtgaaatac   8160
cgcacagatg cgtaaggaga aaataccgca tcaggcgcca ttcgccattc aggctgcgca   8220
actgttggga agggcgatcg gtgcgggcct cttcgctatt acgccagctg gcgaaagggg   8280
gatgtgctgc aaggcgatta agttgggtaa cgccagggtt ttcccagtca cgacgttgta   8340
aaacgacggc cagtgaattg cggccgcatc gatggtggga tgagcttgga gcaggaagaa   8400
tacactatac tggatctaaa gagtacaata gatggataag aatattggca gcgcaaaaag   8460
gcttcaagct tacacaacac ggtttatttc gaaataatat ccttctcgaa agctttaacg   8520
aacgcagaat tttcgagtta ttaaacttaa aatacgctga acccgaacat agaaatatcg   8580
aatgggaaaa aaaaactgca taaaggcatt aaaagaggag cgaatttttt tttaataaaa   8640
atcttaataa tcattaaaag ataaataata gtctatatat acgtatataa ataaaaaata   8700
ttcaaaaaat aaaataaact attattttag cgtaaaggat ggggaaagag aaaagaaaaa   8760
aattgatcta tcgatttcaa ttcaattcaa ttta                               8794
```

<210> SEQ ID NO 4
<211> LENGTH: 11346
<212> TYPE: DNA
<213> ORGANISM: Artificial Sequence
<220> FEATURE:
<223> OTHER INFORMATION: bCBHA0096 vector

<400> SEQUENCE: 4

```
gattaatata attatataaa aatattatct tcttttcttt atatctagtg ttatgtaaaa     60
taaattgatg actacggaaa gctttttat attgtttctt tttcattctg agccacttaa    120
atttcgtgaa tgttcttgta agggacggta gatttacaag tgatacaaca aaaagcaagg    180
cgctttttct aataaaaaga agaaaagcat ttaacaattg aacacctcta tatcaacgaa    240
gaatattact ttgtctctaa atccttgtaa aatgtgtacg atctctatat gggttactca    300
taagtgtacc gaagactgca ttgaaagttt atgtttttc actggaggcg tcattttcgc    360
gttgagaaca attgtcctgt acttccttgt tcatgtgtgt tcaaaaacgt tatatttata    420
ggataattat actctatttc tcaacaagta attggttgtt tggccgagcg gtctaaggcg    480
cctgattcaa gaaatatctt gaccgcagtt aactgtggga atactcaggt atcgtaagat    540
```

```
gcaagagttc gaatctctta gcaaccatta tttttttcct caacataacg agaacacaca    600
ggggcgctat cgcacagaat caaattcgat gactggaaat tttttgttaa tttcagaggt    660
cgcctgacgc atatacettt ttcaactgaa aaattgggag aaaaaggaaa ggtgagagcg    720
ccggaaccgg cttttcatat agaatagaga agcgttcatg actaaatgct tgcatcacaa    780
tacttgaagt tgacaatatt atttaaggac ctattgtttt ttccaatagg tggttagcaa    840
tcgtcttact ttctaacttt tcttaccttt tacatttcag caatatatat atatatttca    900
aggatatacc attctaatgt ctgcccctaa gaagatcgtc gttttgccag gtgaccacgt    960
tggtcaagaa atcacagccg aagccattaa ggttcttaaa gctatttctg atgttcgttc   1020
caatgtcaag ttcgatttcg aaaatcattt aattggtggt gctgctatcg atgctacagg   1080
tgttccactt ccagatgagg cgctggaagc ctccaagaag gctgatgccg ttttgttagg   1140
tgctgtgggt ggtcctaaat ggggtaccgg tagtgttaga cctgaacaag gtttactaaa   1200
aatccgtaaa gaacttcaat tgtacgccaa cttaagacca tgtaactttg catccgactc   1260
tcttttagac ttatctccaa tcaagccaca atttgctaaa aatactgact tcgttgttgt   1320
cagagaatta gtgggaggta tttactttgg taagagaaag gaagacgatg gtgatggtgt   1380
cgcttgggat agtgaacaat acaccgttcc agaagtgcaa agaatcacaa gaatggccgc   1440
tttcatggcc ctacaacatg agccaccatt gcctatttgg tccttggata aagctaatgt   1500
tttggcctct tcaagattat ggagaaaaac tgtggaggaa accatcaaga acgaattccc   1560
tacattgaag gttcaacatc aattgattga ttctgccgcc atgatcctag ttaagaaccc   1620
aacccaccta aatggtatta taatcaccag caacatgttt ggtgatatca tctccgatga   1680
agcctccgtt atcccaggtt ccttgggttt gttgccatct gcgtccttgg cctctttgcc   1740
agacaagaac accgcatttg gtttgtacga accatgccac ggttctgctc cagatttgcc   1800
aaagaataag gtcaacccta tcgccactat cttgtctgct gcaatgatgt tgaaattgtc   1860
attgaacttg cctgaagaag gtaaggccat tgaagatgca gttaaaaagg ttttggatgc   1920
aggtatcaga actggtgatt taggtggttc caacagtacc accgaagtcg gtgatgctgt   1980
cgccgaagaa gttaagaaaa tccttgctta aaaagattct cttttttat gatatttgta   2040
cataaacttt ataaatgaaa ttcataatag aaacgacacg aaattacaaa atggaatatg   2100
ttcatagggt agacgaaact atatacgcaa tctacataca tttatcaaga aggagaaaaa   2160
ggaggatgta aaggaataca ggtaagcaaa ttgatactaa tggctcaacg tgataaggaa   2220
aaagaattgc actttaacat taatattgac aaggaggagg gcaccacaca aaaagttaca   2280
gatctgctgc attaatgaat cggccaacgc gcggggagag gcggtttgcg tattgggcgc   2340
tcttccgctt cctcgctcac tgactcgctg cgctcggtcg ttcggctgcg gcgagcggta   2400
tcagcatcga tgaattccac ggactataga ctatactagt atactccgtc tactgtacga   2460
tacacttccg ctcaggtcct tgtcctttaa cgaggcctta ccactctttt gttactctat   2520
tgatccagct cagcaaaggc agtgtgatct aagattctat cttcgcgatg tagtaaaact   2580
agctagaccg agaaagagac tagaaatgca aaaggcactt ctacaatggc tgccatcatt   2640
attatccgat gtgacgctgc agcttctcaa tgatattcga atacgctttg aggagataca   2700
gcctaatatc cgacaaactg ttttacagat ttacgatcgt atttgttacc catcattgaa   2760
ttttgaacat ccgaacctgg gagttttccc tgaaacagat agtatatttg aacctgtata   2820
ataatatata gtctagcgct ttacggaaga caatgtatgt atttcggttc ctggagaaac   2880
```

```
tattgcatct attgcatagg taatcttgca cgtcgcatcc ccggttcatt ttctgcgttt   2940
ccatcttgca cttcaatagc atatctttgt taacgaagca tctgtgcttc attttgtaga   3000
acaaaaatgc aacgcgagag cgctaatttt tcaaacaaag aatctgagct gcatttttac   3060
agaacagaaa tgcaacgcga aagcgctatt ttaccaacga agaatctgtg cttcattttt   3120
gtaaaacaaa aatgcaacgc gagagcgcta atttttcaaa caaagaatct gagctgcatt   3180
tttacagaac agaaatgcaa cgcgagagcg ctattttacc aacaaagaat ctatacttct   3240
tttttgttct acaaaaatgc atcccgagag cgctattttt ctaacaaagc atcttagatt   3300
actttttttc tcctttgtgc gctctataat gcagtctctt gataactttt tgcactgtag   3360
gtccgttaag gttagaagaa ggctactttg gtgtctattt tctcttccat aaaaaaagcc   3420
tgactccact tcccgcgttt actgattact agcgaagctg cgggtgcatt ttttcaagat   3480
aaaggcatcc ccgattatat tctataccga tgtggattgc gcatactttg tgaacagaaa   3540
gtgatagcgt tgatgattct tcattggtca gaaaattatg aacggtttct tctattttgt   3600
ctctatatac tacgtatagg aaatgtttac attttcgtat tgttttcgat tcactctatg   3660
aatagttctt actacaattt ttttgtctaa agagtaatac tagagataaa cataaaaaat   3720
gtagaggtcg agtttagatg caagttcaag gagcgaaagg tggatgggta ggttatatag   3780
ggatatagca cagagatata tagcaaagag atacttttga gcaatgtttg tggaagcggt   3840
attcgcaata ttttagtagc tcgttacagt ccggtgcgtt tttggttttt tgaaagtgcg   3900
tcttcagagc gcttttggtt ttcaaaagcg ctctgaagtt cctatacttt ctagagaata   3960
ggaacttcgg aataggaact tcaaagcgtt tccgaaaacg agcgcttccg aaaatgcaac   4020
gcgagctgcg cacatacagc tcactgttca cgtcgcacct atatctgcgt gttgcctgta   4080
tatatatata catgagaaga acggcatagt gcgtgtttat gcttaaatgc gtacttatat   4140
gcgtctattt atgtaggatg aaaggtagtc tagtacctcc tgtgatatta tcccattcca   4200
tgcggggtat cgtatgcttc cttcagcact accctttagc tgttctatat gctgccactc   4260
ctcaattgga ttagtctcat ccttcaatgc tatcatttcc tttgatattg gatcatatgc   4320
atagtaccga gaaactagtg cgaagtagtg atcaggtatt gctgttatct gatgagtata   4380
cgttgtcctg gccacggcag aagcacgctt atcgctccaa tttcccacaa cattagtcaa   4440
ctccgttagg cccttcattg aaagaaatga ggtcatcaaa tgtcttccaa tgtgagattt   4500
tgggccattt tttatagcaa agattgaata aggcgcattt ttcttcaaag ctttattgta   4560
cgatctgact aagttatctt ttaataattg gtattcctgt ttattgcttg aagaattgcc   4620
ggtcctattt actcgtttta ggactggttc agaattcatc gatgctcact caaaggcggt   4680
aatacggtta tccacagaat caggggataa cgcaggaaag aacatgtgag caaaaggcca   4740
gcaaaaggcc aggaaccgta aaaaggccgc gttgctggcg tttttccata ggctccgccc   4800
ccctgacgag catcacaaaa atcgacgctc aagtcagagg tggcgaaacc cgacaggact   4860
ataaagatac caggcgtttc cccctggaag ctccctcgtg cgctctcctg ttccgaccct   4920
gccgcttacc ggatacctgt ccgcctttct cccttcggga agcgtggcgc tttctcatag   4980
ctcacgctgt aggtatctca gttcggtgta ggtcgttcgc tccaagctgg gctgtgtgca   5040
cgaacccccc gttcagcccg accgctgcgc cttatccggt aactatcgtc ttgagtccaa   5100
cccggtaaga cacgacttat cgccactggc agcagccact ggtaacagga ttagcagagc   5160
gaggtatgta ggcggtgcta cagagttctt gaagtggtgg cctaactacg gctacactag   5220
aagaacagta tttggtatct gcgctctgct gaagccagtt accttcggaa aaagagttgg   5280
```

```
tagctcttga tccggcaaac aaaccaccgc tggtagcggt ggtttttttg tttgcaagca   5340
gcagattacg cgcagaaaaa aaggatctca agaagatcct ttgatctttt ctacggggtc   5400
tgacgctcag tggaacgaaa actcacgtta agggattttg gtcatgagat tatcaaaaag   5460
gatcttcacc tagatccttt taaattaaaa atgaagtttt aaatcaatct aaagtatata   5520
tgagtaaact tggtctgaca gttaccaatg cttaatcagt gaggcaccta tctcagcgat   5580
ctgtctattt cgttcatcca tagttgcctg actccccgtc gtgtagataa ctacgatacg   5640
ggagggctta ccatctggcc ccagtgctgc aatgataccg cgagacccac gctcaccggc   5700
tccagattta tcagcaataa accagccagc cggaagggcc gagcgcagaa gtggtcctgc   5760
aactttatcc gcctccatcc agtctattaa ttgttgccgg gaagctagag taagtagttc   5820
gccagttaat agtttgcgca acgttgttgc cattgctaca ggcatcgtgg tgtcacgctc   5880
gtcgtttggt atggcttcat tcagctccgg ttcccaacga tcaaggcgag ttacatgatc   5940
ccccatgttg tgcaaaaaag cggttagctc cttcggtcct ccgatcgttg tcagaagtaa   6000
gttggccgca gtgttatcac tcatggttat ggcagcactg cataattctc ttactgtcat   6060
gccatccgta agatgctttt ctgtgactgg tgagtactca accaagtcat tctgagaata   6120
gtgtatgcgg cgaccgagtt gctcttgccc ggcgtcaata cgggataata ccgcgccaca   6180
tagcagaact ttaaaagtgc tcatcattgg aaaacgttct tcggggcgaa aactctcaag   6240
gatcttaccg ctgttgagat ccagttcgat gtaacccact cgtgcaccca actgatcttc   6300
agcatctttt actttcacca gcgtttctgg gtgagcaaaa acaggaaggc aaaatgccgc   6360
aaaaaaggga ataagggcga cacggaaatg ttgaatactc atactcttcc tttttcaata   6420
ttattgaagc atttatcagg gttattgtct catgagcgga tacatatttg aatgtattta   6480
gaaaaataaa caaatagggg ttccgcgcac atttccccga aaagtgccac ctgacgtcta   6540
agaaaccatt attatcatga cattaaccta taaaaatagg cgtatcacga ggccctttcg   6600
tctcgcgcgt ttcggtgatg acggtgaaaa cctctgacac atgcagctcc cggagacggt   6660
cacagcttgt ctgtaagcgg atgccgggag cagacaagcc cgtcagggcg cgtcagcggg   6720
tgttggcggg tgtcggggct ggcttaacta tgcggcatca gagcagattg tactgagagt   6780
gcaccatatg cggtgtggaa taccgcacag atgcgtaagg agaaaatacc gcatcaggcg   6840
ccattcgcca ttcaggctgc gcaactgttg ggaagggcga tcggtgcggg cctcttcgct   6900
attacgccag ctggcgaaag ggggatgtgc tgcaaggcga ttaagttggg taacgccagg   6960
gttttcccag tcacgacgtt gtaaaacgac ggccagtgaa ttgcggccgc atcgatggaa   7020
aagaccaaac ggtgacgtta agagaaagaa attctatgag gcaagtaaga ggcactatta   7080
ctgatgtgat ttcgaccatt gacaaaatgc ttcacaaccc tgatgaatcg gactgggata   7140
aatcaacatt tggactgtcg cctgttaaga tataactgaa aaaagagggg aatttttaga   7200
tactgaaatg atattttaga ataaccagac tatatataag gataaattac aaaaaattaa   7260
ctaatagata agatttaaat ataaaagata tgcaactaga aaagtcttat caatctcctt   7320
attcaaaatg agaaaattgt tgtctcaaga ctcttctcat gatcttattt gtagcagttc   7380
ttggcaaaga tgacaatgga acaactctag taactttaaa caatgggttc aatttctttt   7440
gtaaacccaa attaaaagac aatctcaatt ggttcaaatc aattgtagta tcatttgaat   7500
ctttcaaaac aaagaaaata accaattgtt ctggaccacc acctaatggt ggaacaccaa   7560
tagctgtagt ttcaaaaact ctatcatcaa cttcgttaca aactctttcg atttcgatag   7620
```

-continued

```
atgagatttt aataccacca atattcattg tatcatcagc tctaccatgt gcatggtagt   7680
aaccgttaga agtcaattcg aagatgtcac catgtcttct caaaacttca ccattcaatg   7740
ttggcatacc cttgaagtaa acatcatgat ggttaccgtt caacaaagtc tttgaagcac   7800
cgaacataac tggacctaat gccaattcac caatacctgg cttattttta ggcattgggt   7860
aaccgttctt atccaagatg tacaatgtac aacccataca ttgagatgaa aaagatgaca   7920
aagattgagc ttgcaaaaat gaaccagctg aaaatgcacc accaatttca gtaccaccac   7980
acatttcaat aactggcttg tagttagctc tacccatcaa ccacaaatat tcatcaacgt   8040
tagatgcttc accagatgaa gagaaacatc tgattgtaga ccaatcgtaa cctgaaacac   8100
agttagtaga cttccatgat ctaacgattg atggaacaac acccaacatt gtaaccttag   8160
catcttgaac gaactttgcg aaaccagaaa ccaatggtga accgttgtac aaagcgatag   8220
atgcaccgtt caacaatgaa gcataaacca accatggacc catcatccaa cccaaattag   8280
ttggccaaac aataacgtca ccttttctaa tatccaaatg tgaccaacca tcagctgcag   8340
cttttaatgg tgtagcttga gtccatggaa ttgcttttgg ttcacctgta gtacctgaag   8400
aaaacaagat gtttgtgtaa gcatcaactg gttgttctct tgcagtgaat tcacagtttt   8460
tgaattcctt agctctttcc aaaaagtaat cccatgaaat gtcaccatct cttaattctg   8520
caccaatgtt agaacctgaa catgggataa cgatagccat tggagacttt gcttcaacaa   8580
ctcttgagta caatggaatt ctctttttac ctctaatgat atgatcttgt gtaaaaatag   8640
cctttgcctt agacaatctc aatctagttg agatttctgg agcagaaaat gaatctgcaa   8700
tagaaacaac aacgtaacca gccaaaacga ttgccaaata tataacaaca gcatcaacat   8760
gcattggcat atcaatagca attgcacaac ctttttccaa acccatttct tctaatgcgt   8820
aaccaaccaa ccaaactctt tttctcaatt gatccaatgt caacttattc aatggcaaat   8880
catcgttacc ctcatctctc caaacgatca tagtatcgtt caatttctta ttagagttaa   8940
cgttcaaaca atttttagct gaattcaaat aaccacctgg caaccattca gaaccacctg   9000
gattgttgat atcatctctt ctcaagatac attctggatc tttagaaaat gagatcttca   9060
tttcatccat caaaactgtt ctccagtaaa cttctgggtt tctaacagaa aattcttgaa   9120
aatgtgaaaa tgaagagatt ggatctttgt acttaacacc caagaattct ttacctctct   9180
tttccaacaa agcacccaaa ttagtagact taaccttttc tggatctgga atccaagctg   9240
gtggtgctgg accgaaatcc ttgtaacaac cataaaacaa catttgatgc aaagaaaatg   9300
gcaaatctgg tgacaagata tggtttgcga tgttgatcca tgtttgtgga gttgcagcac   9360
cgtagttaca aacgatttca gccaatctac catgcaatgt ttctgcaact tcagaagtaa   9420
tacccaaagc aatgaaatct gatgcaacaa cagaatccaa tgacttgtaa tttttaccca   9480
tttatattga attttcaaaa attcttactt tttttttgga tggacgcaaa gaagtttaat   9540
aatcatatta catggcatta ccaccatata catatccata tctaatctta cttatatgtt   9600
gtggaaatgt aaagagcccc attatcttag cctaaaaaaa ccttctcttt ggaactttca   9660
gtaatacgct taactgctca ttgctatatt gaagtacgga ttagaagccg ccgagcgggc   9720
gacagccctc cgacggaaga ctctcctccg tgcgtcctcg tcttcaccgg tcgcgttcct   9780
gaaacgcaga tgtgcctcgc gccgcactgc tccgaacaat aaagattcta caatactagc   9840
ttttatggtt atgaagagga aaaattggca gtaacctggc cccacaaacc ttcaaattaa   9900
cgaatcaaat taacaaccat aggatgataa tgcgattagt tttttagcct tatttctggg   9960
gtaattaatc agcgaagcga tgatttttga tctattaaca gatatataaa tggaaaagct  10020
```

```
gcataaccac tttaactaat actttcaaca ttttcagttt gtattacttc ttattcaaat  10080

gtcataaaag tatcaacaaa aaattgttaa tatacctcta tactttaacg tcaaggagaa  10140

aaaactataa tgggtttatc tttggtctgt actttttcat ttcaaactaa ttaccataca  10200

ttgttaaatc cacataataa gaaccctaaa aattctttgt tgtcatatca acatccaaaa  10260

actccaatta ttaaatcttc ttatgataat tttccatcta agtactgttt gactaaaaat  10320

ttccatttgt taggtttaaa ttctcataat agaatttctt cacaatcaag atcaattaga  10380

gctggttctg atcaaattga aggttcacca catcatgaat ctgataactc aatcgcaact  10440

aaaatttga actttggtca tacatgttgg aaattgcaaa gaccatacgt tgttaagggt  10500

atgatttcta ttgcttgtgg tttatttggt agagaattgt ttaataacag acatttgttt  10560

tcttggggtt tgatgtggaa agcatttttc gcattagttc caatcttgtc ttttaatttc  10620

tttgctgcaa tcatgaacca aatatatgat gttgatattg atagaattaa taagccagat  10680

ttgccattgg tttctggtga aatgtcaatc gaaactgctt ggattttatc tatcatcgtt  10740

gcattgactg gtttgatcgt tacaattaaa ttaaaatcag ctccattgtt cgtttttata  10800

tatatcttcg gtatcttcgc tggttttgca tactctgttc caccaattag atggaagcaa  10860

taccctttta ctaatttctt gatcacaatt tcttcacatg ttggtttggc ttttacttct  10920

tactcagcta ctacatctgc attaggtttg ccatttgttt ggaggccagc tttttctttt  10980

attatcgctt ttatgactgt tatgggtatg acaatcgctt tcgcaaagga tatctctgat  11040

attgaaggtg acgctaaata cggtgtttca actgttgcta caaaattggg tgcaagaaac  11100

atgactttcg ttgtttctgg tgttttgttg ttgaactatt tggtttctat ctcaatcggt  11160

attatttggc cacaagtttt taaatctaac atcatgatct tgtcacatgc tatcttggca  11220

ttctgtttga tcttccaaac aagagaatta gctttggcaa attatgcttc tgcaccatca  11280

agacaatttt tcgagtttat ttggttgttg tactacgctg aatattttgt ttacgttttt  11340

atttga                                                            11346
```

```
<210> SEQ ID NO 5
<211> LENGTH: 385
<212> TYPE: PRT
<213> ORGANISM: Cannabis sativa

<400> SEQUENCE: 5

Met Asn His Leu Arg Ala Glu Gly Pro Ala Ser Val Leu Ala Ile Gly
1               5                   10                  15

Thr Ala Asn Pro Glu Asn Ile Leu Ile Gln Asp Glu Phe Pro Asp Tyr
            20                  25                  30

Tyr Phe Arg Val Thr Lys Ser Glu His Met Thr Gln Leu Lys Glu Lys
        35                  40                  45

Phe Arg Lys Ile Cys Asp Lys Ser Met Ile Arg Lys Arg Asn Cys Phe
    50                  55                  60

Leu Asn Glu Glu His Leu Lys Gln Asn Pro Arg Leu Val Glu His Glu
65                  70                  75                  80

Met Gln Thr Leu Asp Ala Arg Gln Asp Met Leu Val Val Glu Val Pro
                85                  90                  95

Lys Leu Gly Lys Asp Ala Cys Ala Lys Ala Ile Lys Glu Trp Gly Gln
            100                 105                 110

Pro Lys Ser Lys Ile Thr His Leu Ile Phe Thr Ser Ala Ser Thr Thr
        115                 120                 125
```

```
Asp Met Pro Gly Ala Asp Tyr His Cys Ala Lys Leu Leu Gly Leu Ser
    130                 135                 140

Pro Ser Val Lys Arg Val Met Met Tyr Gln Leu Gly Cys Tyr Gly Gly
145                 150                 155                 160

Gly Thr Val Leu Arg Ile Ala Lys Asp Ile Ala Glu Asn Asn Lys Gly
                165                 170                 175

Ala Arg Val Leu Ala Val Cys Cys Asp Ile Met Ala Cys Leu Phe Arg
            180                 185                 190

Gly Pro Ser Asp Ser Asp Leu Glu Leu Leu Val Gly Gln Ala Ile Phe
        195                 200                 205

Gly Asp Gly Ala Ala Ala Val Ile Val Gly Ala Glu Pro Asp Glu Ser
    210                 215                 220

Val Gly Glu Arg Pro Ile Phe Glu Leu Val Ser Thr Gly Gln Thr Ile
225                 230                 235                 240

Leu Pro Asn Ser Glu Gly Thr Ile Gly Gly His Ile Arg Glu Ala Gly
                245                 250                 255

Leu Ile Phe Asp Leu His Lys Asp Val Pro Met Leu Ile Ser Asn Asn
            260                 265                 270

Ile Glu Lys Cys Leu Ile Glu Ala Phe Thr Pro Ile Gly Ile Ser Asp
        275                 280                 285

Trp Asn Ser Ile Phe Trp Ile Thr His Pro Gly Gly Lys Ala Ile Leu
    290                 295                 300

Asp Lys Val Glu Glu Lys Leu Asp Leu Lys Lys Glu Lys Phe Val Asp
305                 310                 315                 320

Ser Arg His Val Leu Ser Glu His Gly Asn Met Ser Ser Ser Thr Val
                325                 330                 335

Leu Phe Val Met Asp Glu Leu Arg Lys Arg Ser Leu Glu Glu Gly Lys
            340                 345                 350

Ser Thr Thr Gly Asp Gly Phe Glu Trp Gly Val Leu Phe Gly Phe Gly
        355                 360                 365

Pro Gly Leu Thr Val Glu Arg Val Val Val Arg Ser Val Pro Ile Lys
    370                 375                 380

Tyr
385
```

<210> SEQ ID NO 6
<211> LENGTH: 1155
<212> TYPE: DNA
<213> ORGANISM: Cannabis sativa

<400> SEQUENCE: 6

```
atgaatcatt tgagagctga aggtccagca tcagttttgg ctattggtac tgcaaaccca      60

gaaaacatct tgatccaaga tgaatttcca gattattact tcagagttac taagtcagaa     120

catatgacac aattgaagga aaagtttaga aagatctgtg ataagtctat gattagaaaa     180

agaaattgtt tcttgaacga agaacatttg aagcaaaacc caagattagt tgaacatgaa     240

atgcaaacat tggatgctag acaagatatg ttggttgttg aagttccaaa gttgggtaaa     300

gatgcatgtg ctaaagcaat taaagaatgg ggtcaaccaa agtctaagat cactcatttg     360

atttttacat cagcatctac tacagatatg ccaggtgctg attaccattg tgcaaagttg     420

ttgggtttgt caccatctgt taagagagtt atgatgtacc aattaggttg ttacggtggt     480

ggtactgttt tgagaatcgc taaggatatc gcagaaaaca ataagggtgc tagagtcttg     540

gcagtttgtt gtgatatcat ggcttgtttg tttagaggtc catcagattc tgatttggaa     600
```

```
ttgttagttg gtcaagctat ttttggtgac ggtgctgcag ctgttattgt tggtgcagaa    660

ccagatgaat cagttggtga aagaccaatc ttcgaattag tttcaactgg tcaaacaatt    720

ttgccaaatt ctgaaggtac aattggtggt catatcagag aagctggttt gatcttcgat    780

ttgcataaag atgttccaat gttgatctct aacaacatcg aaaagtgttt gatcgaagct    840

tttactccaa tcggtatctc agattggaac tctattttct ggattacaca tccaggtggt    900

aaagcaatct tggataaggt tgaagaaaaa ttggatttga agaaagaaaa atttgttgat    960

tcaagacatg ttttgtctga acatggtaac atgtcttcat ctactgtttt gttcgttatg   1020

gatgaattga gaaagagatc attagaagag ggtaaatcta ctacaggtga cggttttgaa   1080

tggggtgttt tatttggttt tggtccaggt ttgacagttg aaagagttgt tgttagatct   1140

gttccaatta aatac                                                    1155


<210> SEQ ID NO 7
<211> LENGTH: 104
<212> TYPE: PRT
<213> ORGANISM: Cannabis sativa

<400> SEQUENCE: 7

Met Ala Val Lys His Leu Ile Val Leu Lys Phe Lys Asp Glu Ile Thr
1               5                   10                  15

Glu Ala Gln Lys Glu Glu Phe Phe Lys Thr Tyr Val Asn Leu Val Asn
            20                  25                  30

Ile Ile Pro Ala Met Lys Asp Val Tyr Trp Gly Lys Asp Val Thr Gln
        35                  40                  45

Lys Lys Glu Glu Gly Tyr Thr His Ile Val Glu Val Thr Phe Glu Ser
    50                  55                  60

Val Glu Thr Ile Gln Asp Tyr Ile Ile His Pro Ala His Val Gly Phe
65                  70                  75                  80

Gly Asp Val Tyr Arg Ser Phe Trp Glu Lys Leu Leu Ile Phe Asp Tyr
                85                  90                  95

Thr Pro Arg Lys Leu Lys Pro Lys
            100


<210> SEQ ID NO 8
<211> LENGTH: 312
<212> TYPE: DNA
<213> ORGANISM: Cannabis sativa

<400> SEQUENCE: 8

atggctgtta agcatttgat cgttttgaag tttaaagatg aaattacaga agcacaaaaa     60

gaagaatttt tcaagactta cgttaatttg gttaacatca tcccagctat gaaggatgtt    120

tattggggta aagatgttac acaaaagaaa gaagaaggtt acactcatat cgttgaagtt    180

acattcgaat ctgttgaaac tatccaagat tacattattc atccagcaca tgttggtttt    240

ggtgacgttt acagatcatt ctgggaaaag ttgttaattt ttgattacac tccaagaaaa    300

ttaaaaccaa aa                                                        312


<210> SEQ ID NO 9
<211> LENGTH: 555
<212> TYPE: PRT
<213> ORGANISM: Cannabis sativa

<400> SEQUENCE: 9

Met Asn Cys Ser Ala Phe Ser Phe Trp Phe Val Cys Lys Ile Ile Phe
1               5                   10                  15
```

```
Phe Phe Leu Ser Phe Asn Ile Gln Ile Ser Ile Ala Asn Pro Gln Glu
            20                  25                  30

Asn Phe Leu Lys Cys Phe Ser Glu Tyr Ile Pro Asn Asn Pro Ala Asn
        35                  40                  45

Pro Lys Phe Ile Tyr Thr Gln His Asp Gln Leu Tyr Met Ser Val Leu
    50                  55                  60

Asn Ser Thr Ile Gln Asn Leu Arg Phe Thr Ser Asp Thr Thr Pro Lys
65                  70                  75                  80

Pro Leu Val Ile Val Thr Pro Ser Asn Val Ser His Ile Gln Ala Ser
                85                  90                  95

Ile Leu Cys Ser Lys Lys Val Gly Leu Gln Ile Arg Thr Arg Ser Gly
            100                 105                 110

Gly His Asp Ala Glu Gly Met Ser Tyr Ile Ser Gln Val Pro Phe Val
        115                 120                 125

Val Val Asp Leu Arg Asn Met His Ser Ile Lys Ile Asp Val His Ser
    130                 135                 140

Gln Thr Ala Trp Val Glu Ala Gly Ala Thr Leu Gly Glu Val Tyr Tyr
145                 150                 155                 160

Trp Ile Asn Glu Lys Asn Glu Asn Phe Ser Phe Pro Gly Gly Tyr Cys
                165                 170                 175

Pro Thr Val Gly Val Gly Gly His Phe Ser Gly Gly Gly Tyr Gly Ala
            180                 185                 190

Leu Met Arg Asn Tyr Gly Leu Ala Ala Asp Asn Ile Ile Asp Ala His
        195                 200                 205

Leu Val Asn Val Asp Gly Lys Val Leu Asp Arg Lys Ser Met Gly Glu
    210                 215                 220

Asp Leu Phe Trp Ala Ile Arg Gly Gly Gly Gly Glu Asn Phe Gly Ile
225                 230                 235                 240

Ile Ala Ala Trp Lys Ile Lys Leu Val Ala Val Pro Ser Lys Ser Thr
                245                 250                 255

Ile Phe Ser Val Lys Lys Asn Met Glu Ile His Gly Leu Val Lys Leu
            260                 265                 270

Phe Asn Lys Trp Gln Asn Ile Ala Tyr Lys Tyr Asp Lys Asp Leu Val
        275                 280                 285

Leu Met Thr His Phe Ile Thr Lys Asn Ile Thr Asp Asn His Gly Lys
    290                 295                 300

Asn Lys Thr Thr Val His Gly Tyr Phe Ser Ser Ile Phe His Gly Gly
305                 310                 315                 320

Val Asp Ser Leu Val Asp Leu Met Asn Lys Ser Phe Pro Glu Leu Gly
                325                 330                 335

Ile Lys Lys Thr Asp Cys Lys Glu Phe Ser Trp Ile Asp Thr Thr Ile
            340                 345                 350

Phe Tyr Ser Gly Val Val Asn Phe Asn Thr Ala Asn Phe Lys Lys Glu
        355                 360                 365

Ile Leu Leu Asp Arg Ser Ala Gly Lys Lys Thr Ala Phe Ser Ile Lys
    370                 375                 380

Leu Asp Tyr Val Lys Lys Pro Ile Pro Glu Thr Ala Met Val Lys Ile
385                 390                 395                 400

Leu Glu Lys Leu Tyr Glu Glu Asp Val Gly Val Gly Met Tyr Val Leu
                405                 410                 415

Tyr Pro Tyr Gly Gly Ile Met Glu Glu Ile Ser Glu Ser Ala Ile Pro
            420                 425                 430
```

```
Phe Pro His Arg Ala Gly Ile Met Tyr Glu Leu Trp Tyr Thr Ala Ser
        435                 440                 445

Trp Glu Lys Gln Glu Asp Asn Glu Lys His Ile Asn Trp Val Arg Ser
    450                 455                 460

Val Tyr Asn Phe Thr Thr Pro Tyr Val Ser Gln Asn Pro Arg Leu Ala
465                 470                 475                 480

Tyr Leu Asn Tyr Arg Asp Leu Asp Leu Gly Lys Thr Asn Pro Glu Ser
                485                 490                 495

Pro Asn Asn Tyr Thr Gln Ala Arg Ile Trp Gly Glu Lys Tyr Phe Gly
            500                 505                 510

Lys Asn Phe Asn Arg Leu Val Lys Val Lys Thr Lys Ala Asp Pro Asn
        515                 520                 525

Asn Phe Phe Arg Asn Glu Gln Ser Ile Pro Pro Leu Pro Pro His His
    530                 535                 540

His Glu Gln Lys Leu Ile Ser Glu Glu Asp Leu
545                 550                 555


<210> SEQ ID NO 10
<211> LENGTH: 1665
<212> TYPE: DNA
<213> ORGANISM: Cannabis sativa

<400> SEQUENCE: 10

atgaactgct ccgcattctc tttctggttc gtctgtaaaa taatcttctt cttcttgtcc      60

ttcaacatcc aaatctccat cgcaaatcca caagaaaact tttgaagtg tttctccgaa     120

tacatcccaa acaaccctgc taacccaaag tttatatata ctcaacatga tcaattgtac     180

atgtccgttt tgaacagtac catccaaaat ttgagattca cttctgacac tacaccaaaa     240

cctttagtca ttgttacacc ttccaatgtt agtcacattc aagcttctat attgtgctct     300

aagaaagtag gtttgcaaat cagaactaga tcaggtggtc atgatgcaga aggcatgtct     360

tacatctcac aagttccatt cgttgtagtc gatttgagaa atatgcattc cataaagatc     420

gacgttcaca gtcaaacagc atgggtagaa gcaggtgcca ccttgggtga agtttactac     480

tggatcaacg aaaagaatga aaacttttct ttccctggtg gttactgtcc aacagtaggt     540

gtcggtggtc acttttctgg tggtggttat ggtgcattga tgagaaacta cggtttagct     600

gcagataata ttatagacgc ccatttggtt aacgtagatg gtaaagtttt ggacagaaag     660

tctatgggtg aagatttgtt ttgggccata agaggtggtg gtggtgaaaa tttcggtatc     720

attgccgctt ggaaaattaa gttagtcgct gttccttcca aagtactat tttctctgtc     780

aaaaagaaca tggaaatcca cggtttggtt aagttgttta ataagtggca aaacatcgct     840

tacaagtacg ataaggactt ggttttgatg acccatttca tcactaaaaa tattacagat     900

aaccatggta aaaataagac cactgttcac ggttattttt cttcaatttt ccatggtggt     960

gtagattctt tggttgattt gatgaataag tcattcccag aattgggtat taaaaagaca    1020

gattgcaagg aattttcttg gatagacaca accatcttct attcaggtgt tgtaaacttc    1080

aacaccgcta acttcaaaaa ggaaatcttg ttggatagat ccgctggtaa aaagaccgct    1140

ttttctatta aattggacta cgttaagaaa ccaatccctg aaactgcaat ggtcaagata    1200

ttggaaaagt tgtacgaaga agatgtaggt gtcggcatgt acgttttgta tccatacggt    1260

ggtattatgg aagaaatatc tgaatcagcc ataccatttc ctcacagagc tggtatcatg    1320

tatgaattat ggtacacagc ctcatgggaa aagcaagaag ataacgaaaa gcatatcaac    1380

tgggtcagat ccgtttacaa cttcactaca ccttacgtta gtcaaaaccc aagattggca    1440
```

```
tatttgaact acagagattt ggacttaggt aaaactaacc ctgaatctcc aaataactat   1500

acacaagcaa gaatttgggg tgaaaagtac tttggtaaaa atttcaacag attagttaaa   1560

gtaaagacta aagccgaccc taacaacttt ttcagaaacg aacaatccat cccacctttg   1620

ccacctcacc accacgaaca aaaattaata agtgaagaag atttg                   1665
```

<210> SEQ ID NO 11
<211> LENGTH: 554
<212> TYPE: PRT
<213> ORGANISM: Cannabis sativa

<400> SEQUENCE: 11

```
Met Lys Cys Ser Thr Phe Ser Phe Trp Phe Val Cys Lys Ile Ile Phe
1               5                   10                  15

Phe Phe Phe Ser Phe Asn Ile Gln Thr Ser Ile Ala Asn Pro Arg Glu
            20                  25                  30

Asn Phe Leu Lys Cys Phe Ser Gln Tyr Ile Pro Asn Asn Ala Thr Asn
        35                  40                  45

Leu Lys Leu Val Tyr Thr Gln Asn Asn Pro Leu Tyr Met Ser Val Leu
    50                  55                  60

Asn Ser Thr Ile His Asn Leu Arg Phe Thr Ser Asp Thr Thr Pro Lys
65                  70                  75                  80

Pro Leu Val Ile Val Thr Pro Ser His Val Ser His Ile Gln Gly Thr
                85                  90                  95

Ile Leu Cys Ser Lys Lys Val Gly Leu Gln Ile Arg Thr Arg Ser Gly
            100                 105                 110

Gly His Asp Ser Glu Gly Met Ser Tyr Ile Ser Gln Val Pro Phe Val
        115                 120                 125

Ile Val Asp Leu Arg Asn Met Arg Ser Ile Lys Ile Asp Val His Ser
    130                 135                 140

Gln Thr Ala Trp Val Glu Ala Gly Ala Thr Leu Gly Glu Val Tyr Tyr
145                 150                 155                 160

Trp Val Asn Glu Lys Asn Glu Asn Leu Ser Leu Ala Ala Gly Tyr Cys
                165                 170                 175

Pro Thr Val Cys Ala Gly Gly His Phe Gly Gly Gly Gly Tyr Gly Pro
            180                 185                 190

Leu Met Arg Asn Tyr Gly Leu Ala Ala Asp Asn Ile Ile Asp Ala His
        195                 200                 205

Leu Val Asn Val His Gly Lys Val Leu Asp Arg Lys Ser Met Gly Glu
    210                 215                 220

Asp Leu Phe Trp Ala Leu Arg Gly Gly Gly Ala Glu Ser Phe Gly Ile
225                 230                 235                 240

Ile Val Ala Trp Lys Ile Arg Leu Val Ala Val Pro Lys Ser Thr Met
                245                 250                 255

Phe Ser Val Lys Lys Ile Met Glu Ile His Glu Leu Val Lys Leu Val
            260                 265                 270

Asn Lys Trp Gln Asn Ile Ala Tyr Lys Tyr Asp Lys Asp Leu Leu Leu
        275                 280                 285

Met Thr His Phe Ile Thr Arg Asn Ile Thr Asp Asn Gln Gly Lys Asn
    290                 295                 300

Lys Thr Ala Ile His Thr Tyr Phe Ser Ser Val Phe Leu Gly Gly Val
305                 310                 315                 320

Asp Ser Leu Val Asp Leu Met Asn Lys Ser Phe Pro Glu Leu Gly Ile
                325                 330                 335
```

```
Lys Lys Thr Asp Cys Arg Gln Leu Ser Trp Ile Asp Thr Ile Ile Phe
            340                 345                 350

Tyr Ser Gly Val Val Asn Tyr Asp Thr Asp Asn Phe Asn Lys Glu Ile
        355                 360                 365

Leu Leu Asp Arg Ser Ala Gly Gln Asn Gly Ala Phe Lys Ile Lys Leu
    370                 375                 380

Asp Tyr Val Lys Lys Pro Ile Pro Glu Ser Val Phe Val Gln Ile Leu
385                 390                 395                 400

Glu Lys Leu Tyr Glu Glu Asp Ile Gly Ala Gly Met Tyr Ala Leu Tyr
                405                 410                 415

Pro Tyr Gly Gly Ile Met Asp Glu Ile Ser Glu Ser Ala Ile Pro Phe
            420                 425                 430

Pro His Arg Ala Gly Ile Leu Tyr Glu Leu Trp Tyr Ile Cys Ser Trp
        435                 440                 445

Glu Lys Gln Glu Asp Asn Glu Lys His Leu Asn Trp Ile Arg Asn Ile
    450                 455                 460

Tyr Asn Phe Met Thr Pro Tyr Val Ser Lys Asn Pro Arg Leu Ala Tyr
465                 470                 475                 480

Leu Asn Tyr Arg Asp Leu Asp Ile Gly Ile Asn Asp Pro Lys Asn Pro
                485                 490                 495

Asn Asn Tyr Thr Gln Ala Arg Ile Trp Gly Glu Lys Tyr Phe Gly Lys
            500                 505                 510

Asn Phe Asp Arg Leu Val Lys Val Lys Thr Leu Val Asp Pro Asn Asn
        515                 520                 525

Phe Phe Arg Asn Glu Gln Ser Ile Pro Pro Leu Pro Arg His Arg His
    530                 535                 540

Glu Gln Lys Leu Ile Ser Glu Glu Asp Leu
545                 550
```

<210> SEQ ID NO 12
<211> LENGTH: 1662
<212> TYPE: DNA
<213> ORGANISM: Cannabis sativa

<400> SEQUENCE: 12

```
atgaaatgtt caactttctc cttttggttc gtatgcaaga tcatcttctt tttcttttcc      60

tttaacatcc aaacaagtat cgcaaaccca agagaaaact tttgaagtg cttctcacaa      120

tacataccta ataacgccac caatttgaag ttggtttaca ctcaaaacaa cccattgtac      180

atgtccgtct tgaacagtac aatccataat ttgagattca cttctgatac cactccaaaa      240

cctttggtca ttgtaacccc tagtcatgta tctcacatcc aaggtactat cttatgttct      300

aaaaaggttg gtttgcaaat tagaactaga tccggtggtc atgatagtga aggcatgtca      360

tacatctccc aagttccatt cgttatcgtt gatttgagaa acatgagatc aattaaaata      420

gacgtacact cacaaactgc ttgggttgaa gctggtgcaa cattgggtga agtatactac      480

tgggttaacg aaaagaatga aaacttatca ttggctgctg gttactgtcc aacagtttgc      540

gcaggtggtc attttggtgg tggtggttat ggtcctttaa tgagaaacta cggtttggcc      600

gctgataaca taatcgacgc tcatttggta aatgttcacg gtaaagtttt ggatagaaag      660

tctatgggtg aagacttatt ttgggctttg agaggtggtg gtgcagaatc attcggtatc      720

atagttgctt ggaagataag attagtcgca gtaccaaagt ctactatgtt ctcagtcaaa      780

aagataatgg aaatccatga attagttaaa ttggtcaata agtggcaaaa catcgcatac      840
```

```
aagtacgata aggacttgtt gttgatgact catttcatca caagaaacat caccgataac    900

caaggtaaaa ataagactgc tatccacaca tacttttctt cagttttctt gggtggtgtc    960

gattccttag tagacttgat gaataagtct tttccagaat taggtattaa gaaaactgat   1020

tgtagacaat tgtcttggat cgacaccatc atcttttatt caggtgttgt caactacgat   1080

acagacaact tcaacaaaga aatattattg gatagatccg caggtcaaaa cggtgccttt   1140

aaaattaagt tagactacgt taaaaagcca atacctgaat cagttttcgt ccaaatctta   1200

gaaaaattgt acgaagaaga tattggtgca ggcatgtacg ccttgtatcc atacggtggt   1260

ataatggacg aaatcagtga atctgccatt ccatttcctc atagagctgg tatcttatac   1320

gaattgtggt acatttgttc atgggaaaag caagaagata acgaaaagca cttaaactgg   1380

attagaaaca tctataactt catgactcca tacgtttcta aaaaccctag attggcatat   1440

ttgaactaca gagatttgga catcggtatt aacgatccaa agaatcctaa caactatacc   1500

caagctagaa tttggggtga aaaatacttc ggtaaaaatt tcgatagatt agtaaaggtt   1560

aagacattgg ttgacccaaa caacttcttt agaaacgaac aatccattcc acctttacct   1620

agacatagac acgaacaaaa attaataagt gaagaagatt tg                      1662
```

```
<210> SEQ ID NO 13
<211> LENGTH: 720
<212> TYPE: PRT
<213> ORGANISM: Cannabis sativa

<400> SEQUENCE: 13

Met Gly Lys Asn Tyr Lys Ser Leu Asp Ser Val Val Ala Ser Asp Phe
1               5                   10                  15

Ile Ala Leu Gly Ile Thr Ser Glu Val Ala Glu Thr Leu His Gly Arg
            20                  25                  30

Leu Ala Glu Ile Val Cys Asn Tyr Gly Ala Ala Thr Pro Gln Thr Trp
        35                  40                  45

Ile Asn Ile Ala Asn His Ile Leu Ser Pro Asp Leu Pro Phe Ser Leu
    50                  55                  60

His Gln Met Leu Phe Tyr Gly Cys Tyr Lys Asp Phe Gly Pro Ala Pro
65                  70                  75                  80

Pro Ala Trp Ile Pro Asp Pro Glu Lys Val Lys Ser Thr Asn Leu Gly
                85                  90                  95

Ala Leu Leu Glu Lys Arg Gly Lys Glu Phe Leu Gly Val Lys Tyr Lys
            100                 105                 110

Asp Pro Ile Ser Ser Phe Ser His Phe Gln Glu Phe Ser Val Arg Asn
        115                 120                 125

Pro Glu Val Tyr Trp Arg Thr Val Leu Met Asp Glu Met Lys Ile Ser
    130                 135                 140

Phe Ser Lys Asp Pro Glu Cys Ile Leu Arg Arg Asp Asp Ile Asn Asn
145                 150                 155                 160

Pro Gly Gly Ser Glu Trp Leu Pro Gly Gly Tyr Leu Asn Ser Ala Lys
                165                 170                 175

Asn Cys Leu Asn Val Asn Ser Asn Lys Lys Leu Asn Asp Thr Met Ile
            180                 185                 190

Val Trp Arg Asp Glu Gly Asn Asp Asp Leu Pro Leu Asn Lys Leu Thr
        195                 200                 205

Leu Asp Gln Leu Arg Lys Arg Val Trp Leu Val Gly Tyr Ala Leu Glu
    210                 215                 220

Glu Met Gly Leu Glu Lys Gly Cys Ala Ile Ala Ile Asp Met Pro Met
```

```
225                 230                 235                 240

His Val Asp Ala Val Val Ile Tyr Leu Ala Ile Val Leu Ala Gly Tyr
                245                 250                 255

Val Val Val Ser Ile Ala Asp Ser Phe Ser Ala Pro Glu Ile Ser Thr
            260                 265                 270

Arg Leu Arg Leu Ser Lys Ala Lys Ala Ile Phe Thr Gln Asp His Ile
        275                 280                 285

Ile Arg Gly Lys Lys Arg Ile Pro Leu Tyr Ser Arg Val Val Glu Ala
    290                 295                 300

Lys Ser Pro Met Ala Ile Val Ile Pro Cys Ser Gly Ser Asn Ile Gly
305                 310                 315                 320

Ala Glu Leu Arg Asp Gly Asp Ile Ser Trp Asp Tyr Phe Leu Glu Arg
                325                 330                 335

Ala Lys Glu Phe Lys Asn Cys Glu Phe Thr Ala Arg Glu Gln Pro Val
            340                 345                 350

Asp Ala Tyr Thr Asn Ile Leu Phe Ser Ser Gly Thr Thr Gly Glu Pro
        355                 360                 365

Lys Ala Ile Pro Trp Thr Gln Ala Thr Pro Leu Lys Ala Ala Ala Asp
    370                 375                 380

Gly Trp Ser His Leu Asp Ile Arg Lys Gly Asp Val Ile Val Trp Pro
385                 390                 395                 400

Thr Asn Leu Gly Trp Met Met Gly Pro Trp Leu Val Tyr Ala Ser Leu
                405                 410                 415

Leu Asn Gly Ala Ser Ile Ala Leu Tyr Asn Gly Ser Pro Leu Val Ser
            420                 425                 430

Gly Phe Ala Lys Phe Val Gln Asp Ala Lys Val Thr Met Leu Gly Val
        435                 440                 445

Val Pro Ser Ile Val Arg Ser Trp Lys Ser Thr Asn Cys Val Ser Gly
    450                 455                 460

Tyr Asp Trp Ser Thr Ile Arg Cys Phe Ser Ser Ser Gly Glu Ala Ser
465                 470                 475                 480

Asn Val Asp Glu Tyr Leu Trp Leu Met Gly Arg Ala Asn Tyr Lys Pro
                485                 490                 495

Val Ile Glu Met Cys Gly Gly Thr Glu Ile Gly Gly Ala Phe Ser Ala
            500                 505                 510

Gly Ser Phe Leu Gln Ala Gln Ser Leu Ser Ser Phe Ser Ser Gln Cys
        515                 520                 525

Met Gly Cys Thr Leu Tyr Ile Leu Asp Lys Asn Gly Tyr Pro Met Pro
    530                 535                 540

Lys Asn Lys Pro Gly Ile Gly Glu Leu Ala Leu Gly Pro Val Met Phe
545                 550                 555                 560

Gly Ala Ser Lys Thr Leu Leu Asn Gly Asn His His Asp Val Tyr Phe
                565                 570                 575

Lys Gly Met Pro Thr Leu Asn Gly Glu Val Leu Arg Arg His Gly Asp
            580                 585                 590

Ile Phe Glu Leu Thr Ser Asn Gly Tyr Tyr His Ala His Gly Arg Ala
        595                 600                 605

Asp Asp Thr Met Asn Ile Gly Gly Ile Lys Ile Ser Ser Ile Glu Ile
    610                 615                 620

Glu Arg Val Cys Asn Glu Val Asp Asp Arg Val Phe Glu Thr Thr Ala
625                 630                 635                 640

Ile Gly Val Pro Pro Leu Gly Gly Gly Pro Glu Gln Leu Val Ile Phe
                645                 650                 655
```

```
Phe Val Leu Lys Asp Ser Asn Asp Thr Thr Ile Asp Leu Asn Gln Leu
            660                 665                 670

Arg Leu Ser Phe Asn Leu Gly Leu Gln Lys Lys Leu Asn Pro Leu Phe
        675                 680                 685

Lys Val Thr Arg Val Val Pro Leu Ser Ser Leu Pro Arg Thr Ala Thr
    690                 695                 700

Asn Lys Ile Met Arg Arg Val Leu Arg Gln Gln Phe Ser His Phe Glu
705                 710                 715                 720


<210> SEQ ID NO 14
<211> LENGTH: 2160
<212> TYPE: DNA
<213> ORGANISM: Cannabis sativa

<400> SEQUENCE: 14

atgggtaaaa attacaagtc attggattct gttgttgcat cagatttcat tgctttgggt     60

attacttctg aagttgcaga aacattgcat ggtagattgg ctgaaatcgt ttgtaactac    120

ggtgctgcaa ctccacaaac atggatcaac atcgcaaacc atatcttgtc accagatttg    180

ccatttttctt tgcatcaaat gttgttttat ggttgttaca aggatttcgg tccagcacca    240

ccagcttgga ttccagatcc agaaaaggtt aagtctacta atttgggtgc tttgttggaa    300

aagagaggta aagaattctt gggtgttaag tacaaagatc caatctcttc attttcacat    360

tttcaagaat tttctgttag aaacccagaa gtttactgga gaacagtttt gatggatgaa    420

atgaagatct cattttctaa agatccagaa tgtatcttga gaagagatga tatcaacaat    480

ccaggtggtt ctgaatggtt gccaggtggt tatttgaatt cagctaaaaa ttgtttgaac    540

gttaactcta ataagaaatt gaacgatact atgatcgttt ggagagatga gggtaacgat    600

gatttgccat tgaataagtt gacattggat caattgagaa aaagagtttg gttggttggt    660

tacgcattag aagaaatggg tttggaaaaa ggttgtgcaa ttgctattga tatgccaatg    720

catgttgatg ctgttgttat atatttggca atcgttttgg ctggttacgt tgttgtttct    780

attgcagatt cattttctgc tccagaaatc tcaactagat tgagattgtc taaggcaaag    840

gctattttta cacaagatca tatcattaga ggtaaaaaga gaattccatt gtactcaaga    900

gttgttgaag caaagtctcc aatggctatc gttatcccat gttcaggttc taacattggt    960

gcagaattaa gagatggtga catttcatgg gattactttt tggaaagagc taaggaattc   1020

aaaaactgtg aattcactgc aagagaacaa ccagttgatg cttacacaaa catcttgttt   1080

tcttcaggta ctacaggtga accaaaagca attccatgga ctcaagctac accattaaaa   1140

gctgcagctg atggttggtc acatttggat attagaaaag gtgacgttat tgtttggcca   1200

actaatttgg gttggatgat gggtccatgg ttggtttatg cttcattgtt gaacggtgca   1260

tctatcgctt tgtacaacgg ttcaccattg gtttctggtt tcgcaaagtt cgttcaagat   1320

gctaaggtta caatgttggg tgttgttcca tcaatcgtta gatcatggaa gtctactaac   1380

tgtgtttcag gttacgattg gtctacaatc agatgtttct cttcatctgg tgaagcatct   1440

aacgttgatg aatatttgtg gttgatgggt agagctaact acaagccagt tattgaaatg   1500

tgtggtggta ctgaaattgg tggtgcattt tcagctggtt catttttgca agctcaatct   1560

ttgtcatctt tttcatctca atgtatgggt tgtacattgt acatcttgga taagaacggt   1620

tacccaatgc ctaaaaataa gccaggtatt ggtgaattgg cattaggtcc agttatgttc   1680

ggtgcttcaa agactttgtt gaacggtaac catcatgatg tttacttcaa gggtatgcca   1740
```

```
acattgaatg gtgaagtttt gagaagacat ggtgacatct tcgaattgac ttctaacggt   1800

tactaccatg cacatggtag agctgatgat acaatgaata ttggtggtat taaaatctca   1860

tctatcgaaa tcgaaagagt ttgtaacgaa gttgatgata gagtttttga aactacagct   1920

attggtgttc caccattagg tggtggtcca gaacaattgg ttattttctt tgttttgaaa   1980

gattcaaatg atactacaat tgatttgaac caattgagat tgtcttttaa tttgggttta   2040

caaaagaaat tgaacccatt gtttaaagtt actagagttg ttccattgtc atctttgcca   2100

agaactgcta caaataagat catgagaaga gtcttgagac aacaattttc tcattttgaa   2160
```

```
<210> SEQ ID NO 15
<211> LENGTH: 18
<212> TYPE: PRT
<213> ORGANISM: Artificial Sequence
<220> FEATURE:
<223> OTHER INFORMATION: T2A

<400> SEQUENCE: 15

Glu Gly Arg Gly Ser Leu Leu Thr Cys Gly Asp Val Glu Glu Asn Pro
1               5                   10                  15

Gly Pro
```

```
<210> SEQ ID NO 16
<211> LENGTH: 54
<212> TYPE: DNA
<213> ORGANISM: Artificial Sequence
<220> FEATURE:
<223> OTHER INFORMATION: T2A

<400> SEQUENCE: 16

gaaggtagag gttctttgtt gacctgtggt gacgttgaag aaaatccagg tcct          54
```

```
<210> SEQ ID NO 17
<211> LENGTH: 530
<212> TYPE: PRT
<213> ORGANISM: Cannabis sativa

<400> SEQUENCE: 17

Met Asn Cys Ser Thr Phe Ser Phe Trp Phe Val Cys Lys Ile Ile Phe
1               5                   10                  15

Phe Phe Leu Ser Phe Asn Ile Gln Ile Ser Ile Ala Asn Pro Gln Glu
            20                  25                  30

Asn Phe Leu Lys Cys Phe Ser Glu Tyr Ile Pro Asn Asn Pro Ala Pro
        35                  40                  45

Lys Phe Ile Tyr Thr Gln His Asp Gln Leu Tyr Met Ser Val Leu Asn
    50                  55                  60

Ser Thr Ile Gln Asn Leu Arg Phe Thr Ser Asp Thr Thr Pro Lys Pro
65                  70                  75                  80

Leu Val Ile Val Thr Pro Ser Asn Val Ser His Ile Gln Ala Ser Ile
                85                  90                  95

Leu Cys Ser Lys Val Gly Leu Gln Ile Arg Thr Arg Ser Gly Gly His
            100                 105                 110

Asp Ala Glu Gly Leu Ser Tyr Ile Ser Gln Val Pro Phe Ala Ile Val
        115                 120                 125

Asp Leu Arg Asn Met His Thr Val Val Asp Ile His Ser Gln Thr Ala
    130                 135                 140

Val Glu Ala Gly Ala Thr Leu Gly Glu Val Tyr Tyr Trp Ile Asn Glu
145                 150                 155                 160
```

```
Met Asn Glu Asn Phe Ser Phe Pro Gly Gly Tyr Cys Pro Thr Val Gly
                165                 170                 175

Val Gly Gly His Phe Ser Gly Gly Gly Tyr Gly Ala Leu Met Arg Asn
            180                 185                 190

Tyr Gly Leu Ala Ala Asp Asn Ile Ile Asp Ala His Leu Val Asn Val
        195                 200                 205

Asp Gly Lys Val Leu Asp Arg Lys Ser Met Gly Glu Asp Leu Phe Trp
    210                 215                 220

Ala Ile Arg Gly Gly Gly Gly Glu Asn Phe Gly Ile Ile Ala Ala Cys
225                 230                 235                 240

Ile Lys Leu Trp Val Pro Ser Lys Ala Thr Ile Phe Ser Val Lys Lys
                245                 250                 255

Asn Met Glu Ile His Gly Leu Val Lys Leu Phe Asn Lys Trp Gln Asn
            260                 265                 270

Ile Ala Tyr Tyr Asp Lys Asp Leu Met Leu Thr Thr His Phe Arg Thr
        275                 280                 285

Arg Asn Ile Thr Asp Asn His Gly Asn Lys Thr Thr Val His Gly Tyr
    290                 295                 300

Phe Ser Ser Ile Phe Leu Gly Gly Val Asp Ser Leu Val Asp Leu Met
305                 310                 315                 320

Asn Lys Ser Phe Pro Glu Leu Gly Ile Lys Thr Asp Cys Lys Glu Leu
                325                 330                 335

Ser Trp Ile Asp Thr Thr Ile Phe Tyr Ser Gly Trp Tyr Asn Thr Ala
            340                 345                 350

Phe Lys Lys Glu Ile Leu Leu Asp Arg Ser Ala Gly Lys Lys Thr Ala
        355                 360                 365

Phe Ser Ile Lys Leu Asp Tyr Val Lys Lys Leu Ile Pro Glu Thr Ala
    370                 375                 380

Met Val Lys Ile Leu Glu Leu Tyr Glu Glu Glu Val Gly Val Gly Met
385                 390                 395                 400

Tyr Val Leu Tyr Pro Tyr Gly Gly Ile Met Asp Glu Ile Ser Glu Ser
                405                 410                 415

Ala Ile Pro Phe Pro His Arg Ala Gly Ile Met Tyr Glu Leu Tyr Thr
            420                 425                 430

Ala Thr Glu Lys Gln Glu Asp Asn Glu Lys His Ile Asn Trp Val Arg
        435                 440                 445

Ser Val Tyr Asn Phe Thr Thr Pro Tyr Val Ser Gln Asn Pro Arg Leu
    450                 455                 460

Ala Tyr Leu Asn Tyr Arg Asp Leu Asp Leu Gly Lys Thr Asn Pro Glu
465                 470                 475                 480

Ser Pro Asn Asn Tyr Thr Gln Ala Arg Ile Trp Gly Glu Lys Tyr Phe
                485                 490                 495

Gly Lys Asn Phe Asn Arg Leu Val Lys Val Lys Thr Lys Ala Asp Pro
            500                 505                 510

Asn Asn Phe Phe Arg Asn Glu Gln Ser Ile Pro Pro Leu Pro Pro Arg
        515                 520                 525

His His
    530


<210> SEQ ID NO 18
<211> LENGTH: 1635
<212> TYPE: DNA
<213> ORGANISM: Cannabis sativa

<400> SEQUENCE: 18
```

```
atgaattgct caacattctc cttttggttt gtttgcaaaa taatattttt ctttctctca     60
ttcaatatcc aaatttcaat agctaatcct caagaaaact tccttaaatg cttctcggaa    120
tatattccta acaatccagc aaatccaaaa ttcatataca ctcaacacga ccaattgtat    180
atgtctgtcc tgaattcgac aatacaaaat cttagattca cctctgatac aaccccaaaa    240
ccactcgtta ttgtcactcc ttcaaatgtc tcccatatcc aggccagtat tctctgctcc    300
aagaaagttg gtttgcagat tcgaactcga agcggtggcc atgatgctga gggtttgtcc    360
tacatatctc aagtcccatt tgctatagta gacttgagaa acatgcatac ggtcaaagta    420
gatattcata gccaaactgc gtgggttgaa gccggagcta cccttggaga agtttattat    480
tggatcaatg agatgaatga gaattttagt tttcctggtg ggtattgccc tactgttggc    540
gtaggtggac actttagtgg aggaggctat ggagcattga tgcgaaatta tggccttgcg    600
gctgataata tcattgatgc acacttagtc aatgttgatg gaaaagttct agatcgaaaa    660
tccatgggag aagatctatt ttgggctata cgtggtggag gaggagaaaa ctttggaatc    720
attgcagcat gtaaaatcaa acttgttgtt gtcccatcaa aggctactat attcagtgtt    780
aaaaagaaca tggagataca tggggcttgtc aagttattta acaaatggca aaatattgct    840
tacaagtatg acaaagattt aatgctcacg actcacttca gaactaggaa tattacagat    900
aatcatggga agaataagac tacagtacat ggttacttct cttccatttt tcttggtgga    960
gtggatagtc tagttgactt gatgaacaag agctttcctg agttgggtat taaaaaaact   1020
gattgcaaag aattgagctg gattgataca accatcttct acagtggtgt tgtaaattac   1080
aacactgcta attttaaaaa ggaaattttg cttgatagat cagctgggaa gaagacggct   1140
ttctcaatta agttagacta tgttaagaaa ctaatacctg aaactgcaat ggtcaaaatt   1200
ttggaaaaat tatatgaaga agaggtagga gttgggatgt atgtgttgta cccttacggt   1260
ggtataatgg atgagatttc agaatcagca attccattcc ctcatcgagc tggaataatg   1320
tatgaacttt ggtacactgc tacctgggag aagcaagaag ataacgaaaa gcatataaac   1380
tgggttcgaa gtgtttataa tttcacaact ccttatgtgt cccaaaatcc aagattggcg   1440
tatctcaatt atagggacct tgatttagga aaaactaatc ctgagagtcc taataattac   1500
acacaagcac gtatttgggg tgaaaagtat tttggtaaaa attttaacag gttagttaag   1560
gtgaaaacca aagctgatcc caataatttt tttagaaacg aacaaagtat cccacctctt   1620
ccaccgcgtc atcat                                                    1635
```

<210> SEQ ID NO 19
<211> LENGTH: 3165
<212> TYPE: DNA
<213> ORGANISM: Saccharomyces cerevisiae

<400> SEQUENCE: 19

```
atgccgccgc tattcaaggg actgaaacag atggcaaagc caattgccta tgtttcaaga     60
ttttcggcga aacgaccaat tcatataata ctttttttctc taatcatatc cgcattcgct    120
tatctatccg tcattcagta ttacttcaat ggttggcaac tagattcaaa tagtgttttt    180
gaaactgctc caaataaaga ctccaacact ctatttcaag aatgttccca ttactacaga    240
gattcctctc tagatggttg ggtatcaatc accgcgcatg aagctagtga gttaccagcc    300
ccacaccatt actatctatt aaacctgaac ttcaatagtc ctaatgaaac tgactccatt    360
ccagaactag ctaacacggt tttgagaaa gataatacaa aatatattct gcaagaagat    420
```

```
ctcagtgttt ccaaagaaat ttcttctact gatggaacga aatggaggtt aagaagtgac    480
agaaaaagtc ttttcgacgt aaagacgtta gcatattctc tctacgatgt attttcagaa    540
aatgtaaccc aagcagaccc gtttgacgtc cttattatgg ttactgccta cctaatgatg    600
ttctacacca tattcggcct cttcaatgac atgaggaaga ccgggtcaaa tttttggttg    660
agcgcctcta cagtggtcaa ttctgcatca tcacttttct tagcattgta tgtcacccaa    720
tgtattctag gcaaagaagt ttccgcatta actctttttg aaggtttgcc tttcattgta    780
gttgttgttg gtttcaagca caaaatcaag attgcccagt atgccctgga gaaatttgaa    840
agagtcggtt tatctaaaag gattactacc gatgaaatcg tttttgaatc cgtgagcgaa    900
gagggtggtc gtttgattca agaccatttg ctttgtattt ttgcctttat cggatgctct    960
atgtatgctc accaattgaa gactttgaca aacttctgca tattatcagc atttatccta   1020
atttttgaat tgattttaac tcctacattt tattctgcta tcttagcgct tagactggaa   1080
atgaatgtta tccacagatc tactattatc aagcaaacat tagaagaaga cggtgttgtt   1140
ccatctacag caagaatcat ttctaaagca gaaaagaaat ccgtatcttc tttcttaaat   1200
ctcagtgtgg ttgtcattat catgaaactc tctgtcatac tgttgtttgt cttcatcaac   1260
ttttataact ttggtgcaaa ttgggtcaat gatgccttca attcattgta cttcgataag   1320
gaacgtgttt ctctaccaga ttttattacc tcgaatgcct ctgaaaactt taaagagcaa   1380
gctattgtta gtgtcacccc attattatat tacaaaccca ttaagtccta ccaacgcatt   1440
gaggatatgg ttcttctatt gcttcgtaat gtcagtgttg ccattcgtga taggttcgtc   1500
agtaaattag ttctttccgc cttagtatgc agtgctgtca tcaatgtgta tttattgaat   1560
gctgctagaa ttcataccag ttatactgca gaccaattgg tgaaaactga agtcaccaag   1620
aagtctttta ctgctcctgt acaaaaggct tctacaccag ttttaaccaa taaaacagtc   1680
atttctggat cgaaagtcaa aagtttatca tctgcgcaat cgagctcatc aggaccttca   1740
tcatctagtg aggaagatga ttcccgcgat attgaaagct tggataagaa aatacgtcct   1800
ttagaagaat tagaagcatt attaagtagt ggaaatacaa aacaattgaa gaacaaagag   1860
gtcgctgcct tggttattca cggtaagtta cctttgtacg ctttggagaa aaaattaggt   1920
gatactacga gagcggttgc ggtacgtagg aaggctcttt caattttggc agaagctcct   1980
gtattagcat ctgatcgttt accatataaa aattatgact acgaccgcgt atttggcgct   2040
tgttgtgaaa atgttatagg ttacatgcct ttgcccgttg gtgttatagg cccccttggtt  2100
atcgatggta catcttatca tataccaatg gcaactacag agggttgttt ggtagcttct   2160
gccatgcgtg gctgtaaggc aatcaatgct ggcggtggtg caacaactgt tttaactaag   2220
gatggtatga caagaggccc agtagtccgt ttcccaactt tgaaaagatc tggtgcctgt   2280
aagatatggt tagactcaga agagggacaa aacgcaatta aaaaagcttt taactctaca   2340
tcaagatttg cacgtctgca acatattcaa acttgtctag caggagattt actcttcatg   2400
agatttagaa caactactgg tgacgcaatg ggtatgaata tgatttctaa aggtgtcgaa   2460
tactcattaa agcaaatggt agaagagtat ggctgggaag atatggaggt tgtctccgtt   2520
tctggtaact actgtaccga caaaaaacca gctgccatca actggatcga aggtcgtggt   2580
aagagtgtcg tcgcagaagc tactattcct ggtgatgttg tcagaaaagt gttaaaaagt   2640
gatgtttccg cattggttga gttgaacatt gctaagaatt tggttggatc tgcaatggct   2700
gggtctgttg gtggatttaa cgcacatgca gctaatttag tgacagctgt tttcttggca   2760
ttaggacaag atcctgcaca aaatgttgaa agttccaact gtataacatt gatgaaagaa   2820
```

```
gtggacggtg atttgagaat ttccgtatcc atgccatcca tcgaagtagg taccatcggt   2880

ggtggtactg ttctagaacc acaaggtgcc atgttggact tattaggtgt aagaggcccg   2940

catgctaccg ctcctggtac caacgcacgt caattagcaa gaatagttgc ctgtgccgtc   3000

ttggcaggtg aattatcctt atgtgctgcc ctagcagccg gccatttggt tcaaagtcat   3060

atgacccaca acaggaaacc tgctgaacca acaaaaccta acaatttgga cgccactgat   3120

ataaatcgtt tgaaagatgg gtccgtcacc tgcattaaat cctaa                   3165
```

<210> SEQ ID NO 20
<211> LENGTH: 1054
<212> TYPE: PRT
<213> ORGANISM: Saccharomyces cerevisiae

<400> SEQUENCE: 20

```
Met Pro Pro Leu Phe Lys Gly Leu Lys Gln Met Ala Lys Pro Ile Ala
1               5                   10                  15

Tyr Val Ser Arg Phe Ser Ala Lys Arg Pro Ile His Ile Ile Leu Phe
            20                  25                  30

Ser Leu Ile Ile Ser Ala Phe Ala Tyr Leu Ser Val Ile Gln Tyr Tyr
        35                  40                  45

Phe Asn Gly Trp Gln Leu Asp Ser Asn Ser Val Phe Glu Thr Ala Pro
    50                  55                  60

Asn Lys Asp Ser Asn Thr Leu Phe Gln Glu Cys Ser His Tyr Tyr Arg
65                  70                  75                  80

Asp Ser Ser Leu Asp Gly Trp Val Ser Ile Thr Ala His Glu Ala Ser
                85                  90                  95

Glu Leu Pro Ala Pro His His Tyr Tyr Leu Leu Asn Leu Asn Phe Asn
            100                 105                 110

Ser Pro Asn Glu Thr Asp Ser Ile Pro Glu Leu Ala Asn Thr Val Phe
        115                 120                 125

Glu Lys Asp Asn Thr Lys Tyr Ile Leu Gln Glu Asp Leu Ser Val Ser
    130                 135                 140

Lys Glu Ile Ser Ser Thr Asp Gly Thr Lys Trp Arg Leu Arg Ser Asp
145                 150                 155                 160

Arg Lys Ser Leu Phe Asp Val Lys Thr Leu Ala Tyr Ser Leu Tyr Asp
                165                 170                 175

Val Phe Ser Glu Asn Val Thr Gln Ala Asp Pro Phe Asp Val Leu Ile
            180                 185                 190

Met Val Thr Ala Tyr Leu Met Met Phe Tyr Thr Ile Phe Gly Leu Phe
        195                 200                 205

Asn Asp Met Arg Lys Thr Gly Ser Asn Phe Trp Leu Ser Ala Ser Thr
    210                 215                 220

Val Val Asn Ser Ala Ser Ser Leu Phe Leu Ala Leu Tyr Val Thr Gln
225                 230                 235                 240

Cys Ile Leu Gly Lys Glu Val Ser Ala Leu Thr Leu Phe Glu Gly Leu
                245                 250                 255

Pro Phe Ile Val Val Val Val Gly Phe Lys His Lys Ile Lys Ile Ala
            260                 265                 270

Gln Tyr Ala Leu Glu Lys Phe Glu Arg Val Gly Leu Ser Lys Arg Ile
        275                 280                 285

Thr Thr Asp Glu Ile Val Phe Glu Ser Val Ser Glu Glu Gly Gly Arg
    290                 295                 300

Leu Ile Gln Asp His Leu Leu Cys Ile Phe Ala Phe Ile Gly Cys Ser
```

```
305                 310                 315                 320

Met Tyr Ala His Gln Leu Lys Thr Leu Thr Asn Phe Cys Ile Leu Ser
                325                 330                 335

Ala Phe Ile Leu Ile Phe Glu Leu Ile Leu Thr Pro Thr Phe Tyr Ser
            340                 345                 350

Ala Ile Leu Ala Leu Arg Leu Glu Met Asn Val Ile His Arg Ser Thr
        355                 360                 365

Ile Ile Lys Gln Thr Leu Glu Glu Asp Gly Val Val Pro Ser Thr Ala
    370                 375                 380

Arg Ile Ile Ser Lys Ala Glu Lys Lys Ser Val Ser Ser Phe Leu Asn
385                 390                 395                 400

Leu Ser Val Val Val Ile Ile Met Lys Leu Ser Val Ile Leu Leu Phe
                405                 410                 415

Val Phe Ile Asn Phe Tyr Asn Phe Gly Ala Asn Trp Val Asn Asp Ala
            420                 425                 430

Phe Asn Ser Leu Tyr Phe Asp Lys Glu Arg Val Ser Leu Pro Asp Phe
        435                 440                 445

Ile Thr Ser Asn Ala Ser Glu Asn Phe Lys Glu Gln Ala Ile Val Ser
    450                 455                 460

Val Thr Pro Leu Leu Tyr Tyr Lys Pro Ile Lys Ser Tyr Gln Arg Ile
465                 470                 475                 480

Glu Asp Met Val Leu Leu Leu Leu Arg Asn Val Ser Val Ala Ile Arg
                485                 490                 495

Asp Arg Phe Val Ser Lys Leu Val Leu Ser Ala Leu Val Cys Ser Ala
            500                 505                 510

Val Ile Asn Val Tyr Leu Leu Asn Ala Ala Arg Ile His Thr Ser Tyr
        515                 520                 525

Thr Ala Asp Gln Leu Val Lys Thr Glu Val Thr Lys Lys Ser Phe Thr
    530                 535                 540

Ala Pro Val Gln Lys Ala Ser Thr Pro Val Leu Thr Asn Lys Thr Val
545                 550                 555                 560

Ile Ser Gly Ser Lys Val Lys Ser Leu Ser Ser Ala Gln Ser Ser Ser
                565                 570                 575

Ser Gly Pro Ser Ser Ser Ser Glu Glu Asp Asp Ser Arg Asp Ile Glu
            580                 585                 590

Ser Leu Asp Lys Lys Ile Arg Pro Leu Glu Glu Leu Glu Ala Leu Leu
        595                 600                 605

Ser Ser Gly Asn Thr Lys Gln Leu Lys Asn Lys Glu Val Ala Ala Leu
    610                 615                 620

Val Ile His Gly Lys Leu Pro Leu Tyr Ala Leu Glu Lys Lys Leu Gly
625                 630                 635                 640

Asp Thr Thr Arg Ala Val Ala Val Arg Arg Lys Ala Leu Ser Ile Leu
                645                 650                 655

Ala Glu Ala Pro Val Leu Ala Ser Asp Arg Leu Pro Tyr Lys Asn Tyr
            660                 665                 670

Asp Tyr Asp Arg Val Phe Gly Ala Cys Cys Glu Asn Val Ile Gly Tyr
        675                 680                 685

Met Pro Leu Pro Val Gly Val Ile Gly Pro Leu Val Ile Asp Gly Thr
    690                 695                 700

Ser Tyr His Ile Pro Met Ala Thr Thr Glu Gly Cys Leu Val Ala Ser
705                 710                 715                 720

Ala Met Arg Gly Cys Lys Ala Ile Asn Ala Gly Gly Gly Ala Thr Thr
                725                 730                 735
```

```
Val Leu Thr Lys Asp Gly Met Thr Arg Gly Pro Val Val Arg Phe Pro
            740                 745                 750

Thr Leu Lys Arg Ser Gly Ala Cys Lys Ile Trp Leu Asp Ser Glu Glu
        755                 760                 765

Gly Gln Asn Ala Ile Lys Lys Ala Phe Asn Ser Thr Ser Arg Phe Ala
    770                 775                 780

Arg Leu Gln His Ile Gln Thr Cys Leu Ala Gly Asp Leu Leu Phe Met
785                 790                 795                 800

Arg Phe Arg Thr Thr Thr Gly Asp Ala Met Gly Met Asn Met Ile Ser
                805                 810                 815

Lys Gly Val Glu Tyr Ser Leu Lys Gln Met Val Glu Glu Tyr Gly Trp
            820                 825                 830

Glu Asp Met Glu Val Val Ser Val Ser Gly Asn Tyr Cys Thr Asp Lys
        835                 840                 845

Lys Pro Ala Ala Ile Asn Trp Ile Glu Gly Arg Gly Lys Ser Val Val
    850                 855                 860

Ala Glu Ala Thr Ile Pro Gly Asp Val Val Arg Lys Val Leu Lys Ser
865                 870                 875                 880

Asp Val Ser Ala Leu Val Glu Leu Asn Ile Ala Lys Asn Leu Val Gly
                885                 890                 895

Ser Ala Met Ala Gly Ser Val Gly Gly Phe Asn Ala His Ala Ala Asn
            900                 905                 910

Leu Val Thr Ala Val Phe Leu Ala Leu Gly Gln Asp Pro Ala Gln Asn
        915                 920                 925

Val Glu Ser Ser Asn Cys Ile Thr Leu Met Lys Glu Val Asp Gly Asp
    930                 935                 940

Leu Arg Ile Ser Val Ser Met Pro Ser Ile Glu Val Gly Thr Ile Gly
945                 950                 955                 960

Gly Gly Thr Val Leu Glu Pro Gln Gly Ala Met Leu Asp Leu Leu Gly
                965                 970                 975

Val Arg Gly Pro His Ala Thr Ala Pro Gly Thr Asn Ala Arg Gln Leu
            980                 985                 990

Ala Arg Ile Val Ala Cys Ala Val  Leu Ala Gly Glu Leu  Ser Leu Cys
        995                 1000                 1005

Ala Ala  Leu Ala Ala Gly His  Leu Val Gln Ser His  Met Thr His
    1010                 1015                 1020

Asn Arg  Lys Pro Ala Glu Pro  Thr Lys Pro Asn Asn  Leu Asp Ala
    1025                 1030                 1035

Thr Asp  Ile Asn Arg Leu Lys  Asp Gly Ser Val Thr  Cys Ile Lys
    1040                 1045                 1050

Ser
```

<210> SEQ ID NO 21
<211> LENGTH: 1578
<212> TYPE: DNA
<213> ORGANISM: Saccharomyces cerevisiae

<400> SEQUENCE: 21

```
atggaccaat tggtgaaaac tgaagtcacc aagaagtctt ttactgctcc tgtacaaaag      60

gcttctacac cagttttaac caataaaaca gtcatttctg gatcgaaagt caaaagttta     120

tcatctgcgc aatcgagctc atcaggacct tcatcatcta gtgaggaaga tgattcccgc     180

gatattgaaa gcttggataa gaaaatacgt cctttagaag aattagaagc attattaagt     240
```

```
agtggaaata caaaacaatt gaagaacaaa gaggtcgctg ccttggttat tcacggtaag    300

ttacctttgt acgctttgga gaaaaaatta ggtgatacta cgagagcggt tgcggtacgt    360

aggaaggctc tttcaatttt ggcagaagct cctgtattag catctgatcg tttaccatat    420

aaaaattatg actacgaccg cgtatttggc gcttgttgtg aaaatgttat aggttacatg    480

cctttgcccg ttggtgttat aggccccttg gttatcgatg gtacatctta tcatatacca    540

atggcaacta cagagggttg tttggtagct tctgccatgc gtggctgtaa ggcaatcaat    600

gctggcggtg gtgcaacaac tgttttaact aaggatggta tgacaagagg cccagtagtc    660

cgtttcccaa ctttgaaaag atctggtgcc tgtaagatat ggttagactc agaagaggga    720

caaaacgcaa ttaaaaaagc ttttaactct acatcaagat ttgcacgtct gcaacatatt    780

caaacttgtc tagcaggaga tttactcttc atgagattta gaacaactac tggtgacgca    840

atgggtatga atatgatttc taaaggtgtc gaatactcat taaagcaaat ggtagaagag    900

tatggctggg aagatatgga ggttgtctcc gtttctggta actactgtac cgacaaaaaa    960

ccagctgcca tcaactggat cgaaggtcgt ggtaagagtg tcgtcgcaga agctactatt   1020

cctggtgatg ttgtcagaaa agtgttaaaa agtgatgttt ccgcattggt tgagttgaac   1080

attgctaaga atttggttgg atctgcaatg gctgggtctg ttggtggatt taacgcacat   1140

gcagctaatt tagtgacagc tgttttcttg gcattaggac aagatcctgc acaaaatgtt   1200

gaaagttcca actgtataac attgatgaaa gaagtggacg gtgatttgag aatttccgta   1260

tccatgccat ccatcgaagt aggtaccatc ggtggtggta ctgttctaga accacaaggt   1320

gccatgttgg acttattagg tgtaagaggc ccgcatgcta ccgctcctgg taccaacgca   1380

cgtcaattag caagaatagt tgcctgtgcc gtcttggcag gtgaattatc cttatgtgct   1440

gccctagcag ccggccattt ggttcaaagt catatgaccc acaacaggaa acctgctgaa   1500

ccaacaaaac ctaacaattt ggacgccact gatataaatc gtttgaaaga tgggtccgtc   1560

acctgcatta aatcctaa                                                 1578
```

<210> SEQ ID NO 22
<211> LENGTH: 525
<212> TYPE: PRT
<213> ORGANISM: Saccharomyces cerevisiae

<400> SEQUENCE: 22

```
Met Asp Gln Leu Val Lys Thr Glu Val Thr Lys Lys Ser Phe Thr Ala
1               5                   10                  15

Pro Val Gln Lys Ala Ser Thr Pro Val Leu Thr Asn Lys Thr Val Ile
            20                  25                  30

Ser Gly Ser Lys Val Lys Ser Leu Ser Ser Ala Gln Ser Ser Ser Ser
        35                  40                  45

Gly Pro Ser Ser Ser Ser Glu Glu Asp Asp Ser Arg Asp Ile Glu Ser
    50                  55                  60

Leu Asp Lys Lys Ile Arg Pro Leu Glu Glu Leu Glu Ala Leu Leu Ser
65                  70                  75                  80

Ser Gly Asn Thr Lys Gln Leu Lys Asn Lys Glu Val Ala Ala Leu Val
                85                  90                  95

Ile His Gly Lys Leu Pro Leu Tyr Ala Leu Glu Lys Lys Leu Gly Asp
            100                 105                 110

Thr Thr Arg Ala Val Ala Val Arg Arg Lys Ala Leu Ser Ile Leu Ala
        115                 120                 125

Glu Ala Pro Val Leu Ala Ser Asp Arg Leu Pro Tyr Lys Asn Tyr Asp
```

```
    130                 135                 140

Tyr Asp Arg Val Phe Gly Ala Cys Cys Glu Asn Val Ile Gly Tyr Met
145                 150                 155                 160

Pro Leu Pro Val Gly Val Ile Gly Pro Leu Val Ile Asp Gly Thr Ser
                165                 170                 175

Tyr His Ile Pro Met Ala Thr Thr Glu Gly Cys Leu Val Ala Ser Ala
            180                 185                 190

Met Arg Gly Cys Lys Ala Ile Asn Ala Gly Gly Gly Ala Thr Thr Val
        195                 200                 205

Leu Thr Lys Asp Gly Met Thr Arg Gly Pro Val Val Arg Phe Pro Thr
    210                 215                 220

Leu Lys Arg Ser Gly Ala Cys Lys Ile Trp Leu Asp Ser Glu Glu Gly
225                 230                 235                 240

Gln Asn Ala Ile Lys Lys Ala Phe Asn Ser Thr Ser Arg Phe Ala Arg
                245                 250                 255

Leu Gln His Ile Gln Thr Cys Leu Ala Gly Asp Leu Leu Phe Met Arg
            260                 265                 270

Phe Arg Thr Thr Thr Gly Asp Ala Met Gly Met Asn Met Ile Ser Lys
        275                 280                 285

Gly Val Glu Tyr Ser Leu Lys Gln Met Val Glu Glu Tyr Gly Trp Glu
    290                 295                 300

Asp Met Glu Val Val Ser Val Ser Gly Asn Tyr Cys Thr Asp Lys Lys
305                 310                 315                 320

Pro Ala Ala Ile Asn Trp Ile Glu Gly Arg Gly Lys Ser Val Val Ala
                325                 330                 335

Glu Ala Thr Ile Pro Gly Asp Val Val Arg Lys Val Leu Lys Ser Asp
            340                 345                 350

Val Ser Ala Leu Val Glu Leu Asn Ile Ala Lys Asn Leu Val Gly Ser
        355                 360                 365

Ala Met Ala Gly Ser Val Gly Gly Phe Asn Ala His Ala Ala Asn Leu
    370                 375                 380

Val Thr Ala Val Phe Leu Ala Leu Gly Gln Asp Pro Ala Gln Asn Val
385                 390                 395                 400

Glu Ser Ser Asn Cys Ile Thr Leu Met Lys Glu Val Asp Gly Asp Leu
                405                 410                 415

Arg Ile Ser Val Ser Met Pro Ser Ile Glu Val Gly Thr Ile Gly Gly
            420                 425                 430

Gly Thr Val Leu Glu Pro Gln Gly Ala Met Leu Asp Leu Leu Gly Val
        435                 440                 445

Arg Gly Pro His Ala Thr Ala Pro Gly Thr Asn Ala Arg Gln Leu Ala
    450                 455                 460

Arg Ile Val Ala Cys Ala Val Leu Ala Gly Glu Leu Ser Leu Cys Ala
465                 470                 475                 480

Ala Leu Ala Ala Gly His Leu Val Gln Ser His Met Thr His Asn Arg
                485                 490                 495

Lys Pro Ala Glu Pro Thr Lys Pro Asn Asn Leu Asp Ala Thr Asp Ile
            500                 505                 510

Asn Arg Leu Lys Asp Gly Ser Val Thr Cys Ile Lys Ser
        515                 520                 525
```

<210> SEQ ID NO 23
<211> LENGTH: 1059
<212> TYPE: DNA
<213> ORGANISM: Saccharomyces cerevisiae

<400> SEQUENCE: 23

```
atggcttcag aaaaagaaat taggagagag agattcttga acgttttccc taaattagta     60
gaggaattga acgcatcgct tttggcttac ggtatgccta aggaagcatg tgactggtat    120
gcccactcat tgaactacaa cactccaggc ggtaagctaa atagaggttt gtccgttgtg    180
gacacgtatg ctattctctc caacaagacc gttgaacaat tggggcaaga agaatacgaa    240
aaggttgcca ttctaggttg gtgcattgag ttgttgcagg cttacttctt ggtcgccgat    300
gatatgatgg acaagtccat taccagaaga ggccaaccat gttggtacaa ggttcctgaa    360
gttggggaaa ttgccatcaa tgacgcattc atgttagagg ctgctatcta caagcttttg    420
aaatctcact tcagaaacga aaaatactac atagatatca ccgaattgtt ccatgaggtc    480
accttccaaa ccgaattggg ccaattgatg gacttaatca ctgcacctga agacaaagtc    540
gacttgagta agttctccct aaagaagcac tccttcatag ttactttcaa gactgcttac    600
tattctttct acttgcctgt cgcattggcc atgtacgttg ccggtatcac ggatgaaaag    660
gatttgaaac aagccagaga tgtcttgatt ccattgggtg aatacttcca aattcaagat    720
gactacttag actgcttcgg taccccagaa cagatcggta agatcggtac agatatccaa    780
gataacaaat gttcttgggt aatcaacaag gcattggaac ttgcttccgc agaacaaaga    840
aagactttag acgaaaatta cggtaagaag gactcagtcg cagaagccaa atgcaaaaag    900
attttcaatg acttgaaaat tgaacagcta taccacgaat atgaagagtc tattgccaag    960
gatttgaagg ccaaaatttc tcaggtcgat gagtctcgtg gcttcaaagc tgatgtctta   1020
actgcgttct tgaacaaagt ttacaagaga agcaaatag                          1059
```

<210> SEQ ID NO 24
<211> LENGTH: 352
<212> TYPE: PRT
<213> ORGANISM: Saccharomyces cerevisiae

<400> SEQUENCE: 24

```
Met Ala Ser Glu Lys Glu Ile Arg Arg Glu Arg Phe Leu Asn Val Phe
1               5                   10                  15

Pro Lys Leu Val Glu Glu Leu Asn Ala Ser Leu Leu Ala Tyr Gly Met
            20                  25                  30

Pro Lys Glu Ala Cys Asp Trp Tyr Ala His Ser Leu Asn Tyr Asn Thr
        35                  40                  45

Pro Gly Gly Lys Leu Asn Arg Gly Leu Ser Val Val Asp Thr Tyr Ala
    50                  55                  60

Ile Leu Ser Asn Lys Thr Val Glu Gln Leu Gly Gln Glu Glu Tyr Glu
65                  70                  75                  80

Lys Val Ala Ile Leu Gly Trp Cys Ile Glu Leu Leu Gln Ala Tyr Phe
                85                  90                  95

Leu Val Ala Asp Asp Met Met Asp Lys Ser Ile Thr Arg Arg Gly Gln
            100                 105                 110

Pro Cys Trp Tyr Lys Val Pro Glu Val Gly Glu Ile Ala Ile Asn Asp
        115                 120                 125

Ala Phe Met Leu Glu Ala Ala Ile Tyr Lys Leu Leu Lys Ser His Phe
    130                 135                 140

Arg Asn Glu Lys Tyr Tyr Ile Asp Ile Thr Glu Leu Phe His Glu Val
145                 150                 155                 160

Thr Phe Gln Thr Glu Leu Gly Gln Leu Met Asp Leu Ile Thr Ala Pro
                165                 170                 175
```

```
Glu Asp Lys Val Asp Leu Ser Lys Phe Ser Leu Lys Lys His Ser Phe
            180                 185                 190

Ile Val Thr Phe Lys Thr Ala Tyr Tyr Ser Phe Tyr Leu Pro Val Ala
        195                 200                 205

Leu Ala Met Tyr Val Ala Gly Ile Thr Asp Glu Lys Asp Leu Lys Gln
    210                 215                 220

Ala Arg Asp Val Leu Ile Pro Leu Gly Glu Tyr Phe Gln Ile Gln Asp
225                 230                 235                 240

Asp Tyr Leu Asp Cys Phe Gly Thr Pro Glu Gln Ile Gly Lys Ile Gly
                245                 250                 255

Thr Asp Ile Gln Asp Asn Lys Cys Ser Trp Val Ile Asn Lys Ala Leu
            260                 265                 270

Glu Leu Ala Ser Ala Glu Gln Arg Lys Thr Leu Asp Glu Asn Tyr Gly
        275                 280                 285

Lys Lys Asp Ser Val Ala Glu Ala Lys Cys Lys Lys Ile Phe Asn Asp
    290                 295                 300

Leu Lys Ile Glu Gln Leu Tyr His Glu Tyr Glu Glu Ser Ile Ala Lys
305                 310                 315                 320

Asp Leu Lys Ala Lys Ile Ser Gln Val Asp Glu Ser Arg Gly Phe Lys
                325                 330                 335

Ala Asp Val Leu Thr Ala Phe Leu Asn Lys Val Tyr Lys Arg Ser Lys
            340                 345                 350
```

<210> SEQ ID NO 25
<211> LENGTH: 9186
<212> TYPE: DNA
<213> ORGANISM: Artificial Sequence
<220> FEATURE:
<223> OTHER INFORMATION: bCBGA0306 vector

<400> SEQUENCE: 25

```
ttatattgaa ttttcaaaaa ttcttacttt ttttttggat ggacgcaaag aagtttaata     60

atcatattac atggcattac caccatatac atatccatat ctaatcttac ttatatgttg    120

tggaaatgta aagagcccca ttatcttagc ctaaaaaaac cttctctttg gaactttcag    180

taatacgctt aactgctcat tgctatattg aagtacggat tagaagccgc cgagcgggcg    240

acagccctcc gacggaagac tctcctccgt gcgtcctcgt cttcaccggt cgcgttcctg    300

aaacgcagat gtgcctcgcg ccgcactgct ccgaacaata aagattctac aatactagct    360

tttatggtta tgaagaggaa aaattggcag taacctggcc ccacaaacct tcaaattaac    420

gaatcaaatt aacaaccata ggatgataat gcgattagtt ttttagcctt atttctgggg    480

taattaatca gcgaagcgat gatttttgat ctattaacag atatataaat ggaaaagctg    540

cataaccact ttaactaata ctttcaacat tttcagtttg tattacttct tattcaaatg    600

tcataaaagt atcaacaaaa aattgttaat atacctctat actttaacgt caaggagaaa    660

aaactataat gggtttatct ttggtctgta ctttttcatt tcaaactaat taccatacat    720

tgttaaatcc acataataag aaccctaaaa attctttgtt gtcatatcaa catccaaaaa    780

ctccaattat taaatcttct tatgataatt ttccatctaa gtactgtttg actaaaaatt    840

tccatttgtt aggtttaaat tctcataata gaatttcttc acaatcaaga tcaattagag    900

ctggttctga tcaaattgaa ggttcaccac atcatgaatc tgataactca atcgcaacta    960

aaattttgaa ctttggtcat acatgttgga aattgcaaag accatacgtt gttaagggta   1020

tgatttctat tgcttgtggt ttatttggta gagaattgtt taataacaga catttgtttt   1080
```

```
cttggggttt gatgtggaaa gcatttttcg cattagttcc aatcttgtct tttaatttct   1140
ttgctgcaat catgaaccaa atatatgatg ttgatattga tagaattaat aagccagatt   1200
tgccattggt ttctggtgaa atgtcaatcg aaactgcttg gattttatct atcatcgttg   1260
cattgactgg tttgatcgtt acaattaaat taaaatcagc tccattgttc gtttttatat   1320
atatcttcgg tatcttcgct ggttttgcat actctgttcc accaattaga tggaagcaat   1380
acccttttac taatttcttg atcacaattt cttcacatgt tggtttggct tttacttctt   1440
actcagctac tacatctgca ttaggtttgc catttgtttg gaggccagct tttctttta    1500
ttatcgcttt tatgactgtt atgggtatga caatcgcttt cgcaaaggat atctctgata   1560
ttgaaggtga cgctaaatac ggtgtttcaa ctgttgctac aaaattgggt gcaagaaaca   1620
tgactttcgt tgtttctggt gttttgttgt tgaactattt ggtttctatc tcaatcggta   1680
ttatttggcc acaagttttt aaatctaaca tcatgatctt gtcacatgct atcttggcat   1740
tctgtttgat cttccaaaca agagaattag ctttggcaaa ttatgcttct gcaccatcaa   1800
gacaattttt cgagtttatt tggttgttgt actacgctga atattttgtt tacgtttta    1860
tttgagatta atataattat ataaaaatat tatcttcttt tctttatatc tagtgttatg   1920
taaaataaat tgatgactac ggaaagcttt tttatattgt ttcttttca ttctgagcca    1980
cttaaatttc gtgaatgttc ttgtaaggga cggtagattt acaagtgata caacaaaaag   2040
caaggcgctt tttctaataa aaagaagaaa agcatttaac aattgaacac ctctatatca   2100
acgaagaata ttactttgtc tctaaatcct tgtaaaatgt gtacgatctc tatatgggtt   2160
actcataagt gtaccgaaga ctgcattgaa agtttatgtt ttttcactgg aggcgtcatt   2220
ttcgcgttga gaacaattgt cctgtacttc cttgttcatg tgtgttcaaa aacgttatat   2280
ttataggata attatactct atttctcaac aagtaattgg ttgtttggcc gagcggtcta   2340
aggcgcctga ttcaagaaat atcttgaccg cagttaactg tgggaatact caggtatcgt   2400
aagatgcaag agttcgaatc tcttagcaac cattattttt ttcctcaaca taacgagaac   2460
acacaggggc gctatcgcac agaatcaaat tcgatgactg gaaatttttt gttaatttca   2520
gaggtcgcct gacgcatata cctttttcaa ctgaaaaatt gggagaaaaa ggaaaggtga   2580
gagcgccgga accggctttt catatagaat agagaagcgt tcatgactaa atgcttgcat   2640
cacaatactt gaagttgaca atattattta aggacctatt gtttttcca ataggtggtt    2700
agcaatcgtc ttactttcta acttttctta ccttttacat ttcagcaata tatatatata   2760
tttcaaggat ataccattct aatgtctgcc cctaagaaga tcgtcgtttt gccaggtgac   2820
cacgttggtc aagaaatcac agccgaagcc attaaggttc ttaaagctat ttctgatgtt   2880
cgttccaatg tcaagttcga tttcgaaaat catttaattg gtggtgctgc tatcgatgct   2940
acaggtgttc cacttccaga tgaggcgctg gaagcctcca agaaggctga tgccgttttg   3000
ttaggtgctg tgggtggtcc taaatggggt accggtagtg ttagacctga acaaggttta   3060
ctaaaaatcc gtaaagaact tcaattgtac gccaacttaa gaccatgtaa ctttgcatcc   3120
gactctcttt tagacttatc tccaatcaag ccacaatttg ctaaaaatac tgacttcgtt   3180
gttgtcagag aattagtggg aggtatttac tttggtaaga gaaaggaaga cgatggtgat   3240
ggtgtcgctt gggatagtga acaatacacc gttccagaag tgcaaagaat cacaagaatg   3300
gccgctttca tggccctaca acatgagcca ccattgccta tttggtcctt ggataaagct   3360
aatgttttgg cctcttcaag attatggaga aaaactgtgg aggaaaccat caagaacgaa   3420
```

```
ttccctacat tgaaggttca acatcaattg attgattctg ccgccatgat cctagttaag   3480
aacccaaccc acctaaatgg tattataatc accagcaaca tgtttggtga tatcatctcc   3540
gatgaagcct ccgttatccc aggttccttg ggtttgttgc catctgcgtc cttggcctct   3600
ttgccagaca agaacaccgc atttggtttg tacgaaccat gccacggttc tgctccagat   3660
ttgccaaaga ataaggtcaa ccctatcgcc actatcttgt ctgctgcaat gatgttgaaa   3720
ttgtcattga acttgcctga agaaggtaag gccattgaag atgcagttaa aaaggttttg   3780
gatgcaggta tcagaactgg tgatttaggt ggttccaaca gtaccaccga agtcggtgat   3840
gctgtcgccg aagaagttaa gaaaatcctt gcttaaaaag attctctttt tttatgatat   3900
ttgtacataa actttataaa tgaaattcat aatagaaacg acacgaaatt acaaaatgga   3960
atatgttcat agggtagacg aaactatata cgcaatctac atacatttat caagaaggag   4020
aaaaaggagg atgtaaagga atacaggtaa gcaaattgat actaatggct caacgtgata   4080
aggaaaaaga attgcacttt aacattaata ttgacaagga ggagggcacc acacaaaaag   4140
ttacagatct gctgcattaa tgaatcggcc aacgcgcggg gagaggcggt ttgcgtattg   4200
ggcgctcttc cgcttcctcg ctcactgact cgctgcgctc ggtcgttcgg ctgcggcgag   4260
cggtatcagc atcgatgaat tccacggact atagactata ctagtatact ccgtctactg   4320
tacgatacac ttccgctcag gtccttgtcc tttaacgagg ccttaccact cttttgttac   4380
tctattgatc cagctcagca aaggcagtgt gatctaagat tctatcttcg cgatgtagta   4440
aaactagcta gaccgagaaa gagactagaa atgcaaaagg cacttctaca atggctgcca   4500
tcattattat ccgatgtgac gctgcagctt ctcaatgata ttcgaatacg ctttgaggag   4560
atacagccta atatccgaca aactgtttta cagatttacg atcgtatttg ttacccatca   4620
ttgaattttg aacatccgaa cctgggagtt ttccctgaaa cagatagtat atttgaacct   4680
gtataataat atatagtcta gcgctttacg gaagacaatg tatgtatttc ggttcctgga   4740
gaaactattg catctattgc ataggtaatc ttgcacgtcg catccccggt tcattttctg   4800
cgtttccatc ttgcacttca atagcatatc tttgttaacg aagcatctgt gcttcatttt   4860
gtagaacaaa aatgcaacgc gagagcgcta atttttcaaa caaagaatct gagctgcatt   4920
tttacagaac agaaatgcaa cgcgaaagcg ctattttacc aacgaagaat ctgtgcttca   4980
tttttgtaaa acaaaaatgc aacgcgagag cgctaatttt tcaaacaaag aatctgagct   5040
gcatttttac agaacagaaa tgcaacgcga gagcgctatt ttaccaacaa agaatctata   5100
cttctttttt gttctacaaa aatgcatccc gagagcgcta tttttctaac aaagcatctt   5160
agattacttt ttttctcctt tgtgcgctct ataatgcagt ctcttgataa ctttttgcac   5220
tgtaggtccg ttaaggttag aagaaggcta ctttggtgtc tattttctct tccataaaaa   5280
aagcctgact ccacttcccg cgtttactga ttactagcga agctgcgggt gcattttttc   5340
aagataaagg catccccgat tatattctat accgatgtgg attgcgcata ctttgtgaac   5400
agaaagtgat agcgttgatg attcttcatt ggtcagaaaa ttatgaacgg tttcttctat   5460
tttgtctcta tatactacgt ataggaaatg tttacatttt cgtattgttt tcgattcact   5520
ctatgaatag ttcttactac aatttttttg tctaaagagt aatactagag ataaacataa   5580
aaaatgtaga ggtcgagttt agatgcaagt tcaaggagcg aaaggtggat gggtaggtta   5640
tatagggata tagcacagag atatatagca aagagatact tttgagcaat gtttgtggaa   5700
gcggtattcg caatatttta gtagctcgtt acagtccggt gcgtttttgg tttttttgaaa   5760
gtgcgtcttc agagcgcttt tggttttcaa aagcgctctg aagttcctat actttctaga   5820
```

```
gaataggaac ttcggaatag gaacttcaaa gcgtttccga aaacgagcgc ttccgaaaat   5880
gcaacgcgag ctgcgcacat acagctcact gttcacgtcg cacctatatc tgcgtgttgc   5940
ctgtatatat atatacatga gaagaacggc atagtgcgtg tttatgctta aatgcgtact   6000
tatatgcgtc tatttatgta ggatgaaagg tagtctagta cctcctgtga tattatccca   6060
ttccatgcgg ggtatcgtat gcttccttca gcactaccct ttagctgttc tatatgctgc   6120
cactcctcaa ttggattagt ctcatccttc aatgctatca tttcctttga tattggatca   6180
tatgcatagt accgagaaac tagtgcgaag tagtgatcag gtattgctgt tatctgatga   6240
gtatacgttg tcctggccac ggcagaagca cgcttatcgc tccaatttcc cacaacatta   6300
gtcaactccg ttaggccctt cattgaaaga aatgaggtca tcaaatgtct tccaatgtga   6360
gattttgggc catttttat agcaaagatt gaataaggcg catttttctt caaagcttta   6420
ttgtacgatc tgactaagtt atcttttaat aattggtatt cctgtttatt gcttgaagaa   6480
ttgccggtcc tatttactcg ttttaggact ggttcagaat tcatcgatgc tcactcaaag   6540
gcggtaatac ggttatccac agaatcaggg gataacgcag gaaagaacat gtgagcaaaa   6600
ggccagcaaa aggccaggaa ccgtaaaaag gccgcgttgc tggcgttttt ccataggctc   6660
cgcccccctg acgagcatca caaaaatcga cgctcaagtc agaggtggcg aaacccgaca   6720
ggactataaa gataccaggc gtttccccct ggaagctccc tcgtgcgctc tcctgttccg   6780
accctgccgc ttaccggata cctgtccgcc tttctccctt cgggaagcgt ggcgctttct   6840
catagctcac gctgtaggta tctcagttcg gtgtaggtcg ttcgctccaa gctgggctgt   6900
gtgcacgaac cccccgttca gcccgaccgc tgcgccttat ccggtaacta tcgtcttgag   6960
tccaacccgg taagacacga cttatcgcca ctggcagcag ccactggtaa caggattagc   7020
agagcgaggt atgtaggcgg tgctacagag ttcttgaagt ggtggcctaa ctacggctac   7080
actagaagaa cagtatttgg tatctgcgct ctgctgaagc cagttacctt cggaaaaaga   7140
gttggtagct cttgatccgg caaacaaacc accgctggta gcggtggttt ttttgtttgc   7200
aagcagcaga ttacgcgcag aaaaaaagga tctcaagaag atcctttgat cttttctacg   7260
gggtctgacg ctcagtggaa cgaaaactca cgttaaggga ttttggtcat gagattatca   7320
aaaaggatct tcacctagat ccttttaaat taaaaatgaa gttttaaatc aatctaaagt   7380
atatatgagt aaacttggtc tgacagttac caatgcttaa tcagtgaggc acctatctca   7440
gcgatctgtc tatttcgttc atccatagtt gcctgactcc ccgtcgtgta gataactacg   7500
atacgggagg gcttaccatc tggccccagt gctgcaatga taccgcgaga cccacgctca   7560
ccggctccag atttatcagc aataaaccag ccagccggaa gggccgagcg cagaagtggt   7620
cctgcaactt tatccgcctc catccagtct attaattgtt gccgggaagc tagagtaagt   7680
agttcgccag ttaatagttt gcgcaacgtt gttgccattg ctacaggcat cgtggtgtca   7740
cgctcgtcgt ttggtatggc ttcattcagc tccggttccc aacgatcaag gcgagttaca   7800
tgatccccca tgttgtgcaa aaaagcggtt agctccttcg gtcctccgat cgttgtcaga   7860
agtaagttgg ccgcagtgtt atcactcatg gttatggcag cactgcataa ttctcttact   7920
gtcatgccat ccgtaagatg cttttctgtg actggtgagt actcaaccaa gtcattctga   7980
gaatagtgta tgcggcgacc gagttgctct tgcccggcgt caatacggga taataccgcg   8040
ccacatagca gaactttaaa agtgctcatc attggaaaac gttcttcggg gcgaaaactc   8100
tcaaggatct taccgctgtt gagatccagt tcgatgtaac ccactcgtgc acccaactga   8160
```

tcttcagcat cttttacttt caccagcgtt tctgggtgag caaaaacagg aaggcaaaat 8220
gccgcaaaaa agggaataag ggcgacacgg aaatgttgaa tactcatact cttccttttt 8280
caatattatt gaagcattta tcagggttat tgtctcatga gcggatacat atttgaatgt 8340
atttagaaaa ataaacaaat aggggttccg cgcacatttc cccgaaaagt gccacctgac 8400
gtctaagaaa ccattattat catgacatta acctataaaa ataggcgtat cacgaggccc 8460
tttcgtctcg cgcgtttcgg tgatgacggt gaaaacctct gacacatgca gctcccggag 8520
acggtcacag cttgtctgta agcggatgcc gggagcagac aagcccgtca gggcgcgtca 8580
gcgggtgttg gcgggtgtcg gggctggctt aactatgcgg catcagagca gattgtactg 8640
agagtgcacc atatgcggtg tggaataccg cacagatgcg taaggagaaa ataccgcatc 8700
aggcgccatt cgccattcag gctgcgcaac tgttgggaag ggcgatcggt gcgggcctct 8760
tcgctattac gccagctggc gaaaggggga tgtgctgcaa ggcgattaag ttgggtaacg 8820
ccagggtttt cccagtcacg acgttgtaaa acgacggcca gtgaattgcg gccgcatcga 8880
tggaaaagac caaacggtga cgttaagaga aagaaattct atgaggcaag taagaggcac 8940
tattactgat gtgatttcga ccattgacaa aatgcttcac aaccctgatg aatcggactg 9000
ggataaatca acatttggac tgtcgcctgt taagatataa ctgaaaaaag aggggaattt 9060
ttagatactg aaatgatatt ttagaataac cagactatat ataaggataa attacaaaaa 9120
attaactaat agataagatt taaatataaa agatatgcaa ctagaaaagt cttatcaatc 9180
tcctta 9186

<210> SEQ ID NO 26
<211> LENGTH: 1665
<212> TYPE: DNA
<213> ORGANISM: Artificial Sequence
<220> FEATURE:
<223> OTHER INFORMATION: prenyl transferase

<400> SEQUENCE: 26
atgtctaaag gtgaagaatt attcactggt gttgtcccaa ttttggttga attagatggt 60
gatgttaatg gtcacaaatt ttctgtctcc ggtgaaggtg aaggtgatgc tacttacggt 120
aaattgacct taaaattgat ttgtactact ggtaaattgc cagttccatg gccaacctta 180
gtcactactt taggttatgg tttgcaatgt tttgctagat acccagatca tatgaaacaa 240
catgactttt tcaagtctgc catgccagaa ggttatgttc aagaaagaac tatttttttc 300
aaagatgacg gtaactacaa gaccagagct gaagtcaagt ttgaaggtga taccttagtt 360
aatagaatcg aattaaaagg tattgatttt aaagaagatg gtaacatttt aggtcacaaa 420
ttggaataca actataactc tcacaatgtt tacatcactg ctgacaaaca aaagaatggt 480
atcaaagcta acttcaaaat tagacacaac attgaagatg gtggtgttca attagctgac 540
cattatcaac aaaatactcc aattggtgat ggtccagtct tgttaccaga caaccattac 600
ttatcctatc aatctgcctt atccaaagat ccaaacgaaa agagagacca catggtcttg 660
ttagaatttg ttactgctgc tggtattacc catggtatgg atgaattgta caaaattgaa 720
ggttcaccac atcatgaatc tgataactca atcgcaacta aattttgaa ctttggtcat 780 acatgttgga aattgcaaag accatacgtt gttaagggta tgatttctat tgcttgtggt 840
ttatttggta gagaattgtt taataacaga catttgtttt cttggggttt gatgtggaaa 900
gcatttttcg cattagttcc aatcttgtct tttaatttct ttgctgcaat catgaaccaa 960
atatatgatg ttgatattga tagaattaat aagccagatt tgccattggt ttctggtgaa 1020

```
atgtcaatcg aaactgcttg gattttatct atcatcgttg cattgactgg tttgatcgtt   1080

acaattaaat taaaatcagc tccattgttc gtttttatat atatcttcgg tatcttcgct   1140

ggttttgcat actctgttcc accaattaga tggaagcaat acccttttac taatttcttg   1200

atcacaattt cttcacatgt tggtttggct tttacttctt actcagctac tacatctgca   1260

ttaggtttgc catttgtttg gaggccagct tttctcttta ttatcgcttt tatgactgtt   1320

atgggtatga caatcgcttt cgcaaaggat atctctgata ttgaaggtga cgctaaatac   1380

ggtgtttcaa ctgttgctac aaaattgggt gcaagaaaca tgactttcgt tgtttctggt   1440

gttttgttgt tgaactattt ggtttctatc tcaatcggta ttatttggcc acaagttttt   1500

aaatctaaca tcatgatctt gtcacatgct atcttggcat tctgtttgat cttccaaaca   1560

agagaattag ctttggcaaa ttatgcttct gcaccatcaa gacaattttt cgagtttatt   1620

tggttgttgt actacgctga atattttgtt tacgttttta tttga                   1665
```

```
<210> SEQ ID NO 27
<211> LENGTH: 554
<212> TYPE: PRT
<213> ORGANISM: Artificial Sequence
<220> FEATURE:
<223> OTHER INFORMATION: prenyl transferase

<400> SEQUENCE: 27

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Leu Ile Cys
        35                  40                  45

Thr Thr Gly Lys Leu Pro Val Pro Trp Pro Thr Leu Val Thr Thr Leu
    50                  55                  60

Gly Tyr Gly Leu Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Gly Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Tyr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys Ile Glu
225                 230                 235                 240

Gly Ser Pro His His Glu Ser Asp Asn Ser Ile Ala Thr Lys Ile Leu
```

```
                245                 250                 255

Asn Phe Gly His Thr Cys Trp Lys Leu Gln Arg Pro Tyr Val Val Lys
            260                 265                 270

Gly Met Ile Ser Ile Ala Cys Gly Leu Phe Gly Arg Glu Leu Phe Asn
        275                 280                 285

Asn Arg His Leu Phe Ser Trp Gly Leu Met Trp Lys Ala Phe Phe Ala
    290                 295                 300

Leu Val Pro Ile Leu Ser Phe Asn Phe Phe Ala Ala Ile Met Asn Gln
305                 310                 315                 320

Ile Tyr Asp Val Asp Ile Asp Arg Ile Asn Lys Pro Asp Leu Pro Leu
                325                 330                 335

Val Ser Gly Glu Met Ser Ile Glu Thr Ala Trp Ile Leu Ser Ile Ile
            340                 345                 350

Val Ala Leu Thr Gly Leu Ile Val Thr Ile Lys Leu Lys Ser Ala Pro
        355                 360                 365

Leu Phe Val Phe Ile Tyr Ile Phe Gly Ile Phe Ala Gly Phe Ala Tyr
    370                 375                 380

Ser Val Pro Pro Ile Arg Trp Lys Gln Tyr Pro Phe Thr Asn Phe Leu
385                 390                 395                 400

Ile Thr Ile Ser Ser His Val Gly Leu Ala Phe Thr Ser Tyr Ser Ala
                405                 410                 415

Thr Thr Ser Ala Leu Gly Leu Pro Phe Val Trp Arg Pro Ala Phe Ser
            420                 425                 430

Phe Ile Ile Ala Phe Met Thr Val Met Gly Met Thr Ile Ala Phe Ala
        435                 440                 445

Lys Asp Ile Ser Asp Ile Glu Gly Asp Ala Lys Tyr Gly Val Ser Thr
    450                 455                 460

Val Ala Thr Lys Leu Gly Ala Arg Asn Met Thr Phe Val Val Ser Gly
465                 470                 475                 480

Val Leu Leu Leu Asn Tyr Leu Val Ser Ile Ser Ile Gly Ile Ile Trp
                485                 490                 495

Pro Gln Val Phe Lys Ser Asn Ile Met Ile Leu Ser His Ala Ile Leu
            500                 505                 510

Ala Phe Cys Leu Ile Phe Gln Thr Arg Glu Leu Ala Leu Ala Asn Tyr
        515                 520                 525

Ala Ser Ala Pro Ser Arg Gln Phe Phe Glu Phe Ile Trp Leu Leu Tyr
    530                 535                 540

Tyr Ala Glu Tyr Phe Val Tyr Val Phe Ile
545                 550
```

<210> SEQ ID NO 28
<211> LENGTH: 717
<212> TYPE: DNA
<213> ORGANISM: Artificial Sequence
<220> FEATURE:
<223> OTHER INFORMATION: modified fluorescent protein yEVenus

<400> SEQUENCE: 28

```
atgtctaaag gtgaagaatt attcactggt gttgtcccaa ttttggttga attagatggt     60

gatgttaatg gtcacaaatt ttctgtctcc ggtgaaggtg aaggtgatgc tacttacggt    120

aaattgacct taaaattgat ttgtactact ggtaaattgc cagttccatg gccaacctta    180

gtcactactt taggttatgg tttgcaatgt tttgctagat acccagatca tatgaaacaa    240

catgactttt tcaagtctgc catgccagaa ggttatgttc aagaaagaac tatttttttc    300
```

-continued

```
aaagatgacg gtaactacaa gaccagagct gaagtcaagt ttgaaggtga taccttagtt    360

aatagaatcg aattaaaagg tattgatttt aaagaagatg gtaacatttt aggtcacaaa    420

ttggaataca actataactc tcacaatgtt tacatcactg ctgacaaaca aaagaatggt    480

atcaaagcta acttcaaaat tagacacaac attgaagatg gtggtgttca attagctgac    540

cattatcaac aaaatactcc aattggtgat ggtccagtct tgttaccaga caaccattac    600

ttatcctatc aatctgcctt atccaaagat ccaaacgaaa agagagacca catggtcttg    660

ttagaatttg ttactgctgc tggtattacc catggtatgg atgaattgta caaataa       717
```

<210> SEQ ID NO 29
<211> LENGTH: 9654
<212> TYPE: DNA
<213> ORGANISM: Artificial Sequence
<220> FEATURE:
<223> OTHER INFORMATION: bCBGA0385 vector

<400> SEQUENCE: 29

```
ttttctacgg ggtctgacgc tcagtggaac gaaaactcac gttaagggat tttggtcatg      60

agattatcaa aaaggatctt cacctagatc cttttaaatt aaaaatgaag ttttaaatca    120

atctaaagta tatatgagta aacttggtct gacagttacc aatgcttaat cagtgaggca    180

cctatctcag cgatctgtct atttcgttca tccatagttg cctgactccc cgtcgtgtag    240

ataactacga tacgggaggg cttaccatct ggccccagtg ctgcaatgat accgcgagac    300

ccacgctcac cggctccaga tttatcagca ataaaccagc cagccggaag ggccgagcgc    360

agaagtggtc ctgcaacttt atccgcctcc atccagtcta ttaattgttg ccgggaagct    420

agagtaagta gttcgccagt taatagtttg cgcaacgttg ttgccattgc tacaggcatc    480

gtggtgtcac gctcgtcgtt tggtatggct tcattcagct ccggttccca acgatcaagg    540

cgagttacat gatcccccat gttgtgcaaa aaagcggtta gctccttcgg tcctccgatc    600

gttgtcagaa gtaagttggc cgcagtgtta tcactcatgg ttatggcagc actgcataat    660

tctcttactg tcatgccatc cgtaagatgc ttttctgtga ctggtgagta ctcaaccaag    720

tcattctgag aatagtgtat gcggcgaccg agttgctctt gcccggcgtc aatacgggat    780

aataccgcgc cacatagcag aactttaaaa gtgctcatca ttggaaaacg ttcttcgggg    840

cgaaaactct caaggatctt accgctgttg agatccagtt cgatgtaacc cactcgtgca    900

cccaactgat cttcagcatc ttttactttc accagcgttt ctgggtgagc aaaaacagga    960

aggcaaaatg ccgcaaaaaa gggaataagg gcgacacgga aatgttgaat actcatactc   1020

ttcctttttc aatattattg aagcatttat cagggttatt gtctcatgag cggatacata   1080

tttgaatgta tttagaaaaa taaacaaata ggggttccgc gcacatttcc ccgaaaagtg   1140

ccacctgacg tctaagaaac cattattatc atgacattaa cctataaaaa taggcgtatc   1200

acgaggccct ttcgtctcgc gcgtttcggt gatgacggtg aaaacctctg acacatgcag   1260

ctcccggaga cggtcacagc ttgtctgtaa gcggatgccg ggagcagaca agcccgtcag   1320

ggcgcgtcag cgggtgttgg cgggtgtcgg ggctggctta actatgcggc atcagagcag   1380

attgtactga gagtgcacca tatgcggtgt ggaataccgc acagatgcgt aaggagaaaa   1440

taccgcatca ggcgccattc gccattcagg ctgcgcaact gttgggaagg gcgatcggtg   1500

cgggcctctt cgctattacg ccagctggcg aaagggggat gtgctgcaag gcgattaagt   1560

tgggtaacgc cagggttttc ccagtcacga cgttgtaaaa cgacggccag tgaattgcgg   1620

ccgcatcgat ggaaaagacc aaacggtgac gttaagagaa agaaattcta tgaggcaagt   1680
```

```
aagaggcact attactgatg tgatttcgac cattgacaaa atgcttcaca accctgatga   1740
atcggactgg gataaatcaa catttggact gtcgcctgtt aagatataac tgaaaaaaga   1800
ggggaatttt tagatactga aatgatattt tagaataacc agactatata taaggataaa   1860
ttacaaaaaa ttaactaata gataagattt aaatataaaa gatatgcaac tagaaaagtc   1920
ttatcaatct ccttattata ttgaattttc aaaaattctt actttttttt tggatggacg   1980
caaagaagtt taataatcat attacatggc attaccacca tatacatatc catatctaat   2040
cttacttata tgttgtggaa atgtaaagag ccccattatc ttagcctaaa aaaaccttct   2100
ctttggaact ttcagtaata cgcttaactg ctcattgcta tattgaagta cggattagaa   2160
gccgccgagc gggcgacagc cctccgacgg aagactctcc tccgtgcgtc ctcgtcttca   2220
ccggtcgcgt tcctgaaacg cagatgtgcc tcgcgccgca ctgctccgaa caataaagat   2280
tctacaatac tagcttttat ggttatgaag aggaaaaatt ggcagtaacc tggccccaca   2340
aaccttcaaa ttaacgaatc aaattaacaa ccataggatg ataatgcgat tagtttttta   2400
gccttatttc tggggtaatt aatcagcgaa gcgatgattt ttgatctatt aacagatata   2460
taaatggaaa agctgcataa ccactttaac taatactttc aacattttca gtttgtatta   2520
cttcttattc aaatgtcata aaagtatcaa caaaaaattg ttaatatacc tctatacttt   2580
aacgtcaagg agaaaaaact ataatgtcta aaggtgaaga attattcact ggtgttgtcc   2640
caattttggt tgaattagat ggtgatgtta atggtcacaa attttctgtc tccggtgaag   2700
gtgaaggtga tgctacttac ggtaaattga ccttaaaatt gatttgtact actggtaaat   2760
tgccagttcc atggccaacc ttagtcacta ctttaggtta tggtttgcaa tgttttgcta   2820
gatacccaga tcatatgaaa caacatgact ttttcaagtc tgccatgcca gaaggttatg   2880
ttcaagaaag aactattttt ttcaaagatg acggtaacta caagaccaga gctgaagtca   2940
agtttgaagg tgatacctta gttaatagaa tcgaattaaa aggtattgat tttaaagaag   3000
atggtaacat tttaggtcac aaattggaat acaactataa ctctcacaat gtttacatca   3060
ctgctgacaa acaaaagaat ggtatcaaag ctaacttcaa aattagacac aacattgaag   3120
atggtggtgt tcaattagct gaccattatc aacaaaatac tccaattggt gatggtccag   3180
tcttgttacc agacaaccat tacttatcct atcaatctgc cttatccaaa gatccaaacg   3240
aaaagagaga ccacatggtc ttgttagaat ttgttactgc tgctggtatt acccatggta   3300
tggatgaatt gtacaaaatt gaaggttcac cacatcatga atctgataac tcaatcgcaa   3360
ctaaaatttt gaactttggt catacatgtt ggaaattgca aagaccatac gttgttaagg   3420
gtatgatttc tattgcttgt ggtttatttg gtagagaatt gtttaataac agacatttgt   3480
tttcttgggg tttgatgtgg aaagcatttt tcgcattagt tccaatcttg tcttttaatt   3540
tctttgctgc aatcatgaac caaatatatg atgttgatat tgatagaatt aataagccag   3600
atttgccatt ggtttctggt gaaatgtcaa tcgaaactgc ttggatttta tctatcatcg   3660
ttgcattgac tggtttgatc gttacaatta aattaaaatc agctccattg ttcgttttta   3720
tatatatctt cggtatcttc gctggttttg catactctgt tccaccaatt agatggaagc   3780
aatacccttt tactaatttc ttgatcacaa tttcttcaca tgttggtttg gcttttactt   3840
cttactcagc tactacatct gcattaggtt tgccatttgt ttggaggcca gctttttctt   3900
ttattatcgc ttttatgact gttatgggta tgacaatcgc tttcgcaaag gatatctctg   3960
atattgaagg tgacgctaaa tacggtgttt caactgttgc tacaaaattg ggtgcaagaa   4020
```

```
acatgacttt cgttgtttct ggtgttttgt tgttgaacta tttggtttct atctcaatcg   4080

gtattatttg gccacaagtt tttaaatcta acatcatgat cttgtcacat gctatcttgg   4140

cattctgttt gatcttccaa acaagagaat tagctttggc aaattatgct tctgcaccat   4200

caagacaatt tttcgagttt atttggttgt tgtactacgc tgaatatttt gtttacgttt   4260

ttatttgaga ttaatataat tatataaaaa tattatcttc ttttctttat atctagtgtt   4320

atgtaaaata aattgatgac tacggaaagc ttttttatat tgtttctttt tcattctgag   4380

ccacttaaat ttcgtgaatg ttcttgtaag ggacggtaga tttacaagtg atacaacaaa   4440

aagcaaggcg ctttttctaa taaaaagaag aaaagcattt aacaattgaa cacctctata   4500

tcaacgaaga atattacttt gtctctaaat ccttgtaaaa tgtgtacgat ctctatatgg   4560

gttactcata agtgtaccga agactgcatt gaaagtttat gttttttcac tggaggcgtc   4620

attttcgcgt tgagaacaat tgtcctgtac ttccttgttc atgtgtgttc aaaaacgtta   4680

tatttatagg ataattatac tctatttctc aacaagtaat tggttgtttg gccgagcggt   4740

ctaaggcgcc tgattcaaga aatatcttga ccgcagttaa ctgtgggaat actcaggtat   4800

cgtaagatgc aagagttcga atctcttagc aaccattatt tttttcctca acataacgag   4860

aacacacagg ggcgctatcg cacagaatca aattcgatga ctggaaattt tttgttaatt   4920

tcagaggtcg cctgacgcat ataccttttt caactgaaaa attgggagaa aaaggaaagg   4980

tgagagcgcc ggaaccggct tttcatatag aatagagaag cgttcatgac taaatgcttg   5040

catcacaata cttgaagttg acaatattat ttaaggacct attgtttttt ccaataggtg   5100

gttagcaatc gtcttacttt ctaacttttc ttacctttta catttcagca atatatatat   5160

atatttcaag gatataccat tctaatgtct gcccctaaga agatcgtcgt tttgccaggt   5220

gaccacgttg gtcaagaaat cacagccgaa gccattaagg ttcttaaagc tatttctgat   5280

gttcgttcca atgtcaagtt cgatttcgaa aatcatttaa ttggtggtgc tgctatcgat   5340

gctacaggtg ttccacttcc agatgaggcg ctggaagcct ccaagaaggc tgatgccgtt   5400

ttgttaggtg ctgtgggtgg tcctaaatgg ggtaccggta gtgttagacc tgaacaaggt   5460

ttactaaaaa tccgtaaaga acttcaattg tacgccaact taagaccatg taactttgca   5520

tccgactctc ttttagactt atctccaatc aagccacaat ttgctaaaaa tactgacttc   5580

gttgttgtca gagaattagt gggaggtatt tactttggta agagaaagga agacgatggt   5640

gatggtgtcg cttgggatag tgaacaatac accgttccag aagtgcaaag aatcacaaga   5700

atggccgctt tcatggccct acaacatgag ccaccattgc ctatttggtc cttggataaa   5760

gctaatgttt tggcctcttc aagattatgg agaaaaactg tggaggaaac catcaagaac   5820

gaattcccta cattgaaggt tcaacatcaa ttgattgatt ctgccgccat gatcctagtt   5880

aagaacccaa cccacctaaa tggtattata atcaccagca acatgtttgg tgatatcatc   5940

tccgatgaag cctccgttat cccaggttcc ttgggtttgt tgccatctgc gtccttggcc   6000

tctttgccag acaagaacac cgcatttggt ttgtacgaac catgccacgg ttctgctcca   6060

gatttgccaa agaataaggt caaccctatc gccactatct tgtctgctgc aatgatgttg   6120

aaattgtcat tgaacttgcc tgaagaaggt aaggccattg aagatgcagt taaaaaggtt   6180

ttggatgcag gtatcagaac tggtgattta ggtggttcca acagtaccac cgaagtcggt   6240

gatgctgtcg ccgaagaagt taagaaaatc cttgcttaaa aagattctct ttttttatga   6300

tatttgtaca taaactttat aaatgaaatt cataatagaa acgacacgaa attacaaaat   6360

ggaatatgtt catagggtag acgaaactat atacgcaatc tacatacatt tatcaagaag   6420
```

```
gagaaaaagg aggatgtaaa ggaatacagg taagcaaatt gatactaatg gctcaacgtg   6480
ataaggaaaa agaattgcac tttaacatta atattgacaa ggaggagggc accacacaaa   6540
aagttacaga tctgctgcat taatgaatcg gccaacgcgc ggggagaggc ggtttgcgta   6600
ttgggcgctc ttccgcttcc tcgctcactg actcgctgcg ctcggtcgtt cggctgcggc   6660
gagcggtatc agcatcgatg aattccacgg actatagact atactagtat actccgtcta   6720
ctgtacgata cacttccgct caggtccttg tcctttaacg aggccttacc actcttttgt   6780
tactctattg atccagctca gcaaaggcag tgtgatctaa gattctatct tcgcgatgta   6840
gtaaaactag ctagaccgag aaagagacta gaaatgcaaa aggcacttct acaatggctg   6900
ccatcattat tatccgatgt gacgctgcag cttctcaatg atattcgaat acgctttgag   6960
gagatacagc ctaatatccg acaaactgtt ttacagattt acgatcgtat ttgttaccca   7020
tcattgaatt ttgaacatcc gaacctggga gttttccctg aaacagatag tatatttgaa   7080
cctgtataat aatatatagt ctagcgcttt acggaagaca atgtatgtat ttcggttcct   7140
ggagaaacta ttgcatctat tgcataggta atcttgcacg tcgcatcccc ggttcatttt   7200
ctgcgtttcc atcttgcact tcaatagcat atctttgtta acgaagcatc tgtgcttcat   7260
tttgtagaac aaaaatgcaa cgcgagagcg ctaatttttc aaacaaagaa tctgagctgc   7320
atttttacag aacagaaatg caacgcgaaa gcgctatttt accaacgaag aatctgtgct   7380
tcatttttgt aaaacaaaaa tgcaacgcga gagcgctaat ttttcaaaca aagaatctga   7440
gctgcatttt tacagaacag aaatgcaacg cgagagcgct attttaccaa caaagaatct   7500
atacttcttt tttgttctac aaaaatgcat cccgagagcg ctatttttct aacaaagcat   7560
cttagattac tttttttctc ctttgtgcgc tctataatgc agtctcttga taactttttg   7620
cactgtaggt ccgttaaggt tagaagaagg ctactttggt gtctattttc tcttccataa   7680
aaaaagcctg actccacttc ccgcgtttac tgattactag cgaagctgcg ggtgcatttt   7740
ttcaagataa aggcatcccc gattatattc tataccgatg tggattgcgc atactttgtg   7800
aacagaaagt gatagcgttg atgattcttc attggtcaga aaattatgaa cggtttcttc   7860
tattttgtct ctatatacta cgtataggaa atgtttacat tttcgtattg ttttcgattc   7920
actctatgaa tagttcttac tacaattttt ttgtctaaag agtaatacta gagataaaca   7980
taaaaaatgt agaggtcgag tttagatgca agttcaagga gcgaaaggtg gatgggtagg   8040
ttatataggg atatagcaca gagatatata gcaaagagat acttttgagc aatgtttgtg   8100
gaagcggtat tcgcaatatt ttagtagctc gttacagtcc ggtgcgtttt tggttttttg   8160
aaagtgcgtc ttcagagcgc ttttggtttt caaaagcgct ctgaagttcc tatactttct   8220
agagaatagg aacttcggaa taggaacttc aaagcgtttc cgaaaacgag cgcttccgaa   8280
aatgcaacgc gagctgcgca catacagctc actgttcacg tcgcacctat atctgcgtgt   8340
tgcctgtata tatatataca tgagaagaac ggcatagtgc gtgtttatgc ttaaatgcgt   8400
acttatatgc gtctatttat gtaggatgaa aggtagtcta gtacctcctg tgatattatc   8460
ccattccatg cggggtatcg tatgcttcct tcagcactac cctttagctg ttctatatgc   8520
tgccactcct caattggatt agtctcatcc ttcaatgcta tcatttcctt tgatattgga   8580
tcatatgcat agtaccgaga aactagtgcg aagtagtgat caggtattgc tgttatctga   8640
tgagtatacg ttgtcctggc cacggcagaa gcacgcttat cgctccaatt tcccacaaca   8700
ttagtcaact ccgttaggcc cttcattgaa agaaatgagg tcatcaaatg tcttccaatg   8760
```

```
tgagattttg ggccattttt tatagcaaag attgaataag gcgcattttt cttcaaagct   8820

ttattgtacg atctgactaa gttatctttt aataattggt attcctgttt attgcttgaa   8880

gaattgccgg tcctatttac tcgttttagg actggttcag aattcatcga tgctcactca   8940

aaggcggtaa tacggttatc cacagaatca ggggataacg caggaaagaa catgtgagca   9000

aaaggccagc aaaaggccag gaaccgtaaa aaggccgcgt tgctggcgtt tttccatagg   9060

ctccgccccc ctgacgagca tcacaaaaat cgacgctcaa gtcagaggtg gcgaaacccg   9120

acaggactat aaagatacca ggcgtttccc cctggaagct ccctcgtgcg ctctcctgtt   9180

ccgaccctgc cgcttaccgg atacctgtcc gcctttctcc cttcgggaag cgtggcgctt   9240

tctcatagct cacgctgtag gtatctcagt tcggtgtagg tcgttcgctc caagctgggc   9300

tgtgtgcacg aaccccccgt tcagcccgac cgctgcgcct tatccggtaa ctatcgtctt   9360

gagtccaacc cggtaagaca cgacttatcg ccactggcag cagccactgg taacaggatt   9420

agcagagcga ggtatgtagg cggtgctaca gagttcttga agtggtggcc taactacggc   9480

tacactagaa gaacagtatt tggtatctgc gctctgctga agccagttac cttcggaaaa   9540

agagttggta gctcttgatc cggcaaacaa accaccgctg gtagcggtgg tttttttgtt   9600

tgcaagcagc agattacgcg cagaaaaaaa ggatctcaag aagatccttt gatc         9654
```

```
<210> SEQ ID NO 30
<211> LENGTH: 9067
<212> TYPE: DNA
<213> ORGANISM: Artificial Sequence
<220> FEATURE:
<223> OTHER INFORMATION: bCBGA0305 vector

<400> SEQUENCE: 30

taagattaat ataattatat aaaaatatta tcttcttttc tttatatcta gtgttatgta     60

aaataaattg atgactacgg aaagcttttt tatattgttt ctttttcatt ctgagccact    120

taaatttcgt gaatgttctt gtaagggacg gtagatttac aagtgataca acaaaaagca    180

aggcgctttt tctaataaaa agaagaaaag catttaacaa ttgaacacct ctatatcaac    240

gaagaatatt actttgtctc taaatccttg taaaatgtgt acgatctcta tatgggttac    300

tcataagtgt accgaagact gcattgaaag tttatgtttt ttcactggag gcgtcatttt    360

cgcgttgaga aaattcggtc gaaaaaagaa aaggagaggg ccaagaggga gggcattggt    420

gactattgag cacgtgagta tatacgtgat taagcacaca aaggcagctt ggagttatgt    480

ctgttattaa tttcacaggt agttctggtc cattggtgaa agtttgcggc ttgcagagca    540

cagaggccgc agaatgtgct ctagattccg atgctgactt gctgggtatt atatgtgtgc    600

ccaatagaaa gagaacaatt gacccggtta ttgcaaggaa aatttcaagt cttgtaaaag    660

catataaaaa tagttcaggc actccgaaat acttggttgg cgtgtttcgt aatcaaccta    720

aggaggatgt tttggctctg gtcaatgatt acggcattga tatcgtccaa ctgcatggag    780

atgagtcgtg gcaagaatac caagagttcc tcggtttgcc agttattaaa agactcgtat    840

ttccaaaaga ctgcaacata ctactcagtg cagcttcaca gaaacctcac tcgtttattc    900

ccttgtttga ttcagaagca ggtgggacag gtgaactttt ggattggaac tcgatttctg    960

actgggttgg aaggcaagag agccccgaaa gtttacattt tatgttagct ggtggactga   1020

cgccagaaaa tgttggtgat gcgcttagat taaatggcgt tattggtgtt gatgtaagcg   1080

gaggtgtgga gacaaatggt gtaaaagact ctaacaaaat agcaaatttc gtcaaaaatg   1140

ctaagaaata ggttattact gagtagtatt tatttaagta ttgtttgtgc acttgcccag   1200
```

```
atctgctgca ttaatgaatc ggccaacgcg cggggagagg cggtttgcgt attgggcgct   1260
cttccgcttc ctcgctcact gactcgctgc gctcggtcgt tcggctgcgg cgagcggtat   1320
cagcatcgat gaattccacg gactatagac tatactagta tactccgtct actgtacgat   1380
acacttccgc tcaggtcctt gtcctttaac gaggccttac cactcttttg ttactctatt   1440
gatccagctc agcaaaggca gtgtgatcta agattctatc ttcgcgatgt agtaaaacta   1500
gctagaccga gaaagagact agaaatgcaa aaggcacttc tacaatggct gccatcatta   1560
ttatccgatg tgacgctgca gcttctcaat gatattcgaa tacgctttga ggagatacag   1620
cctaatatcc gacaaactgt tttacagatt tacgatcgta tttgttaccc atcattgaat   1680
tttgaacatc cgaacctggg agttttccct gaaacagata gtatatttga acctgtataa   1740
taatatatag tctagcgctt tacggaagac aatgtatgta tttcggttcc tggagaaact   1800
attgcatcta ttgcataggt aatcttgcac gtcgcatccc cggttcattt tctgcgtttc   1860
catcttgcac ttcaatagca tatctttgtt aacgaagcat ctgtgcttca ttttgtagaa   1920
caaaaatgca acgcgagagc gctaattttt caaacaaaga atctgagctg catttttaca   1980
gaacagaaat gcaacgcgaa agcgctattt taccaacgaa gaatctgtgc ttcatttttg   2040
taaaacaaaa atgcaacgcg agagcgctaa tttttcaaac aaagaatctg agctgcattt   2100
ttacagaaca gaaatgcaac gcgagagcgc tattttacca acaaagaatc tatacttctt   2160
ttttgttcta caaaaatgca tcccgagagc gctatttttc taacaaagca tcttagatta   2220
cttttttct cctttgtgcg ctctataatg cagtctcttg ataacttttt gcactgtagg   2280
tccgttaagg ttagaagaag gctactttgg tgtctatttt ctcttccata aaaaaagcct   2340
gactccactt cccgcgttta ctgattacta gcgaagctgc gggtgcattt tttcaagata   2400
aaggcatccc cgattatatt ctataccgat gtggattgcg catactttgt gaacagaaag   2460
tgatagcgtt gatgattctt cattggtcag aaaattatga acggtttctt ctattttgtc   2520
tctatatact acgtatagga aatgtttaca ttttcgtatt gttttcgatt cactctatga   2580
atagttctta ctacaatttt tttgtctaaa gagtaatact agagataaac ataaaaaatg   2640
tagaggtcga gtttagatgc aagttcaagg agcgaaaggt ggatgggtag gttatatagg   2700
gatatagcac agagatatat agcaaagaga tacttttgag caatgtttgt ggaagcggta   2760
ttcgcaatat tttagtagct cgttacagtc cggtgcgttt ttggtttttt gaaagtgcgt   2820
cttcagagcg cttttggttt tcaaaagcgc tctgaagttc ctatactttc tagagaatag   2880
gaacttcgga ataggaactt caaagcgttt ccgaaaacga gcgcttccga aaatgcaacg   2940
cgagctgcgc acatacagct cactgttcac gtcgcaccta tatctgcgtg ttgcctgtat   3000
atatatatac atgagaagaa cggcatagtg cgtgtttatg cttaaatgcg tacttatatg   3060
cgtctattta tgtaggatga aaggtagtct agtacctcct gtgatattat cccattccat   3120
gcggggtatc gtatgcttcc ttcagcacta ccctttagct gttctatatg ctgccactcc   3180
tcaattggat tagtctcatc cttcaatgct atcatttcct ttgatattgg atcatatgca   3240
tagtaccgag aaactagtgc gaagtagtga tcaggtattg ctgttatctg atgagtatac   3300
gttgtcctgg ccacggcaga agcacgctta tcgctccaat ttcccacaac attagtcaac   3360
tccgttaggc ccttcattga aagaaatgag gtcatcaaat gtcttccaat gtgagatttt   3420
gggccatttt ttatagcaaa gattgaataa ggcgcatttt tcttcaaagc tttattgtac   3480
gatctgacta agttatcttt taataattgg tattcctgtt tattgcttga agaattgccg   3540
```

```
gtcctattta ctcgttttag gactggttca gaattcatcg atgctcactc aaaggcggta   3600
atacggttat ccacagaatc aggggataac gcaggaaaga acatgtgagc aaaaggccag   3660
caaaaggcca ggaaccgtaa aaaggccgcg ttgctggcgt ttttccatag gctccgcccc   3720
cctgacgagc atcacaaaaa tcgacgctca agtcagaggt ggcgaaaccc gacaggacta   3780
taaagatacc aggcgtttcc ccctggaagc tccctcgtgc gctctcctgt tccgaccctg   3840
ccgcttaccg gatacctgtc cgcctttctc ccttcgggaa gcgtggcgct ttctcatagc   3900
tcacgctgta ggtatctcag ttcggtgtag gtcgttcgct ccaagctggg ctgtgtgcac   3960
gaaccccccg ttcagcccga ccgctgcgcc ttatccggta actatcgtct tgagtccaac   4020
ccggtaagac acgacttatc gccactggca gcagccactg gtaacaggat tagcagagcg   4080
aggtatgtag gcggtgctac agagttcttg aagtggtggc ctaactacgg ctacactaga   4140
agacagtatt tggtatctgc gctctgctga agccagttac cttcggaaaa agagttggta   4200
gctcttgatc cggcaaacaa accaccgctg gtagcggtgg tttttttgtt tgcaagcagc   4260
agattacgcg cagaaaaaaa ggatctcaag aagatccttt gatcttttct acggggtctg   4320
acgctcagtg gaacgaaaac tcacgttaag ggattttggt catgagatta tcaaaaagga   4380
tcttcaccta gatcctttta aattaaaaat gaagttttaa atcaatctaa agtatatatg   4440
agtaaacttg gtctgacagt taccaatgct taatcagtga ggcacctatc tcagcgatct   4500
gtctatttcg ttcatccata gttgcctgac tccccgtcgt gtagataact acgatacggg   4560
agggcttacc atctggcccc agtgctgcaa tgataccgcg agacccacgc tcaccggctc   4620
cagatttatc agcaataaac cagccagccg gaagggccga gcgcagaagt ggtcctgcaa   4680
ctttatccgc ctccatccag tctattaatt gttgccggga agctagagta agtagttcgc   4740
cagttaatag tttgcgcaac gttgttgcca ttgctacagg catcgtggtg tcacgctcgt   4800
cgtttggtat ggcttcattc agctccggtt cccaacgatc aaggcgagtt acatgatccc   4860
ccatgttgtg caaaaaagcg gttagctcct tcggtcctcc gatcgttgtc agaagtaagt   4920
tggccgcagt gttatcactc atggttatgg cagcactgca taattctctt actgtcatgc   4980
catccgtaag atgcttttct gtgactggtg agtactcaac caagtcattc tgagaatagt   5040
gtatgcggcg accgagttgc tcttgcccgg cgtcaatacg ggataatacc gcgccacata   5100
gcagaacttt aaaagtgctc atcattggaa aacgttcttc ggggcgaaaa ctctcaagga   5160
tcttaccgct gttgagatcc agttcgatgt aacccactcg tgcacccaac tgatcttcag   5220
catcttttac tttcaccagc gtttctgggt gagcaaaaac aggaaggcaa aatgccgcaa   5280
aaaagggaat aagggcgaca cggaaatgtt gaatactcat actcttcctt tttcaatatt   5340
attgaagcat ttatcagggt tattgtctca tgagcggata catatttgaa tgtatttaga   5400
aaaataaaca aataggggtt ccgcgcacat ttccccgaaa agtgccacct gacgtctaag   5460
aaaccattat tatcatgaca ttaacctata aaaataggcg tatcacgagg ccctttcgtc   5520
tcgcgcgttt cggtgatgac ggtgaaaacc tctgacacat gcagctcccg gagacggtca   5580
cagcttgtct gtaagcggat gccgggagca gacaagcccg tcagggcgcg tcagcgggtg   5640
ttggcgggtg tcggggctgg cttaactatg cggcatcaga gcagattgta ctgagagtgc   5700
accatatgcg gtgtgaaata ccgcacagat gcgtaaggag aaaataccgc atcaggcgcc   5760
attcgccatt caggctgcgc aactgttggg aagggcgatc ggtgcgggcc tcttcgctat   5820
tacgccagct ggcgaaaggg ggatgtgctg caaggcgatt aagttgggta acgccagggt   5880
tttcccagtc acgacgttgt aaaacgacgg ccagtgaatt gcggccgcat cgatggaaaa   5940
```

```
gaccaaacgg tgacgttaag agaaagaaat tctatgaggc aagtaagagg cactattact   6000
gatgtgattt cgaccattga caaaatgctt cacaaccctg atgaatcgga ctgggataaa   6060
tcaacatttg gactgtcgcc tgttaagata taactgaaaa aagaggggaa tttttagata   6120
ctgaaatgat attttagaat aaccagacta tatataagga taaattacaa aaaattaact   6180
aatagataag atttaaatat aaaagatatg caactagaaa agtcttatca atctccttat   6240
tcaaaatgag aaaattgttg tctcaagact cttctcatga tcttatttgt agcagttctt   6300
ggcaaagatg acaatggaac aactctagta actttaaaca atgggttcaa tttcttttgt   6360
aaacccaaat taaaagacaa tctcaattgg ttcaaatcaa ttgtagtatc atttgaatct   6420
ttcaaaacaa agaaaataac caattgttct ggaccaccac ctaatggtgg aacaccaata   6480
gctgtagttt caaaaactct atcatcaact tcgttacaaa ctctttcgat ttcgatagat   6540
gagattttaa taccaccaat attcattgta tcatcagctc taccatgtgc atggtagtaa   6600
ccgttagaag tcaattcgaa gatgtcacca tgtcttctca aaacttcacc attcaatgtt   6660
ggcataccct tgaagtaaac atcatgatgg ttaccgttca acaaagtctt tgaagcaccg   6720
aacataactg gacctaatgc caattcacca atacctggct tatttttagg cattgggtaa   6780
ccgttcttat ccaagatgta caatgtacaa cccatacatt gagatgaaaa agatgacaaa   6840
gattgagctt gcaaaaatga accagctgaa aatgcaccac caatttcagt accaccacac   6900
atttcaataa ctggcttgta gttagctcta cccatcaacc acaaatattc atcaacgtta   6960
gatgcttcac cagatgaaga gaaacatctg attgtagacc aatcgtaacc tgaaacacag   7020
ttagtagact tccatgatct aacgattgat ggaacaacac ccaacattgt aaccttagca   7080
tcttgaacga actttgcgaa accagaaacc aatggtgaac cgttgtacaa agcgatagat   7140
gcaccgttca acaatgaagc ataaaccaac catggaccca tcatccaacc caaattagtt   7200
ggccaaacaa taacgtcacc ttttctaata tccaaatgtg accaaccatc agctgcagct   7260
tttaatggtg tagcttgagt ccatggaatt gcttttggtt cacctgtagt acctgaagaa   7320
aacaagatgt ttgtgtaagc atcaactggt tgttctcttg cagtgaattc acagtttttg   7380
aattccttag ctctttccaa aaagtaatcc catgaaatgt caccatctct taattctgca   7440
ccaatgttag aacctgaaca tgggataacg atagccattg gagactttgc ttcaacaact   7500
cttgagtaca atggaattct ctttttacct ctaatgatat gatcttgtgt aaaaatagcc   7560
tttgccttag acaatctcaa tctagttgag atttctggag cagaaaatga atctgcaata   7620
gaaacaacaa cgtaaccagc caaaacgatt gccaaatata taacaacagc atcaacatgc   7680
attggcatat caatagcaat tgcacaacct tttccaaac ccatttcttc taatgcgtaa   7740
ccaaccaacc aaactctttt tctcaattga tccaatgtca acttattcaa tggcaaatca   7800
tcgttaccct catctctcca aacgatcata gtatcgttca atttcttatt agagttaacg   7860
ttcaaacaat ttttagctga attcaaataa ccacctggca accattcaga accacctgga   7920
ttgttgatat catctcttct caagatacat tctggatctt tagaaaatga gatcttcatt   7980
tcatccatca aaactgttct ccagtaaact tctgggtttc taacagaaaa ttcttgaaaa   8040
tgtgaaaatg aagagattgg atctttgtac ttaacaccca agaattcttt acctctcttt   8100
tccaacaaag cacccaaatt agtagactta accttttctg gatctggaat ccaagctggt   8160
ggtgctggac cgaaatcctt gtaacaacca taaaacaaca tttgatgcaa agaaaatggc   8220
aaatctggtg acaagatatg gtttgcgatg ttgatccatg tttgtggagt tgcagcaccg   8280
```

```
tagttacaaa cgatttcagc caatctacca tgcaatgttt ctgcaacttc agaagtaata   8340

cccaaagcaa tgaaatctga tgcaacaaca gaatccaatg acttgtaatt tttacccatt   8400

tatattgaat tttcaaaaat tcttactttt tttttggatg gacgcaaaga agtttaataa   8460

tcatattaca tggcattacc accatataca tatccatatc taatcttact tatatgttgt   8520

ggaaatgtaa agagccccat tatcttagcc taaaaaaacc ttctctttgg aactttcagt   8580

aatacgctta actgctcatt gctatattga agtacggatt agaagccgcc gagcgggcga   8640

cagccctccg acggaagact ctcctccgtg cgtcctcgtc ttcaccggtc gcgttcctga   8700

aacgcagatg tgcctcgcgc cgcactgctc cgaacaataa agattctaca atactagctt   8760

ttatggttat gaagaggaaa aattggcagt aacctggccc cacaaacctt caaattaacg   8820

aatcaaatta acaaccatag gatgataatg cgattagttt tttagcctta tttctggggt   8880

aattaatcag cgaagcgatg atttttgatc tattaacaga tatataaatg gaaaagctgc   8940

ataaccactt taactaatac tttcaacatt ttcagtttgt attacttctt attcaaatgt   9000

cataaaagta tcaacaaaaa attgttaata tacctctata ctttaacgtc aaggagaaaa   9060

aactata                                                             9067
```

```
<210> SEQ ID NO 31
<211> LENGTH: 2037
<212> TYPE: DNA
<213> ORGANISM: Artificial Sequence
<220> FEATURE:
<223> OTHER INFORMATION: ERG20mut-dPT

<400> SEQUENCE: 31

atggcttcag aaaaagaaat taggagagag agattcttga acgttttccc taaattagta     60

gaggaattga acgcatcgct tttggcttac ggtatgccta aggaagcatg tgactggtat    120

gcccactcat tgaactacaa cactccaggc ggtaagctaa atagaggttt gtccgttgtg    180

gacacgtatg ctattctctc caacaagacc gttgaacaat tggggcaaga agaatacgaa    240

aaggttgcca ttctaggttg gtgcattgag ttgttgcagg cttactggtt ggtcgccgat    300

gatatgatgg acaagtccat taccagaaga ggccaaccat gttggtacaa ggttcctgaa    360

gttggggaaa ttgccatctg ggacgcattc atgttagagg ctgctatcta caagcttttg    420

aaatctcact tcagaaacga aaaatactac atagatatca ccgaattgtt ccatgaggtc    480

accttccaaa ccgaattggg ccaattgatg gacttaatca ctgcacctga agacaaagtc    540

gacttgagta agttctccct aaagaagcac tccttcatag ttactttcaa gactgcttac    600

tattctttct acttgcctgt cgcattggcc atgtacgttg ccggtatcac ggatgaaaag    660

gatttgaaac aagccagaga tgtcttgatt ccattgggtg aatacttcca aattcaagat    720

gactacttag actgcttcgg taccccagaa cagatcggta agatcggtac agatatccaa    780

gataacaaat gttcttgggt aatcaacaag gcattggaac ttgcttccgc agaacaaaga    840

aagactttag acgaaaatta cggtaagaag gactcagtcg cagaagccaa atgcaaaaag    900

attttcaatg acttgaaaat tgaacagcta taccacgaat atgaagagtc tattgccaag    960

gatttgaagg ccaaaatttc tcaggtcgat gagtctcgtg gcttcaaagc tgatgtctta   1020

actgcgttct tgaacaaagt ttacaagaga agcaaaggta gcggcagcgg tagcggtagc   1080

ggcagcattg aaggttcacc acatcatgaa tctgataact caatcgcaac taaaattttg   1140

aactttggtc atacatgttg gaaattgcaa agaccatacg ttgttaaggg tatgatttct   1200

attgcttgtg gtttatttgg tagagaattg tttaataaca gacatttgtt ttcttggggt   1260
```

```
ttgatgtgga aagcattttt cgcattagtt ccaatcttgt cttttaattt ctttgctgca   1320

atcatgaacc aaatatatga tgttgatatt gatagaatta ataagccaga tttgccattg   1380

gtttctggtg aaatgtcaat cgaaactgct tggattttat ctatcatcgt tgcattgact   1440

ggtttgatcg ttacaattaa attaaaatca gctccattgt tcgtttttat atatatcttc   1500

ggtatcttcg ctggttttgc atactctgtt ccaccaatta gatggaagca ataccctttt   1560

actaatttct tgatcacaat ttcttcacat gttggtttgg cttttacttc ttactcagct   1620

actacatctg cattaggttt gccatttgtt tggaggccag ctttttcttt tattatcgct   1680

tttatgactg ttatgggtat gacaatcgct ttcgcaaagg atatctctga tattgaaggt   1740

gacgctaaat acggtgtttc aactgttgct acaaaattgg gtgcaagaaa catgactttc   1800

gttgtttctg gtgttttgtt gttgaactat ttggtttcta tctcaatcgg tattatttgg   1860

ccacaagttt ttaaatctaa catcatgatc ttgtcacatg ctatcttggc attctgtttg   1920

atcttccaaa caagagaatt agctttggca aattatgctt ctgcaccatc aagacaattt   1980

ttcgagttta tttggttgtt gtactacgct gaatattttg tttacgtttt tatttga      2037
```

<210> SEQ ID NO 32
<211> LENGTH: 678
<212> TYPE: PRT
<213> ORGANISM: Artificial Sequence
<220> FEATURE:
<223> OTHER INFORMATION: ERG20mut-dPT

<400> SEQUENCE: 32

```
Met Ala Ser Glu Lys Glu Ile Arg Arg Glu Arg Phe Leu Asn Val Phe
1               5                   10                  15

Pro Lys Leu Val Glu Glu Leu Asn Ala Ser Leu Leu Ala Tyr Gly Met
            20                  25                  30

Pro Lys Glu Ala Cys Asp Trp Tyr Ala His Ser Leu Asn Tyr Asn Thr
        35                  40                  45

Pro Gly Gly Lys Leu Asn Arg Gly Leu Ser Val Val Asp Thr Tyr Ala
    50                  55                  60

Ile Leu Ser Asn Lys Thr Val Glu Gln Leu Gly Gln Glu Glu Tyr Glu
65                  70                  75                  80

Lys Val Ala Ile Leu Gly Trp Cys Ile Glu Leu Leu Gln Ala Tyr Trp
                85                  90                  95

Leu Val Ala Asp Asp Met Met Asp Lys Ser Ile Thr Arg Arg Gly Gln
            100                 105                 110

Pro Cys Trp Tyr Lys Val Pro Glu Val Gly Glu Ile Ala Ile Trp Asp
        115                 120                 125

Ala Phe Met Leu Glu Ala Ala Ile Tyr Lys Leu Leu Lys Ser His Phe
    130                 135                 140

Arg Asn Glu Lys Tyr Tyr Ile Asp Ile Thr Glu Leu Phe His Glu Val
145                 150                 155                 160

Thr Phe Gln Thr Glu Leu Gly Gln Leu Met Asp Leu Ile Thr Ala Pro
                165                 170                 175

Glu Asp Lys Val Asp Leu Ser Lys Phe Ser Leu Lys Lys His Ser Phe
            180                 185                 190

Ile Val Thr Phe Lys Thr Ala Tyr Tyr Ser Phe Tyr Leu Pro Val Ala
        195                 200                 205

Leu Ala Met Tyr Val Ala Gly Ile Thr Asp Glu Lys Asp Leu Lys Gln
    210                 215                 220
```

-continued

```
Ala Arg Asp Val Leu Ile Pro Leu Gly Glu Tyr Phe Gln Ile Gln Asp
225                 230                 235                 240

Asp Tyr Leu Asp Cys Phe Gly Thr Pro Glu Gln Ile Gly Lys Ile Gly
                245                 250                 255

Thr Asp Ile Gln Asp Asn Lys Cys Ser Trp Val Ile Asn Lys Ala Leu
            260                 265                 270

Glu Leu Ala Ser Ala Glu Gln Arg Lys Thr Leu Asp Glu Asn Tyr Gly
        275                 280                 285

Lys Lys Asp Ser Val Ala Glu Ala Lys Cys Lys Lys Ile Phe Asn Asp
    290                 295                 300

Leu Lys Ile Glu Gln Leu Tyr His Glu Tyr Glu Glu Ser Ile Ala Lys
305                 310                 315                 320

Asp Leu Lys Ala Lys Ile Ser Gln Val Asp Glu Ser Arg Gly Phe Lys
                325                 330                 335

Ala Asp Val Leu Thr Ala Phe Leu Asn Lys Val Tyr Lys Arg Ser Lys
            340                 345                 350

Gly Ser Gly Ser Gly Ser Gly Ser Gly Ser Ile Glu Gly Ser Pro His
        355                 360                 365

His Glu Ser Asp Asn Ser Ile Ala Thr Lys Ile Leu Asn Phe Gly His
    370                 375                 380

Thr Cys Trp Lys Leu Gln Arg Pro Tyr Val Val Lys Gly Met Ile Ser
385                 390                 395                 400

Ile Ala Cys Gly Leu Phe Gly Arg Glu Leu Phe Asn Asn Arg His Leu
                405                 410                 415

Phe Ser Trp Gly Leu Met Trp Lys Ala Phe Phe Ala Leu Val Pro Ile
            420                 425                 430

Leu Ser Phe Asn Phe Phe Ala Ala Ile Met Asn Gln Ile Tyr Asp Val
        435                 440                 445

Asp Ile Asp Arg Ile Asn Lys Pro Asp Leu Pro Leu Val Ser Gly Glu
    450                 455                 460

Met Ser Ile Glu Thr Ala Trp Ile Leu Ser Ile Ile Val Ala Leu Thr
465                 470                 475                 480

Gly Leu Ile Val Thr Ile Lys Leu Lys Ser Ala Pro Leu Phe Val Phe
                485                 490                 495

Ile Tyr Ile Phe Gly Ile Phe Ala Gly Phe Ala Tyr Ser Val Pro Pro
            500                 505                 510

Ile Arg Trp Lys Gln Tyr Pro Phe Thr Asn Phe Leu Ile Thr Ile Ser
        515                 520                 525

Ser His Val Gly Leu Ala Phe Thr Ser Tyr Ser Ala Thr Thr Ser Ala
    530                 535                 540

Leu Gly Leu Pro Phe Val Trp Arg Pro Ala Phe Ser Phe Ile Ile Ala
545                 550                 555                 560

Phe Met Thr Val Met Gly Met Thr Ile Ala Phe Ala Lys Asp Ile Ser
                565                 570                 575

Asp Ile Glu Gly Asp Ala Lys Tyr Gly Val Ser Thr Val Ala Thr Lys
            580                 585                 590

Leu Gly Ala Arg Asn Met Thr Phe Val Val Ser Gly Val Leu Leu Leu
        595                 600                 605

Asn Tyr Leu Val Ser Ile Ser Ile Gly Ile Ile Trp Pro Gln Val Phe
    610                 615                 620

Lys Ser Asn Ile Met Ile Leu Ser His Ala Ile Leu Ala Phe Cys Leu
625                 630                 635                 640

Ile Phe Gln Thr Arg Glu Leu Ala Leu Ala Asn Tyr Ala Ser Ala Pro
```

```
                645                 650                 655

Ser Arg Gln Phe Phe Glu Phe Ile Trp Leu Leu Tyr Tyr Ala Glu Tyr
            660                 665                 670

Phe Val Tyr Val Phe Ile
        675
```

<210> SEQ ID NO 33
<211> LENGTH: 9996
<212> TYPE: DNA
<213> ORGANISM: Artificial Sequence
<220> FEATURE:
<223> OTHER INFORMATION: bCBGA0559 vector

<400> SEQUENCE: 33

```
attgaaggtt caccacatca tgaatctgat aactcaatcg caactaaaat tttgaacttt      60
ggtcatacat gttggaaatt gcaaagacca tacgttgtta agggtatgat ttctattgct     120
tgtggtttat ttggtagaga attgtttaat aacagacatt tgttttcttg ggtttgatg      180
tggaaagcat tttcgcatt agttccaatc ttgtctttta atttctttgc tgcaatcatg      240
aaccaaatat atgatgttga tattgataga attaataagc cagatttgcc attggtttct     300
ggtgaaatgt caatcgaaac tgcttggatt ttatctatca tcgttgcatt gactggtttg     360
atcgttacaa ttaaattaaa atcagctcca ttgttcgttt ttatatatat cttcggtatc     420
ttcgctggtt ttgcatactc tgttccacca attagatgga agcaataccc ttttactaat     480
ttcttgatca caatttcttc acatgttggt ttggctttta cttcttactc agctactaca     540
tctgcattag gtttgccatt tgtttggagg ccagcttttt cttttattat cgcttttatg     600
actgttatgg gtatgacaat cgctttcgca aaggatatct ctgatattga aggtgacgct     660
aaatacggtg tttcaactgt tgctacaaaa ttgggtgcaa gaaacatgac tttcgttgtt     720
tctggtgttt tgttgttgaa ctatttggtt tctatctcaa tcggtattat ttggccacaa     780
gtttttaaat ctaacatcat gatcttgtca catgctatct tggcattctg tttgatcttc     840
caaacaagag aattagcttt ggcaaattat gcttctgcac catcaagaca atttttcgag     900
tttatttggt tgttgtacta cgctgaatat tttgtttacg tttttatttg agattaatat     960
aattatataa aaatattatc ttcttttctt tatatctagt gttatgtaaa ataaattgat    1020
gactacggaa agcttttta tattgtttct ttttcattct gagccactta aatttcgtga     1080
atgttcttgt aagggacggt agatttacaa gtgatacaac aaaaagcaag gcgcttttc     1140
taataaaaag aagaaaagca tttaacaatt gaacacctct atatcaacga agaatattac    1200
tttgtctcta aatccttgta aaatgtgtac gatctctata tgggttactc ataagtgtac    1260
cgaagactgc attgaaagtt tatgtttttt cactggaggc gtcattttcg cgttgagaac    1320
aattgtcctg tacttccttg ttcatgtgtg ttcaaaaacg ttatatttat aggataatta    1380
tactctattt ctcaacaagt aattggttgt ttggccgagc ggtctaaggc gcctgattca    1440
agaaatatct tgaccgcagt taactgtggg aatactcagg tatcgtaaga tgcaagagtt    1500
cgaatctctt agcaaccatt attttttcc tcaacataac gagaacacac aggggcgcta     1560
tcgcacagaa tcaaattcga tgactggaaa ttttttgtta atttcagagg tcgcctgacg    1620
catatacctt tttcaactga aaaattggga gaaaaaggaa aggtgagagc gccggaaccg    1680
gcttttcata tagaatagag aagcgttcat gactaaatgc ttgcatcaca atacttgaag    1740
ttgacaatat tatttaagga cctattgttt tttccaatag gtggttagca atcgtcttac    1800
tttctaactt ttcttacctt ttacatttca gcaatatata tatatatttc aaggatatac    1860
```

```
cattctaatg tctgccccta agaagatcgt cgttttgcca ggtgaccacg ttggtcaaga   1920
aatcacagcc gaagccatta aggttcttaa agctatttct gatgttcgtt ccaatgtcaa   1980
gttcgatttc gaaaatcatt taattggtgg tgctgctatc gatgctacag gtgttccact   2040
tccagatgag gcgctggaag cctccaagaa ggctgatgcc gttttgttag gtgctgtggg   2100
tggtcctaaa tggggtaccg gtagtgttag acctgaacaa ggtttactaa aaatccgtaa   2160
agaacttcaa ttgtacgcca acttaagacc atgtaacttt gcatccgact ctcttttaga   2220
cttatctcca atcaagccac aatttgctaa aaatactgac ttcgttgttg tcagagaatt   2280
agtgggaggt atttactttg gtaagagaaa ggaagacgat ggtgatggtg tcgcttggga   2340
tagtgaacaa tacaccgttc cagaagtgca aagaatcaca agaatggccg ctttcatggc   2400
cctacaacat gagccaccat tgcctatttg gtccttggat aaagctaatg ttttggcctc   2460
ttcaagatta tggagaaaaa ctgtggagga aaccatcaag aacgaattcc ctacattgaa   2520
ggttcaacat caattgattg attctgccgc catgatccta gttaagaacc caacccacct   2580
aaatggtatt ataatcacca gcaacatgtt tggtgatatc atctccgatg aagcctccgt   2640
tatcccaggt tccttgggtt tgttgccatc tgcgtccttg gcctctttgc cagacaagaa   2700
caccgcattt ggtttgtacg aaccatgcca cggttctgct ccagatttgc caaagaataa   2760
ggtcaaccct atcgccacta tcttgtctgc tgcaatgatg ttgaaattgt cattgaactt   2820
gcctgaagaa ggtaaggcca ttgaagatgc agttaaaaag gttttggatg caggtatcag   2880
aactggtgat ttaggtggtt ccaacagtac caccgaagtc ggtgatgctg tcgccgaaga   2940
agttaagaaa atccttgctt aaaaagattc tcttttttta tgatatttgt acataaactt   3000
tataaatgaa attcataata gaaacgacac gaaattacaa aatggaatat gttcataggg   3060
tagacgaaac tatatacgca atctacatac atttatcaag aaggagaaaa aggaggatgt   3120
aaaggaatac aggtaagcaa attgatacta atggctcaac gtgataagga aaaagaattg   3180
cactttaaca ttaatattga caaggaggag ggcaccacac aaaaagttac agatctgctg   3240
cattaatgaa tcggccaacg cgcggggaga ggcggtttgc gtattgggcg ctcttccgct   3300
tcctcgctca ctgactcgct gcgctcggtc gttcggctgc ggcgagcggt atcagcatcg   3360
atgaattcca cggactatag actatactag tatactccgt ctactgtacg atacacttcc   3420
gctcaggtcc ttgtccttta acgaggcctt accactcttt tgttactcta ttgatccagc   3480
tcagcaaagg cagtgtgatc taagattcta tcttcgcgat gtagtaaaac tagctagacc   3540
gagaaagaga ctagaaatgc aaaaggcact tctacaatgg ctgccatcat tattatccga   3600
tgtgacgctg cagcttctca atgatattcg aatacgcttt gaggagatac agcctaatat   3660
ccgacaaact gttttacaga tttacgatcg tatttgttac ccatcattga attttgaaca   3720
tccgaacctg ggagttttcc ctgaaacaga tagtatattt gaacctgtat aataatatat   3780
agtctagcgc tttacggaag acaatgtatg tatttcggtt cctggagaaa ctattgcatc   3840
tattgcatag gtaatcttgc acgtcgcatc cccggttcat ttctgcgtt tccatcttgc   3900
acttcaatag catatctttg ttaacgaagc atctgtgctt cattttgtag aacaaaaatg   3960
caacgcgaga gcgctaattt ttcaaacaaa gaatctgagc tgcattttta cagaacagaa   4020
atgcaacgcg aaagcgctat tttaccaacg aagaatctgt gcttcatttt tgtaaaacaa   4080
aaatgcaacg cgagagcgct aatttttcaa acaaagaatc tgagctgcat tttacagaa   4140
cagaaatgca acgcgagagc gctattttac caacaaagaa tctatacttc tttttgttc   4200
```

```
tacaaaaatg catcccgaga gcgctatttt tctaacaaag catcttagat tacttttttt   4260
ctcctttgtg cgctctataa tgcagtctct tgataacttt ttgcactgta ggtccgttaa   4320
ggttagaaga aggctacttt ggtgtctatt ttctcttcca taaaaaaagc ctgactccac   4380
ttcccgcgtt tactgattac tagcgaagct gcgggtgcat tttttcaaga taaaggcatc   4440
cccgattata ttctataccg atgtggattg cgcatacttt gtgaacagaa agtgatagcg   4500
ttgatgattc ttcattggtc agaaaattat gaacggtttc ttctattttg tctctatata   4560
ctacgtatag gaaatgttta cattttcgta ttgttttcga ttcactctat gaatagttct   4620
tactacaatt tttttgtcta aagagtaata ctagagataa acataaaaaa tgtagaggtc   4680
gagtttagat gcaagttcaa ggagcgaaag gtggatgggt aggttatata gggatatagc   4740
acagagatat atagcaaaga gatacttttg agcaatgttt gtggaagcgg tattcgcaat   4800
attttagtag ctcgttacag tccggtgcgt ttttggtttt ttgaaagtgc gtcttcagag   4860
cgcttttggt tttcaaaagc gctctgaagt tcctatactt tctagagaat aggaacttcg   4920
gaataggaac ttcaaagcgt ttccgaaaac gagcgcttcc gaaaatgcaa cgcgagctgc   4980
gcacatacag ctcactgttc acgtcgcacc tatatctgcg tgttgcctgt atatatatat   5040
acatgagaag aacggcatag tgcgtgttta tgcttaaatg cgtacttata tgcgtctatt   5100
tatgtaggat gaaaggtagt ctagtacctc ctgtgatatt atcccattcc atgcggggta   5160
tcgtatgctt ccttcagcac taccctttag ctgttctata tgctgccact cctcaattgg   5220
attagtctca tccttcaatg ctatcatttc ctttgatatt ggatcatatg catagtaccg   5280
agaaactagt gcgaagtagt gatcaggtat tgctgttatc tgatgagtat acgttgtcct   5340
ggccacggca gaagcacgct tatcgctcca atttcccaca acattagtca actccgttag   5400
gcccttcatt gaaagaaatg aggtcatcaa atgtcttcca atgtgagatt ttgggccatt   5460
ttttatagca aagattgaat aaggcgcatt tttcttcaaa gctttattgt acgatctgac   5520
taagttatct tttaataatt ggtattcctg tttattgctt gaagaattgc cggtcctatt   5580
tactcgtttt aggactggtt cagaattcat cgatgctcac tcaaaggcgg taatacggtt   5640
atccacagaa tcaggggata acgcaggaaa gaacatgtga gcaaaaggcc agcaaaaggc   5700
caggaaccgt aaaaaggccg cgttgctggc gtttttccat aggctccgcc cccctgacga   5760
gcatcacaaa aatcgacgct caagtcagag gtggcgaaac ccgacaggac tataaagata   5820
ccaggcgttt ccccctggaa gctccctcgt gcgctctcct gttccgaccc tgccgcttac   5880
cggatacctg tccgcctttc tcccttcggg aagcgtggcg ctttctcata gctcacgctg   5940
taggtatctc agttcggtgt aggtcgttcg ctccaagctg ggctgtgtgc acgaaccccc   6000
cgttcagccc gaccgctgcg ccttatccgg taactatcgt cttgagtcca acccggtaag   6060
acacgactta tcgccactgg cagcagccac tggtaacagg attagcagag cgaggtatgt   6120
aggcggtgct acagagttct tgaagtggtg gcctaactac ggctacacta gaagaacagt   6180
atttggtatc tgcgctctgc tgaagccagt taccttcgga aaaagagttg gtagctcttg   6240
atccggcaaa caaaccaccg ctggtagcgg tggttttttt gtttgcaagc agcagattac   6300
gcgcagaaaa aaaggatctc aagaagatcc tttgatcttt tctacggggt ctgacgctca   6360
gtggaacgaa aactcacgtt aagggatttt ggtcatgaga ttatcaaaaa ggatcttcac   6420
ctagatcctt ttaaattaaa aatgaagttt taaatcaatc taaagtatat atgagtaaac   6480
ttggtctgac agttaccaat gcttaatcag tgaggcacct atctcagcga tctgtctatt   6540
tcgttcatcc atagttgcct gactccccgt cgtgtagata actacgatac gggagggctt   6600
```

```
accatctggc cccagtgctg caatgatacc gcgagaccca cgctcaccgg ctccagattt   6660
atcagcaata aaccagccag ccggaagggc cgagcgcaga agtggtcctg caactttatc   6720
cgcctccatc cagtctatta attgttgccg ggaagctaga gtaagtagtt cgccagttaa   6780
tagtttgcgc aacgttgttg ccattgctac aggcatcgtg gtgtcacgct cgtcgtttgg   6840
tatggcttca ttcagctccg gttcccaacg atcaaggcga gttacatgat cccccatgtt   6900
gtgcaaaaaa gcggttagct ccttcggtcc tccgatcgtt gtcagaagta agttggccgc   6960
agtgttatca ctcatggtta tggcagcact gcataattct cttactgtca tgccatccgt   7020
aagatgcttt tctgtgactg gtgagtactc aaccaagtca ttctgagaat agtgtatgcg   7080
gcgaccgagt tgctcttgcc cggcgtcaat acgggataat accgcgccac atagcagaac   7140
tttaaaagtg ctcatcattg gaaaacgttc ttcggggcga aaactctcaa ggatcttacc   7200
gctgttgaga tccagttcga tgtaacccac tcgtgcaccc aactgatctt cagcatcttt   7260
tactttcacc agcgtttctg ggtgagcaaa aacaggaagg caaaatgccg caaaaaaggg   7320
aataagggcg acacggaaat gttgaatact catactcttc ctttttcaat attattgaag   7380
catttatcag ggttattgtc tcatgagcgg atacatattt gaatgtattt agaaaaataa   7440
acaaataggg gttccgcgca catttccccg aaaagtgcca cctgacgtct aagaaaccat   7500
tattatcatg acattaacct ataaaaatag gcgtatcacg aggccctttc gtctcgcgcg   7560
tttcggtgat gacggtgaaa acctctgaca catgcagctc ccggagacgg tcacagcttg   7620
tctgtaagcg gatgccggga gcagacaagc ccgtcagggc gcgtcagcgg gtgttggcgg   7680
gtgtcggggc tggcttaact atgcggcatc agagcagatt gtactgagag tgcaccatat   7740
gcggtgtgga ataccgcaca gatgcgtaag gagaaaatac cgcatcaggc gccattcgcc   7800
attcaggctg cgcaactgtt gggaagggcg atcggtgcgg gcctcttcgc tattacgcca   7860
gctggcgaaa gggggatgtg ctgcaaggcg attaagttgg gtaacgccag ggttttccca   7920
gtcacgacgt tgtaaaacga cggccagtga attgcggccg catcgatgga aaagaccaaa   7980
cggtgacgtt aagagaaaga aattctatga ggcaagtaag aggcactatt actgatgtga   8040
tttcgaccat tgacaaaatg cttcacaacc ctgatgaatc ggactgggat aaatcaacat   8100
ttggactgtc gcctgttaag atataactga aaaaagaggg gaatttttag atactgaaat   8160
gatattttag aataaccaga ctatatataa ggataaatta caaaaaatta actaatagat   8220
aagatttaaa tataaaagat atgcaactag aaaagtctta tcaatctcct tattatattg   8280
aattttcaaa aattcttact ttttttttgg atggacgcaa agaagtttaa taatcatatt   8340
acatggcatt accaccatat acatatccat atctaatctt acttatatgt tgtggaaatg   8400
taaagagccc cattatctta gcctaaaaaa accttctctt tggaactttc agtaatacgc   8460
ttaactgctc attgctatat tgaagtacgg attagaagcc gccgagcggg cgacagccct   8520
ccgacggaag actctcctcc gtgcgtcctc gtcttcaccg gtcgcgttcc tgaaacgcag   8580
atgtgcctcg cgccgcactg ctccgaacaa taaagattct acaatactag cttttatggt   8640
tatgaagagg aaaaattggc agtaacctgg ccccacaaac cttcaaatta acgaatcaaa   8700
ttaacaacca taggatgata atgcgattag tttttagcc ttatttctgg ggtaattaat   8760
cagcgaagcg atgattttg atctattaac agatatataa atggaaaagc tgcataacca   8820
ctttaactaa tactttcaac attttcagtt tgtattactt cttattcaaa tgtcataaaa   8880
gtatcaacaa aaaattgtta atatacctct atactttaac gtcaaggaga aaaaactata   8940
```

```
atggcttcag aaaaagaaat taggagagag agattcttga acgttttccc taaattagta   9000

gaggaattga acgcatcgct tttggcttac ggtatgccta aggaagcatg tgactggtat   9060

gcccactcat tgaactacaa cactccaggc ggtaagctaa atagaggttt gtccgttgtg   9120

gacacgtatg ctattctctc caacaagacc gttgaacaat tggggcaaga agaatacgaa   9180

aaggttgcca ttctaggttg gtgcattgag ttgttgcagg cttactggtt ggtcgccgat   9240

gatatgatgg acaagtccat taccagaaga ggccaaccat gttggtacaa ggttcctgaa   9300

gttggggaaa ttgccatctg ggacgcattc atgttagagg ctgctatcta caagcttttg   9360

aaatctcact tcagaaacga aaaatactac atagatatca ccgaattgtt ccatgaggtc   9420

accttccaaa ccgaattggg ccaattgatg gacttaatca ctgcacctga agacaaagtc   9480

gacttgagta agttctccct aaagaagcac tccttcatag ttactttcaa gactgcttac   9540

tattctttct acttgcctgt cgcattggcc atgtacgttg ccggtatcac ggatgaaaag   9600

gatttgaaac aagccagaga tgtcttgatt ccattgggtg aatacttcca aattcaagat   9660

gactacttag actgcttcgg taccccagaa cagatcggta agatcggtac agatatccaa   9720

gataacaaat gttcttgggt aatcaacaag gcattggaac ttgcttccgc agaacaaaga   9780

aagactttag acgaaaatta cggtaagaag gactcagtcg cagaagccaa atgcaaaaag   9840

attttcaatg acttgaaaat tgaacagcta taccacgaat atgaagagtc tattgccaag   9900

gatttgaagg ccaaaatttc tcaggtcgat gagtctcgtg gcttcaaagc tgatgtctta   9960

actgcgttct tgaacaaagt ttacaagaga agcaaa                             9996
```

<210> SEQ ID NO 34
<211> LENGTH: 8817
<212> TYPE: DNA
<213> ORGANISM: Artificial Sequence
<220> FEATURE:
<223> OTHER INFORMATION: RUNM001233_51.1 vector

<400> SEQUENCE: 34

```
aaaagaccaa acggtgacgt taagagaaag aaattctatg aggcaagtaa gaggcactat     60

tactgatgtg atttcgacca ttgacaaaat gcttcacaac cctgatgaat cggactggga    120

taaatcaaca tttggactgt cgcctgttaa gatataactg aaaaaagagg ggaattttta    180

gatactgaaa tgatatttta gaataaccag actatatata aggataaatt acaaaaaatt    240

aactaataga taagatttaa atataaaaga tatgcaacta gaaaagtctt atcaatctcc    300

ttatattgaa ttttcaaaaa ttcttacttt ttttttggat ggacgcaaag aagtttaata    360

atcatattac atggcattac caccatatac atatccatat ctaatcttac ttatatgttg    420

tggaaatgta aagagcccca ttatcttagc ctaaaaaaac cttctctttg gaactttcag    480

taatacgctt aactgctcat tgctatattg aagtacggat tagaagccgc cgagcgggcg    540

acagccctcc gacggaagac tctcctccgt gcgtcctcgt cttcaccggt cgcgttcctg    600

aaacgcagat gtgcctcgcg ccgcactgct ccgaacaata aagattctac aatactagct    660

tttatggtta tgaagaggaa aaattggcag taacctggcc ccacaaacct tcaaattaac    720

gaatcaaatt aacaaccata ggatgataat gcgattagtt ttttagcctt atttctgggg    780

taattaatca gcgaagcgat gatttttgat ctattaacag atatataaat ggaaaagctg    840

cataaccact ttaactaata ctttcaacat tttcagtttg tattacttct tattcaaatg    900

tcataaaagt atcaacaaaa aattgttaat atacctctat actttaacgt caaggagaaa    960

aaactataat gaactgctcc gcattctctt tctggttcgt ctgtaaaata atcttcttct   1020
```

```
tcttgtcctt caacatccaa atctccatcg caaatccaca agaaaacttt ttgaagtgtt   1080
tctccgaata catcccaaac aaccctgcta acccaaagtt tatatatact caacatgatc   1140
aattgtacat gtccgttttg aacagtacca tccaaaattt gagattcact tctgacacta   1200
caccaaaacc tttagtcatt gttacacctt ccaatgttag tcacattcaa gcttctatat   1260
tgtgctctaa gaaagtaggt ttgcaaatca gaactagatc aggtggtcat gatgcagaag   1320
gcatgtctta catctcacaa gttccattcg ttgtagtcga tttgagaaat atgcattcca   1380
taaagatcga cgttcacagt caaacagcat gggtagaagc aggtgccacc ttgggtgaag   1440
tttactactg gatcaacgaa aagaatgaaa actttcttt ccctggtggt tactgtccaa   1500
cagtaggtgt cggtggtcac ttttctggtg gtggttatgg tgcattgatg agaaactacg   1560
gtttagctgc agataatatt atagacgccc atttggttaa cgtagatggt aaagttttgg   1620
acagaaagtc tatgggtgaa gatttgtttt gggccataag aggtggtggt ggtgaaaatt   1680
tcggtatcat tgccgcttgg aaaattaagt tagtcgctgt tccttccaaa agtactattt   1740
tctctgtcaa aaagaacatg gaaatccacg gtttggttaa gttgtttaat aagtggcaaa   1800
acatcgctta caagtacgat aaggacttgg ttttgatgac ccatttcatc actaaaaata   1860
ttacagataa ccatggtaaa aataagacca ctgttcacgg ttatttttct tcaattttcc   1920
atggtggtgt agattctttg gttgatttga tgaataagtc attcccagaa ttgggtatta   1980
aaaagacaga ttgcaaggaa ttttcttgga tagacacaac catcttctat tcaggtgttg   2040
taaacttcaa caccgctaac ttcaaaaagg aaatcttgtt ggatagatcc gctggtaaaa   2100
agaccgcttt ttctattaaa ttggactacg ttaagaaacc aatccctgaa actgcaatgg   2160
tcaagatatt ggaaaagttg tacgaagaag atgtaggtgt cggcatgtac gttttgtatc   2220
catacggtgg tattatggaa gaaatatctg aatcagccat accatttcct cacagagctg   2280
gtatcatgta tgaattatgg tacacagcct catgggaaaa gcaagaagat aacgaaaagc   2340
atatcaactg ggtcagatcc gtttacaact tcactacacc ttacgttagt caaaacccaa   2400
gattggcata tttgaactac agagatttgg acttaggtaa aactaaccct gaatctccaa   2460
ataactatac acaagcaaga atttggggtg aaaagtactt tggtaaaaat ttcaacagat   2520
tagttaaagt aaagactaaa gccgacccta acaacttttt cagaaacgaa caatccatcc   2580
caccttgcc acctcaccac cactaataag attaatataa ttatataaaa atattatctt   2640
cttttcttta tatctagtgt tatgtaaaat aaattgatga ctacggaaag ctttttata   2700
ttgtttcttt ttcattctga gccacttaaa tttcgtgaat gttcttataa gggacggtag   2760
atttacaagt gatacaacaa aaagcaaggc gctttttcta ataaaaagaa gaaaagcatt   2820
taacaattga acacctctat atcaacgaag aatattactt tgtctctaaa tccttgtaaa   2880
atgtgtacga tctctatatg ggttactcag aagtgtaccg aagactgcat tgaaagttta   2940
tgttttttca ctgcaagcgt cattttcgcg ttgagaagaa tttcatcatt tttttttat   3000
tcttttttt gatttcggtt tccttgaaat tttttgatt cggtaatctc cgaacagaag   3060
gaagaacgaa ggaaggagca cagacttaga ttggtatata tacgcatatg tagtgttgaa   3120
gaaacatgaa attgcccagt attcttaacc caactgcaca gaacaaaaac ctgcaggaaa   3180
cgaagataaa tcatgtcgaa agctacatat aaggaacgtg ctgctactca tcctagtcct   3240
gttgctgcca agctatttaa tatcatgcac gaaaagcaaa caaacttgtg tgcttcattg   3300
gatgttcgta ccaccaagga attactggag ttagttgaag cattaggtcc caaaatttgt   3360
```

-continued

```
ttactaaaaa cacatgtgga tatcttgact gatttttcca tggagggcac agttaagccg   3420
ctaaaggcat tatccgccaa gtacaatttt ttactcttcg aagacagaaa atttgctgac   3480
attggtaata cagtcaaatt gcagtactct gcgggtgtat acagaatagc agaatgggca   3540
gacattacga atgcacacgg tgtggtgggc ccaggtattg ttagcggttt gaagcaggcg   3600
gcagaagaag taacaaagga acctagaggc cttttgatgt tagcagaatt gtcatgcaag   3660
ggctccctat ctactggaga atatactaag ggtactgttg acattgcgaa gagcgacaaa   3720
gattttgtta tcggctttat tgctcaaaga gacatgggtg gaagagatga aggttacgat   3780
tggttgatta tgacacccgg tgtgggttta gatgacaagg gagacgcatt gggtcaacag   3840
tatagaaccg tggatgatgt ggtctctaca ggatctgaca ttattattgt tggaagagga   3900
ctatttgcaa agggaaggga tgctaaggta gagggtgaac gttacagaaa agcaggctgg   3960
gaagcatatt tgagaagatg cggccagcaa aactaaaaaa ctgtattata agtaaatgca   4020
tgtatactaa actcacaaat tagagcttca atttaattat atcagttatt acccaatcag   4080
atctgctgca ttaatgaatc ggccaacgcg cggggagagg cggtttgcgt attgggcgct   4140
cttccgcttc ctcgctcact gactcgctgc gctcggtcgt tcggctgcgg cgagcggtat   4200
cagcatcgat gaattccacg gactatagac tatactagta tactccgtct actgtacgat   4260
acacttccgc tcaggtcctt gtcctttaac gaggccttac cactcttttg ttactctatt   4320
gatccagctc agcaaaggca gtgtgatcta agattctatc ttcgcgatgt agtaaaacta   4380
gctagaccga gaaagagact agaaatgcaa aaggcacttc tacaatggct gccatcatta   4440
ttatccgatg tgacgctgca gcttctcaat gatattcgaa tacgctttga ggagatacag   4500
cctaatatcc gacaaactgt tttacagatt tacgatcgta tttgttaccc atcattgaat   4560
tttgaacatc cgaacctggg agttttccct gaaacagata gtatatttga acctgtataa   4620
taatatatag tctagcgctt tacggaagac aatgtatgta tttcggttcc tggagaaact   4680
attgcatcta ttgcataggt aatcttgcac gtcgcatccc cggttcattt tctgcgtttc   4740
catcttgcac ttcaatagca tatctttgtt aacgaagcat ctgtgcttca ttttgtagaa   4800
caaaaatgca acgcgagagc gctaattttt caaacaaaga atctgagctg catttttaca   4860
gaacagaaat gcaacgcgaa agcgctattt taccaacgaa gaatctgtgc ttcatttttg   4920
taaaacaaaa atgcaacgcg agagcgctaa tttttcaaac aaagaatctg agctgcattt   4980
ttacagaaca gaaatgcaac gcgagagcgc tattttacca acaaagaatc tatacttctt   5040
ttttgttcta caaaaatgca tcccgagagc gctatttttc taacaaagca tcttagatta   5100
ctttttttct cctttgtgcg ctctataatg cagtctcttg ataacttttt gcactgtagg   5160
tccgttaagg ttagaagaag gctactttgg tgtctatttt ctcttccata aaaaaagcct   5220
gactccactt cccgcgttta ctgattacta gcgaagctgc gggtgcattt tttcaagata   5280
aaggcatccc cgattatatt ctataccgat gtggattgcg catactttgt gaacagaaag   5340
tgatagcgtt gatgattctt cattggtcag aaaattatga acggtttctt ctattttgtc   5400
tctatatact acgtatagga aatgtttaca ttttcgtatt gttttcgatt cactctatga   5460
atagttctta ctacaatttt tttgtctaaa gagtaatact agagataaac ataaaaaatg   5520
tagaggtcga gtttagatgc aagttcaagg agcgaaaggt ggatgggtag gttatatagg   5580
gatatagcac agagatatat agcaaagaga tacttttgag caatgtttgt ggaagcggta   5640
ttcgcaatat tttagtagct cgttacagtc cggtgcgttt ttggtttttt gaaagtgcgt   5700
cttcagagcg cttttggttt tcaaaagcgc tctgaagttc ctatactttc tagagaatag   5760
```

gaacttcgga ataggaactt caaagcgttt ccgaaaacga gcgcttccga aaatgcaacg 5820
cgagctgcgc acatacagct cactgttcac gtcgcaccta tatctgcgtg ttgcctgtat 5880
atatatatac atgagaagaa cggcatagtg cgtgtttatg cttaaatgcg tacttatatg 5940
cgtctattta tgtaggatga aaggtagtct agtacctcct gtgatattat cccattccat 6000
gcggggtatc gtatgcttcc ttcagcacta ccctttagct gttctatatg ctgccactcc 6060
tcaattggat tagtctcatc cttcaatgct atcatttcct ttgatattgg atcatatgca 6120
tagtaccgag aaactagtgc gaagtagtga tcaggtattg ctgttatctg atgagtatac 6180
gttgtcctgg ccacggcaga agcacgctta tcgctccaat ttcccacaac attagtcaac 6240
tccgttaggc ccttcattga aagaaatgag gtcatcaaat gtcttccaat gtgagatttt 6300
gggccatttt ttatagcaaa gattgaataa ggcgcatttt tcttcaaagc tttattgtac 6360
gatctgacta agttatcttt taataattgg tattcctgtt tattgcttga agaattgccg 6420
gtcctattta ctcgttttag gactggttca gaattcatcg atgctcactc aaaggcggta 6480
atacggttat ccacagaatc aggggataac gcaggaaaga acatgtgagc aaaaggccag 6540
caaaaggcca ggaaccgtaa aaaggccgcg ttgctggcgt ttttccatag gctccgcccc 6600
cctgacgagc atcacaaaaa tcgacgctca agtcagaggt ggcgaaaccc gacaggacta 6660
taaagatacc aggcgtttcc ccctggaagc tccctcgtgc gctctcctgt tccgaccctg 6720
ccgcttaccg gatacctgtc cgcctttctc ccttcgggaa gcgtggcgct ttctcatagc 6780
tcacgctgta ggtatctcag ttcggtgtag gtcgttcgct ccaagctggg ctgtgtgcac 6840
gaaccccccg ttcagcccga ccgctgcgcc ttatccggta actatcgtct tgagtccaac 6900
ccggtaagac acgacttatc gccactggca gcagccactg gtaacaggat tagcagagcg 6960
aggtatgtag gcggtgctac agagttcttg aagtggtggc ctaactacgg ctacactaga 7020
agaacagtat ttggtatctg cgctctgctg aagccagtta ccttcggaaa aagagttggt 7080
agctcttgat ccggcaaaca aaccaccgct ggtagcggtg gtttttttgt ttgcaagcag 7140
cagattacgc gcagaaaaaa aggatctcaa gaagatcctt tgatcttttc tacggggtct 7200
gacgctcagt ggaacgaaaa ctcacgttaa gggattttgg tcatgagatt atcaaaaagg 7260
atcttcacct agatcctttt aaattaaaaa tgaagtttta aatcaatcta aagtatatat 7320
gagtaaactt ggtctgacag ttaccaatgc ttaatcagtg aggcacctat ctcagcgatc 7380
tgtctatttc gttcatccat agttgcctga ctccccgtcg tgtagataac tacgatacgg 7440
gagggcttac catctggccc cagtgctgca atgataccgc gagacccacg ctcaccggct 7500
ccagatttat cagcaataaa ccagccagcc ggaagggccg agcgcagaag tggtcctgca 7560
actttatccg cctccatcca gtctattaat tgttgccggg aagctagagt aagtagttcg 7620
ccagttaata gtttgcgcaa cgttgttgcc attgctacag gcatcgtggt gtcacgctcg 7680
tcgtttggta tggcttcatt cagctccggt tcccaacgat caaggcgagt tacatgatcc 7740
cccatgttgt gcaaaaaagc ggttagctcc ttcggtcctc cgatcgttgt cagaagtaag 7800
ttggccgcag tgttatcact catggttatg gcagcactgc ataattctct tactgtcatg 7860
ccatccgtaa gatgcttttc tgtgactggt gagtactcaa ccaagtcatt ctgagaatag 7920
tgtatgcggc gaccgagttg ctcttgcccg gcgtcaatac gggataatac cgcgccacat 7980
agcagaactt taaaagtgct catcattgga aaacgttctt cggggcgaaa actctcaagg 8040
atcttaccgc tgttgagatc cagttcgatg taacccactc gtgcacccaa ctgatcttca 8100

```
gcatctttta ctttcaccag cgtttctggg tgagcaaaaa caggaaggca aaatgccgca   8160
aaaaagggaa taagggcgac acggaaatgt tgaatactca tactcttcct ttttcaatat   8220
tattgaagca tttatcaggg ttattgtctc atgagcggat acatatttga atgtatttag   8280
aaaaataaac aaataggggt tccgcgcaca tttccccgaa aagtgccacc tgacgtctaa   8340
gaaaccatta ttatcatgac attaacctat aaaaataggc gtatcacgag gccctttcgt   8400
ctcgcgcgtt tcggtgatga cggtgaaaac ctctgacaca tgcagctccc ggagacggtc   8460
acagcttgtc tgtaagcgga tgccgggagc agacaagccc gtcagggcgc gtcagcgggt   8520
gttggcgggt gtcggggctg gcttaactat gcggcatcag agcagattgt actgagagtg   8580
caccatatgc ggtgtgaaat accgcacaga tgcgtaagga gaaaataccg catcaggcgc   8640
cattcgccat tcaggctgcg caactgttgg gaagggcgat cggtgcgggc ctcttcgcta   8700
ttacgccagc tggcgaaagg gggatgtgct gcaaggcgat taagttgggt aacgccaggg   8760
ttttcccagt cacgacgttg taaaacgacg gccagtgaat tgcggccgca tcgatgg      8817
```

<210> SEQ ID NO 35
<211> LENGTH: 11894
<212> TYPE: DNA
<213> ORGANISM: Artificial Sequence
<220> FEATURE:
<223> OTHER INFORMATION: RUNM001210_96.1 vector

<400> SEQUENCE: 35

```
cgtacattta attttcaacg tattctataa gaaattgcgg gagttttttt catgtagatg     60
atactgactg cacgcaaata taggcatgat ttataggcat gatttgatgg ctgtaccgat    120
aggaacgcta agagtaactt cagaatcgtt atcctggcgg aaaaaattca tttgtaaact    180
ttaaaaaaaa aagccaatat ccccaaaatt attaagagcg cctccattat taactaaaat    240
ttcactcagc atccacaatg tatcaggtat ctactacaga tattacatgt ggcgaaaaag    300
acaagaacaa tgcaatagcg catcaagaaa aaacacaaag ctttcaatca atgaatcgaa    360
aatgtcatta aaatagtata taaattgaaa ctaagtcata aagctataaa aagaaaattt    420
atttaaatgc aagatttaaa gtaaattcac gtatttaatt ggaacagatc taacaacaac    480
tctttcaact gtcaaacctg gaccaaaacc aaataaaaca ccccattcaa aaccgtcacc    540
tgtagtagat ttaccctctt ctaatgatct ctttctcaat tcatccataa cgaacaaaac    600
agtagatgaa gacatgttac catgttcaga caaaacatgt cttgaatcaa caaatttttc    660
tttcttcaaa tccaattttt cttcaacctt atccaagatt gctttaccac ctggatgtgt    720
aatccagaaa atagagttcc aatctgagat accgattgga gtaaaagctt cgatcaaaca    780
cttttcgatg ttgttagaga tcaacattgg aacatcttta tgcaaatcga agatcaaacc    840
agcttctctg atatgaccac caattgtacc ttcagaattt ggcaaaattg tttgaccagt    900
tgaaactaat tcgaagattg gtctttcacc aactgattca tctggttctg caccaacaat    960
aacagctgca gcaccgtcac caaaaatagc ttgaccaact aacaattcca aatcagaatc   1020
tgatggacct ctaaacaaac aagccatgat atcacaacaa actgccaaga ctctagcacc   1080
cttattgttt tctgcgatat ccttagcgat tctcaaaaca gtaccaccac cgtaacaacc   1140
taattggtac atcataactc tcttaacaga tggtgacaaa cccaacaact ttgcacaatg   1200
gtaatcagca cctggcatat ctgtagtaga tgctgatgta aaaatcaaat gagtgatctt   1260
agactttggt tgaccccatt ctttaattgc tttagcacat gcatctttac ccaactttgg   1320
aacttcaaca accaacatat cttgtctagc atccaatgtt tgcatttcat gttcaactaa   1380
```

```
tcttgggttt tgcttcaaat gttcttcgtt caagaaacaa tttctttttc taatcataga   1440
cttatcacag atctttctaa acttttcctt caattgtgtc atatgttctg acttagtaac   1500
tctgaagtaa taatctggaa attcatcttg gatcaagatg ttttctgggt ttgcagtacc   1560
aatagccaaa actgatgctg gaccttcagc tctcaaatga ttcatttata ttgaattttc   1620
aaaaattctt actttttttt tggatggacg caaagaagtt taataatcat attacatggc   1680
attaccacca tatacatatc catatctaat cttacttata tgttgtggaa atgtaaagag   1740
ccccattatc ttagcctaaa aaaaccttct ctttggaact ttcagtaata cgcttaactg   1800
ctcattgcta tattgaagta cggattagaa gccgccgagc gggcgacagc cctccgacgg   1860
aagactctcc tccgtgcgtc ctcgtcttca ccggtcgcgt tcctgaaacg cagatgtgcc   1920
tcgcgccgca ctgctccgaa caataaagat tctacaatac tagcttttat ggttatgaag   1980
aggaaaaatt ggcagtaacc tggccccaca aaccttcaaa ttaacgaatc aaattaacaa   2040
ccataggatg ataatgcgat tagtttttta gccttatttc tggggtaatt aatcagcgaa   2100
gcgatgattt ttgatctatt aacagatata taaatggaaa agctgcataa ccactttaac   2160
taatactttc aacattttca gtttgtatta cttcttattc aaatgtcata aaagtatcaa   2220
caaaaaattg ttaatatacc tctatacttt aacgtcaagg agaaaaaact ataatggctg   2280
ttaagcattt gatcgttttg aagtttaaag atgaaattac agaagcacaa aaagaagaat   2340
ttttcaagac ttacgttaat ttggttaaca tcatcccagc tatgaaggat gtttattggg   2400
gtaaagatgt tacacaaaag aaagaagaag gttacactca tatcgttgaa gttacattcg   2460
aatctgttga aactatccaa gattacatta ttcatccagc acatgttggt tttggtgacg   2520
tttacagatc attctgggaa aagttgttaa tttttgatta cactccaaga aaattaaaac   2580
caaaaattga attgaattga aaacgataga tcaatttttt tcttttctct ttccccatcc   2640
tttacgctaa aataatagtt tattttattt tttgaatatt ttttatttat atacgtatat   2700
atagactatt atttatcttt taatgattat taagattttt attaaaaaaa aattcgctcc   2760
tcttttaatg cctttatgca gtttttttttt cccattcgat atttctatgt tcgggttcag   2820
cgtattttaa gtttaataac tcgaaaattc tgcgttcgtt aaagctttcg agaaggatat   2880
tatttcgaaa taaaccgtgt tgtgtaagct tgaagccttt ttgcgctgcc aatattctta   2940
tccatctatt gtactcttta gatccagtat agtgtattct tcctgctcca agctcatccc   3000
acttgcaaca aaaaaagtct aatcttctgc aataatttcc atccttggca ttcagagaca   3060
tatattggtc aatcggtttt aattttgttt cttcatcaag tttcctttaa agggatatat   3120
aacagattct aaaactgaca gaaatatttc gagtgaagaa gaagcgttaa atattggatc   3180
tttccgcagt tctactctga tacatttttg aagtaggaga gtcatttaga aggcgtattg   3240
ctcaatagta gaaagcaggc ctgtgcacat gaattaatta aaaaatataa aggtagtgat   3300
tagacgacac atgtccatag gtaacctgtc ataattttga acaatttccc ttcttttctt   3360
ttttttttt gggtgcggcg atatgtagct tgttaattta cacatcatgt actttctgc   3420
atcaaaatat gaaaggcgat agtagctaaa gaaaataccg agaatttcct cgaaaagttg   3480
acgacaaaag aaaggcataa aaaagtaatt tgaaaatatt ttaaaactgt tttaacccat   3540
ctagcatccg cgctaaaaaa ggaagataca ggatacagcg gaaacaactt ttaaatgggt   3600
aaaaattaca agtcattgga ttctgttgtt gcatcagatt tcattgcttt gggtattact   3660
tctgaagttg cagaaacatt gcatggtaga ttggctgaaa tcgtttgtaa ctacggtgct   3720
```

```
gcaactccac aaacatggat caacatcgca aaccatatct tgtcaccaga tttgccattt   3780
tctttgcatc aaatgttgtt ttatggttgt tacaaggatt tcggtccagc accaccagct   3840
tggattccag atccagaaaa ggttaagtct actaatttgg gtgctttgtt ggaaaagaga   3900
ggtaaagaat tcttgggtgt taagtacaaa gatccaatct cttcattttc acattttcaa   3960
gaattttctg ttagaaaccc agaagtttac tggagaacag ttttgatgga tgaaatgaag   4020
atctcatttt ctaaagatcc agaatgtatc ttgagaagag atgatatcaa caatccaggt   4080
ggttctgaat ggttgccagg tggttatttg aattcagcta aaaattgttt gaacgttaac   4140
tctaataaga aattgaacga tactatgatc gtttggagag atgagggtaa cgatgatttg   4200
ccattgaata agttgacatt ggatcaattg agaaaaagag tttggttggt tggttacgca   4260
ttagaagaaa tgggtttgga aaaaggttgt gcaattgcta ttgatatgcc aatgcatgtt   4320
gatgctgttg ttatatattt ggcaatcgtt ttggctggtt acgttgttgt ttctattgca   4380
gattcatttt ctgctccaga aatctcaact agattgagat tgtctaaggc aaaggctatt   4440
tttacacaag atcatatcat tagaggtaaa aagagaattc cattgtactc aagagttgtt   4500
gaagcaaagt ctccaatggc tatcgttatc ccatgttcag gttctaacat tggtgcagaa   4560
ttaagagatg gtgacatttc atgggattac tttttggaaa gagctaagga attcaaaaac   4620
tgtgaattca ctgcaagaga acaaccagtt gatgcttaca caaacatctt gttttcttca   4680
ggtactacag gtgaaccaaa agcaattcca tggactcaag ctacaccatt aaaagctgca   4740
gctgatggtt ggtcacattt ggatattaga aaaggtgacg ttattgtttg gccaactaat   4800
ttgggttgga tgatgggtcc atggttggtt tatgcttcat tgttgaacgg tgcatctatc   4860
gctttgtaca acggttcacc attggtttct ggtttcgcaa agttcgttca agatgctaag   4920
gttacaatgt tgggtgttgt tccatcaatc gttagatcat ggaagtctac taactgtgtt   4980
tcaggttacg attggtctac aatcagatgt ttctcttcat ctggtgaagc atctaacgtt   5040
gatgaatatt tgtggttgat gggtagagct aactacaagc cagttattga aatgtgtggt   5100
ggtactgaaa ttggtggtgc attttcagct ggttcatttt tgcaagctca atctttgtca   5160
tctttttcat ctcaatgtat gggttgtaca ttgtacatct tggataagaa cggttaccca   5220
atgcctaaaa ataagccagg tattggtgaa ttggcattag gtccagttat gttcggtgct   5280
tcaaagactt tgttgaacgg taaccatcat gatgtttact tcaagggtat gccaacattg   5340
aatggtgaag ttttgagaag acatggtgac atcttcgaat tgacttctaa cggttactac   5400
catgcacatg gtagagctga tgatacaatg aatattggtg gtattaaaat ctcatctatc   5460
gaaatcgaaa gagtttgtaa cgaagttgat gatagagttt ttgaaactac agctattggt   5520
gttccaccat taggtggtgg tccagaacaa ttggttattt tctttgtttt gaaagattca   5580
aatgatacta caattgattt gaaccaattg agattgtctt ttaatttggg tttacaaaag   5640
aaattgaacc cattgtttaa agttactaga gttgttccat tgtcatcttt gccaagaact   5700
gctacaaata agatcatgag aagagtcttg agacaacaat ttctcattt tgaaggagat   5760
tgataagact tttctagttg catatctttt atatttaaat cttatctatt agttaatttt   5820
ttgtaattta tccttatata tagtctggtt attctaaaat atcatttcag tatctaaaaa   5880
ttcccctctt ttttcagtta tatcttaaca ggcgacagtc caaatgttga tttatcccag   5940
tccgattcat cagggttgtg aagcattttg tcaatggtcg aaatcacatc agtaatagtg   6000
cctcttactt gcctcataga atttctttct cttaacgtca ccgtttggtc ttttgaattt   6060
catcattttt tttttattct ttttttgat ttcggtttcc ttgaaatttt tttgattcgg   6120
```

```
taatctccga acagaaggaa gaacgaagga aggagcacag acttagattg gtatatatac   6180
gcatatgtag tgttgaagaa acatgaaatt gcccagtatt cttaacccaa ctgcacagaa   6240
caaaaacctg caggaaacga agataaatca tgtcgaaagc tacatataag gaacgtgctg   6300
ctactcatcc tagtcctgtt gctgccaagc tatttaatat catgcacgaa aagcaaacaa   6360
acttgtgtgc ttcattggat gttcgtacca ccaaggaatt actggagtta gttgaagcat   6420
taggtcccaa aatttgttta ctaaaaacac atgtggatat cttgactgat ttttccatgg   6480
agggcacagt taagccgcta aaggcattat ccgccaagta caattttttta ctcttcgaag   6540
acagaaaatt tgctgacatt ggtaatacag tcaaattgca gtactctgcg ggtgtataca   6600
gaatagcaga atgggcagac attacgaatg cacacggtgt ggtgggccca ggtattgtta   6660
gcggtttgaa gcaggcggca gaagaagtaa caaaggaacc tagaggcctt ttgatgttag   6720
cagaattgtc atgcaagggc tccctatcta ctggagaata tactaagggt actgttgaca   6780
ttgcgaagag cgacaaagat tttgttatcg gctttattgc tcaaagagac atgggtggaa   6840
gagatgaagg ttacgattgg ttgattatga cacccggtgt gggtttagat gacaagggag   6900
acgcattggg tcaacagtat agaaccgtgg atgatgtggt ctctacagga tctgacatta   6960
ttattgttgg aagaggacta tttgcaaagg gaagggatgc taaggtagag ggtgaacgtt   7020
acagaaaagc aggctgggaa gcatatttga gaagatgcgg ccagcaaaac taaaaaactg   7080
tattataagt aaatgcatgt atactaaact cacaaattag agcttcaatt taattatatc   7140
agttattacc caatcagatc tgctgcatta atgaatcggc caacgcgcgg ggagaggcgg   7200
tttgcgtatt gggcgctctt ccgcttcctc gctcactgac tcgctgcgct cggtcgttcg   7260
gctgcggcga gcggtatcag catcgatgaa ttccacggac tatagactat actagtatac   7320
tccgtctact gtacgataca cttccgctca ggtccttgtc ctttaacgag gccttaccac   7380
tcttttgtta ctctattgat ccagctcagc aaaggcagtg tgatctaaga ttctatcttc   7440
gcgatgtagt aaaactagct agaccgagaa agagactaga aatgcaaaag gcacttctac   7500
aatggctgcc atcattatta tccgatgtga cgctgcagct tctcaatgat attcgaatac   7560
gctttgagga gatacagcct aatatccgac aaactgtttt acagatttac gatcgtattt   7620
gttacccatc attgaatttt gaacatccga acctgggagt tttccctgaa acagatagta   7680
tatttgaacc tgtataataa tatatagtct agcgctttac ggaagacaat gtatgtattt   7740
cggttcctgg agaaactatt gcatctattg cataggtaat cttgcacgtc gcatccccgg   7800
ttcattttct gcgtttccat cttgcacttc aatagcatat ctttgttaac gaagcatctg   7860
tgcttcattt tgtagaacaa aaatgcaacg cgagagcgct aatttttcaa acaaagaatc   7920
tgagctgcat ttttacagaa cagaaatgca acgcgaaagc gctattttac caacgaagaa   7980
tctgtgcttc atttttgtaa aacaaaaatg caacgcgaga gcgctaattt ttcaaacaaa   8040
gaatctgagc tgcattttta cagaacagaa atgcaacgcg agagcgctat tttaccaaca   8100
aagaatctat acttcttttt tgttctacaa aaatgcatcc cgagagcgct atttttctaa   8160
caaagcatct tagattactt tttttctcct ttgtgcgctc tataatgcag tctcttgata   8220
actttttgca ctgtaggtcc gttaaggtta gaagaaggct actttggtgt ctattttctc   8280
ttccataaaa aaagcctgac tccacttccc gcgtttactg attactagcg aagctgcggg   8340
tgcatttttt caagataaag gcatccccga ttatattcta taccgatgtg gattgcgcat   8400
actttgtgaa cagaaagtga tagcgttgat gattcttcat tggtcagaaa attatgaacg   8460
```

```
gtttcttcta ttttgtctct atatactacg tataggaaat gtttacattt tcgtattgtt   8520
ttcgattcac tctatgaata gttcttacta caattttttt gtctaaagag taatactaga   8580
gataaacata aaaaatgtag aggtcgagtt tagatgcaag ttcaaggagc gaaaggtgga   8640
tgggtaggtt atatagggat atagcacaga gatatatagc aaagagatac ttttgagcaa   8700
tgtttgtgga agcggtattc gcaatatttt agtagctcgt tacagtccgg tgcgtttttg   8760
gtttttgaa agtgcgtctt cagagcgctt ttggttttca aaagcgctct gaagttccta   8820
tactttctag agaataggaa cttcggaata ggaacttcaa agcgtttccg aaaacgagcg   8880
cttccgaaaa tgcaacgcga gctgcgcaca tacagctcac tgttcacgtc gcacctatat   8940
ctgcgtgttg cctgtatata tatatacatg agaagaacgg catagtgcgt gtttatgctt   9000
aaatgcgtac ttatatgcgt ctatttatgt aggatgaaag gtagtctagt acctcctgtg   9060
atattatccc attccatgcg gggtatcgta tgcttccttc agcactaccc tttagctgtt   9120
ctatatgctg ccactcctca attggattag tctcatcctt caatgctatc atttcctttg   9180
atattggatc atatgcatag taccgagaaa ctagtgcgaa gtagtgatca ggtattgctg   9240
ttatctgatg agtatacgtt gtcctggcca cggcagaagc acgcttatcg ctccaatttc   9300
ccacaacatt agtcaactcc gttaggccct tcattgaaag aaatgaggtc atcaaatgtc   9360
ttccaatgtg agattttggg ccattttta tagcaaagat tgaataaggc gcatttttct   9420
tcaaagcttt attgtacgat ctgactaagt tatcttttaa taattggtat tcctgtttat   9480
tgcttgaaga attgccggtc ctatttactc gttttaggac tggttcagaa ttcatcgatg   9540
ctcactcaaa ggcggtaata cggttatcca cagaatcagg ggataacgca ggaaagaaca   9600
tgtgagcaaa aggccagcaa aaggccagga accgtaaaaa ggccgcgttg ctggcgtttt   9660
tccataggct ccgcccccct gacgagcatc acaaaaatcg acgctcaagt cagaggtggc   9720
gaaacccgac aggactataa agataccagg cgtttccccc tggaagctcc ctcgtgcgct   9780
ctcctgttcc gaccctgccg cttaccggat acctgtccgc ctttctccct tcgggaagcg   9840
tggcgctttc tcatagctca cgctgtaggt atctcagttc ggtgtaggtc gttcgctcca   9900
agctgggctg tgtgcacgaa ccccccgttc agcccgaccg ctgcgcctta tccggtaact   9960
atcgtcttga gtccaacccg gtaagacacg acttatcgcc actggcagca gccactggta  10020
acaggattag cagagcgagg tatgtaggcg gtgctacaga gttcttgaag tggtggccta  10080
actacggcta cactagaaga acagtatttg gtatctgcgc tctgctgaag ccagttacct  10140
tcggaaaaag agttggtagc tcttgatccg gcaaacaaac caccgctggt agcggtggtt  10200
tttttgtttg caagcagcag attacgcgca gaaaaaaagg atctcaagaa gatcctttga  10260
tcttttctac ggggtctgac gctcagtgga acgaaaactc acgttaaggg attttggtca  10320
tgagattatc aaaaaggatc ttcacctaga tccttttaaa ttaaaaatga agttttaaat  10380
caatctaaag tatatatgag taaacttggt ctgacagtta ccaatgctta atcagtgagg  10440
cacctatctc agcgatctgt ctatttcgtt catccatagt tgcctgactc cccgtcgtgt  10500
agataactac gatacgggag ggcttaccat ctggccccag tgctgcaatg ataccgcgag  10560
acccacgctc accggctcca gatttatcag caataaacca gccagccgga agggccgagc  10620
gcagaagtgg tcctgcaact ttatccgcct ccatccagtc tattaattgt tgccgggaag  10680
ctagagtaag tagttcgcca gttaatagtt tgcgcaacgt tgttgccatt gctacaggca  10740
tcgtggtgtc acgctcgtcg tttggtatgg cttcattcag ctccggttcc caacgatcaa  10800
ggcgagttac atgatccccc atgttgtgca aaaaagcggt tagctccttc ggtcctccga  10860
```

```
tcgttgtcag aagtaagttg gccgcagtgt tatcactcat ggttatggca gcactgcata  10920

attctcttac tgtcatgcca tccgtaagat gcttttctgt gactggtgag tactcaacca  10980

agtcattctg agaatagtgt atgcggcgac cgagttgctc ttgcccggcg tcaatacggg  11040

ataataccgc gccacatagc agaactttaa aagtgctcat cattggaaaa cgttcttcgg  11100

ggcgaaaact ctcaaggatc ttaccgctgt tgagatccag ttcgatgtaa cccactcgtg  11160

cacccaactg atcttcagca tcttttactt tcaccagcgt ttctgggtga gcaaaaacag  11220

gaaggcaaaa tgccgcaaaa aagggaataa gggcgacacg gaaatgttga atactcatac  11280

tcttcctttt tcaatattat tgaagcattt atcagggtta ttgtctcatg agcggataca  11340

tatttgaatg tatttagaaa aataaacaaa taggggttcc gcgcacattt ccccgaaaag  11400

tgccacctga cgtctaagaa accattatta tcatgacatt aacctataaa aataggcgta  11460

tcacgaggcc ctttcgtctc gcgcgtttcg gtgatgacgg tgaaaacctc tgacacatgc  11520

agctcccgga gacggtcaca gcttgtctgt aagcggatgc cgggagcaga caagcccgtc  11580

agggcgcgtc agcgggtgtt ggcgggtgtc ggggctggct taactatgcg gcatcagagc  11640

agattgtact gagagtgcac catatgcggt gtgaaatacc gcacagatgc gtaaggagaa  11700

aataccgcat caggcgccat tcgccattca ggctgcgcaa ctgttgggaa gggcgatcgg  11760

tgcgggcctc ttcgctatta cgccagctgg cgaaaggggg atgtgctgca aggcgattaa  11820

gttgggtaac gccagggttt tcccagtcac gacgttgtaa aacgacggcc agtgaattgc  11880

ggccgcatcg atgg                                                    11894
```

```
<210> SEQ ID NO 36
<211> LENGTH: 10821
<212> TYPE: DNA
<213> ORGANISM: Artificial Sequence
<220> FEATURE:
<223> OTHER INFORMATION: bCBGA0409 vector

<400> SEQUENCE: 36
```

```
gtggtggtga ggtggcaaag gtgggatgga ttgttcgttt ctgaaaaagt tgttagggtc     60

ggctttagtc tttactttaa ctaatctgtt gaaattttta ccaaagtact tttcacccca    120

aattcttgct tgtgtatagt tatttggaga ttcagggtta gttttaccta agtccaaatc    180

tctgtagttc aaatatgcca atcttgggtt ttgactaacg taaggtgtag tgaagttgta    240

aacggatctg acccagttga tatgcttttc gttatcttct tgcttttccc atgaggctgt    300

gtaccataat tcatacatga taccagctct gtgaggaaat ggtatggctg attcagatat    360

ttcttccata ataccaccgt atggatacaa aacgtacatg ccgacaccta catcttcttc    420

gtacaacttt tccaatatct tgaccattgc agtttcaggg attggtttct taacgtagtc    480

caatttaata gaaaaagcgg tctttttacc agcggatcta tccaacaaga tttccttttt    540

gaagttagcg gtgttgaagt ttacaacacc tgaatagaag atggttgtgt ctatccaaga    600

aaattccttg caatctgtct ttttaatacc caattctggg aatgacttat tcatcaaatc    660

aaccaaagaa tctacaccac catggaaaat tgaagaaaaa taaccgtgaa cagtggtctt    720

atttttacca tggttatctg taatattttt agtgatgaaa tgggtcatca aaaccaagtc    780

cttatcgtac ttgtaagcga tgttttgcca cttattaaac aacttaacca aaccgtggat    840

ttccatgttc tttttgacag agaaaatagt acttttggaa ggaacagcga ctaacttaat    900

tttccaagcg gcaatgatac cgaaattttc accaccacca cctcttatgg cccaaaacaa    960
```

```
atcttcaccc atagactttc tgtccaaaac tttaccatct acgttaacca aatgggcgtc   1020
tataatatta tctgcagcta aaccgtagtt tctcatcaat gcaccataac caccaccaga   1080
aaagtgacca ccgacaccta ctgttggaca gtaaccacca gggaaagaaa agttttcatt   1140
cttttcgttg atccagtagt aaacttcacc caaggtggca cctgcttcta cccatgctgt   1200
ttgactgtga acgtcgatct ttatggaatg catatttctc aaatcgacta caacgaatgg   1260
aacttgtgag atgtaagaca tgccttctgc atcatgacca cctgatctag ttctgatttg   1320
caaacctact ttcttagagc acaatataga agcttgaatg tgactaacat tggaaggtgt   1380
aacaatgact aaaggttttg gtgtagtgtc agaagtgaat ctcaaatttt ggatggtact   1440
gttcaaaacg gacatgtaca attgatcatg ttgagtatat ataaactttg ggttagcagg   1500
gttgtttggg atgtattcgg agaaacactt caaaaagttt tcttgtggat ttgcgatgga   1560
gatttggatg ttgaaggaca agaagaagaa gattatttta cagacgaacc agaaagagaa   1620
tgcggagcag ttcatttata ttgaattttc aaaaattctt actttttttt tggatggacg   1680
caaagaagtt taataatcat attacatggc attaccacca tatacatatc catatctaat   1740
cttacttata tgttgtggaa atgtaaagag ccccattatc ttagcctaaa aaaaccttct   1800
ctttggaact ttcagtaata cgcttaactg ctcattgcta tattgaagta cggattagaa   1860
gccgccgagc gggcgacagc cctccgacgg aagactctcc tccgtgcgtc ctcgtcttca   1920
ccggtcgcgt tcctgaaacg cagatgtgcc tcgcgccgca ctgctccgaa caataaagat   1980
tctacaatac tagcttttat ggttatgaag aggaaaaatt ggcagtaacc tggccccaca   2040
aaccttcaaa ttaacgaatc aaattaacaa ccataggatg ataatgcgat tagtttttta   2100
gccttatttc tggggtaatt aatcagcgaa gcgatgattt ttgatctatt aacagatata   2160
taaatggaaa agctgcataa ccactttaac taatactttc aacattttca gtttgtatta   2220
cttcttattc aaatgtcata aaagtatcaa caaaaaattg ttaatatacc tctatacttt   2280
aacgtcaagg agaaaaaact ataatgggtt tatctttggt ctgtactttt tcatttcaaa   2340
ctaattacca tacattgtta aatccacata ataagaaccc taaaaattct ttgttgtcat   2400
atcaacatcc aaaaactcca attattaaat cttcttatga taattttcca tctaagtact   2460
gtttgactaa aaatttccat ttgttaggtt taaattctca taatagaatt tcttcacaat   2520
caagatcaat tagagctggt tctgatcaaa ttgaaggttc accacatcat gaatctgata   2580
actcaatcgc aactaaaatt ttgaactttg gtcatacatg ttggaaattg caaagaccat   2640
acgttgttaa gggtatgatt tctattgctt gtggtttatt tggtagagaa ttgtttaata   2700
acagacattt gttttcttgg ggtttgatgt ggaaagcatt tttcgcatta gttccaatct   2760
tgtcttttaa tttctttgct gcaatcatga accaaatata tgatgttgat attgatagaa   2820
ttaataagcc agatttgcca ttggtttctg gtgaaatgtc aatcgaaact gcttggattt   2880
tatctatcat cgttgcattg actggtttga tcgttacaat taaattaaaa tcagctccat   2940
tgttcgtttt tatatatatc ttcggtatct tcgctggttt tgcatactct gttccaccaa   3000
ttagatggaa gcaatacccc tttactaatt tcttgatcac aatttcttca catgttggtt   3060
tggcttttac ttcttactca gctactacat ctgcattagg tttgccattt gtttggaggc   3120
cagctttttc ttttattatc gcttttatga ctgttatggg tatgacaatc gctttcgcaa   3180
aggatatctc tgatattgaa ggtgacgcta aatacggtgt ttcaactgtt gctacaaaat   3240
tgggtgcaag aaacatgact ttcgttgttt ctggtgtttt gttgttgaac tatttggttt   3300
ctatctcaat cggtattatt tggccacaag tttttaaatc taacatcatg atcttgtcac   3360
```

```
atgctatctt ggcattctgt ttgatcttcc aaacaagaga attagctttg gcaaattatg   3420
cttctgcacc atcaagacaa tttttcgagt ttatttggtt gttgtactac gctgaatatt   3480
ttgtttacgt ttttatttga gattaatata attatataaa aatattatct tcttttcttt   3540
atatctagtg ttatgtaaaa taaattgatg actacggaaa gctttttttat attgtttctt   3600
tttcattctg agccacttaa atttcgtgaa tgttcttgta agggacggta gatttacaag   3660
tgatacaaca aaaagcaagg cgctttttct aataaaaaga agaaaagcat ttaacaattg   3720
aacacctcta tatcaacgaa gaatattact ttgtctctaa atccttgtaa aatgtgtacg   3780
atctctatat gggttactca taagtgtacc gaagactgca ttgaaagttt atgtttttc   3840
actggaggcg tcattttcgc gttgagaaca attgtcctgt acttccttgt tcatgtgtgt   3900
tcaaaaacgt tatatttata ggataattat actctatttc tcaacaagta attggttgtt   3960
tggccgagcg gtctaaggcg cctgattcaa gaaatatctt gaccgcagtt aactgtggga   4020
atactcaggt atcgtaagat gcaagagttc gaatctctta gcaaccatta tttttttcct   4080
caacataacg agaacacaca ggggcgctat cgcacagaat caaattcgat gactggaaat   4140
tttttgttaa tttcagaggt cgcctgacgc atataccttt ttcaactgaa aaattgggag   4200
aaaaaggaaa ggtgagagcg ccggaaccgg cttttcatat agaatagaga agcgttcatg   4260
actaaatgct tgcatcacaa tacttgaagt tgacaatatt atttaaggac ctattgtttt   4320
ttccaatagg tggttagcaa tcgtcttact ttctaacttt tcttaccttt tacatttcag   4380
caatatatat atatatttca aggatatacc attctaatgt ctgcccctaa gaagatcgtc   4440
gttttgccag gtgaccacgt tggtcaagaa atcacagccg aagccattaa ggttcttaaa   4500
gctatttctg atgttcgttc caatgtcaag ttcgatttcg aaaatcattt aattggtggt   4560
gctgctatcg atgctacagg tgttccactt ccagatgagg cgctggaagc ctccaagaag   4620
gctgatgccg ttttgttagg tgctgtgggt ggtcctaaat ggggtaccgg tagtgttaga   4680
cctgaacaag gtttactaaa aatccgtaaa gaacttcaat tgtacgccaa cttaagacca   4740
tgtaactttg catccgactc tcttttagac ttatctccaa tcaagccaca atttgctaaa   4800
aatactgact tcgttgttgt cagagaatta gtgggaggta tttactttgg taagagaaag   4860
gaagacgatg gtgatggtgt cgcttgggat agtgaacaat acaccgttcc agaagtgcaa   4920
agaatcacaa gaatggccgc tttcatggcc ctacaacatg agccaccatt gcctatttgg   4980
tccttggata aagctaatgt tttggcctct tcaagattat ggagaaaaac tgtggaggaa   5040
accatcaaga acgaattccc tacattgaag gttcaacatc aattgattga ttctgccgcc   5100
atgatcctag ttaagaaccc aacccaccta aatggtatta taatcaccag caacatgttt   5160
ggtgatatca tctccgatga agcctccgtt atcccaggtt ccttgggttt gttgccatct   5220
gcgtccttgg cctctttgcc agacaagaac accgcatttg gtttgtacga accatgccac   5280
ggttctgctc cagatttgcc aaagaataag gtcaacccta tcgccactat cttgtctgct   5340
gcaatgatgt tgaaattgtc attgaacttg cctgaagaag gtaaggccat tgaagatgca   5400
gttaaaaagg ttttggatgc aggtatcaga actggtgatt taggtggttc caacagtacc   5460
accgaagtcg gtgatgctgt cgccgaagaa gttaagaaaa tccttgctta aaaagattct   5520
ctttttttat gatatttgta cataaacttt ataaatgaaa ttcataatag aaacgacacg   5580
aaattacaaa atggaatatg ttcatagggt agacgaaact atatacgcaa tctacataca   5640
tttatcaaga aggagaaaaa ggaggatgta aaggaataca ggtaagcaaa ttgatactaa   5700
```

```
tggctcaacg tgataaggaa aaagaattgc actttaacat taatattgac aaggaggagg   5760
gcaccacaca aaaagttaca gatctgctgc attaatgaat cggccaacgc gcggggagag   5820
gcggtttgcg tattgggcgc tcttccgctt cctcgctcac tgactcgctg cgctcggtcg   5880
ttcggctgcg gcgagcggta tcagcatcga tgaattccac ggactataga ctatactagt   5940
atactccgtc tactgtacga tacacttccg ctcaggtcct tgtcctttaa cgaggcctta   6000
ccactctttt gttactctat tgatccagct cagcaaaggc agtgtgatct aagattctat   6060
cttcgcgatg tagtaaaact agctagaccg agaaagagac tagaaatgca aaaggcactt   6120
ctacaatggc tgccatcatt attatccgat gtgacgctgc agcttctcaa tgatattcga   6180
atacgctttg aggagataca gcctaatatc cgacaaactg ttttacagat ttacgatcgt   6240
atttgttacc catcattgaa ttttgaacat ccgaacctgg gagttttccc tgaaacagat   6300
agtatatttg aacctgtata ataatatata gtctagcgct ttacggaaga caatgtatgt   6360
atttcggttc ctggagaaac tattgcatct attgcatagg taatcttgca cgtcgcatcc   6420
ccggttcatt ttctgcgttt ccatcttgca cttcaatagc atatctttgt taacgaagca   6480
tctgtgcttc attttgtaga acaaaaatgc aacgcgagag cgctaatttt tcaaacaaag   6540
aatctgagct gcatttttac agaacagaaa tgcaacgcga aagcgctatt ttaccaacga   6600
agaatctgtg cttcattttt gtaaaacaaa aatgcaacgc gagagcgcta atttttcaaa   6660
caaagaatct gagctgcatt tttacagaac agaaatgcaa cgcgagagcg ctattttacc   6720
aacaaagaat ctatacttct tttttgttct acaaaaatgc atcccgagag cgctattttt   6780
ctaacaaagc atcttagatt actttttttc tcctttgtgc gctctataat gcagtctctt   6840
gataactttt tgcactgtag gtccgttaag gttagaagaa ggctactttg gtgtctattt   6900
tctcttccat aaaaaaagcc tgactccact tcccgcgttt actgattact agcgaagctg   6960
cgggtgcatt ttttcaagat aaaggcatcc ccgattatat tctataccga tgtggattgc   7020
gcatactttg tgaacagaaa gtgatagcgt tgatgattct tcattggtca gaaaattatg   7080
aacggtttct tctattttgt ctctatatac tacgtatagg aaatgtttac attttcgtat   7140
tgttttcgat tcactctatg aatagttctt actacaattt ttttgtctaa agagtaatac   7200
tagagataaa cataaaaaat gtagaggtcg agtttagatg caagttcaag gagcgaaagg   7260
tggatgggta ggttatatag ggatatagca cagagatata tagcaaagag atacttttga   7320
gcaatgtttg tggaagcggt attcgcaata ttttagtagc tcgttacagt ccggtgcgtt   7380
tttggttttt tgaaagtgcg tcttcagagc gcttttggtt ttcaaaagcg ctctgaagtt   7440
cctatacttt ctagagaata ggaacttcgg aataggaact tcaaagcgtt tccgaaaacg   7500
agcgcttccg aaaatgcaac gcgagctgcg cacatacagc tcactgttca cgtcgcacct   7560
atatctgcgt gttgcctgta tatatatata catgagaaga acggcatagt gcgtgtttat   7620
gcttaaatgc gtacttatat gcgtctattt atgtaggatg aaaggtagtc tagtacctcc   7680
tgtgatatta tcccattcca tgcggggtat cgtatgcttc cttcagcact accctttagc   7740
tgttctatat gctgccactc ctcaattgga ttagtctcat ccttcaatgc tatcatttcc   7800
tttgatattg gatcatatgc atagtaccga gaaactagtg cgaagtagtg atcaggtatt   7860
gctgttatct gatgagtata cgttgtcctg gccacggcag aagcacgctt atcgctccaa   7920
tttcccacaa cattagtcaa ctccgttagg ccccttcattg aaagaaatga ggtcatcaaa   7980
tgtcttccaa tgtgagattt tgggccattt tttatagcaa agattgaata aggcgcattt   8040
ttcttcaaag ctttattgta cgatctgact aagttatctt ttaataattg gtattcctgt   8100
```

```
ttattgcttg aagaattgcc ggtcctattt actcgtttta ggactggttc agaattcatc   8160
gatgctcact caaaggcggt aatacggtta tccacagaat caggggataa cgcaggaaag   8220
aacatgtgag caaaaggcca gcaaaaggcc aggaaccgta aaaaggccgc gttgctggcg   8280
tttttccata ggctccgccc ccctgacgag catcacaaaa atcgacgctc aagtcagagg   8340
tggcgaaacc cgacaggact ataaagatac caggcgtttc cccctggaag ctccctcgtg   8400
cgctctcctg ttccgaccct gccgcttacc ggatacctgt ccgcctttct cccttcggga   8460
agcgtggcgc tttctcatag ctcacgctgt aggtatctca gttcggtgta ggtcgttcgc   8520
tccaagctgg gctgtgtgca cgaacccccc gttcagcccg accgctgcgc cttatccggt   8580
aactatcgtc ttgagtccaa cccggtaaga cacgacttat cgccactggc agcagccact   8640
ggtaacagga ttagcagagc gaggtatgta ggcggtgcta cagagttctt gaagtggtgg   8700
cctaactacg gctacactag aagaacagta tttggtatct gcgctctgct gaagccagtt   8760
accttcggaa aaagagttgg tagctcttga tccggcaaac aaaccaccgc tggtagcggt   8820
ggtttttttg tttgcaagca gcagattacg cgcagaaaaa aaggatctca agaagatcct   8880
ttgatctttt ctacggggtc tgacgctcag tggaacgaaa actcacgtta agggattttg   8940
gtcatgagat tatcaaaaag gatcttcacc tagatccttt taaattaaaa atgaagtttt   9000
aaatcaatct aaagtatata tgagtaaact tggtctgaca gttaccaatg cttaatcagt   9060
gaggcaccta tctcagcgat ctgtctattt cgttcatcca tagttgcctg actccccgtc   9120
gtgtagataa ctacgatacg ggagggctta ccatctggcc ccagtgctgc aatgataccg   9180
cgagacccac gctcaccggc tccagattta tcagcaataa accagccagc cggaagggcc   9240
gagcgcagaa gtggtcctgc aactttatcc gcctccatcc agtctattaa ttgttgccgg   9300
gaagctagag taagtagttc gccagttaat agtttgcgca acgttgttgc cattgctaca   9360
ggcatcgtgg tgtcacgctc gtcgtttggt atggcttcat tcagctccgg ttcccaacga   9420
tcaaggcgag ttacatgatc ccccatgttg tgcaaaaaag cggttagctc cttcggtcct   9480
ccgatcgttg tcagaagtaa gttggccgca gtgttatcac tcatggttat ggcagcactg   9540
cataattctc ttactgtcat gccatccgta agatgctttt ctgtgactgg tgagtactca   9600
accaagtcat tctgagaata gtgtatgcgg cgaccgagtt gctcttgccc ggcgtcaata   9660
cgggataata ccgcgccaca tagcagaact ttaaaagtgc tcatcattgg aaaacgttct   9720
tcggggcgaa aactctcaag gatcttaccg ctgttgagat ccagttcgat gtaacccact   9780
cgtgcaccca actgatcttc agcatctttt actttcacca gcgtttctgg gtgagcaaaa   9840
acaggaaggc aaaatgccgc aaaaaaggga ataagggcga cacggaaatg ttgaatactc   9900
atactcttcc tttttcaata ttattgaagc atttatcagg gttattgtct catgagcgga   9960
tacatatttg aatgtattta gaaaaataaa caaatagggg ttccgcgcac atttccccga  10020
aaagtgccac ctgacgtcta agaaaccatt attatcatga cattaaccta taaaaatagg  10080
cgtatcacga ggccctttcg tctcgcgcgt ttcggtgatg acggtgaaaa cctctgacac  10140
atgcagctcc cggagacggt cacagcttgt ctgtaagcgg atgccgggag cagacaagcc  10200
cgtcagggcg cgtcagcggg tgttggcggg tgtcggggct ggcttaacta tgcggcatca  10260
gagcagattg tactgagagt gcaccatatg cggtgtggaa taccgcacag atgcgtaagg  10320
agaaaatacc gcatcaggcg ccattcgcca ttcaggctgc gcaactgttg ggaagggcga  10380
tcggtgcggg cctcttcgct attacgccag ctggcgaaag ggggatgtgc tgcaaggcga  10440
```

```
ttaagttggg taacgccagg gttttcccag tcacgacgtt gtaaaacgac ggccagtgaa  10500

ttgcggccgc atcgatggaa aagaccaaac ggtgacgtta agagaaagaa attctatgag  10560

gcaagtaaga ggcactatta ctgatgtgat ttcgaccatt gacaaaatgc ttcacaaccc  10620

tgatgaatcg gactgggata aatcaacatt tggactgtcg cctgttaaga tataactgaa  10680

aaaagagggg aatttttaga tactgaaatg atattttaga ataaccagac tatatataag  10740

gataaattac aaaaaattaa ctaatagata agatttaaat ataaaagata tgcaactaga  10800

aaagtcttat caatctcctt a                                            10821
```

```
<210> SEQ ID NO 37
<211> LENGTH: 951
<212> TYPE: DNA
<213> ORGANISM: Artificial Sequence
<220> FEATURE:
<223> OTHER INFORMATION: Truncated Prenyltransferase

<400> SEQUENCE: 37

attgaaggtt caccacatca tgaatctgat aactcaatcg caactaaaat tttgaacttt     60

ggtcatacat gttggaaatt gcaaagacca tacgttgtta agggtatgat ttctattgct    120

tgtggtttat ttggtagaga attgtttaat aacagacatt tgttttcttg ggtttgatg     180

tggaaagcat tttcgcatt agttccaatc ttgtctttta atttctttgc tgcaatcatg     240

aaccaaatat atgatgttga tattgataga attaataagc cagatttgcc attggtttct    300

ggtgaaatgt caatcgaaac tgcttggatt ttatctatca tcgttgcatt gactggtttg    360

atcgttacaa ttaaattaaa atcagctcca ttgttcgttt ttatatatat cttcggtatc    420

ttcgctggtt ttgcatactc tgttccacca attagatgga agcaataccc ttttactaat    480

ttcttgatca caatttcttc acatgttggt ttggctttta cttcttactc agctactaca    540

tctgcattag gtttgccatt tgtttggagg ccagcttttt cttttattat cgcttttatg    600

actgttatgg gtatgacaat cgctttcgca aaggatatct ctgatattga aggtgacgct    660

aaatacggtg tttcaactgt tgctacaaaa ttgggtgcaa gaaacatgac tttcgttgtt    720

tctggtgttt tgttgttgaa ctatttggtt tctatctcaa tcggtattat ttggccacaa    780

gtttttaaat ctaacatcat gatcttgtca catgctatct tggcattctg tttgatcttc    840

caaacaagag aattagcttt ggcaaattat gcttctgcac catcaagaca atttttcgag    900

tttatttggt tgttgtacta cgctgaatat tttgtttacg tttttatttg a             951
```

```
<210> SEQ ID NO 38
<211> LENGTH: 316
<212> TYPE: PRT
<213> ORGANISM: Artificial Sequence
<220> FEATURE:
<223> OTHER INFORMATION: Truncated Prenyltransferase

<400> SEQUENCE: 38

Ile Glu Gly Ser Pro His His Glu Ser Asp Asn Ser Ile Ala Thr Lys
1               5                   10                  15

Ile Leu Asn Phe Gly His Thr Cys Trp Lys Leu Gln Arg Pro Tyr Val
            20                  25                  30

Val Lys Gly Met Ile Ser Ile Ala Cys Gly Leu Phe Gly Arg Glu Leu
        35                  40                  45

Phe Asn Asn Arg His Leu Phe Ser Trp Gly Leu Met Trp Lys Ala Phe
    50                  55                  60

Phe Ala Leu Val Pro Ile Leu Ser Phe Asn Phe Phe Ala Ala Ile Met
```

```
65                  70                  75                  80

Asn Gln Ile Tyr Asp Val Asp Ile Asp Arg Ile Asn Lys Pro Asp Leu
                85                  90                  95

Pro Leu Val Ser Gly Glu Met Ser Ile Glu Thr Ala Trp Ile Leu Ser
            100                 105                 110

Ile Ile Val Ala Leu Thr Gly Leu Ile Val Thr Ile Lys Leu Lys Ser
        115                 120                 125

Ala Pro Leu Phe Val Phe Ile Tyr Ile Phe Gly Ile Phe Ala Gly Phe
    130                 135                 140

Ala Tyr Ser Val Pro Pro Ile Arg Trp Lys Gln Tyr Pro Phe Thr Asn
145                 150                 155                 160

Phe Leu Ile Thr Ile Ser Ser His Val Gly Leu Ala Phe Thr Ser Tyr
                165                 170                 175

Ser Ala Thr Thr Ser Ala Leu Gly Leu Pro Phe Val Trp Arg Pro Ala
            180                 185                 190

Phe Ser Phe Ile Ile Ala Phe Met Thr Val Met Gly Met Thr Ile Ala
        195                 200                 205

Phe Ala Lys Asp Ile Ser Asp Ile Glu Gly Asp Ala Lys Tyr Gly Val
    210                 215                 220

Ser Thr Val Ala Thr Lys Leu Gly Ala Arg Asn Met Thr Phe Val Val
225                 230                 235                 240

Ser Gly Val Leu Leu Leu Asn Tyr Leu Val Ser Ile Ser Ile Gly Ile
                245                 250                 255

Ile Trp Pro Gln Val Phe Lys Ser Asn Ile Met Ile Leu Ser His Ala
            260                 265                 270

Ile Leu Ala Phe Cys Leu Ile Phe Gln Thr Arg Glu Leu Ala Leu Ala
        275                 280                 285

Asn Tyr Ala Ser Ala Pro Ser Arg Gln Phe Phe Glu Phe Ile Trp Leu
    290                 295                 300

Leu Tyr Tyr Ala Glu Tyr Phe Val Tyr Val Phe Ile
305                 310                 315


<210> SEQ ID NO 39
<211> LENGTH: 4247
<212> TYPE: DNA
<213> ORGANISM: Saccharomyces cerevisiae
<220> FEATURE:
<221> NAME/KEY: misc_feature
<222> LOCATION: (836)..(837)
<223> OTHER INFORMATION: n is a, c, g, or t

<400> SEQUENCE: 39

tcactcaacc atctccaaaa aataacaggt tcatctaaag taaaagactt taacttgctc     60

ttagtttcca aattaaatat ctgcacgata gtaccatttg ctctaacgga aataaccatc    120

tgagatggat gcatgatagc agaatcaccg cccatattct tccttgtcac ttcattgcct    180

ttggccaaat ccacgattgc aacagagttt gtaccgtcct ttgtttctct aacagtgacg    240

aagtggtcac tctcgaaagt agttgatctg aagtcaagga attgagggga aattcctaag    300

gacgtcagat cgaccaattc ggtaaattca atgggtaggt cactcattgg ttagaacttt    360

cgtgataatt tatttttata gttgaatatc ttctttctct ctcaactctg atccggattg    420

tcgaggtttc aataagttac tctgaacaac taatcaaaat atctccttat ttctgtagat    480

tccttcagtt ccactttttg cttttcttaa ttctctttgt atttattcct agcgacgaaa    540

aatgcgagat ctcgaccaaa aaaagggggt agggtaataa aattarccct attatttttg    600
```

```
aactttaaaa cctataatgt gctaatattt tattatacac ctcctttttt tgtgtttaaa    660
ccctgacaca ttttaagccc tatatttacg gtattagttg attaaactcc gaagcgaaag    720
gaattcggtc attagcggct aatagccgtt ggggtaaatc acctacaagc aagtacacaa    780
gagaacgttg gcgttgttaa gtcaaagcac taatacattg gggctttaag agtgtnnata    840
aaggtctgac ctgtaaaaat tatttaaaca acttgaacag gccttaaagt tttcctcatt    900
ccgctcatca tcactaatat tgctctccgt tttgaatac acacttgaca ctaataagta    960
tcacagaaaa aaagaaaata taataaatta gtattgcgat atgacgagac gtactactat   1020
taatcccgat tcggtggttc tgaatcctca aaaatttatc cagaaagaaa gggcggattc   1080
caaaatcaaa gttgaccaag ttaacacatt tttagagtca tccccggaga ggagaactct   1140
gacgcacgcc ttaatagacc aaatagtgaa tgatcctata ttgaagactg acacggacta   1200
ttacgatgct acaaaactgc aagagagaga aattactgcc aaaaaaatag ctaggcttgc   1260
tagttatatg gagcacgata tcaaaacagt gcgcaaacac tttcgcaaca ctgacctgat   1320
gaaagagttg caagcaaatg atccagacaa agcttcgcct ttaacaaaca aagacctttt   1380
tatattcgat aagagattat cacttgtagc aaatattgat cctcaattgg gtacgcgcgt   1440
gggtgtacac ttggggctat ttggtaattg tatcaagggc aatggtactg atgagcaaat   1500
ccggtattgg ttgcaggaga gaggtgccac tttgatgaaa ggtatatatg gctgttttgc   1560
aatgactgag ttaggacatg gttccaatgt tgcccagctg cagactaggg ctgtgtacga   1620
taagcaaaat gatactttta taattgatac acctgatcta actgccacca aatggtggat   1680
tggtggggct gcccattctg ccacgcacgc tgccgtgtac gccagattga tcgttgaagg   1740
taaagactac ggtgtaaaaa cattcgttgt tcctctgaga gacccttcga ctttccaact   1800
gttagctggt gtttccatag gggatattgg agcgaagatg ggtcgtgacg gtattgataa   1860
tggctggatc cagttcagaa acgtagttat ccctagagaa tttatgctaa gtagatttac   1920
caaagttgtc cgttctccag atggttcagt caccgtcaaa actgagccac aattggatca   1980
aatttctggt tatagtgcat tgttaagtgg tagagttaac atggtcatgg attcatttag   2040
gtttggctcc aaatttgcta ctattgctgt acgttacgcg gttggtcgtc agcaattcgc   2100
acctagaaag ggattgtctg aaacacaatt aatcgactat ccccttcacc aatatcgtgt   2160
tttaccacaa ttgtgtgttc catatttggt gtcacctgta gcttttaagt taatggacaa   2220
ctattattcc actttggacg agttatacaa cgcttcctca tctgcagaca aagctgctct   2280
ggttaccgtg agtaaaaagt tgaagaattt atttattgat agcgccagct tgaaagccac   2340
caatacttgg ttaattgcta cactgattga tgagttgaga cagacttgcg gaggacatgg   2400
gtattcacag tataacggat ttggtaaagg ctatgacgac tgggtggttc agtgcacatg   2460
ggagggtgat aataatgttt tatctttaac ttcagcaaaa tcaatattga aaaaatttat   2520
cgattcagcc acaaagggta gatttgacaa cacactggat gtggactcat tctcttactt   2580
aaaacctcag tacataggat ctgtggtttc tggagaaaca aagagtagtt taaaggagtt   2640
gggtgattat actgaaattt ggtctatcac cttaatcaaa ttattggcac atattggtac   2700
tttagttgaa aaatcaagaa gtattgatag cgtttctaag cttttagtct tagtatccaa   2760
atttcatgcc ttgcgctgca tgttgaaaac ctattacgac aagttaaact ctcgcgattc   2820
acatatttcc gatgaaatta caaaggaatc aatgtggaat gtttataagt tattttcctt   2880
gtattttatt gacaagcatt ccggagaatt ccaacaattc aagattttca ctcctgatca   2940
gatctctaaa gttgtgcagc cacaactatt ggctcttttk ccaattgtga ggaaagactg   3000
```

```
tataggtgtg acagactcct ttgaattacc tgacgcgatg ttaaattctc ctataggtta   3060
ctttgatggc gatatctatc acaattactt caatgaagtt tgccgcaata atccagtgga   3120
ggcagatggg gcagggaagc cttcttatca tgcgctgttg agcagcatgc tcggtagagg   3180
tttcgaattt gaccaaaagt taggtggtgc agctaatgcg gaaattttat cgaaaataaa   3240
caagtgagta gaggtttcct gttttccttc gaaccctctg ttttgcgact tttgtttcaa   3300
ttcaactagt gtcgccaagt tttaacaaaa agttacaaaa tcctagtgag aggccatctt   3360
ttgtgcataa cggtactctc tatctattta catatctaat actattcaca taactatgac   3420
gaatcaatga catgactaca tttaccaatg tatagtagta aaaaawttgc catctcctag   3480
aatcgaacca gggtttcatc ggccacaacg atgtgtacta accactatac taagatggca   3540
ggtaattatt gagtgtttac tcaatatctc agaattatat acgtaacaaa taataaatgt   3600
gctgtgttgg cacttgttgg aatgaagctc taaaatatca tgatgattgt gtggattctg   3660
atgtaattgt tgggattcca tttttaataa ggcaatatgt tggaacgaga gtaattaata   3720
gtgacatgag ttgctatggt aacaatctaa tgcttacatc gtatattaat gtacacatcg   3780
tatacgttta agtgtgattg cgcctattgc agaaggaatg ttaaacgaga agctcagaca   3840
atactgaagc tgtgttaaag acctattagc tgaacatgat atggtaggta catatatgag   3900
gaatatgagt cgtcacatca atgtatagta actaccggaa tcactattat attggtcatg   3960
attaatatga ccaatcggcg tgtgttttat atacctctct tatttagtat aagaagatca   4020
gtactcactt cttcattaat actaattttt aacctctaat tatcaacaca ataatattag   4080
gtatgtagat atactagaag ttctcctcca ggatttagga atccataaaa gggagtctgc   4140
aattctacac aattctataa atattatcat catcgtttta tatgttaata ttcattgatc   4200
ctattacatt atcaatcctt gcgtttcagc ttccactaat ttagatg                 4247
```